US009187535B2

(12) United States Patent
Lindborg et al.

(10) Patent No.: US 9,187,535 B2
(45) Date of Patent: Nov. 17, 2015

(54) POLYPEPTIDE DERIVED FROM PROTEIN A AND ABLE TO BIND PDGF

(75) Inventors: Malin Lindborg, Bromma (SE); Elin Gunneriusson, Saltsjöbaden (SE); Christofer Lendel, Farsta (SE)

(73) Assignee: AFFIBODY AB, Solna (SE)

( * ) Notice: Subject to any disclaimer, the term of this patent is extended or adjusted under 35 U.S.C. 154(b) by 907 days.

(21) Appl. No.: 12/735,070

(22) PCT Filed: Dec. 17, 2008

(86) PCT No.: PCT/EP2008/010776
§ 371 (c)(1),
(2), (4) Date: Oct. 6, 2010

(87) PCT Pub. No.: WO2009/077175
PCT Pub. Date: Jun. 25, 2009

(65) Prior Publication Data
US 2011/0021424 A1 Jan. 27, 2011

Related U.S. Application Data

(63) Continuation-in-part of application No. 12/002,972, filed on Dec. 19, 2007, now Pat. No. 8,937,047.

(60) Provisional application No. 61/009,171, filed on Dec. 26, 2007.

(30) Foreign Application Priority Data

Dec. 21, 2007 (EP) .................................. 07150394

(51) Int. Cl.
*C07K 14/31* (2006.01)
(52) U.S. Cl.
CPC .............. *C07K 14/31* (2013.01); *C07K 2318/20* (2013.01); *C07K 2319/00* (2013.01)
(58) Field of Classification Search
None
See application file for complete search history.

(56) References Cited

U.S. PATENT DOCUMENTS

| | | | |
|---|---|---|---|
| 5,831,012 A | 11/1998 | Nilsson et al. | |
| 6,534,628 B1 | 3/2003 | Nilsson et al. | |
| 6,602,977 B1 | 8/2003 | Ljungqvist et al. | |
| 6,740,734 B1 | 5/2004 | Nilsson et al. | |
| 7,993,650 B2 | 8/2011 | Carlsson et al. | |
| 8,124,725 B2* | 2/2012 | Marino et al. | 530/324 |
| 2009/0180954 A1* | 7/2009 | Marino et al. | 424/1.69 |
| 2009/0191124 A1* | 7/2009 | Marino et al. | 424/1.69 |
| 2011/0021424 A1* | 1/2011 | Lindborg et al. | 514/7.5 |

FOREIGN PATENT DOCUMENTS

| | | |
|---|---|---|
| EP | 2 077 272 A1 | 7/2009 |
| WO | WO 91/01743 | 2/1991 |
| WO | WO 92/00091 | 1/1992 |
| WO | WO 95/19374 | 7/1995 |
| WO | WO 2005/003156 | 1/2005 |
| WO | 2005097202 A2 | 10/2005 |
| WO | 2006092338 A2 | 9/2006 |
| WO | WO 2007/065635 | 6/2007 |
| WO | 2009019117 A1 | 2/2009 |
| WO | WO 2009/077569 A1 | 6/2009 |
| WO | WO 2009/080810 A1 | 7/2009 |
| WO | WO 2009/080811 A1 | 7/2009 |

OTHER PUBLICATIONS

Orlova, Anna et al., "Tumor Imaging Using a Picomolar Affinity HER2 Binding Affibody Molecule", Cancer Research, vol. 66, No. 8., pp. 4339-4348 (Apr. 15, 2006).
Wikman, M. et al., Election and characterization of HER2/neu-binding affibody ligands, Protein Engineering, Design & Selection, vol. 17, No. 5, pp. 455-462 (Jun. 18, 2004).
Orlova, Anna et al., "Affibody Molecules for Molecular Imaging and Therapy for Cancer", Cancer Biotherapy & Radiopharmaceuticals, vol. 22, No. 6, pp. 573-584 (2007).
Orlova, Anna et al., "Synthetic Ajjbody Molecules: A Novel Class of Affinity Ligands for Molecular Imaging of HER2-Expressing Malignant Tumors", Cancer Research, vol. 67, No. 5, pp. 2178-2186 (Mar. 1, 2007).
Tran, Thuy et al., "$^{99m}$Te-maEEE-$Z_{HER2:342}$, an Affibody Molecule-Based Tracer for the Detection of HER2 Expression in Malignant Tumors", Bioconjugate Chemistry, vol. 18, No. 6, pp. 1956-1964 (2007).
Tolmachev, Vladimir et al., "Radionuclide Therapy of HER2-Positive Microzenografts Using a $^{177}$Lu-Labeled HER2-Specific Affibody Molecule", Cancer Research, vol. 67, No. 6, (Mar. 15, 2007).
Linhult, Martin et al., "Improving the Tolerance of a Protein A Analogue to Repeated Alkaline Exposures Using a Bypass Mutagenesis Approach", Proteins, vol. 55, pp. 407-416 (2004).
Alvarez et al., "Biology of Platelet-Derived Growth Factor and its Involvement in Disease", Mayo Clinic Proceedings, Sep. 2006; vol. 81, No. 9, pp. 241-1257.
Baranowska-Kortylewicz et al., "Effect of Platelet-Derived Growth Factor Receptor-β Inhibition with STI157 on Radioimmunotherapy", Cancer Research 2005, vol. 65, No. 17, Sep. 1, 2005, pp. 7824-7831.
Bohmer et al., "A Single Amino Acid Exchange Inverts Susceptibility of Related Receptor Tyrosine Kinases for the ATP Site Inhibitor STI-571*", The Journal of Biological Chemistry, 2003 vol. 278, No. 7, Issue of Feb. 14, pp. 5148-5155.
Jones et al., "Oncogenic derivatives of platelet-derived growth factor receptors", Cellular and Molecular Life Sciences, vol. 61, (2004), pp. 2912-2923.

(Continued)

*Primary Examiner* — Maury Audet
(74) *Attorney, Agent, or Firm* — Cantor Colburn LLP

(57) ABSTRACT

The invention provides a platelet derived growth factor receptor beta (PDGF-Rβ) binding polypeptide, comprising a platelet derived growth factor receptor beta binding motif, PBM, which motif consists of an amino acid sequence as defined herein, wherein the PDGF-Rβ-binding polypeptide binds to PDGF-Rβ such that the $K_D$ value of the interaction is at most $1 \times 10^{-6}$ M. Also provided are methods and uses of said polypeptide in treatment and diagnosis of PDGF-Rβ-related conditions.

44 Claims, 27 Drawing Sheets

(56) References Cited

OTHER PUBLICATIONS

Levitzki, "PDGF receptor kinase inhibitors for the treatment of PDGF driven diseases", Cytokine & Growth Factor Reviews, vol. 15, (2004), pp. 229-235.
Lindborg et al., "Engineered High-Affinity Affbody Molecules Targeting Platelet-Derived Growth Factor Receptor β In Vivo", Journal of Molecular Biology, (2011), vol. 407, pp. 298-315.
Ostman et al., "PDGF Receptors as Targets in Tumor Treatment", Advances in Cancer Research, 2007, vol. 97, pp. 247-274.
Paulsson et al., "Prognostic Significance of Stromal Platelet-Derived Growth Factor β-Receptor Expression in Human Breast Cancer", The American Journal of Pathology, vol. 175, No. 1, Jul. 2009, pp. 334-341.
Pietras et al., "PDGF receptors as cancer drug targets", Cancer Cell, May 2003, vol. 3, pp. 439-443.
Rossi et al., "PDGFR expression in differential diagnosis between KIT-negative gastrointestinal stromal tumours and other primary soft-tissue tumours of the gastrointestinal tract", Histopathology 2005, vol. 46, pp. 522-531, DOI:10.1111/j.1365-2559.2005.02128.x.
Shen et al., "An antibody directed against PDGF receptor β enhances the antitumor and the anti-angiogenic activties of an anti-VEGF receptor 2 antibody", Biochemical and Biophysical Research Communications 357, (2007), pp. 1141-1127.
Tolmachev et al., "Imaging of Platelet-Derived Growth Factor Receptor β Expression in Glioblastoma Xenografts Using Affibody Molecule 111 In-DOTA-Z09591", Journal of Nuclear Medicine, published on Jan. 9, 2014, as doi:10.2967/jnumed.113.121814, pp. 1-7.
Alvarez et al., "Biology of Platelet-Derived Growth Factor and its Involvement in Disease", Mayo Clinic Proceedings, Sep. 2006; vol. 81, No. 9, pp. 1241-1257.
Rossi et al., "PDGFR expression in differential diagnosis between KIT-negative gastrointestinal stromal tumours and other primary soft-tissue tumours of the gastrointestinal tract", Histopathology 2005, vol. 46, pp. 522-531.
Tolmachev et al., "Imaging of Platelet-Derived Growth Factor Receptor β Expression in Glioblastoma Xenografts Using Affibody Molecule 111-In-DOTA-Z09591", Journal of Nuclear Medicine, 2014, 55: 1-7; epublished on Jan. 9, 2014, as doi:10.2967/jnumed.113.121814.
Gronwall et al. "Selection and Characterization of Affibody Ligands Binding to Alzheimer Amyloid β Peptides" Journal of Biotechnology, 128 (2007) 162-183.
Nord et al. "Binding Proteins Selected from Combinatorial Libraries of an a-helical Bacterial Receptor Domain" Nature Biotechnology, vol. 15, pp. 772-777 (1997).
Nord et al. "A Combinatorial Library of an a-helical Bacterial Receptor Domain" Protein Engineering, vol. 8, No. 6, pp. 601-608 (1995).
Hosse et al., "A New Generation of Protein Display Scaffolds for Molecular Recognition", Protein Science; 15 (2006); pp. 14-27.
Informational Pamphlet "Phusion® Flash, High-idelity PCR Master Mix" Finnzymes; Version 1.4; Oct. 2010; 2 Pages.
Sörensen et al., "First-in-Human Molecular Imaging of HER2 Expressin in Breast Cancer Metastases Using the 111 In-ABY-025 Affibody Molecule", The Journal of Nuclear Medicine; 55; 2014; (pp. 730-735).

\* cited by examiner

| Polypeptide | Amino acid sequence | SEQ ID NO |
|---|---|---|
| PBM01976 | ERAEAAQEIDQLPNLNRGQWNAFIASLVD | SEQ ID NO:1 |
| PBM01977 | ERQVAAAEIDALPNLNRGQWNAFIASLVD | SEQ ID NO:2 |
| PBM01978 | ELSDAAQEIDSLPNLNRSQWNAFIKSLID | SEQ ID NO:3 |
| PBM01979 | ERREAAAEIDNIPNLNRSQWNAFIQSLVD | SEQ ID NO:4 |
| PBM01980 | ERREAAKEIDSLPNLNRTQWNAFIRSLAD | SEQ ID NO:5 |
| PBM01981 | ELRHAASEIDDLPNLNRAQWNAFIRSLRD | SEQ ID NO:6 |
| PBM01982 | ELVRAAQEIDELPNLNRGQWNAFIKSLVD | SEQ ID NO:7 |
| PBM01983 | EIKQAAREIDALPNLNKKQWNAFIQSLAD | SEQ ID NO:8 |
| PBM01993 | ERHRAAQEIDQLPNLNRRQWNAFIKSLVD | SEQ ID NO:9 |
| PBM01994 | EIKFAAGEIDNLPNLNRKQWNAFIGSLRD | SEQ ID NO:10 |
| PBM01995 | ERLKAAAEIDALPNLNRKQWNAFISSLRD | SEQ ID NO:11 |
| PBM02417 | ELRAAAAEIDSLPNLNRKQWNAFIKSLVD | SEQ ID NO:12 |
| PBM02418 | ERLEAAAEIDSLPNLNRAQWNAFIKSLVD | SEQ ID NO:13 |
| PBM02419 | ELIKAAAEIDALPNLNRRQWNAFIRSLVD | SEQ ID NO:14 |
| PBM02420 | ERIHAAREIDALPNLNRKQWNAFIKSLVD | SEQ ID NO:15 |
| PBM02421 | ELIKAAAEIDGLPNLNRKQWNAFIKSLVD | SEQ ID NO:16 |
| PBM02422 | ELVEAAREIDSLPNLNRRQWNAFIKSLVD | SEQ ID NO:17 |
| PBM02423 | ELIKAAREIDELPNLNRRQWNAFIKSLVD | SEQ ID NO:18 |
| PBM02424 | ELLAAAAEIDSLPNLNRAQWNAFIKSLVD | SEQ ID NO:19 |
| PBM02425 | ELINAAKEIDDLPNLNRRQWNAFIKSLVD | SEQ ID NO:20 |
| PBM02426 | ELVEAAREIDALPNLNRKQWNAFIKSLVD | SEQ ID NO:21 |
| PBM02427 | ELRDAAAEIDRLPNLNRRQWNAFIKSLVD | SEQ ID NO:22 |
| PBM02428 | ELSAAAREIDNLPNLNRRQWNAFIKSLVD | SEQ ID NO:23 |
| PBM02429 | ELISAAAEIDDLPNLNRRQWNAFIKSLVD | SEQ ID NO:24 |
| PBM02430 | ELVDAAREIDELPNLNRVQWNAFIKSLVD | SEQ ID NO:25 |
| PBM02431 | ELIEAAREIDALPNLNRSQWNAFIKSLRD | SEQ ID NO:26 |
| PBM02432 | ELVEAAKEIDKLPNLNRRQWNAFIKSLVD | SEQ ID NO:27 |
| PBM02433 | ELRQAAKEIDNLPNLNRAQWNAFIKSLVD | SEQ ID NO:28 |
| PBM02434 | ELVAAAREIDSLPNLNRTQWNAFIKSLVD | SEQ ID NO:29 |

Figure 1 A

| Polypeptide | Amino acid sequence | SEQ ID NO |
|---|---|---|
| PBM02435 | ELRNAAKEIDSLPNLNRRQWNAFIRSLVD | SEQ ID NO:30 |
| PBM02436 | ELVQAAREIDELPNLNRTQWNAFIKSLVD | SEQ ID NO:31 |
| PBM02437 | ELREAAEEIDNLPNLNRVQWNAFIKSLVD | SEQ ID NO:32 |
| PBM02438 | ELIEAAREIDNLPNLNRAQWNAFIKSLVD | SEQ ID NO:33 |
| PBM02439 | ELINAAREIDGLPNLNRMQWNAFIRSLVD | SEQ ID NO:34 |
| PBM02440 | ERIAAAQEIDGLPNLNRRQWNAFIKSLVD | SEQ ID NO:35 |
| PBM02441 | ELINAAKEIDDLPNLNRRQWNAFIKSLVD | SEQ ID NO:36 |
| PBM02442 | ERSHAAQEIDALPNLNRVQWNAFIKSLVD | SEQ ID NO:37 |
| PBM02443 | ELIAAAKEIDELPNLNRRQWNAFIKSLVD | SEQ ID NO:38 |
| PBM02444 | ERIRAAEEIDGLPNLNRWQWNAFIKSLVD | SEQ ID NO:39 |
| PBM02445 | ELVQAAREIDALPNLNRQQWNAFIKSLVD | SEQ ID NO:40 |
| PBM02446 | ERREAAREIDNLPNLNRRQWNAFIKSLVD | SEQ ID NO:41 |
| PBM02447 | ELRWAAGEIDKLPNLNRKQWNAFIKSLVD | SEQ ID NO:42 |
| PBM02448 | ELSRAAEEIDRLPNLNRVQWNAFIKSLVD | SEQ ID NO:43 |
| PBM02449 | ELIEAAREIDELPNLNRRQWNAFIKSLVD | SEQ ID NO:44 |
| PBM02450 | ELIAAAKEIDDLPNLNREQWNAFIKSLVD | SEQ ID NO:45 |
| PBM02451 | ERVRAAEEIDSLPNLNRQQWNAFIKSLVD | SEQ ID NO:46 |
| PBM02452 | ELIDAAAEIDKLPNLNRGQWNAFIKSLVD | SEQ ID NO:47 |
| PBM02453 | ELIDAAAEIDKLPNLNRSQWNAFIKSLVD | SEQ ID NO:48 |
| PBM02454 | ELIEAAEEIDRLPNLNRQQWNAFIKSLVD | SEQ ID NO:49 |
| PBM02455 | ELIEAAREIDELPNLNRKQWNAFIKSLVD | SEQ ID NO:50 |
| PBM02456 | ELREAAEEIDSLPNLNRKQWNAFIKSLVD | SEQ ID NO:51 |
| PBM02457 | ELVDAAREIDDLPNLNRGQWNAFIKSLVD | SEQ ID NO:52 |
| PBM02458 | ELREAAAEIDALPNLNRKQWNAFIKSLVD | SEQ ID NO:53 |
| PBM02459 | ELIEAAAEIDKLPNLNRAQWNAFIKSLVD | SEQ ID NO:54 |
| PBM02460 | ELREAAGEIDRLPNLNRRQWNAFIKSLVD | SEQ ID NO:55 |
| PBM02461 | ELVRAAEEIDALPNLNRKQWNAFIKSLVD | SEQ ID NO:56 |
| PBM02462 | ERSRAAAEIDALPNLNRRQWNAFIKSLVD | SEQ ID NO:57 |
| PBM02463 | ELIRAASEIDKLPNLNRRQWNAFIKSLRD | SEQ ID NO:58 |

Figure 1B

| Polypeptide | Amino acid sequence | SEQ ID NO |
|---|---|---|
| PBM02464 | ELIKAAQEIDRLPNLNRTQWNAFIRSLVD | SEQ ID NO:59 |
| PBM02465 | ELIEAAAEIDALPNLNRRQWNAFIKSLVD | SEQ ID NO:60 |
| PBM02466 | ELIWAAGEIDKLPNLNRRQWNAFIKSLVD | SEQ ID NO:61 |
| PBM02467 | ERLAAAAEIDNLPNLNRRQWNAFIKSLVD | SEQ ID NO:62 |
| PBM02468 | ELRKAAAEIDALPNLNRKQWNAFIKSLVD | SEQ ID NO:63 |
| PBM02469 | ELIAAAREIDSLPNLNRRQWNAFIKSLVD | SEQ ID NO:64 |
| PBM02470 | ERVKAAAEIDKLPNLNRRQWNAFIKSLVD | SEQ ID NO:65 |
| PBM02471 | ELIHAAEEIDRLPNLNRNQWNAFIKSLVD | SEQ ID NO:66 |
| PBM02472 | ELINAAGEIDKLPNLNRKQWNAFIKSLVD | SEQ ID NO:67 |
| PBM02473 | ELIEAAAEIDALPNLNRAQWNAFIKSLVD | SEQ ID NO:68 |
| PBM02474 | ELIAAAREIDSLPNLNRRQWNAFIKSLVD | SEQ ID NO:69 |
| PBM02475 | ERVDAAREIDNLPNLNREQWNAFIRSLVD | SEQ ID NO:70 |
| PBM02476 | ELRDAAAEIDRLPNLNRKQWNAFIKSLVD | SEQ ID NO:71 |
| PBM02477 | ELIAAAAEIDRLPNLNRVQWNAFIKSLVD | SEQ ID NO:72 |
| PBM02478 | ELRAAEEIDKLPNLNRRQWNAFIKSLID | SEQ ID NO:73 |
| PBM02479 | ELIWAAAEIDRLPNLNREQWNAFIRSLVD | SEQ ID NO:74 |
| PBM02480 | ELRAAAAKEIDNLPNLNRRQWNAFIRSLVD | SEQ ID NO:75 |
| PBM02481 | ELVQAAKEIDNLPNLNRSQWNAFIRSLVD | SEQ ID NO:76 |
| PBM02482 | ELIEAAGEIDALPNLNRRQWNAFIKSLVD | SEQ ID NO:77 |
| PBM02483 | ELVKAAAEIDALPNLNRRQWNAFIKSLVD | SEQ ID NO:78 |
| PBM02484 | ELREAAREIDSLPNLNRSQWNAFIKSLVD | SEQ ID NO:79 |
| PBM02485 | ELIEAAKEIDELPNLNRRQWNAFIKSLVD | SEQ ID NO:80 |
| PBM02486 | ELVEAAREIDELPNLNRSQWNAFIKSLVD | SEQ ID NO:81 |
| PBM02487 | ELREAAREIDALPNLNRSQWNAFIKSLVD | SEQ ID NO:82 |
| PBM02488 | ELVRAAAEIDRLPNLNRAQWNAFIKSLVD | SEQ ID NO:83 |
| PBM02489 | ELRAAAAEIDSLPNLNRGQWNAFIKSLVD | SEQ ID NO:84 |
| PBM02490 | ELIRAAREIDELPNLNRMQWNAFIKSLVD | SEQ ID NO:85 |
| PBM02491 | ELRDAAREIDSLPNLNRRQWNAFIRSLVD | SEQ ID NO:86 |
| PBM02492 | ELREAAREIDELPNLNRRQWNAFIKSLVD | SEQ ID NO:87 |

Figure 1C

| Polypeptide | Amino acid sequence | SEQ ID NO |
|---|---|---|
| PBM02493 | ELIRAAEEIDKLPNLNRKQWNAFIKSLVD | SEQ ID NO:88 |
| PBM02494 | ELIKAAREIDELPNLNRRQWNAFIRSLVD | SEQ ID NO:89 |
| PBM02495 | ELIAAAREIDGLPNLNRKQWNAFIKSLVD | SEQ ID NO:90 |
| PBM02496 | ELVAAAAEIDGLPNLNRKQWNAFIHSLVD | SEQ ID NO:91 |
| PBM02497 | ELRDAAREIDALPNLNRAQWNAFIKSLVD | SEQ ID NO:92 |
| PBM02498 | ERINAAKEIDSLPNLNRRQWNAFIKSLVD | SEQ ID NO:93 |
| PBM02499 | ELRQAAAEIDALPNLNRQQWNAFIKSLVD | SEQ ID NO:94 |
| PBM02500 | ELVEAAAEIDRLPNLNRGQWNAFIKSLVD | SEQ ID NO:95 |
| PBM02501 | ELREAAAEIDRLPNLNRKQWNAFIKSLVD | SEQ ID NO:96 |
| PBM02502 | ELIQAAKEIDSLPNLNRRQWNAFIKSLVD | SEQ ID NO:97 |
| PBM02503 | ERSMAAKEIDSLPNLNRRQWNAFIKSLVD | SEQ ID NO:98 |
| PBM02504 | ELVAAAREIDDLPNLNRKQWNAFIRSLVD | SEQ ID NO:99 |
| PBM02505 | ELVRAAEEIDRLPNLNRLQWNAFIKSLID | SEQ ID NO:100 |
| PBM02506 | ELREAAAEIDDLPNLNRAQWNAFIKSLVD | SEQ ID NO:101 |
| PBM02507 | ELVEAAKEIDSLPNLNRRQWNAFIKSLVD | SEQ ID NO:102 |
| PBM02508 | ELINAAGEIDRLPNLNRRQWNAFIKSLVD | SEQ ID NO:103 |
| PBM02509 | ELSAAAAEIDSLPNLNRKQWNAFIKSLVD | SEQ ID NO:104 |
| PBM02510 | ELRDAAAEIDKLPNLNRRQWNAFIKSLVD | SEQ ID NO:105 |
| PBM02511 | ELRQAAAEIDKLPNLNRSQWNAFIQSLVD | SEQ ID NO:106 |
| PBM02512 | ELREAAAEIDALPNLNRVQWNAFIKSLRD | SEQ ID NO:107 |
| PBM02513 | ELVAAAEIDRLPNLNRAQWNAFIKSLVD | SEQ ID NO:108 |
| PBM02514 | ELIDAAAEIDKLPNLNRNQWNAFIKSLVD | SEQ ID NO:109 |
| PBM02515 | ERINAAAEIDGLPNLNRQQWNAFIKSLVD | SEQ ID NO:110 |
| PBM02516 | ELVRAAEEIDNLPNLNRKQWNAFIKSLVD | SEQ ID NO:111 |
| PBM02517 | ELIRAAKEIDELPNLNRRQWNAFIRSLVD | SEQ ID NO:112 |
| PBM02518 | ELIQAAREIDSLPNLNRRQWNAFIKSLVD | SEQ ID NO:113 |
| PBM02519 | ELIDAAREIDDLPNLNRQQWNAFIKSIID | SEQ ID NO:114 |
| PBM02520 | ELLKAADEIDALPNLNRAQWNAFIKSLVD | SEQ ID NO:115 |
| PBM02521 | ELLEAAAEIDSLPNLNRRQWNAFIKSLVD | SEQ ID NO:116 |

Figure 1D

| Polypeptide | Amino acid sequence | SEQ ID NO |
|---|---|---|
| PBM02522 | ELVDAAREIDTLPNLNRRQWNAFIKSLVD | SEQ ID NO:117 |
| PBM02523 | ELIEAAREIDKLPNLNRRQWNAFIRSLVD | SEQ ID NO:118 |
| PBM02524 | ELVAAAREIDNLPNLNRRQWNAFIRSLVD | SEQ ID NO:119 |
| PBM02525 | ELVEAAAEIDGLPNLNRRQWNAFIKSLRD | SEQ ID NO:120 |
| PBM02526 | ELRNAAKEIDGLPNLNRRQWNAFIKSLVD | SEQ ID NO:121 |
| PBM02527 | ELRHAAREIDGLPNLNRITQWNAFIKSLVD | SEQ ID NO:122 |
| PBM02528 | ELVEAAREIDTLPNLNRRQWNAFIKSLRD | SEQ ID NO:123 |
| PBM02529 | ELVAAAAEIDALPNLNRRQWNAFIKSLVD | SEQ ID NO:124 |
| PBM02530 | ELRTAAKEIDDLPNLNRRQWNAFIKSLVD | SEQ ID NO:125 |
| PBM02531 | ELIRAAREIDSLPNLNRTQWNAFIKSLVD | SEQ ID NO:126 |
| PBM02532 | ERIRAAREIDALPNLNRQQWNAFIKSLVD | SEQ ID NO:127 |
| PBM02533 | ELRAAAEEIDRLPNLNRRQWNAFIKSLVD | SEQ ID NO:128 |
| PBM02534 | ELIEAAAEIDALPNLNRKQWNAFISSLVD | SEQ ID NO:129 |
| PBM02535 | ERIEAAREIDELPNLNRKQWNAFISSLVD | SEQ ID NO:130 |
| PBM02536 | ELIAAAKEIDELPNLNRAQWNAFIKSLVD | SEQ ID NO:131 |
| PBM02537 | ELINAAREIDELPNLNRRQWNAFIKSLVD | SEQ ID NO:132 |
| PBM02538 | ELVKAAAEIDALPNLNRRQWNAFIKSLVD | SEQ ID NO:133 |
| PBM02539 | ELIAAAKEIDELPNLNRRQWNAFIKSLVD | SEQ ID NO:134 |
| PBM02540 | ELISAAREIDKLPNLPNLNRQQWNAFIKSLVD | SEQ ID NO:135 |
| PBM02541 | ELREAAEEIDKLPNLNRWQWNAFIKSLVD | SEQ ID NO:136 |
| PBM02542 | ELVEAAREIDGLPNLNRAQWNAFIKSLVD | SEQ ID NO:137 |
| PBM02543 | ELVAAAQEIDNLPNLNRKQWNAFISSLVD | SEQ ID NO:138 |
| PBM02544 | ELRNAAAEIDKLPNLNRRQWNAFIRSLVD | SEQ ID NO:139 |
| PBM02545 | ELIQAASEIDALPNLNRTQWNAFIKSLVD | SEQ ID NO:140 |
| PBM02546 | ELVEAAAEIDSLPNLNRRQWNAFIKSLVD | SEQ ID NO:141 |
| PBM02547 | ERIAAAQEIDALPNLNRRQWNAFIRSLVD | SEQ ID NO:142 |
| PBM02548 | ELRDAAKEIDSLPNLNRRQWNAFIKSLVD | SEQ ID NO:143 |
| PBM02549 | ELVAAAKEIDKLPNLNRKQWNAFIKSLVD | SEQ ID NO:144 |
| PBM02550 | ELIKAAREIDELPNLNRKQWNAFIKSLID | SEQ ID NO:145 |

Figure 1E

| Polypeptide | Amino acid sequence | SEQ ID NO |
|---|---|---|
| PBM02551 | ELVEAASEIDGLPNLNRNQWNAFIKSLVD | SEQ ID NO:146 |
| PBM02552 | ELLRAAAEEIDNLPNLNRAQWNAFIKSLVD | SEQ ID NO:147 |
| PBM02553 | ELIKAAKEIDALPNLNRRQWNAFIKSLVD | SEQ ID NO:148 |
| PBM02554 | ELRRAAAEIDSLPNLNRDQWNAFIKSLID | SEQ ID NO:149 |
| PBM02555 | ELVEAAREIDGLPNLNRAQWNAFIRSLVD | SEQ ID NO:150 |
| PBM02556 | ELVEAAREIDRLPNLNRRQWNAFIRSLVD | SEQ ID NO:151 |
| PBM02557 | ELVWAAAEIDRLPNLNRCQWNAFIKSLVD | SEQ ID NO:152 |
| PBM02558 | ERIRAAREIDELPNLNREQWNAFIKSLVD | SEQ ID NO:153 |
| PBM02559 | ELRQAAKEIDALPNLNRRQWNAFIKSLVD | SEQ ID NO:154 |
| PBM02560 | ELREAAAEIDKLPNLNRKQWNAFIKSLVD | SEQ ID NO:155 |
| PBM02561 | ELRRAAAEIDKLPNLNRQQWNAFIKSLVD | SEQ ID NO:156 |
| PBM02562 | ELVQAAREIDALPNLNRQQWNAFIKSLVD | SEQ ID NO:157 |
| PBM02563 | ELRAAAAEIDALPNLNRRQWNAFIRSLVD | SEQ ID NO:158 |
| PBM02564 | ELRAAAAEIDKLPNLNRKQWNAFIKSLVD | SEQ ID NO:159 |
| PBM02565 | ERIQAAKEIDELPNLNREQWNAFIKSLVD | SEQ ID NO:160 |
| PBM02566 | ELVAAAAEIDKLPNLNRRQWNAFIKSLVD | SEQ ID NO:161 |
| PBM02568 | ELVRAAAEIDNLPNLNRKQWNAFIKSLVD | SEQ ID NO:162 |
| PBM02569 | ELRTAAAEIDALPNLNREQWNAFIRSLVD | SEQ ID NO:163 |
| PBM02570 | ELVEAAAEIDALPNLNRKQWNAFIKSLVD | SEQ ID NO:164 |
| PBM02571 | ELIKAAREIDKLPNLNRMQWNAFIRSLVD | SEQ ID NO:165 |
| PBM02572 | ELRRBAAAEIDNLPNLNRRQWNAFIKSLID | SEQ ID NO:166 |
| PBM02573 | ELIEAAAREIDALPNLNRKQWNAFIRSLVD | SEQ ID NO:167 |
| PBM02574 | ELREAAQEIDSLPNLNRQQWNAFIKSLVD | SEQ ID NO:168 |
| PBM02575 | ELRSAAEEIDSLPNLNRRQWNAFIKSLVD | SEQ ID NO:169 |
| PBM02576 | ELVEAAAEIDNLPNLNRMQWNAFIRSLVD | SEQ ID NO:170 |
| PBM02577 | ELVEAAGEIDNLPNLNRRQWNAFIKSLVD | SEQ ID NO:171 |
| PBM02578 | ELSKAAIDALPNLNRRQWNAFIKSLVD | SEQ ID NO:172 |
| PBM02579 | ELLWAAGEIDRLPNLNRRQWNAFIKSLVD | SEQ ID NO:173 |
| PBM02580 | ELRQAAAEIDGLPNLNRRQWNAFIKSLVD | SEQ ID NO:174 |

Figure 1F

| Polypeptide | Amino acid sequence | SEQ ID NO |
|---|---|---|
| PBM02831 | ELVKAAAEIDALPNLTRRQWNAFIKSLVD | SEQ ID NO:175 |
| PBM02832 | ELVKAAAEIDALPNLNRRQWNAFIKKLVD | SEQ ID NO:176 |
| PBM02833 | ELVKAAAEIDALPNLTRRQWNAFIKKLVD | SEQ ID NO:177 |
| PBM02834 | ELVKAAAEIDALPNLTRRQWNAFIKKLVK | SEQ ID NO:178 |
| PBM03358 | ELIEAAAEIDALPNLTRRQWNAFIKKLVD | SEQ ID NO:179 |
| PB01976 | KERAEAAQEIDQLPNLNRGQWNAFIASLVDDPSQSANLLAEAKKLNDAQ | SEQ ID NO:180 |
| PB01977 | KERQVAAAEIDALPNLNRGQWNAFIASLVDDPSQSANLLAEAKKLNDAQ | SEQ ID NO:181 |
| PB01978 | KELSDAAQEIDSLPNLNRSQWNAFIKSLIDDPSQSANLLAEAKKLNDAQ | SEQ ID NO:182 |
| PB01979 | KERREAAAEIDNLPNLNRSQWNAFIQSLVDDPSQSANLLAEAKKLNDAQ | SEQ ID NO:183 |
| PB01980 | KERREAAKEIDSLPNLNRTQWNAFIRSLADDPSQSANLLAEAKKLNDAQ | SEQ ID NO:184 |
| PB01981 | KELHAASEIDDLPNLNRAQWNAFIRSLRDDPSQSANLLAEAKKLNDAQ | SEQ ID NO:185 |
| PB01982 | KELVRAAQEIDELPNLNRGQWNAFIKSLVDDPSQSANLLAEAKKLNDAQ | SEQ ID NO:186 |
| PB01983 | KETKQAAREIDALPNLNKKQWNAFIQSLADDPSQSANLLAEAKKLNDAQ | SEQ ID NO:187 |
| PB01993 | KERHRAAQEIDQLPNLPNLNRRQWNAFIKSLVDDPSQSANLLAEAKKLNDAQ | SEQ ID NO:188 |
| PB01994 | KEIKFAAGEIDNLPNLNRKOWNAFIGSLRDDPSQSANLLAEAKKLNDAQ | SEQ ID NO:189 |
| PB01995 | KERLKAAAEIDALPNLNRKQWNAFISSLRDDPSQSANLLAEAKKLNDAQ | SEQ ID NO:190 |
| PB02417 | KELRAAAAEIDSLPNLNRKQWNAFIKSLVDDPSQSANLLAEAKKLNDAQ | SEQ ID NO:191 |
| PB02418 | KERLEAAAEIDSLPNLNRAQWNAFIKSLVDDPSQSANLLAEAKKLNDAQ | SEQ ID NO:192 |
| PB02419 | KELIKAAAEIDALPNLNRRQWNAFIRSLVDDPSQSANLLAEAKKLNDAQ | SEQ ID NO:193 |
| PB02420 | KERIHAAREIDALPNLNRKQWNAFIKSLVDDPSQSANLLAEAKKLNDAQ | SEQ ID NO:194 |
| PB02421 | KELIKAAAEIDGLPNLNRKQWNAFIKSLVDDPSQSANLLAEAKKLNDAQ | SEQ ID NO:195 |
| PB02422 | KELVEAAREIDSLPNLNRRQWNAFIKSLVDDPSQSANLLAEAKKLNDAQ | SEQ ID NO:196 |
| PB02423 | KELIKAAAREIDELPNLNRRQWNAFIKSLVDDPSQSANLLAEAKKLNDAQ | SEQ ID NO:197 |
| PB02424 | KELLAAAAEIDSLPNLNRAQWNAFIKSLVDDPSQSANLLAEAKKLNDAQ | SEQ ID NO:198 |
| PB02425 | KELINAAKEIDDLPNLNRRQWNAFIKSLVDDPSQSANLLAEAKKLNDAQ | SEQ ID NO:199 |
| PB02426 | KELVEAAREIDALPNLNRKQWNAFIKSLVDDPSQSANLLAEAKKLNDAQ | SEQ ID NO:200 |
| PB02427 | KELRDAAAEIDRLPNLNRRQWNAFIKSLVDDPSQSANLLAEAKKLNDAQ | SEQ ID NO:201 |
| PB02428 | KELSAAAREIDNLPNLNRRQWNAFIKSLVDDPSQSANLLAEAKKLNDAQ | SEQ ID NO:202 |
| PB02429 | KELISAABEIDDLPNLNRRQWNAFIKSLVDDPSQSANLLAEAKKLNDAQ | SEQ ID NO:203 |

Figure 1 G

| Polypeptide | Amino acid sequence | SEQ ID NO |
| --- | --- | --- |
| PB02430 | KELVDAAREIDELPNLNRVQWNAFIKSLVDDPSQSANLLAEAKKLNDAQ | SEQ ID NO:204 |
| PB02431 | KELIEAAREIDALPNLNRSQWNAFIKSLRDDPSQSANLLAEAKKLNDAQ | SEQ ID NO:205 |
| PB02432 | KELVEAAKEIDKLPNLNRRQWNAFIKSLVDDPSQSANLLAEAKKLNDAQ | SEQ ID NO:206 |
| PB02433 | KELRQAAKEIDNLPNLNRAQWNAFIKSLVDDPSQSANLLAEAKKLNDAQ | SEQ ID NO:207 |
| PB02434 | KELVAAAREIDSLPNLNRTQWNAFIKSLVDDPSQSANLLAEAKKLNDAQ | SEQ ID NO:208 |
| PB02435 | KELRNAAKEIDSLPNLNRRQWNAFIRSLVDDPSQSANLLAEAKKLNDAQ | SEQ ID NO:209 |
| PB02436 | KELVQAAREIDELPNLNRTQWNAFIKSLVDDPSQSANLLAEAKKLNDAQ | SEQ ID NO:210 |
| PB02437 | KELREAAEEIDNLPNLNRVQWNAFIKSLVDDPSQSANLLAEAKKLNDAQ | SEQ ID NO:211 |
| PB02438 | KELIEAAREIDNLPNLNRAQWNAFIKSLVDDPSQSANLLAEAKKLNDAQ | SEQ ID NO:212 |
| PB02439 | KELINAAREIDGLPNLNRMQWNAFIRSLVDDPSQSANLLAEAKKLNDAQ | SEQ ID NO:213 |
| PB02440 | KERIAAAQEIDGLPNLNRRQWNAFIKSLVDDPSQSANLLAEAKKLNDAQ | SEQ ID NO:214 |
| PB02441 | KELINAAKEIDDLPNLNRRQWNAFIKSLVDDPSQSANLLAEAKKLNDAQ | SEQ ID NO:215 |
| PB02442 | KERSHAAQEIDALPNLNRVQWNAFIKSLVDDPSQSANLLAEAKKLNDAQ | SEQ ID NO:216 |
| PB02443 | KELIAAAKEIDELPNLNRRQWNAFIKSLVDDPSQSANLLAEAKKLNDAQ | SEQ ID NO:217 |
| PB02444 | KERIRAABEIDGLPNLNRWQWNAFIKSLVDDPSQSANLLAEAKKLNDAQ | SEQ ID NO:218 |
| PB02445 | KELVQAAREIDALPNLNRQQWNAFIKSLVDDPSQSANLLAEAKKLNDAQ | SEQ ID NO:219 |
| PB02446 | KERREAAAREIDNLPNLNRRQWNAFIKSLVDDPSQSANLLAEAKKLNDAQ | SEQ ID NO:220 |
| PB02447 | KELRWAAGEIDDLPNLNREQWNAFIKSLVDDPSQSANLLAEAKKLNDAQ | SEQ ID NO:221 |
| PB02448 | KELSRAAAEIDSLPNLNRQQWNAFIKSLVDDPSQSANLLAEAKKLNDAQ | SEQ ID NO:222 |
| PB02449 | KELIEAAAREIDKLPNLNRRQWNAFIKSLVDDPSQSANLLAEAKKLNDAQ | SEQ ID NO:223 |
| PB02450 | KELIAAAKEIDDLPNLNRQQWNAFIKSLVDDPSQSANLLAEAKKLNDAQ | SEQ ID NO:224 |
| PB02451 | KERVRAAEEIDSLPNLNRQQWNAFIKSLVDDPSQSANLLAEAKKLNDAQ | SEQ ID NO:225 |
| PB02452 | KELIDAAABIDKLPNLNRGQWNAFIKSLVDDPSQSANLLAEAKKLNDAQ | SEQ ID NO:226 |
| PB02453 | KELIDAAAEIDKLPNLNRSQWNAFIKSLVDDPSQSANLLAEAKKLNDAQ | SEQ ID NO:227 |
| PB02454 | KELIEAAEEIDRLPNLNRQQWNAFIKSLVDDPSQSANLLAEAKKLNDAQ | SEQ ID NO:228 |
| PB02455 | KELIEAAAREIDELPNLNRKQWNAFIKSLVDDPSQSANLLAEAKKLNDAQ | SEQ ID NO:229 |
| PB02456 | KELREAAAEIDSLPNLNRKQWNAFIKSLVDDPSQSANLLAEAKKLNDAQ | SEQ ID NO:230 |
| PB02457 | KELVDAAREIDDLPNLNRGQWNAFIKSLVDDPSQSANLLAEAKKLNDAQ | SEQ ID NO:231 |
| PB02458 | KELREAAABEIDALPNLNRKQWNAFIKSLVDDPSQSANLLAEAKKLNDAQ | SEQ ID NO:232 |

Figure 1H

| Polypeptide | Amino acid sequence | SEQ ID NO |
|---|---|---|
| PB02459 | KELIEAAAEIDKLPNLNRAQWNAFIKSLVDDPSQSANLLAEAKKLNDAQ | SEQ ID NO:233 |
| PB02460 | KELREAAGEIDRLPNLNRRQWNAFIKSLVDDPSQSANLLAEAKKLNDAQ | SEQ ID NO:234 |
| PB02461 | KELVRAAEEIDALPNLNRKQWNAFIKSLVDDPSQSANLLAEAKKLNDAQ | SEQ ID NO:235 |
| PB02462 | KERSRAAAEIDALPNLNRRQWNAFIKSLVDDPSQSANLLAEAKKLNDAQ | SEQ ID NO:236 |
| PB02463 | KELIRAASEIDKLPNLNRRQWNAFIKSLRDDPSQSANLLAEAKKLNDAQ | SEQ ID NO:237 |
| PB02464 | KELIKAAQEIDRLPNLNRTQWNAFIRSLVDDPSQSANLLAEAKKLNDAQ | SEQ ID NO:238 |
| PB02465 | KELIEAAAEIDALPNLNRRQWNAFIKSLVDDPSQSANLLAEAKKLNDAQ | SEQ ID NO:239 |
| PB02466 | KELIWAAGEIDKLPNLNRRQWNAFIKSLVDDPSQSANLLAEAKKLNDAQ | SEQ ID NO:240 |
| PB02467 | KERLAAAEEIDNLPNLNRRQWNAFIKSLVDDPSQSANLLAEAKKLNDAQ | SEQ ID NO:241 |
| PB02468 | KELRKAAEEIDALPNLNRKQWNAFIKSLVDDPSQSANLLAEAKKLNDAQ | SEQ ID NO:242 |
| PB02469 | KELIAAAREIDSLPNLNRRQWNAFIKSLVDDPSQSANLLAEAKKLNDAQ | SEQ ID NO:243 |
| PB02470 | KERVKAAREIDSLPNLNRRQWNAFIKSLVDDPSQSANLLAEAKKLNDAQ | SEQ ID NO:244 |
| PB02471 | KELIHAABEIDRLPNLNRNQWNAFIKSLVDDPSQSANLLAEAKKLNDAQ | SEQ ID NO:245 |
| PB02472 | KELINAAGEIDKLPNLNRKQWNAFIKSLVDDPSQSANLLAEAKKLNDAQ | SEQ ID NO:246 |
| PB02473 | KELIEAAAEIDALPNLNRRQWNAFIKSLVDDPSQSANLLAEAKKLNDAQ | SEQ ID NO:247 |
| PB02474 | KELIAAAREIDSLPNLNRRQWNAFIKSLVDDPSQSANLLAEAKKLNDAQ | SEQ ID NO:248 |
| PB02475 | KERVDAAREIDNLPNLNREQWNAFIRSLVDDPSQSANLLAEAKKLNDAQ | SEQ ID NO:249 |
| PB02476 | KELRDAAAEIDRLPNLNRRQWNAFIKSLVDDPSQSANLLAEAKKLNDAQ | SEQ ID NO:250 |
| PB02477 | KELIAAAAEIDRLPNLNRVQWNAFIKSLVDDPSQSANLLAEAKKLNDAQ | SEQ ID NO:251 |
| PB02478 | KELRAAAEEIDKLPNLNRRQWNAFIKSLIDDPSQSANLLAEAKKLNDAQ | SEQ ID NO:252 |
| PB02479 | KELIWAAAEIDRLPNLNREQWNAFIKSLVDDPSQSANLLAEAKKLNDAQ | SEQ ID NO:253 |
| PB02480 | KELRAAAKEIDNLPNLNRRQWNAFIKSLVDDPSQSANLLAEAKKLNDAQ | SEQ ID NO:254 |
| PB02481 | KELVQAAKEIDNLPNLNRRQWNAFIRSLVDDPSQSANLLAEAKKLNDAQ | SEQ ID NO:255 |
| PB02482 | KELIEAAGEIDALPNLNRRQWNAFIKSLVDDPSQSANLLAEAKKLNDAQ | SEQ ID NO:256 |
| PB02483 | KELVKAAAEIDALPNLNRRQWNAFIKSLVDDPSQSANLLAEAKKLNDAQ | SEQ ID NO:257 |
| PB02484 | KELREAAREIDSLPNLNRSQWNAFIKSLVDDPSQSANLLAEAKKLNDAQ | SEQ ID NO:258 |
| PB02485 | KELLEAAKEIDELPNLNRRQWNAFIKSLVDDPSQSANLLAEAKKLNDAQ | SEQ ID NO:259 |
| PB02486 | KELVEAAREIDELPNLNRSQWNAFIKSLVDDPSQSANLLAEAKKLNDAQ | SEQ ID NO:260 |
| PB02487 | KELREAAAEIDALPNLNRSQWNAFIKSLVDDPSQSANLLAEAKKLNDAQ | SEQ ID NO:261 |

Figure 1 I

| Polypeptide | Amino acid sequence | SEQ ID NO |
|---|---|---|
| PB02488 | KELVRAAEEIDRLPNLNRAQWNAFIKSLVDDPSQSANLLAEAKKLNDAQ | SEQ ID NO:262 |
| PB02489 | KELRAAAAEIDSLPNLNRGQWNAFIKSLVDDPSQSANLLAEAKKLNDAQ | SEQ ID NO:263 |
| PB02490 | KELIRAAREIDELPNLNRMQWNAFIKSLVDDPSQSANLLAEAKKLNDAQ | SEQ ID NO:264 |
| PB02491 | KELRDAAREIDSLPNLNRRQWNAFIRSLVDDPSQSANLLAEAKKLNDAQ | SEQ ID NO:265 |
| PB02492 | KELRAAREIDELPNLNRRQWNAFIKSLVDDPSQSANLLAEAKKLNDAQ | SEQ ID NO:266 |
| PB02493 | KELIRAAREIDKLPNLNRKQWNAFIKSLVDDPSQSANLLAEAKKLNDAQ | SEQ ID NO:267 |
| PB02494 | KELLKAAREIDELPNLNRRQWNAFIRSLVDDPSQSANLLAEAKKLNDAQ | SEQ ID NO:268 |
| PB02495 | KELIAAAREIDGLPNLNRKQWNAFIKSLVDDPSQSANLLAEAKKLNDAQ | SEQ ID NO:269 |
| PB02496 | KELVAAAAEIDGLPNLNRKQWNAFTHSLVDDPSQSANLLAEAKKLNDAQ | SEQ ID NO:270 |
| PB02497 | KELRDAAREIDALPNLNRAQWNAFIKSLVDDPSQSANLLAEAKKLNDAQ | SEQ ID NO:271 |
| PB02498 | KERINAAKEIDSLPNLNRRQWNAFIKSLVDDPSQSANLLAEAKKLNDAQ | SEQ ID NO:272 |
| PB02499 | KELRQAAAEIDALPNLNRGQWNAFIKSLVDDPSQSANLLAEAKKLNDAQ | SEQ ID NO:273 |
| PB02500 | KELVAAAREIDRLPNLNRGQWNAFIKSLVDDPSQSANLLAEAKKLNDAQ | SEQ ID NO:274 |
| PB02501 | KELREAAAEIDRLPNLNRKQWNAFIKSLVDDPSQSANLLAEAKKLNDAQ | SEQ ID NO:275 |
| PB02502 | KELIQAAKEIDSLPNLNRRQWNAFIKSLVDDPSQSANLLAEAKKLNDAQ | SEQ ID NO:276 |
| PB02503 | KERSMAAKEIDSLPNLNRRQWNAFIKSLVDDPSQSANLLAEAKKLNDAQ | SEQ ID NO:277 |
| PB02504 | KELVAAAREIDDLPNLNRKQWNAFIRSLVDDPSQSANLLAEAKKLNDAQ | SEQ ID NO:278 |
| PB02505 | KELVRAAEEIDRLPNLNRLQWNAFIKSLIDDPSQSANLLAEAKKLNDAQ | SEQ ID NO:279 |
| PB02506 | KELREAAAEIDDLPNLNRAQWNAFIKSLVDDPSQSANLLAEAKKLNDAQ | SEQ ID NO:280 |
| PB02507 | KELVEAAKEIDSLPNLNRRQWNAFIKSLVDDPSQSANLLAEAKKLNDAQ | SEQ ID NO:281 |
| PB02508 | KELINAAGEIDKLPNLNRSQWNAFIQSLVDDPSQSANLLAEAKKLNDAQ | SEQ ID NO:282 |
| PB02509 | KELLSAAAEIDSLPNLNRRQWNAFIKSLRDDPSQSANLLAEAKKLNDAQ | SEQ ID NO:283 |
| PB02510 | KELRDAAAEIDKLPNLNRRQWNAFIKSLVDDPSQSANLLAEAKKLNDAQ | SEQ ID NO:284 |
| PB02511 | KELRQAAAEIDKLPNLNRVQWNAFIKSLVDDPSQSANLLAEAKKLNDAQ | SEQ ID NO:285 |
| PB02512 | KELREAAAEIDALPNLNRVQWNAFIKSLVDDPSQSANLLAEAKKLNDAQ | SEQ ID NO:286 |
| PB02513 | KELVAAAEEIDRLPNLNRAQWNAFIKSLVDDPSQSANLLAEAKKLNDAQ | SEQ ID NO:287 |
| PB02514 | KELIDAAAEIDKLPNLNRNQWNAFIKSLVDDPSQSANLLAEAKKLNDAQ | SEQ ID NO:288 |
| PB02515 | KERINAAAEIDGLPNLNRQQWNAFIKSLVDDPSQSANLLAEAKKLNDAQ | SEQ ID NO:289 |
| PB02516 | KELVRAAEEIDNLPNLNRKQWNAFIKSLVDDPSQSANLLAEAKKLNDAQ | SEQ ID NO:290 |

Figure 1 J

| Polypeptide | Amino acid sequence | SEQ ID NO |
|---|---|---|
| PB02517 | KELIRAAKEIDELPNLNRRQWNAFIRSLVDDPSQSANLLAEAKKLNDAQ | SEQ ID NO:291 |
| PB02518 | KELIQAAREIDSLPNLNRRQWNAFIKSLVDDPSQSANLLAEAKKLNDAQ | SEQ ID NO:292 |
| PB02519 | KELIDAAREIDDLPNLNRRQWNAFIKSLLDDPSQSANLLAEAKKLNDAQ | SEQ ID NO:293 |
| PB02520 | KELIKAADEIDALPNLNRRAQWNAFIKSLVDDPSQSANLLAEAKKLNDAQ | SEQ ID NO:294 |
| PB02521 | KELLEAAAREIDSLPNLNRRQWNAFIKSLVDDPSQSANLLAEAKKLNDAQ | SEQ ID NO:295 |
| PB02522 | KELVDAAREIDTLPNLNRRQWNAFIKSLVDDPSQSANLLAEAKKLNDAQ | SEQ ID NO:296 |
| PB02523 | KELIEAAREIDKLPNLNRRQWNAFIRSLVDDPSQSANLLAEAKKLNDAQ | SEQ ID NO:297 |
| PB02524 | KELVAAAREIDNLPNLNRRQWNAFIKSLVDDPSQSANLLAEAKKLNDAQ | SEQ ID NO:298 |
| PB02525 | KELVEAAARIDGLPNLNRDQWNAFIKSLRDDPSQSANLLAEAKKLNDAQ | SEQ ID NO:299 |
| PB02526 | KELRNAAKEIDGLPNLNRRQWNAFIKSLVDDPSQSANLLAEAKKLNDAQ | SEQ ID NO:300 |
| PB02527 | KELRHAAREIDGLPNLNRTQWNAFIKSLVDDPSQSANLLAEAKKLNDAQ | SEQ ID NO:301 |
| PB02528 | KELVEAAREIDTLPNLNRRQWNAFIKSLRDDPSQSANLLAEAKKLNDAQ | SEQ ID NO:302 |
| PB02529 | KELVAAAAEIDALPNLNRRQWNAFIKSLVDDPSQSANLLAEAKKLNDAQ | SEQ ID NO:303 |
| PB02530 | KELRTAAKEIDDLPNLNRKQWNAFIKSLVDDPSQSANLLAEAKKLNDAQ | SEQ ID NO:304 |
| PB02531 | KELRAAREIDSLPNLNRTQWNAFIKSLVDDPSQSANLLAEAKKLNDAQ | SEQ ID NO:305 |
| PB02532 | KERIRAAREIDALPNLNRQQWNAFIKSLVDDPSQSANLLAEAKKLNDAQ | SEQ ID NO:306 |
| PB02533 | KELRAAAEEIDRLPNLNRRQWNAFIKSLVDDPSQSANLLAEAKKLNDAQ | SEQ ID NO:307 |
| PB02534 | KELIEAAAEIDALPNLNRRQWNAFISSLVDDPSQSANLLAEAKKLNDAQ | SEQ ID NO:308 |
| PB02535 | KERIEAAREIDELPNLNRRQWNAFIRSLVDDPSQSANLLAEAKKLNDAQ | SEQ ID NO:309 |
| PB02536 | KELLAAAKEIDELPNLNRRAQWNAFIKSLVDDPSQSANLLAEAKKLNDAQ | SEQ ID NO:310 |
| PB02537 | KELISAAREIDKLPNLNRQQWNAFIKSLVDDPSQSANLLAEAKKLNDAQ | SEQ ID NO:311 |
| PB02538 | KELNAAAEIDELPNLNRRQWNAFIKSLVDDPSQSANLLAEAKKLNDAQ | SEQ ID NO:312 |
| PB02539 | KELREAAEIDKLPNLNRWQWNAFIKSLVDDPSQSANLLAEAKKLNDAQ | SEQ ID NO:313 |
| PB02540 | KELVKAAAEIDALPNLNRRQWNAFIKSLVDDPSQSANLLAEAKKLNDAQ | SEQ ID NO:314 |
| PB02541 | KELVEAAREIDGLPNLNRRQWNAFIKSLVDDPSQSANLLAEAKKLNDAQ | SEQ ID NO:315 |
| PB02542 | KELVAAAQEIDNLPNLNRRKQWNAFISSLVDDPSQSANLLAEAKKLNDAQ | SEQ ID NO:316 |
| PB02543 | KELRNAAAEIDKLPNLNRRQWNAFIKSLVDDPSQSANLLAEAKKLNDAQ | SEQ ID NO:317 |
| PB02544 | KELIQAASEIDALPNLNRTQWNAFIKSLVDDPSQSANLLAEAKKLNDAQ | SEQ ID NO:318 |
| PB02545 | KELIQAASEIDALPNLNRTQWNAFIKSLVDDPSQSANLLAEAKKLNDAQ | SEQ ID NO:319 |

Figure 1 K

| Polypeptide | Amino acid sequence | SEQ ID NO |
|---|---|---|
| PB02546 | KELVEAAAEIDSLPNLNRRQWNAFIKSLVDDPSQSANLLAEAKKLNDAQ | SEQ ID NO:320 |
| PB02547 | KERIAAAQEIDALPNLNRRQWNAFIRSLVDDPSQSANLLAEAKKLNDAQ | SEQ ID NO:321 |
| PB02548 | KELRDAAKEIDSLPNLNRKQWNAFIKSLVDDPSQSANLLAEAKKLNDAQ | SEQ ID NO:322 |
| PB02549 | KELVAAAKEIDKLPNLNRKQWNAFIKSLVDDPSQSANLLAEAKKLNDAQ | SEQ ID NO:323 |
| PB02550 | KELIKAAREIDELPNLNRKQWNAFIKSLIDDPSQSANLLAEAKKLNDAQ | SEQ ID NO:324 |
| PB02551 | KELVEAASEIDGLPNLNRMQWNAFIKSLVDDPSQSANLLAEAKKLNDAQ | SEQ ID NO:325 |
| PB02552 | KELLRAAAEIDNLPNLNRAQWNAFIKSLVDDPSQSANLLAEAKKLNDAQ | SEQ ID NO:326 |
| PB02553 | KELIKAAKEIDALPNLNRRQWNAFIKSLVDDPSQSANLLAEAKKLNDAQ | SEQ ID NO:327 |
| PB02554 | KELRRAAAEIDSLPNLNRDQWNAFIRSLIDDPSQSANLLAEAKKLNDAQ | SEQ ID NO:328 |
| PB02555 | KELVEAAREIDGLPNLNRIQWNAFIKSLVDDPSQSANLLAEAKKLNDAQ | SEQ ID NO:329 |
| PB02556 | KELVEAAREIDELPNLNRQWNAFIRSLVDDPSQSANLLAEAKKLNDAQ | SEQ ID NO:330 |
| PB02557 | KELVWAAAEIDRLPNLNRCQWNAFIKSLVDDPSQSANLLAEAKKLNDAQ | SEQ ID NO:331 |
| PB02558 | KERIRAAREIDELPNLNREQWNAFIKSLVDDPSQSANLLAEAKKLNDAQ | SEQ ID NO:332 |
| PB02559 | KELRQAAKEIDALPNLNRRQWNAFIKSLVDDPSQSANLLAEAKKLNDAQ | SEQ ID NO:333 |
| PB02560 | KELREAAAEIDKLPNLNRKQWNAFIRSLVDDPSQSANLLAEAKKLNDAQ | SEQ ID NO:334 |
| PB02561 | KELRRAAEEIDKLPNLNRQQWNAFIKSLVDDPSQSANLLAEAKKLNDAQ | SEQ ID NO:335 |
| PB02562 | KELVQAAREIDALPNLNRQQWNAFIKSLVDDPSQSANLLAEAKKLNDAQ | SEQ ID NO:336 |
| PB02563 | KELVEAAREIDALPNLNRRQWNAFIRSLVDDPSQSANLLAEAKKLNDAQ | SEQ ID NO:337 |
| PB02564 | KELRAAAAEIDKLPNLNRKQWNAFIKSLVDDPSQSANLLAEAKKLNDAQ | SEQ ID NO:338 |
| PB02565 | KERIQAAKEIDELPNLNREQWNAFIKSLVDDPSQSANLLAEAKKLNDAQ | SEQ ID NO:339 |
| PB02566 | KELVAAAEEIDKLPNLNRRQWNAFIKSLVDDPSQSANLLAEAKKLNDAQ | SEQ ID NO:340 |
| PB02568 | KELVRAAAEIDNLPNLNRKQWNAFIKSLVDDPSQSANLLAEAKKLNDAQ | SEQ ID NO:341 |
| PB02569 | KELRTAAAEIDALPNLNRKQWNAFIRSLVDDPSQSANLLAEAKKLNDAQ | SEQ ID NO:342 |
| PB02570 | KELVEAAAEIDALPNLNRKQWNAFIKSLVDDPSQSANLLAEAKKLNDAQ | SEQ ID NO:343 |
| PB02571 | KELIKAAEEIDKLPNLNRMQWNAFIRSLVDDPSQSANLLAEAKKLNDAQ | SEQ ID NO:344 |
| PB02572 | KELREAAAEIDNLPNLNRRQWNAFIKSLIDDPSQSANLLAEAKKLNDAQ | SEQ ID NO:345 |
| PB02573 | KELIEAAREIDALPNLNRKQWNAFIKSLVDDPSQSANLLAEAKKLNDAQ | SEQ ID NO:346 |
| PB02574 | KELRBAAQEIDSLPNLNRQQWNAFIKSLVDDPSQSANLLAEAKKLNDAQ | SEQ ID NO:347 |
| PB02575 | KELRSAAEEIDSLPNLNRRQWNAFIKSLVDDPSQSANLLAEAKKLNDAQ | SEQ ID NO:348 |

Figure 1 L

| Polypeptide | Amino acid sequence | SEQ ID NO |
|---|---|---|
| PB02576 | KELVEAAAEIDNLPNLNRMQWNAFIKSLVDDPSQSANLLAEAKKLNDAQ | SEQ ID NO:349 |
| PB02577 | KELVEAAGEIDNLPNLNRRQWNAFIRSLVDDPSQSANLLAEAKKLNDAQ | SEQ ID NO:350 |
| PB02578 | KELSKAAAEIDALPNLNRRQWNAFIKSLVDDPSQSANLLAEAKKLNDAQ | SEQ ID NO:351 |
| PB02579 | KELLWAAGEIDRLPNLNRQQWNAFIKSLVDDPSQSANLLAEAKKLNDAQ | SEQ ID NO:352 |
| PB02580 | KELRQAAAEIDGLPNLNRRQWNAFIKSLVDDPSQSANLLAEAKKLNDAQ | SEQ ID NO:353 |
| PB02831 | KELVKAAAEIDALPNLITRRQWNAFIKSLVDDPSQSSELLSEAKKLNDSQ | SEQ ID NO:354 |
| PB02832 | KELVKAAAEIDALPNLNRRQWNAFIKKLVDDPSQSSELLSEAKKLNDSQ | SEQ ID NO:355 |
| PB02833 | KELVKAAAEIDALPNLTRRQWNAFIKKLVDDPSQSSELLSEAKKLNDSQ | SEQ ID NO:356 |
| PB02834 | KELVKAAAEIDALPNLTRRQWNAFIKKLVKDPSQSSELLSEAKKLNDSQ | SEQ ID NO:357 |
| PB03358 | KELIEAAAEIDALPNLITRRQWNAFIKKLVDDPSQSSELLSEAKKLNDSQ | SEQ ID NO:358 |
| Z01976 | VDNKFNKERAEFAAQEIDQLPNLNRGQWNAFIASLVDDPSQSANLLAEAKKLNDAQAPK | SEQ ID NO:359 |
| Z01977 | VDNKFNKERQVAAAEIDALPNLNRGQWNAFIASLVDDPSQSANLLAEAKKLNDAQAPK | SEQ ID NO:360 |
| Z01978 | VDNKFNKELSDAAAQEIDSLPNLNRSQWNAFIKSLIDDPSQSANLLAEAKKLNDAQAPK | SEQ ID NO:361 |
| Z01979 | VDNKFNKERREAAAEIDNLPNLNRSQWNAFIQSLVDDPSQSANLLAEAKKLNDAQAPK | SEQ ID NO:362 |
| Z01980 | VDNKFNKERREAAKEIDSLPNLNRTQWNAFIRSLADDPSQSANLLAEAKKLNDAQAPK | SEQ ID NO:363 |
| Z01981 | VDNKFNKELRHAASEIDDLPNLNRAQWNAFIRSLRDDPSQSANLLAEAKKLNDAQAPK | SEQ ID NO:364 |
| Z01982 | VDNKFNKELVRAAQEIDELPNLNRGQWNAFIKSLVDDPSQSANLLAEAKKLNDAQAPK | SEQ ID NO:365 |
| Z01983 | VDNKFNKEIKQAAREIDALPNLNKKQWNAFIQSLADDPSQSANLLAEAKKLNDAQAPK | SEQ ID NO:366 |
| Z01993 | VDNKFNKERHRAAQEIDQLPNLNRRQWNAFIKSLVDDPSQSANLLAEAKKLNDAQAPK | SEQ ID NO:367 |
| Z01994 | VDNKFNKEIKFAAGEIDNLPNLNRKQWNAFIGSLRDDPSQSANLLAEAKKLNDAQAPK | SEQ ID NO:368 |
| Z01995 | VDNKFNKERLKAAAEIDALPNLNRKQWNAFISSLRDDPSQSANLLAEAKKLNDAQAPK | SEQ ID NO:369 |
| Z02417 | VDNKFNKELRAAAAEIDSLPNLNRKQWNAFIKSLVDDPSQSANLLAEAKKLNDAQAPK | SEQ ID NO:370 |
| Z02418 | VDNKFNKERLEAAEEIDSLPNLNRAQWNAFIKSLVDDPSQSANLLAEAKKLNDAQAPK | SEQ ID NO:371 |
| Z02419 | VDNKFNKELIKAAAEIDALPNLNRRQWNAFIRSLVDDPSQSANLLAEAKKLNDAQAPK | SEQ ID NO:372 |
| Z02420 | VDNKFNKERIHAAREIDALPNLNRKQWNAFIKSLVDDPSQSANLLAEAKKLNDAQAPK | SEQ ID NO:373 |
| Z02421 | VDNKFNKELIKAAAEIDGLPNLNRKQWNAFIKSLVDDPSQSANLLAEAKKLNDAQAPK | SEQ ID NO:374 |
| Z02422 | VDNKFNKELVRAAREIDSLPNLNRRQWNAFIKSLVDDPSQSANLLAEAKKLNDAQAPK | SEQ ID NO:375 |
| Z02423 | VDNKFNKELIKAAREIDELPNLNRRQWNAFIKSLVDDPSQSANLLAEAKKLNDAQAPK | SEQ ID NO:376 |
| Z02424 | VDNKFNKELLAAAAEIDSLPNLNRAQWNAFIKSLVDDPSQSANLLAEAKKLNDAQAPK | SEQ ID NO:377 |

Figure 1M

| Polypeptide | Amino acid sequence | SEQ ID NO |
|---|---|---|
| Z02425 | VDNKFNKELINAAKEIDDLPNLNRRQWNAFIKSLVDDPSQSANLLAEAKKLNDAQAPK | SEQ ID NO:378 |
| Z02426 | VDNKFNKELVEAAREIDALPNLNRKQWNAFIKSLVDDPSQSANLLAEAKKLNDAQAPK | SEQ ID NO:379 |
| Z02427 | VDNKFNKELRDAAAEIDRLPNLNRRQWNAFIKSLVDDPSQSANLLAEAKKLNDAQAPK | SEQ ID NO:380 |
| Z02428 | VDNKFNKELSAAAREIDNLPNLNRRQWNAFIKSLVDDPSQSANLLAEAKKLNDAQAPK | SEQ ID NO:381 |
| Z02429 | VDNKFNKELISAAEEIDDLPNLNRRQWNAFIKSLVDDPSQSANLLAEAKKLNDAQAPK | SEQ ID NO:382 |
| Z02430 | VDNKFNKELVDAAREIDELPNLNRVQWNAFIKSLVDDPSQSANLLAEAKKLNDAQAPK | SEQ ID NO:383 |
| Z02431 | VDNKFNKELIEAAAREIDALPNLNRSQWNAFIKSLRDDPSQSANLLAEAKKLNDAQAPK | SEQ ID NO:384 |
| Z02432 | VDNKFNKELVEAAKEIDKLPNLNRRQWNAFIKSLVDDPSQSANLLAEAKKLNDAQAPK | SEQ ID NO:385 |
| Z02433 | VDNKFNKELRQAAKEIDNLPNLNRAQWNAFIKSLVDDPSQSANLLAEAKKLNDAQAPK | SEQ ID NO:386 |
| Z02434 | VDNKFNKELVAAAREIDSLPNLNRTQWNAFIKSLVDDPSQSANLLAEAKKLNDAQAPK | SEQ ID NO:387 |
| Z02435 | VDNKFNKELRNAAKEIDSLPNLNRRQWNAFIRSLVDDPSQSANLLAEAKKLNDAQAPK | SEQ ID NO:388 |
| Z02436 | VDNKFNKELVQAAREIDELPNLNRTQWNAFIKSLVDDPSQSANLLAEAKKLNDAQAPK | SEQ ID NO:389 |
| Z02437 | VDNKFNKELREAAEEIDNLPNLNRVQWNAFIKSLVDDPSQSANLLAEAKKLNDAQAPK | SEQ ID NO:390 |
| Z02438 | VDNKFNKELIEAAREIDNLPNLNRAQWNAFIRSLVDDPSQSANLLAEAKKLNDAQAPK | SEQ ID NO:391 |
| Z02439 | VDNKFNKELINAAREIDGLPNLNRMQWNAFIRSLVDDPSQSANLLAEAKKLNDAQAPK | SEQ ID NO:392 |
| Z02440 | VDNKFNKERIAAAQEIDGLPNLNRRQWNAFIKSLVDDPSQSANLLAEAKKLNDAQAPK | SEQ ID NO:393 |
| Z02441 | VDNKFNKELINAAKEIDDLPNLNRRQWNAFIKSLVDDPSQSANLLAEAKKLNDAQAPK | SEQ ID NO:394 |
| Z02442 | VDNKFNKERSHAAQEIDALPNLNRVQWNAFIKSLVDDPSQSANLLAEAKKLNDAQAPK | SEQ ID NO:395 |
| Z02443 | VDNKFNKELIAAAKEIDELPNLNRRQWNAFIKSLVDDPSQSANLLAEAKKLNDAQAPK | SEQ ID NO:396 |
| Z02444 | VDNKFNKERIRAAEEIDGLPNLNRWQWNAFIKSLVDDPSQSANLLAEAKKLNDAQAPK | SEQ ID NO:397 |
| Z02445 | VDNKFNKELVQAAREIDALPNLNRQQWNAFIKSLVDDPSQSANLLAEAKKLNDAQAPK | SEQ ID NO:398 |
| Z02446 | VDNKFNKERREAAREIDNLPNLNRRQWNAFIKSLVDDPSQSANLLAEAKKLNDAQAPK | SEQ ID NO:399 |
| Z02447 | VDNKFNKELRWAAGEIDKLPNLNRKQWNAFIKSLVDDPSQSANLLAEAKKLNDAQAPK | SEQ ID NO:400 |
| Z02448 | VDNKFNKELSRAAAEIDRLPNLNRVQWNAFIKSLVDDPSQSANLLAEAKKLNDAQAPK | SEQ ID NO:401 |
| Z02449 | VDNKFNKELIEAAREIDELPNLNRRQWNAFIKSLVDDPSQSANLLAEAKKLNDAQAPK | SEQ ID NO:402 |
| Z02450 | VDNKFNKELIAAAKEIDDLPNLNREQWNAFIKSLVDDPSQSANLLAEAKKLNDAQAPK | SEQ ID NO:403 |
| Z02451 | VDNKFNKERVRAAEIDSLPNLNRQQWNAFIKSLVDDPSQSANLLAEAKKLNDAQAPK | SEQ ID NO:404 |
| Z02452 | VDNKFNKELIDAAAEIDKLPNLNRGQWNAFIKSLVDDPSQSANLLAEAKKLNDAQAPK | SEQ ID NO:405 |
| Z02453 | VDNKFNKELIDAAAEIDKLPNLNRSQWNAFIKSLVDDPSQSANLLAEAKKLNDAQAPK | SEQ ID NO:406 |

Figure 1N

| Polypeptide | Amino acid sequence | SEQ ID NO |
|---|---|---|
| Z02454 | VDNKFNKELIEAAEEIDRLPNLNRQQWNAFIKSLVDDPSQSANLLAEAKKLNDAQAPK | SEQ ID NO:407 |
| Z02455 | VDNKFNKELIEAAREIDELPNLNRKQWNAFIKSLVDDPSQSANLLAEAKKLNDAQAPK | SEQ ID NO:408 |
| Z02456 | VDNKFNKELREAAEEIDSLPNLNRKQWNAFIKSLVDDPSQSANLLAEAKKLNDAQAPK | SEQ ID NO:409 |
| Z02457 | VDNKFNKELVDAAREIDDLPNLNRGQWNAFIKSLVDDPSQSANLLAEAKKLNDAQAPK | SEQ ID NO:410 |
| Z02458 | VDNKFNKELREAAAEIDALPNLNRKQWNAFIKSLVDDPSQSANLLAEAKKLNDAQAPK | SEQ ID NO:411 |
| Z02459 | VDNKFNKELIEAAAEIDKLPNLNRAQWNAFIKSLVDDPSQSANLLAEAKKLNDAQAPK | SEQ ID NO:412 |
| Z02460 | VDNKFNKELREAAGEIDRLPNLNRRQWNAFIKSLVDDPSQSANLLAEAKKLNDAQAPK | SEQ ID NO:413 |
| Z02461 | VDNKFNKELVRAAEEIDALPNLNRKQWNAFIKSLVDDPSQSANLLAEAKKLNDAQAPK | SEQ ID NO:414 |
| Z02462 | VDNKFNKERSRAAAEIDALPNLNRRQWNAFIKSLVDDPSQSANLLAEAKKLNDAQAPK | SEQ ID NO:415 |
| Z02463 | VDNKFNKELIRAASEIDKLPNLNRRQWNAFIKSLRDDPSQSANLLAEAKKLNDAQAPK | SEQ ID NO:416 |
| Z02464 | VDNKFNKELIKAAQEIDRLPNLNRTQWNAFIRSLVDDPSQSANLLAEAKKLNDAQAPK | SEQ ID NO:417 |
| Z02465 | VDNKFNKELIEAAAEIDALPNLNRRQWNAFIKSLVDDPSQSANLLAEAKKLNDAQAPK | SEQ ID NO:418 |
| Z02466 | VDNKFNKELIWAAGEIDKLPNLNRRQWNAFIKSLVDDPSQSANLLAEAKKLNDAQAPK | SEQ ID NO:419 |
| Z02467 | VDNKFNKERLAAAEEIDNLPNLNRRQWNAFIKSLVDDPSQSANLLAEAKKLNDAQAPK | SEQ ID NO:420 |
| Z02468 | VDNKFNKELRKAAEEIDALPNLNRRQWNAFIKSLVDDPSQSANLLAEAKKLNDAQAPK | SEQ ID NO:421 |
| Z02469 | VDNKFNKELIAAAREIDSLPNLNRRQWNAFIKSLVDDPSQSANLLAEAKKLNDAQAPK | SEQ ID NO:422 |
| Z02470 | VDNKFNKERVKAAEEIDALPNLNRRQWNAFIKSLVDDPSQSANLLAEAKKLNDAQAPK | SEQ ID NO:423 |
| Z02471 | VDNKFNKELHAAEEIDRLPNLNRMQWNAFIKSLVDDPSQSANLLAEAKKLNDAQAPK | SEQ ID NO:424 |
| Z02472 | VDNKFNKELINAAGEIDKLPNLNRKQWNAFIKSLVDDPSQSANLLAEAKKLNDAQAPK | SEQ ID NO:425 |
| Z02473 | VDNKFNKELIEAAAEIDALPNLNRAQWNAFIKSLVDDPSQSANLLAEAKKLNDAQAPK | SEQ ID NO:426 |
| Z02474 | VDNKFNKELLAAAREIDSLPNLNRRQWNAFIKSLVDDPSQSANLLAEAKKLNDAQAPK | SEQ ID NO:427 |
| Z02475 | VDNKFNKERVDAAREIDNLPNLNREQWNAFIRSLVDDPSQSANLLAEAKKLNDAQAPK | SEQ ID NO:428 |
| Z02476 | VDNKFNKELRDAAAEIDRLPNLNRKQWNAFIKSLVDDPSQSANLLAEAKKLNDAQAPK | SEQ ID NO:429 |
| Z02477 | VDNKFNKELIAAAAEIDRLPNLNRVQWNAFIKSLVDDPSQSANLLAEAKKLNDAQAPK | SEQ ID NO:430 |
| Z02478 | VDNKFNKELRAAAEEIDKLPNLNRRQWNAFIKSLIDDPSQSANLLAEAKKLNDAQAPK | SEQ ID NO:431 |
| Z02479 | VDNKFNKELIWAAAEEIDNLPNLNRREQWNAFIRSLVDDPSQSANLLAEAKKLNDAQAPK | SEQ ID NO:432 |
| Z02480 | VDNKFNKELIEAAKEIDNLPNLNRQWNAFIKSLVDDPSQSANLLAEAKKLNDAQAPK | SEQ ID NO:433 |
| Z02481 | VDNKFNKELVQAAKEIDNLPNLNRSQWNAFIRSLVDDPSQSANLLAEAKKLNDAQAPK | SEQ ID NO:434 |
| Z02482 | VDNKFNKELIEAAGEIDALPNLNRRQWNAFIKSLVDDPSQSANLLAEAKKLNDAQAPK | SEQ ID NO:435 |

Figure 10

| Polypeptide | Amino acid sequence | SEQ ID NO |
|---|---|---|
| Z02483 | VDNKFNKELVKAAAEIDALPNLNRRQWNAFIKSLVDDPSQSANLLAEAKKLNDAQAPK | SEQ ID NO:436 |
| Z02484 | VDNKFNKELREAAREIDSLPNLNRSQWNAFIKSLVDDPSQSANLLAEAKKLNDAQAPK | SEQ ID NO:437 |
| Z02485 | VDNKFNKELLEAAKEIDELPNLNRRQWNAFIKSLVDDPSQSANLLAEAKKLNDAQAPK | SEQ ID NO:438 |
| Z02486 | VDNKFNKELVEAAREIDELPNLNRSQWNAFIKSLVDDPSQSANLLAEAKKLNDAQAPK | SEQ ID NO:439 |
| Z02487 | VDNKFNKELREAAAEIDALPNLNRSQWNAFIKSLVDDPSQSANLLAEAKKLNDAQAPK | SEQ ID NO:440 |
| Z02488 | VDNKFNKELVRAAEEIDRLPNLNRAQWNAFIKSLVDDPSQSANLLAEAKKLNDAQAPK | SEQ ID NO:441 |
| Z02489 | VDNKFNKELRAAAAEIDSLPNLNRGQWNAFIKSLVDDPSQSANLLAEAKKLNDAQAPK | SEQ ID NO:442 |
| Z02490 | VDNKFNKELIRAAREIDELPNLNRMQWNAFIKSLVDDPSQSANLLAEAKKLNDAQAPK | SEQ ID NO:443 |
| Z02491 | VDNKFNKELRDAAREIDAARELDSLPNLNRRQWNAFIRSLVDDPSQSANLLAEAKKLNDAQAPK | SEQ ID NO:444 |
| Z02492 | VDNKFNKELREAAREIDELPNLNRRQWNAFIKSLVDDPSQSANLLAEAKKLNDAQAPK | SEQ ID NO:445 |
| Z02493 | VDNKFNKELIRAAEEIDKLPNLNRKQWNAFIKSLVDDPSQSANLLAEAKKLNDAQAPK | SEQ ID NO:446 |
| Z02494 | VDNKFNKELLKAAREIDELPNLNRRQWNAFIRSLVDDPSQSANLLAEAKKLNDAQAPK | SEQ ID NO:447 |
| Z02495 | VDNKFNKELIAAAREIDGLPNLNRKQWNAFIKSLVDDPSQSANLLAEAKKLNDAQAPK | SEQ ID NO:448 |
| Z02496 | VDNKFNKELVAAAEIDGLPNLNRKQWNAFIHSLVDDPSQSANLLAEAKKLNDAQAPK | SEQ ID NO:449 |
| Z02497 | VDNKFNKELRDAAREIDALPNLNRAQWNAFIKSLVDDPSQSANLLAEAKKLNDAQAPK | SEQ ID NO:450 |
| Z02498 | VDNKFNKERINAAKEIDSLPNLNRRQWNAFIKSLVDDPSQSANLLAEAKKLNDAQAPK | SEQ ID NO:451 |
| Z02499 | VDNKFNKELRQAAAEIDALPNLNRQQWNAFIKSLVDDPSQSANLLAEAKKLNDAQAPK | SEQ ID NO:452 |
| Z02500 | VDNKFNKELVEAAAEIDRLPNLNRGQWNAFIKSLVDDPSQSANLLAEAKKLNDAQAPK | SEQ ID NO:453 |
| Z02501 | VDNKFNKELRFAAAEIDRLPNLNRRQWNAFIKSLVDDPSQSANLLAEAKKLNDAQAPK | SEQ ID NO:454 |
| Z02502 | VDNKFNKELIQAAKEIDSLPNLNRRQWNAFIKSLVDDPSQSANLLAEAKKLNDAQAPK | SEQ ID NO:455 |
| Z02503 | VDNKFNKERSMAAKEIDSLPNLNRRQWNAFIKSLVDDPSQSANLLAEAKKLNDAQAPK | SEQ ID NO:456 |
| Z02504 | VDNKFNKELVAAAREIDDLPNLNRAFIRSLVDDPSQSANLLAEAKKLNDAQAPK | SEQ ID NO:457 |
| Z02505 | VDNKFNKELVRAAEEIDRLPNLNRLQWNAFIKSLIDDPSQSANLLAEAKKLNDAQAPK | SEQ ID NO:458 |
| Z02506 | VDNKFNKELRFAAAEIDDLPNLNRAQWNAFIKSLVDDPSQSANLLAEAKKLNDAQAPK | SEQ ID NO:459 |
| Z02507 | VDNKFNKELVEAAKEIDSLPNLNRRQWNAFIKSLVDDPSQSANLLAEAKKLNDAQAPK | SEQ ID NO:460 |
| Z02508 | VDNKFNKELINAAGEIDRLPNLNRRQWNAFIKSLVDDPSQSANLLAEAKKLNDAQAPK | SEQ ID NO:461 |
| Z02509 | VDNKFNKELLSAAAEIDSLPNLNRKQWNAFIKSLVDDPSQSANLLAEAKKLNDAQAPK | SEQ ID NO:462 |
| Z02510 | VDNKFNKELRDAAAEIDKLPNLNRAQWNAFIKSLVDDPSQSANLLAEAKKLNDAQAPK | SEQ ID NO:463 |
| Z02511 | VDNKFNKELRQAAAEIDKLPNLNRSQWNAFIQSLVDDPSQSANLLAEAKKLNDAQAPK | SEQ ID NO:464 |

Figure 1 P

| Polypeptide | Amino acid sequence | SEQ ID NO |
|---|---|---|
| Z02512 | VDNKFNKELRBAAAEIDALPNLNRVQWNAFIKSLRDDPSQSANLLAEAKKLNDAQAPK | SEQ ID NO:465 |
| Z02513 | VDNKFNKELVAAAEEIDRLPNLNRAQWNAFIKSLVDDPSQSANLLAEAKKLNDAQAPK | SEQ ID NO:466 |
| Z02514 | VDNKFNKELIDAAAEIDKLPNLNRNQWNAFIKSLVDDPSQSANLLAEAKKLNDAQAPK | SEQ ID NO:467 |
| Z02515 | VDNKFNKERINAAAEIDGLPNLNRQQWNAFIKSLVDDPSQSANLLAEAKKLNDAQAPK | SEQ ID NO:468 |
| Z02516 | VDNKFNKELVRAAAEIDNLPNLNRKQWNAFIKSLVDDPSQSANLLAEAKKLNDAQAPK | SEQ ID NO:469 |
| Z02517 | VDNKFNKELIRAAAEIDELPNLNRRQWNAFIRSLVDDPSQSANLLAEAKKLNDAQAPK | SEQ ID NO:470 |
| Z02518 | VDNKFNKELIQAAREIDSLPNLNRQWNAFIKSLLDDPSQSANLLAEAKKLNDAQAPK | SEQ ID NO:471 |
| Z02519 | VDNKFNKELIDAAREIDDLPNLNRQQWNAFIKSLVDDPSQSANLLAEAKKLNDAQAPK | SEQ ID NO:472 |
| Z02520 | VDNKFNKELLKAADEIDALPNLNRACWNAFIKSLVDDPSQSANLLAEAKKLNDAQAPK | SEQ ID NO:473 |
| Z02521 | VDNKFNKELLEAAAEIDSLPNLNRRQWNAFIKSLVDDPSQSANLLAEAKKLNDAQAPK | SEQ ID NO:474 |
| Z02522 | VDNKFNKELVDAAREIDTLPNLNRRQWNAFIKSLVDDPSQSANLLAEAKKLNDAQAPK | SEQ ID NO:475 |
| Z02523 | VDNKFNKELIEAAREIDKLPNLNRRQWNAFIKSLVDDPSQSANLLAEAKKLNDAQAPK | SEQ ID NO:476 |
| Z02524 | VDNKFNKELVAAAREIDNLPNLNRRQWNAFIKSLVDDPSQSANLLAEAKKLNDAQAPK | SEQ ID NO:477 |
| Z02525 | VDNKFNKELVEAAAEIDGLPNLNRDQWNAFIKSLRDDPSQSANLLAEAKKLNDAQAPK | SEQ ID NO:478 |
| Z02526 | VDNKFNKELRNAAKEIDGLPNLNRRQWNAFIKSLVDDPSQSANLLAEAKKLNDAQAPK | SEQ ID NO:479 |
| Z02527 | VDNKFNKELRHAAREIDGLPNLNRTQWNAFIKSLVDDPSQSANLLAEAKKLNDAQAPK | SEQ ID NO:480 |
| Z02528 | VDNKFNKELVEAAREIDTLPNLNRRQWNAFIKSLVDDPSQSANLLAEAKKLNDAQAPK | SEQ ID NO:481 |
| Z02529 | VDNKFNKELVAAAREIDALPNLNRRQWNAFIKSLVDDPSQSANLLAEAKKLNDAQAPK | SEQ ID NO:482 |
| Z02530 | VDNKFNKELRTAAKEIDDLPNLNRKQWNAFIKSLVDDPSQSANLLAEAKKLNDAQAPK | SEQ ID NO:483 |
| Z02531 | VDNKFNKELLRAAAREIDSLPNLNRTQWNAFIKSLVDDPSQSANLLAEAKKLNDAQAPK | SEQ ID NO:484 |
| Z02532 | VDNKFNKERIRAAREIDALPNLNRQQWNAFIKSLVDDPSQSANLLAEAKKLNDAQAPK | SEQ ID NO:485 |
| Z02533 | VDNKFNKELRAAAEIDRLPNLNRRQWNAFIKSLVDDPSQSANLLAEAKKLNDAQAPK | SEQ ID NO:486 |
| Z02534 | VDNKFNKELIEAAREIDALPNLNRKQWNAFISSLVDDPSQSANLLAEAKKLNDAQAPK | SEQ ID NO:487 |
| Z02535 | VDNKFNKERIEAAREIDAAREIDELPNLNRKQWNAFIKSLVDDPSQSANLLAEAKKLNDAQAPK | SEQ ID NO:488 |
| Z02536 | VDNKFNKELLAAAKEIDELPNLNRAQWNAFIKSLVDDPSQSANLLAEAKKLNDAQAPK | SEQ ID NO:489 |
| Z02537 | VDNKFNKELINAAREIDELPNLNRRQWNAFIKSLVDDPSQSANLLAEAKKLNDAQAPK | SEQ ID NO:490 |
| Z02538 | VDNKFNKELVKAAAEIDALPNLNRRQWNAFIKSLVDDPSQSANLLAEAKKLNDAQAPK | SEQ ID NO:491 |
| Z02539 | VDNKFNKELIAAAAKEIDELPNLNRKQWNAFIKSLVDDPSANLLAEAKKLNDAQAPK | SEQ ID NO:492 |
| Z02540 | VDNKFNKELISAAREIDKLPNLNRQQWNAFIKSLVDDPSQSANLLAEAKKLNDAQAPK | SEQ ID NO:493 |

Figure 1 Q

| Polypeptide | Amino acid sequence | SEQ ID NO |
|---|---|---|
| Z02541 | VDNKFNKELREAAEEIDKLPNLNRWQWNAFIKSLVDDPSQSANLLAEAKKLNDAQAPK | SEQ ID NO:494 |
| Z02542 | VDNKFNKELVEAAREIDGLPNLNRAQWNAFIKSLVDDPSQSANLLAEAKKLNDAQAPK | SEQ ID NO:495 |
| Z02543 | VDNKFNKELVAAAQEIDNLPNLNRQWNAFISSLVDDPSQSANLLAEAKKLNDAQAPK | SEQ ID NO:496 |
| Z02544 | VDNKFNKELRNAAAEIDKLPNLNRRQWNAFIKSLVDDPSQSANLLAEAKKLNDAQAPK | SEQ ID NO:497 |
| Z02545 | VDNKFNKELIQAASEIDALPNLNRTQWNAFIKSLVDDPSQSANLLAEAKKLNDAQAPK | SEQ ID NO:498 |
| Z02546 | VDNKFNKELVRAAAEIDSLPNLNRRQWNAFIKSLVDDPSQSANLLAEAKKLNDAQAPK | SEQ ID NO:499 |
| Z02547 | VDNKFNKERIAAAQEIDALPNLNRRQWNAFIRSLVDDPSQSANLLAEAKKLNDAQAPK | SEQ ID NO:500 |
| Z02548 | VDNKFNKELRDAAKEIDSLPNLNRRQWNAFIKSLVDDPSQSANLLAEAKKLNDAQAPK | SEQ ID NO:501 |
| Z02549 | VDNKFNKELVAAAKEIDKLPNLNRKQWNAFIKSLVDDPSQSANLLAEAKKLNDAQAPK | SEQ ID NO:502 |
| Z02550 | VDNKFNKELIKAAREIDELPNLNRKQWNAFIKSLIDDPSQSANLLAEAKKLNDAQAPK | SEQ ID NO:503 |
| Z02551 | VDNKFNKELVRAASEIDGLPNLNRNQWNAFIKSLVDDPSQSANLLAEAKKLNDAQAPK | SEQ ID NO:504 |
| Z02552 | VDNKFNKELLRAAAEIDNLPNLNRAQWNAFIKSLVDDPSQSANLLAEAKKLNDAQAPK | SEQ ID NO:505 |
| Z02553 | VDNKFNKELIKAAKEIDALPNLNRRQWNAFIKSLVDDPSQSANLLAEAKKLNDAQAPK | SEQ ID NO:506 |
| Z02554 | VDNKFNKELRAAAEIDSLPNLNRDQWNAFIRSLIDDPSQSANLLAEAKKLNDAQAPK | SEQ ID NO:507 |
| Z02555 | VDNKFNKELVEAAREIDGLPNLNRAQWNAFIKSLVDDPSQSANLLAEAKKLNDAQAPK | SEQ ID NO:508 |
| Z02556 | VDNKFNKELVEAAREIDELPNLNRRQWNAFIRSLVDDPSQSANLLAEAKKLNDAQAPK | SEQ ID NO:509 |
| Z02557 | VDNKFNKELVWAAAEIDRLPNLNRCQWNAFIKSLVDDPSQSANLLAEAKKLNDAQAPK | SEQ ID NO:510 |
| Z02558 | VDNKFNKERIRAAREIDELPNLNREQWNAFIKSLVDDPSQSANLLAEAKKLNDAQAPK | SEQ ID NO:511 |
| Z02559 | VDNKFNKELRQAAKEIDKLPNLNRRQWNAFIKSLVDDPSQSANLLAEAKKLNDAQAPK | SEQ ID NO:512 |
| Z02560 | VDNKFNKELREAAAEIDKLPNLNRKQWNAFIKSLVDDPSQSANLLAEAKKLNDAQAPK | SEQ ID NO:513 |
| Z02561 | VDNKFNKELRRAAAEIDKLPNLNRRQWNAFIRSLVDDPSQSANLLAEAKKLNDAQAPK | SEQ ID NO:514 |
| Z02562 | VDNKFNKELVQAAREIDALPNLNRQQWNAFIKSLVDDPSQSANLLAEAKKLNDAQAPK | SEQ ID NO:515 |
| Z02563 | VDNKFNKELRAAAEIDALPNLNRRQWNAFIKSLVDDPSQSANLLAEAKKLNDAQAPK | SEQ ID NO:516 |
| Z02564 | VDNKFNKELRAAAEIDKLPNLNRKQWNAFIKSLVDDPSQSANLLAEAKKLNDAQAPK | SEQ ID NO:517 |
| Z02565 | VDNKFNKERIQAAKEIDELPNLNREQWNAFIKSLVDDPSQSANLLAEAKKLNDAQAPK | SEQ ID NO:518 |
| Z02566 | VDNKFNKELVAAAEEIDKLPNLNRRQWNAFIKSLVDDPSQSANLLAEAKKLNDAQAPK | SEQ ID NO:519 |
| Z02568 | VDNKFNKELVRAAEIDNLPNLNRQWNAFIKSLVDDPSQSANLLAEAKKLNDAQAPK | SEQ ID NO:520 |
| Z02569 | VDNKFNKELRTAAAEIDALPNLNREQWNAFIRSLVDDPSQSANLLAEAKKLNDAQAPK | SEQ ID NO:521 |
| Z02570 | VDNKFNKELVRAAAEIDALPNLNRKQWNAFIKSLVDDPSQSANLLAEAKKLNDAQAPK | SEQ ID NO:522 |

Figure 1 R

| Polypeptide | Amino acid sequence | SEQ ID NO |
|---|---|---|
| Z02571 | VDNKFNKELIKAAEEIDKLPNLNRMQWNAFIRSLVDDPSQSANLLAEAKKLNDAQAPK | SEQ ID NO:523 |
| Z02572 | VDNKFNKELREAAAEIDNLPNLNRRQWNAFIKSLIDDPSQSANLLAEAKKLNDAQAPK | SEQ ID NO:524 |
| Z02573 | VDNKFNKELIEAAREIDALPNLNRKQWNAFIRSLVDDPSQSANLLAEAKKLNDAQAPK | SEQ ID NO:525 |
| Z02574 | VDNKFNKELREAAQEIDSLPNLNRQQWNAFIKSLVDDPSQSANLLAEAKKLNDAQAPK | SEQ ID NO:526 |
| Z02575 | VDNKFNKELRSAAEEIDSLPNLNRRQWNAFIKSLVDDPSQSANLLAEAKKLNDAQAPK | SEQ ID NO:527 |
| Z02576 | VDNKFNKELVEAAAEIDNLPNLNRMQWNAFIKSLVDDPSQSANLLAEAKKLNDAQAPK | SEQ ID NO:528 |
| Z02577 | VDNKFNKELVEAAGEIDNLPNLNRRQWNAFIRSLVDDPSQSANLLAEAKKLNDAQAPK | SEQ ID NO:529 |
| Z02578 | VDNKFNKELSKAAAEIDALPNLNRRQWNAFIKSLVDDPSQSANLLAEAKKLNDAQAPK | SEQ ID NO:530 |
| Z02579 | VDNKFNKELLWAAGEIDRLPNLNRQQWNAFIKSLVDDPSQSANLLAEAKKLNDAQAPK | SEQ ID NO:531 |
| Z02580 | VDNKFNKELRQAAAEIDGLPNLNRRQWNAFIKSLVDDPSQSSELLSEAKKLNDAQAPK | SEQ ID NO:532 |
| Z02831 | VDAFAKELVKAAAEIDALPNLNRRQWNAFIKSLVDDPSQSSELLSEAKKLNDSQAPK | SEQ ID NO:533 |
| Z02832 | VDAKFAKELVKAAAEIDALPNLNRQQWNAFIKKLVDDPSQSSELLSEAKKLNDSQAPK | SEQ ID NO:534 |
| Z02833 | VDAKFAKELVKAAAEIDALPNLTRRQWNAFIKKLVDDPSQSSELLSEAKKLNDSQAPK | SEQ ID NO:535 |
| Z02834 | VDAKFAKELVKAAAEIDALPNLTRRQWNAFIKKLVKDPSQSSELLSEAKKLNDSQAPK | SEQ ID NO:536 |
| Z03358 | AEAKYAKELIEAAAEIDALPNLTRRQWNAFIKKLVDDPSQSSELLSEAKKLNDSQAPS | SEQ ID NO:537 |
| Z00000 | VDNKFNKEQQ NAFYEILHLP NLNEEQRNAF IQSLKDDPSQ SANLLAEAKK LNDAQAPK | SEQ ID NO:538 |

Figure 1 S

| Polypeptide | Amino acid sequence | SEQ ID NO |
|---|---|---|
| PDGF-Rβ | MRLPGAMPAL ALKGELLLLS LLLLLEPQIS QGLVVTPPGP ELVLNVSSTF VLTCSGSAPV VWERMSQEPP QEMAKAQDGT FSSVLTLTNL TGLDTGEYFC THNDSRGLET DERKRLYIFV PDPTVGFLPN DAEELFIFLT EITEITIPCR VTDPQLVVTL HEKKGDVALP VPYDHQRGFS GIFEDRSYIC KTTIGDREVD SDAYYVYRLQ VSSINVSVNA VQTVVRQGEN ITLMCIVIGN EVVNFEWTYP RKESGRLVEP VTDFLLDMPY HIRSILHIPS AELEDSGTYT CNVTESVNDH QDEKAINITV VESGYVRLLG EVGTLQFAEL HRSRTLQVVF EAYPPPTVLW FKDNRTLGDS SAGEIALSTR NVSETRYVSE LTLVRVKVAE AGHYTMRAFH EDAEVQLSFQ LQINVPVRVL ELSESHPDSG EQTVRCRGRG MPQPNIIWSA CRDLKRCPRE LPPTLLGNSS EEESQLETNV TYWEEEQEFE VVSTLRLQHV DRPLSVRCTL RNAVGQDTQE VIVVPHSLPF KVVVISAILA LVVLTIISLI ILIMLWQKKP RYEIRWKVIE SVSSDGHEYI YVDPMQLPYD STWELPRDQL VLGRTLGSGA FGQVVEATAH GLSHSQATMK VAVKMLKSTA RSSEKQALMS ELKIMSHLGP HLNVVNLLGA CTKGGPIYII TEYCRYGDLV DYLHRNKHTF LQHHSDKRRP PSAELYSNAL PVGLPLPSHV SLTGESDGGY MDMSKDESVD YVPMLDMKGD VKYADIESSN YMAPYDNYVP SAPERTCRAT LINESPVLSY MDLVGFSYQV ANGMEFLASK NCVHRDLAAR NVLICEGKLV KICDFGLARD IMRDSNYISK GSTFLPLKWM APESIFNSLY TTLSDVWSFG ILLWEIFTLG GTPYPELPMN EQFYNAIKRG YRMAQPAHAS DEIYEIMQKC WEEKFEIRPP FSQLVLLLER LLGEGYKKKY QQVDEEFLRS DHPAILRSQA RLPGFHGLRS PLDTSSVLYT AVQPNEGDND YIIPLPDPKP EVADEGPLEG SPSLASSTLN EVNTSSTISC DSPLEPQDEP EPEPQLELQV EPEPELEQLP DSGCPAPRAE AEDSFL | SEQ ID NO:539 |
| PDGF-RβEC | VVTPPGP ELVLNVSSTF VLTCSGSAPV VWERMSQEPP QEMAKAQDGT FSSVLTLTNL TGLDTGEYFC THNDSRGLET DERKRLYIFV PDPTVGFLPN DAEELFIFLT EITEITIPCR VTDPQLVVTL HEKKGDVALP VPYDHQRGFS GIFEDRSYIC KTTIGDREVD SDAYYVYRLQ VSSINVSVNA VQTVVRQGEN ITLMCIVIGN EVVNFEWTYP RKESGRLVEP VTDFLLDMPY HIRSILHIPS AELEDSGTYT CNVTESVNDH QDEKAINITV VESGYVRLLG EVGTLQFAEL HRSRTLQVVF EAYPPPTVLW FKDNRTLGDS SAGEIALSTR NVSETRYVSE LTLVRVKVAE AGHYTMRAFH EDAEVQLSFQ LQINVPVRVL ELSESHPDSG EQTVRCRGRG MPQPNIIWSA CRDLKRCPRE LPPTLLGNSS EEESQLETNV TYWEEEQEFE VVSTLRLQHV DRPLSVRCTL RNAVGQDTQE VIVVPHSLPF K | SEQ ID NO:540 |

Figure 1 T

A
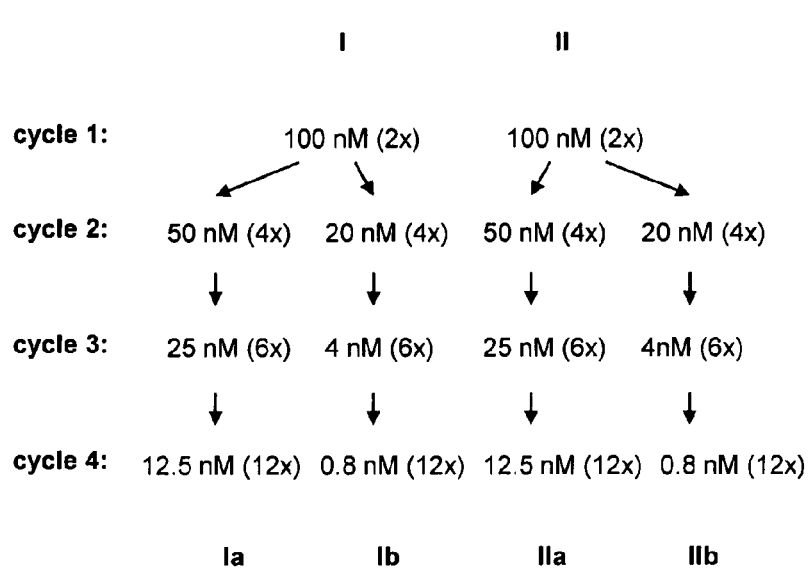
B
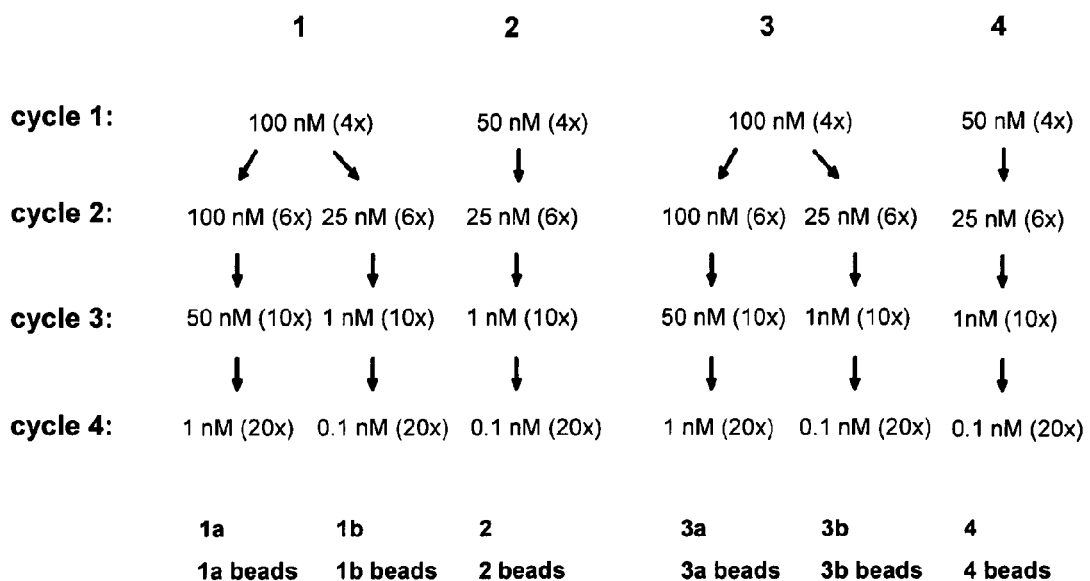
Figure 4

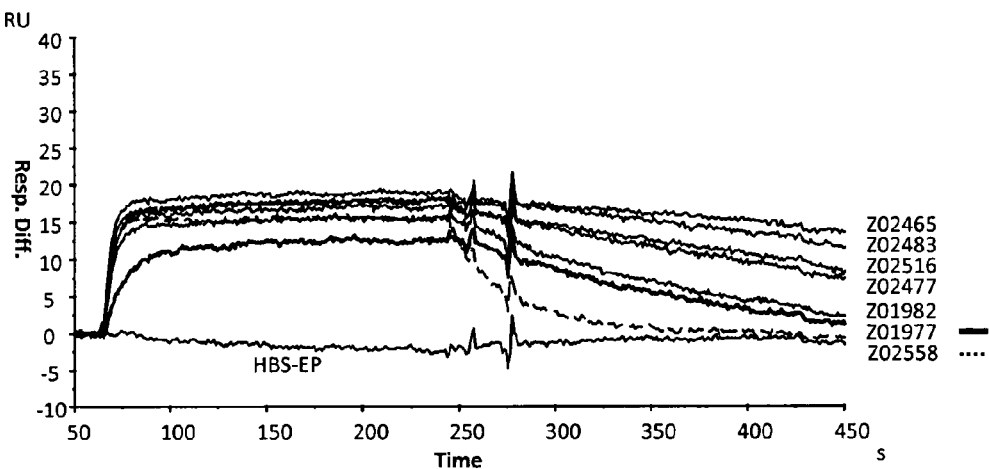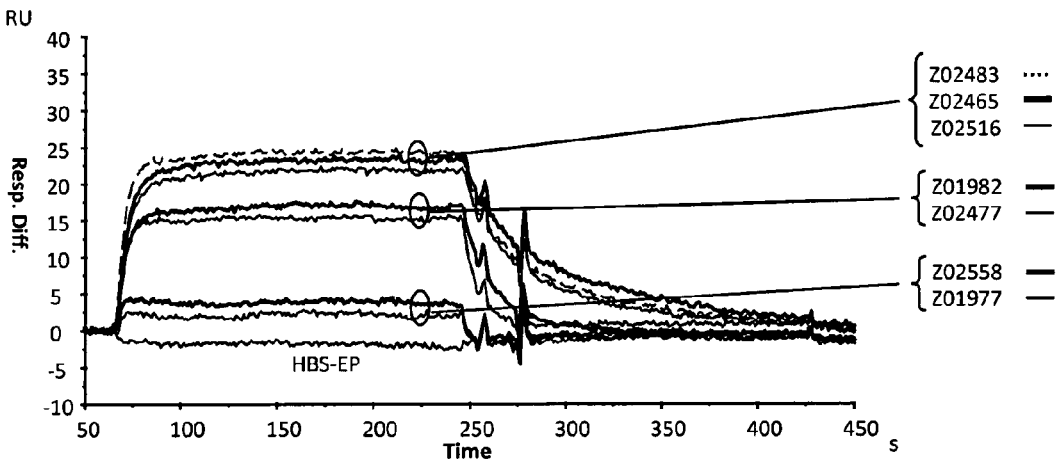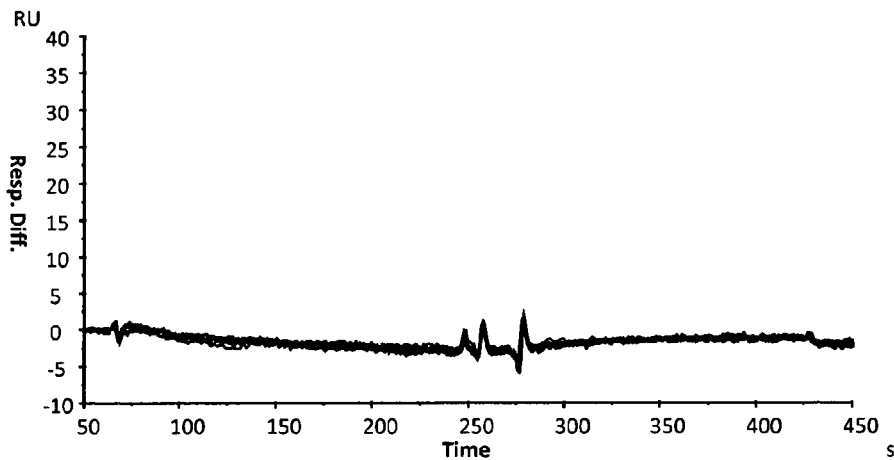
Figure 5

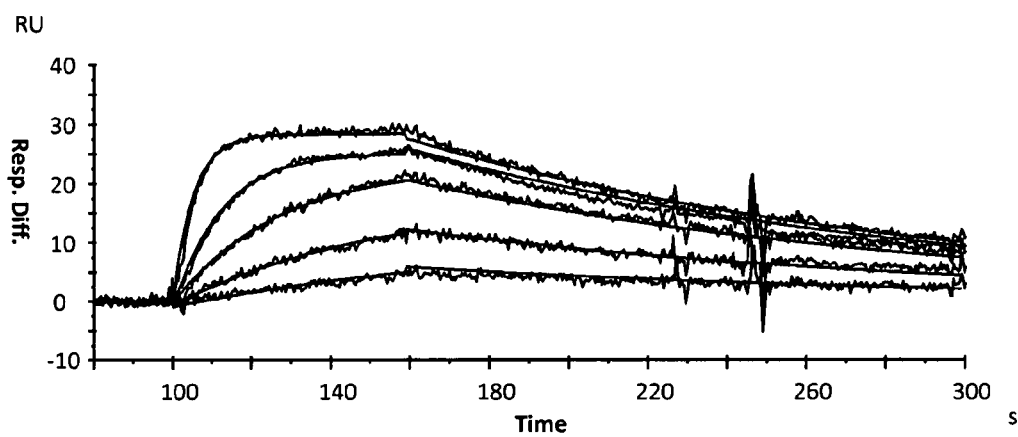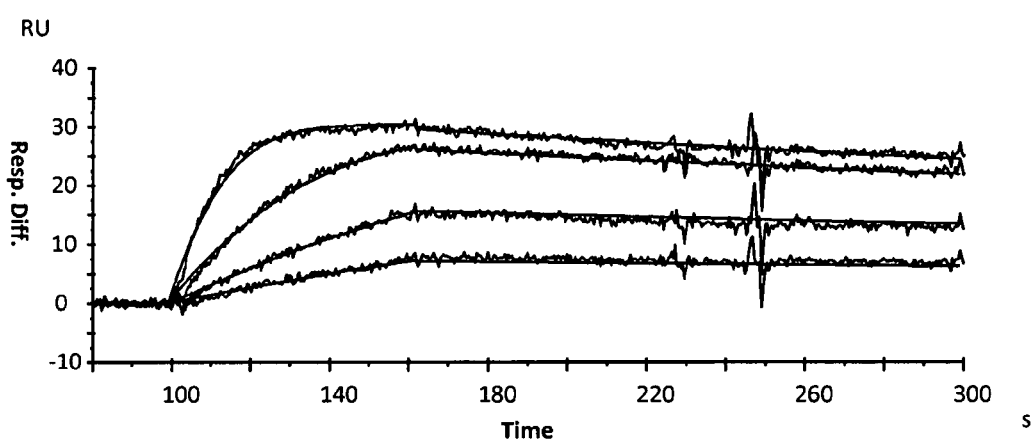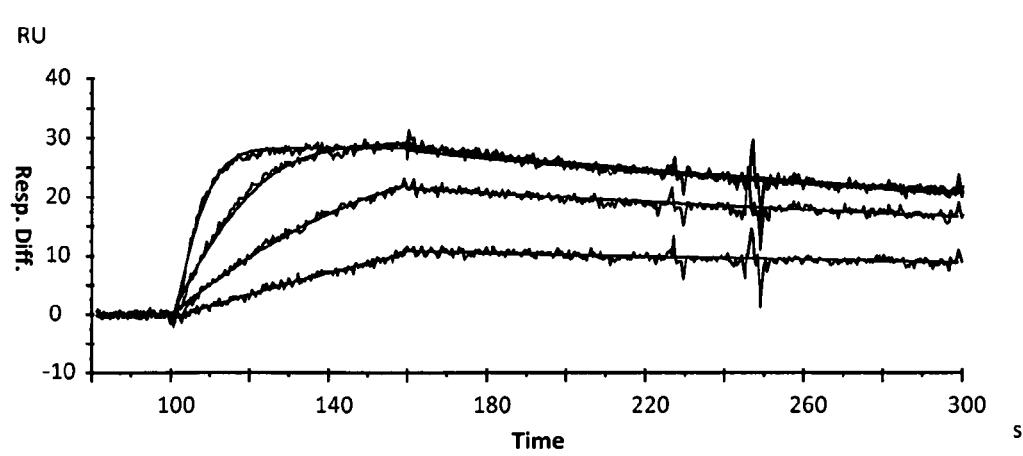
Figure 6

SEQUENCE LISTING

<160> NUMBER OF SEQ ID NOS: 550

<210> SEQ ID NO 1
<211> LENGTH: 29
<212> TYPE: PRT
<213> ORGANISM: Artificial
<220> FEATURE:
<223> OTHER INFORMATION: Engineered polypeptide

<400> SEQUENCE: 1

Glu Arg Ala Glu Ala Ala Gln Glu Ile Asp Gln Leu Pro Asn Leu Asn
1               5                   10                  15

Arg Gly Gln Trp Asn Ala Phe Ile Ala Ser Leu Val Asp
            20                  25

<210> SEQ ID NO 2
<211> LENGTH: 29
<212> TYPE: PRT
<213> ORGANISM: Artificial
<220> FEATURE:
<223> OTHER INFORMATION: Engineered polypeptide

<400> SEQUENCE: 2

Glu Arg Gln Val Ala Ala Ala Glu Ile Asp Ala Leu Pro Asn Leu Asn
1               5                   10                  15

Arg Gly Gln Trp Asn Ala Phe Ile Ala Ser Leu Val Asp
            20                  25

<210> SEQ ID NO 3
<211> LENGTH: 29
<212> TYPE: PRT
<213> ORGANISM: Artificial
<220> FEATURE:
<223> OTHER INFORMATION: Engineered polypeptide

<400> SEQUENCE: 3

Glu Leu Ser Asp Ala Ala Gln Glu Ile Asp Ser Leu Pro Asn Leu Asn
1               5                   10                  15

Arg Ser Gln Trp Asn Ala Phe Ile Lys Ser Leu Ile Asp
            20                  25

<210> SEQ ID NO 4
<211> LENGTH: 29
<212> TYPE: PRT
<213> ORGANISM: Artificial
<220> FEATURE:
<223> OTHER INFORMATION: Engineered polypeptide

<400> SEQUENCE: 4

Glu Arg Arg Glu Ala Ala Ala Glu Ile Asp Asn Leu Pro Asn Leu Asn
1               5                   10                  15

Arg Ser Gln Trp Asn Ala Phe Ile Gln Ser Leu Val Asp
            20                  25

<210> SEQ ID NO 5
<211> LENGTH: 29
<212> TYPE: PRT
<213> ORGANISM: Artificial
<220> FEATURE:
<223> OTHER INFORMATION: Engineered polypeptide

<400> SEQUENCE: 5

Glu Arg Arg Glu Ala Ala Lys Glu Ile Asp Ser Leu Pro Asn Leu Asn
1               5                   10                  15

Arg Thr Gln Trp Asn Ala Phe Ile Arg Ser Leu Ala Asp
            20                  25

<210> SEQ ID NO 6
<211> LENGTH: 29
<212> TYPE: PRT
<213> ORGANISM: Artificial
<220> FEATURE:
<223> OTHER INFORMATION: Engineered polypeptide

<400> SEQUENCE: 6

Glu Leu Arg His Ala Ala Ser Glu Ile Asp Asp Leu Pro Asn Leu Asn
1               5                   10                  15

Arg Ala Gln Trp Asn Ala Phe Ile Arg Ser Leu Arg Asp
            20                  25

<210> SEQ ID NO 7
<211> LENGTH: 29
<212> TYPE: PRT
<213> ORGANISM: Artificial
<220> FEATURE:
<223> OTHER INFORMATION: Engineered polypeptide

<400> SEQUENCE: 7

Glu Leu Val Arg Ala Ala Gln Glu Ile Asp Glu Leu Pro Asn Leu Asn
1               5                   10                  15

Arg Gly Gln Trp Asn Ala Phe Ile Lys Ser Leu Val Asp
            20                  25

<210> SEQ ID NO 8
<211> LENGTH: 29
<212> TYPE: PRT
<213> ORGANISM: Artificial
<220> FEATURE:
<223> OTHER INFORMATION: Engineered polypeptide

<400> SEQUENCE: 8

Glu Ile Lys Gln Ala Ala Arg Glu Ile Asp Ala Leu Pro Asn Leu Asn
1               5                   10                  15

Lys Lys Gln Trp Asn Ala Phe Ile Gln Ser Leu Ala Asp
            20                  25

<210> SEQ ID NO 9
<211> LENGTH: 29
<212> TYPE: PRT
<213> ORGANISM: Artificial
<220> FEATURE:
<223> OTHER INFORMATION: Engineered polypeptide

<400> SEQUENCE: 9

Glu Arg His Arg Ala Ala Gln Glu Ile Asp Gln Leu Pro Asn Leu Asn
1               5                   10                  15

Arg Arg Gln Trp Asn Ala Phe Ile Lys Ser Leu Val Asp
            20                  25

<210> SEQ ID NO 10
<211> LENGTH: 29
<212> TYPE: PRT
<213> ORGANISM: Artificial
<220> FEATURE:
<223> OTHER INFORMATION: Engineered polypeptide

<400> SEQUENCE: 10

Glu Ile Lys Phe Ala Ala Gly Glu Ile Asp Asn Leu Pro Asn Leu Asn
1               5                   10                  15

```
Arg Lys Gln Trp Asn Ala Phe Ile Gly Ser Leu Arg Asp
            20                  25

<210> SEQ ID NO 11
<211> LENGTH: 29
<212> TYPE: PRT
<213> ORGANISM: Artificial
<220> FEATURE:
<223> OTHER INFORMATION: Engineered polypeptide

<400> SEQUENCE: 11

Glu Arg Leu Lys Ala Ala Ala Glu Ile Asp Ala Leu Pro Asn Leu Asn
1               5                   10                  15

Arg Lys Gln Trp Asn Ala Phe Ile Ser Ser Leu Arg Asp
            20                  25

<210> SEQ ID NO 12
<211> LENGTH: 29
<212> TYPE: PRT
<213> ORGANISM: Artificial
<220> FEATURE:
<223> OTHER INFORMATION: Engineered polypeptide

<400> SEQUENCE: 12

Glu Leu Arg Ala Ala Ala Ala Glu Ile Asp Ser Leu Pro Asn Leu Asn
1               5                   10                  15

Arg Lys Gln Trp Asn Ala Phe Ile Lys Ser Leu Val Asp
            20                  25

<210> SEQ ID NO 13
<211> LENGTH: 29
<212> TYPE: PRT
<213> ORGANISM: Artificial
<220> FEATURE:
<223> OTHER INFORMATION: Engineered polypeptide

<400> SEQUENCE: 13

Glu Arg Leu Glu Ala Ala Gly Glu Ile Asp Ser Leu Pro Asn Leu Asn
1               5                   10                  15

Arg Ala Gln Trp Asn Ala Phe Ile Lys Ser Leu Val Asp
            20                  25

<210> SEQ ID NO 14
<211> LENGTH: 29
<212> TYPE: PRT
<213> ORGANISM: Artificial
<220> FEATURE:
<223> OTHER INFORMATION: Engineered polypeptide

<400> SEQUENCE: 14

Glu Leu Ile Lys Ala Ala Ala Glu Ile Asp Ala Leu Pro Asn Leu Asn
1               5                   10                  15

Arg Arg Gln Trp Asn Ala Phe Ile Arg Ser Leu Val Asp
            20                  25

<210> SEQ ID NO 15
<211> LENGTH: 29
<212> TYPE: PRT
<213> ORGANISM: Artificial
<220> FEATURE:
<223> OTHER INFORMATION: Engineered polypeptide

<400> SEQUENCE: 15

Glu Arg Ile His Ala Ala Arg Glu Ile Asp Ala Leu Pro Asn Leu Asn
```

```
1               5                   10                  15
Arg Lys Gln Trp Asn Ala Phe Ile Lys Ser Leu Val Asp
            20                  25
```

<210> SEQ ID NO 16
<211> LENGTH: 29
<212> TYPE: PRT
<213> ORGANISM: Artificial
<220> FEATURE:
<223> OTHER INFORMATION: Engineered polypeptide

<400> SEQUENCE: 16

```
Glu Leu Ile Lys Ala Ala Ala Glu Ile Asp Gly Leu Pro Asn Leu Asn
1               5                   10                  15

Arg Lys Gln Trp Asn Ala Phe Ile Lys Ser Leu Val Asp
            20                  25
```

<210> SEQ ID NO 17
<211> LENGTH: 29
<212> TYPE: PRT
<213> ORGANISM: Artificial
<220> FEATURE:
<223> OTHER INFORMATION: Engineered polypeptide

<400> SEQUENCE: 17

```
Glu Leu Val Glu Ala Ala Arg Glu Ile Asp Ser Leu Pro Asn Leu Asn
1               5                   10                  15

Arg Arg Gln Trp Asn Ala Phe Ile Lys Ser Leu Val Asp
            20                  25
```

<210> SEQ ID NO 18
<211> LENGTH: 29
<212> TYPE: PRT
<213> ORGANISM: Artificial
<220> FEATURE:
<223> OTHER INFORMATION: Engineered polypeptide

<400> SEQUENCE: 18

```
Glu Leu Ile Lys Ala Ala Arg Glu Ile Asp Glu Leu Pro Asn Leu Asn
1               5                   10                  15

Arg Arg Gln Trp Asn Ala Phe Ile Lys Ser Leu Val Asp
            20                  25
```

<210> SEQ ID NO 19
<211> LENGTH: 29
<212> TYPE: PRT
<213> ORGANISM: Artificial
<220> FEATURE:
<223> OTHER INFORMATION: Engineered polypeptide

<400> SEQUENCE: 19

```
Glu Leu Leu Ala Ala Ala Ala Glu Ile Asp Ser Leu Pro Asn Leu Asn
1               5                   10                  15

Arg Ala Gln Trp Asn Ala Phe Ile Lys Ser Leu Val Asp
            20                  25
```

<210> SEQ ID NO 20
<211> LENGTH: 29
<212> TYPE: PRT
<213> ORGANISM: Artificial
<220> FEATURE:
<223> OTHER INFORMATION: Engineered polypeptide

<400> SEQUENCE: 20

```
Glu Leu Ile Asn Ala Ala Lys Glu Ile Asp Leu Pro Asn Leu Asn
1               5                  10                  15

Arg Arg Gln Trp Asn Ala Phe Ile Lys Ser Leu Val Asp
            20                  25
```

<210> SEQ ID NO 21
<211> LENGTH: 29
<212> TYPE: PRT
<213> ORGANISM: Artificial
<220> FEATURE:
<223> OTHER INFORMATION: Engineered polypeptide

<400> SEQUENCE: 21

```
Glu Leu Val Glu Ala Ala Arg Glu Ile Asp Ala Leu Pro Asn Leu Asn
1               5                  10                  15

Arg Lys Gln Trp Asn Ala Phe Ile Lys Ser Leu Val Asp
            20                  25
```

<210> SEQ ID NO 22
<211> LENGTH: 29
<212> TYPE: PRT
<213> ORGANISM: Artificial
<220> FEATURE:
<223> OTHER INFORMATION: Engineered polypeptide

<400> SEQUENCE: 22

```
Glu Leu Arg Asp Ala Ala Ala Glu Ile Asp Arg Leu Pro Asn Leu Asn
1               5                  10                  15

Arg Arg Gln Trp Asn Ala Phe Ile Lys Ser Leu Val Asp
            20                  25
```

<210> SEQ ID NO 23
<211> LENGTH: 29
<212> TYPE: PRT
<213> ORGANISM: Artificial
<220> FEATURE:
<223> OTHER INFORMATION: Engineered polypeptide

<400> SEQUENCE: 23

```
Glu Leu Ser Ala Ala Ala Arg Glu Ile Asp Asn Leu Pro Asn Leu Asn
1               5                  10                  15

Arg Arg Gln Trp Asn Ala Phe Ile Lys Ser Leu Val Asp
            20                  25
```

<210> SEQ ID NO 24
<211> LENGTH: 29
<212> TYPE: PRT
<213> ORGANISM: Artificial
<220> FEATURE:
<223> OTHER INFORMATION: Engineered polypeptide

<400> SEQUENCE: 24

```
Glu Leu Ile Ser Ala Ala Glu Glu Ile Asp Asp Leu Pro Asn Leu Asn
1               5                  10                  15

Arg Arg Gln Trp Asn Ala Phe Ile Lys Ser Leu Val Asp
            20                  25
```

<210> SEQ ID NO 25
<211> LENGTH: 29
<212> TYPE: PRT
<213> ORGANISM: Artificial
<220> FEATURE:
<223> OTHER INFORMATION: Engineered polypeptide

<400> SEQUENCE: 25

Glu Leu Val Asp Ala Ala Arg Glu Ile Asp Glu Leu Pro Asn Leu Asn
1               5                   10                  15

Arg Val Gln Trp Asn Ala Phe Ile Lys Ser Leu Val Asp
            20                  25

<210> SEQ ID NO 26
<211> LENGTH: 29
<212> TYPE: PRT
<213> ORGANISM: Artificial
<220> FEATURE:
<223> OTHER INFORMATION: Engineered polypeptide

<400> SEQUENCE: 26

Glu Leu Ile Glu Ala Ala Arg Glu Ile Asp Ala Leu Pro Asn Leu Asn
1               5                   10                  15

Arg Ser Gln Trp Asn Ala Phe Ile Lys Ser Leu Arg Asp
            20                  25

<210> SEQ ID NO 27
<211> LENGTH: 29
<212> TYPE: PRT
<213> ORGANISM: Artificial
<220> FEATURE:
<223> OTHER INFORMATION: Engineered polypeptide

<400> SEQUENCE: 27

Glu Leu Val Glu Ala Ala Lys Glu Ile Asp Lys Leu Pro Asn Leu Asn
1               5                   10                  15

Arg Arg Gln Trp Asn Ala Phe Ile Lys Ser Leu Val Asp
            20                  25

<210> SEQ ID NO 28
<211> LENGTH: 29
<212> TYPE: PRT
<213> ORGANISM: Artificial
<220> FEATURE:
<223> OTHER INFORMATION: Engineered polypeptide

<400> SEQUENCE: 28

Glu Leu Arg Gln Ala Ala Lys Glu Ile Asp Asn Leu Pro Asn Leu Asn
1               5                   10                  15

Arg Ala Gln Trp Asn Ala Phe Ile Lys Ser Leu Val Asp
            20                  25

<210> SEQ ID NO 29
<211> LENGTH: 29
<212> TYPE: PRT
<213> ORGANISM: Artificial
<220> FEATURE:
<223> OTHER INFORMATION: Engineered polypeptide

<400> SEQUENCE: 29

Glu Leu Val Ala Ala Ala Arg Glu Ile Asp Ser Leu Pro Asn Leu Asn
1               5                   10                  15

Arg Thr Gln Trp Asn Ala Phe Ile Lys Ser Leu Val Asp
            20                  25

<210> SEQ ID NO 30
<211> LENGTH: 29
<212> TYPE: PRT
<213> ORGANISM: Artificial
<220> FEATURE:
<223> OTHER INFORMATION: Engineered polypeptide

```
<400> SEQUENCE: 30

Glu Leu Arg Asn Ala Ala Lys Glu Ile Asp Ser Leu Pro Asn Leu Asn
1               5                   10                  15

Arg Arg Gln Trp Asn Ala Phe Ile Arg Ser Leu Val Asp
            20                  25

<210> SEQ ID NO 31
<211> LENGTH: 29
<212> TYPE: PRT
<213> ORGANISM: Artificial
<220> FEATURE:
<223> OTHER INFORMATION: Engineered polypeptide

<400> SEQUENCE: 31

Glu Leu Val Gln Ala Ala Arg Glu Ile Asp Glu Leu Pro Asn Leu Asn
1               5                   10                  15

Arg Thr Gln Trp Asn Ala Phe Ile Lys Ser Leu Val Asp
            20                  25

<210> SEQ ID NO 32
<211> LENGTH: 29
<212> TYPE: PRT
<213> ORGANISM: Artificial
<220> FEATURE:
<223> OTHER INFORMATION: Engineered polypeptide

<400> SEQUENCE: 32

Glu Leu Arg Glu Ala Ala Glu Glu Ile Asp Asn Leu Pro Asn Leu Asn
1               5                   10                  15

Arg Val Gln Trp Asn Ala Phe Ile Lys Ser Leu Val Asp
            20                  25

<210> SEQ ID NO 33
<211> LENGTH: 29
<212> TYPE: PRT
<213> ORGANISM: Artificial
<220> FEATURE:
<223> OTHER INFORMATION: Engineered polypeptide

<400> SEQUENCE: 33

Glu Leu Ile Glu Ala Ala Arg Glu Ile Asp Asn Leu Pro Asn Leu Asn
1               5                   10                  15

Arg Ala Gln Trp Asn Ala Phe Ile Lys Ser Leu Val Asp
            20                  25

<210> SEQ ID NO 34
<211> LENGTH: 29
<212> TYPE: PRT
<213> ORGANISM: Artificial
<220> FEATURE:
<223> OTHER INFORMATION: Engineered polypeptide

<400> SEQUENCE: 34

Glu Leu Ile Asn Ala Ala Arg Glu Ile Asp Gly Leu Pro Asn Leu Asn
1               5                   10                  15

Arg Met Gln Trp Asn Ala Phe Ile Arg Ser Leu Val Asp
            20                  25

<210> SEQ ID NO 35
<211> LENGTH: 29
<212> TYPE: PRT
<213> ORGANISM: Artificial
<220> FEATURE:
<223> OTHER INFORMATION: Engineered polypeptide
```

<400> SEQUENCE: 35

Glu Arg Ile Ala Ala Gln Glu Ile Asp Gly Leu Pro Asn Leu Asn
1               5                   10                  15

Arg Arg Gln Trp Asn Ala Phe Ile Lys Ser Leu Val Asp
            20                  25

<210> SEQ ID NO 36
<211> LENGTH: 29
<212> TYPE: PRT
<213> ORGANISM: Artificial
<220> FEATURE:
<223> OTHER INFORMATION: Engineered polypeptide

<400> SEQUENCE: 36

Glu Leu Ile Asn Ala Ala Lys Glu Ile Asp Asp Leu Pro Asn Leu Asn
1               5                   10                  15

Arg Arg Gln Trp Asn Ala Phe Ile Lys Ser Leu Val Asp
            20                  25

<210> SEQ ID NO 37
<211> LENGTH: 29
<212> TYPE: PRT
<213> ORGANISM: Artificial
<220> FEATURE:
<223> OTHER INFORMATION: Engineered polypeptide

<400> SEQUENCE: 37

Glu Arg Ser His Ala Ala Gln Glu Ile Asp Ala Leu Pro Asn Leu Asn
1               5                   10                  15

Arg Val Gln Trp Asn Ala Phe Ile Lys Ser Leu Val Asp
            20                  25

<210> SEQ ID NO 38
<211> LENGTH: 29
<212> TYPE: PRT
<213> ORGANISM: Artificial
<220> FEATURE:
<223> OTHER INFORMATION: Engineered polypeptide

<400> SEQUENCE: 38

Glu Leu Ile Ala Ala Ala Lys Glu Ile Asp Glu Leu Pro Asn Leu Asn
1               5                   10                  15

Arg Arg Gln Trp Asn Ala Phe Ile Lys Ser Leu Val Asp
            20                  25

<210> SEQ ID NO 39
<211> LENGTH: 29
<212> TYPE: PRT
<213> ORGANISM: Artificial
<220> FEATURE:
<223> OTHER INFORMATION: Engineered polypeptide

<400> SEQUENCE: 39

Glu Arg Ile Arg Ala Ala Glu Glu Ile Asp Gly Leu Pro Asn Leu Asn
1               5                   10                  15

Arg Trp Gln Trp Asn Ala Phe Ile Lys Ser Leu Val Asp
            20                  25

<210> SEQ ID NO 40
<211> LENGTH: 29
<212> TYPE: PRT
<213> ORGANISM: Artificial
<220> FEATURE:

```
<223> OTHER INFORMATION: Engineered polypeptide

<400> SEQUENCE: 40

Glu Leu Val Gln Ala Ala Arg Glu Ile Asp Ala Leu Pro Asn Leu Asn
1               5                   10                  15
Arg Gln Gln Trp Asn Ala Phe Ile Lys Ser Leu Val Asp
            20                  25

<210> SEQ ID NO 41
<211> LENGTH: 29
<212> TYPE: PRT
<213> ORGANISM: Artificial
<220> FEATURE:
<223> OTHER INFORMATION: Engineered polypeptide

<400> SEQUENCE: 41

Glu Arg Arg Glu Ala Ala Arg Glu Ile Asp Asn Leu Pro Asn Leu Asn
1               5                   10                  15
Arg Arg Gln Trp Asn Ala Phe Ile Lys Ser Leu Val Asp
            20                  25

<210> SEQ ID NO 42
<211> LENGTH: 29
<212> TYPE: PRT
<213> ORGANISM: Artificial
<220> FEATURE:
<223> OTHER INFORMATION: Engineered polypeptide

<400> SEQUENCE: 42

Glu Leu Arg Trp Ala Ala Gly Glu Ile Asp Lys Leu Pro Asn Leu Asn
1               5                   10                  15
Arg Lys Gln Trp Asn Ala Phe Ile Lys Ser Leu Val Asp
            20                  25

<210> SEQ ID NO 43
<211> LENGTH: 29
<212> TYPE: PRT
<213> ORGANISM: Artificial
<220> FEATURE:
<223> OTHER INFORMATION: Engineered polypeptide

<400> SEQUENCE: 43

Glu Leu Ser Arg Ala Ala Glu Glu Ile Asp Arg Leu Pro Asn Leu Asn
1               5                   10                  15
Arg Val Gln Trp Asn Ala Phe Ile Lys Ser Leu Val Asp
            20                  25

<210> SEQ ID NO 44
<211> LENGTH: 29
<212> TYPE: PRT
<213> ORGANISM: Artificial
<220> FEATURE:
<223> OTHER INFORMATION: Engineered polypeptide

<400> SEQUENCE: 44

Glu Leu Ile Glu Ala Ala Arg Glu Ile Asp Glu Leu Pro Asn Leu Asn
1               5                   10                  15
Arg Arg Gln Trp Asn Ala Phe Ile Lys Ser Leu Val Asp
            20                  25

<210> SEQ ID NO 45
<211> LENGTH: 29
<212> TYPE: PRT
<213> ORGANISM: Artificial
```

```
<220> FEATURE:
<223> OTHER INFORMATION: Engineered polypeptide

<400> SEQUENCE: 45

Glu Leu Ile Ala Ala Ala Lys Glu Ile Asp Asp Leu Pro Asn Leu Asn
1               5                   10                  15

Arg Glu Gln Trp Asn Ala Phe Ile Lys Ser Leu Val Asp
            20                  25

<210> SEQ ID NO 46
<211> LENGTH: 29
<212> TYPE: PRT
<213> ORGANISM: Artificial
<220> FEATURE:
<223> OTHER INFORMATION: Engineered polypeptide

<400> SEQUENCE: 46

Glu Arg Val Arg Ala Ala Glu Glu Ile Asp Ser Leu Pro Asn Leu Asn
1               5                   10                  15

Arg Gln Gln Trp Asn Ala Phe Ile Lys Ser Leu Val Asp
            20                  25

<210> SEQ ID NO 47
<211> LENGTH: 29
<212> TYPE: PRT
<213> ORGANISM: Artificial
<220> FEATURE:
<223> OTHER INFORMATION: Engineered polypeptide

<400> SEQUENCE: 47

Glu Leu Ile Asp Ala Ala Ala Glu Ile Asp Lys Leu Pro Asn Leu Asn
1               5                   10                  15

Arg Gly Gln Trp Asn Ala Phe Ile Lys Ser Leu Val Asp
            20                  25

<210> SEQ ID NO 48
<211> LENGTH: 29
<212> TYPE: PRT
<213> ORGANISM: Artificial
<220> FEATURE:
<223> OTHER INFORMATION: Engineered polypeptide

<400> SEQUENCE: 48

Glu Leu Ile Asp Ala Ala Ala Glu Ile Asp Lys Leu Pro Asn Leu Asn
1               5                   10                  15

Arg Ser Gln Trp Asn Ala Phe Ile Lys Ser Leu Val Asp
            20                  25

<210> SEQ ID NO 49
<211> LENGTH: 29
<212> TYPE: PRT
<213> ORGANISM: Artificial
<220> FEATURE:
<223> OTHER INFORMATION: Engineered polypeptide

<400> SEQUENCE: 49

Glu Leu Ile Glu Ala Ala Glu Glu Ile Asp Arg Leu Pro Asn Leu Asn
1               5                   10                  15

Arg Gln Gln Trp Asn Ala Phe Ile Lys Ser Leu Val Asp
            20                  25

<210> SEQ ID NO 50
<211> LENGTH: 29
<212> TYPE: PRT
```

```
<213> ORGANISM: Artificial
<220> FEATURE:
<223> OTHER INFORMATION: Engineered polypeptide

<400> SEQUENCE: 50

Glu Leu Ile Glu Ala Ala Arg Glu Ile Asp Glu Leu Pro Asn Leu Asn
1               5                   10                  15

Arg Lys Gln Trp Asn Ala Phe Ile Lys Ser Leu Val Asp
            20                  25

<210> SEQ ID NO 51
<211> LENGTH: 29
<212> TYPE: PRT
<213> ORGANISM: Artificial
<220> FEATURE:
<223> OTHER INFORMATION: Engineered polypeptide

<400> SEQUENCE: 51

Glu Leu Arg Glu Ala Ala Glu Glu Ile Asp Ser Leu Pro Asn Leu Asn
1               5                   10                  15

Arg Lys Gln Trp Asn Ala Phe Ile Lys Ser Leu Val Asp
            20                  25

<210> SEQ ID NO 52
<211> LENGTH: 29
<212> TYPE: PRT
<213> ORGANISM: Artificial
<220> FEATURE:
<223> OTHER INFORMATION: Engineered polypeptide

<400> SEQUENCE: 52

Glu Leu Val Asp Ala Ala Arg Glu Ile Asp Asp Leu Pro Asn Leu Asn
1               5                   10                  15

Arg Gly Gln Trp Asn Ala Phe Ile Lys Ser Leu Val Asp
            20                  25

<210> SEQ ID NO 53
<211> LENGTH: 29
<212> TYPE: PRT
<213> ORGANISM: Artificial
<220> FEATURE:
<223> OTHER INFORMATION: Engineered polypeptide

<400> SEQUENCE: 53

Glu Leu Arg Glu Ala Ala Ala Glu Ile Asp Ala Leu Pro Asn Leu Asn
1               5                   10                  15

Arg Lys Gln Trp Asn Ala Phe Ile Lys Ser Leu Val Asp
            20                  25

<210> SEQ ID NO 54
<211> LENGTH: 29
<212> TYPE: PRT
<213> ORGANISM: Artificial
<220> FEATURE:
<223> OTHER INFORMATION: Engineered polypeptide

<400> SEQUENCE: 54

Glu Leu Ile Glu Ala Ala Ala Glu Ile Asp Lys Leu Pro Asn Leu Asn
1               5                   10                  15

Arg Ala Gln Trp Asn Ala Phe Ile Lys Ser Leu Val Asp
            20                  25

<210> SEQ ID NO 55
<211> LENGTH: 29
```

```
<212> TYPE: PRT
<213> ORGANISM: Artificial
<220> FEATURE:
<223> OTHER INFORMATION: Engineered polypeptide

<400> SEQUENCE: 55

Glu Leu Arg Glu Ala Ala Gly Glu Ile Asp Arg Leu Pro Asn Leu Asn
1               5                   10                  15

Arg Arg Gln Trp Asn Ala Phe Ile Lys Ser Leu Val Asp
            20                  25

<210> SEQ ID NO 56
<211> LENGTH: 29
<212> TYPE: PRT
<213> ORGANISM: Artificial
<220> FEATURE:
<223> OTHER INFORMATION: Engineered polypeptide

<400> SEQUENCE: 56

Glu Leu Val Arg Ala Ala Glu Glu Ile Asp Ala Leu Pro Asn Leu Asn
1               5                   10                  15

Arg Lys Gln Trp Asn Ala Phe Ile Lys Ser Leu Val Asp
            20                  25

<210> SEQ ID NO 57
<211> LENGTH: 29
<212> TYPE: PRT
<213> ORGANISM: Artificial
<220> FEATURE:
<223> OTHER INFORMATION: Engineered polypeptide

<400> SEQUENCE: 57

Glu Arg Ser Arg Ala Ala Ala Glu Ile Asp Ala Leu Pro Asn Leu Asn
1               5                   10                  15

Arg Arg Gln Trp Asn Ala Phe Ile Lys Ser Leu Val Asp
            20                  25

<210> SEQ ID NO 58
<211> LENGTH: 29
<212> TYPE: PRT
<213> ORGANISM: Artificial
<220> FEATURE:
<223> OTHER INFORMATION: Engineered polypeptide

<400> SEQUENCE: 58

Glu Leu Ile Arg Ala Ala Ser Glu Ile Asp Lys Leu Pro Asn Leu Asn
1               5                   10                  15

Arg Arg Gln Trp Asn Ala Phe Ile Lys Ser Leu Arg Asp
            20                  25

<210> SEQ ID NO 59
<211> LENGTH: 29
<212> TYPE: PRT
<213> ORGANISM: Artificial
<220> FEATURE:
<223> OTHER INFORMATION: Engineered polypeptide

<400> SEQUENCE: 59

Glu Leu Ile Lys Ala Ala Gln Glu Ile Asp Arg Leu Pro Asn Leu Asn
1               5                   10                  15

Arg Thr Gln Trp Asn Ala Phe Ile Arg Ser Leu Val Asp
            20                  25

<210> SEQ ID NO 60
```

```
<211> LENGTH: 29
<212> TYPE: PRT
<213> ORGANISM: Artificial
<220> FEATURE:
<223> OTHER INFORMATION: Engineered polypeptide

<400> SEQUENCE: 60

Glu Leu Ile Glu Ala Ala Ala Glu Ile Asp Ala Leu Pro Asn Leu Asn
1               5                   10                  15

Arg Arg Gln Trp Asn Ala Phe Ile Lys Ser Leu Val Asp
            20                  25

<210> SEQ ID NO 61
<211> LENGTH: 29
<212> TYPE: PRT
<213> ORGANISM: Artificial
<220> FEATURE:
<223> OTHER INFORMATION: Engineered polypeptide

<400> SEQUENCE: 61

Glu Leu Ile Trp Ala Ala Gly Glu Ile Asp Lys Leu Pro Asn Leu Asn
1               5                   10                  15

Arg Arg Gln Trp Asn Ala Phe Ile Lys Ser Leu Val Asp
            20                  25

<210> SEQ ID NO 62
<211> LENGTH: 29
<212> TYPE: PRT
<213> ORGANISM: Artificial
<220> FEATURE:
<223> OTHER INFORMATION: Engineered polypeptide

<400> SEQUENCE: 62

Glu Arg Leu Ala Ala Ala Glu Glu Ile Asp Asn Leu Pro Asn Leu Asn
1               5                   10                  15

Arg Arg Gln Trp Asn Ala Phe Ile Lys Ser Leu Val Asp
            20                  25

<210> SEQ ID NO 63
<211> LENGTH: 29
<212> TYPE: PRT
<213> ORGANISM: Artificial
<220> FEATURE:
<223> OTHER INFORMATION: Engineered polypeptide

<400> SEQUENCE: 63

Glu Leu Arg Lys Ala Ala Glu Glu Ile Asp Ala Leu Pro Asn Leu Asn
1               5                   10                  15

Arg Lys Gln Trp Asn Ala Phe Ile Lys Ser Leu Val Asp
            20                  25

<210> SEQ ID NO 64
<211> LENGTH: 29
<212> TYPE: PRT
<213> ORGANISM: Artificial
<220> FEATURE:
<223> OTHER INFORMATION: Engineered polypeptide

<400> SEQUENCE: 64

Glu Leu Ile Ala Ala Ala Arg Glu Ile Asp Ser Leu Pro Asn Leu Asn
1               5                   10                  15

Arg Arg Gln Trp Asn Ala Phe Ile Lys Ser Leu Val Asp
            20                  25
```

```
<210> SEQ ID NO 65
<211> LENGTH: 29
<212> TYPE: PRT
<213> ORGANISM: Artificial
<220> FEATURE:
<223> OTHER INFORMATION: Engineered polypeptide

<400> SEQUENCE: 65

Glu Arg Val Lys Ala Ala Glu Glu Ile Asp Lys Leu Pro Asn Leu Asn
1               5                   10                  15

Arg Arg Gln Trp Asn Ala Phe Ile Lys Ser Leu Val Asp
            20                  25

<210> SEQ ID NO 66
<211> LENGTH: 29
<212> TYPE: PRT
<213> ORGANISM: Artificial
<220> FEATURE:
<223> OTHER INFORMATION: Engineered polypeptide

<400> SEQUENCE: 66

Glu Leu Ile His Ala Ala Glu Glu Ile Asp Arg Leu Pro Asn Leu Asn
1               5                   10                  15

Arg Asn Gln Trp Asn Ala Phe Ile Lys Ser Leu Val Asp
            20                  25

<210> SEQ ID NO 67
<211> LENGTH: 29
<212> TYPE: PRT
<213> ORGANISM: Artificial
<220> FEATURE:
<223> OTHER INFORMATION: Engineered polypeptide

<400> SEQUENCE: 67

Glu Leu Ile Asn Ala Ala Gly Glu Ile Asp Lys Leu Pro Asn Leu Asn
1               5                   10                  15

Arg Lys Gln Trp Asn Ala Phe Ile Lys Ser Leu Val Asp
            20                  25

<210> SEQ ID NO 68
<211> LENGTH: 29
<212> TYPE: PRT
<213> ORGANISM: Artificial
<220> FEATURE:
<223> OTHER INFORMATION: Engineered polypeptide

<400> SEQUENCE: 68

Glu Leu Ile Glu Ala Ala Ala Glu Ile Asp Ala Leu Pro Asn Leu Asn
1               5                   10                  15

Arg Ala Gln Trp Asn Ala Phe Ile Lys Ser Leu Val Asp
            20                  25

<210> SEQ ID NO 69
<211> LENGTH: 29
<212> TYPE: PRT
<213> ORGANISM: Artificial
<220> FEATURE:
<223> OTHER INFORMATION: Engineered polypeptide

<400> SEQUENCE: 69

Glu Leu Ile Ala Ala Ala Arg Glu Ile Asp Ser Leu Pro Asn Leu Asn
1               5                   10                  15

Arg Arg Gln Trp Asn Ala Phe Ile Lys Ser Leu Val Asp
            20                  25
```

<210> SEQ ID NO 70
<211> LENGTH: 29
<212> TYPE: PRT
<213> ORGANISM: Artificial
<220> FEATURE:
<223> OTHER INFORMATION: Engineered polypeptide

<400> SEQUENCE: 70

Glu Arg Val Asp Ala Ala Arg Glu Ile Asp Asn Leu Pro Asn Leu Asn
1               5                   10                  15

Arg Glu Gln Trp Asn Ala Phe Ile Arg Ser Leu Val Asp
            20                  25

<210> SEQ ID NO 71
<211> LENGTH: 29
<212> TYPE: PRT
<213> ORGANISM: Artificial
<220> FEATURE:
<223> OTHER INFORMATION: Engineered polypeptide

<400> SEQUENCE: 71

Glu Leu Arg Asp Ala Ala Ala Glu Ile Asp Arg Leu Pro Asn Leu Asn
1               5                   10                  15

Arg Lys Gln Trp Asn Ala Phe Ile Lys Ser Leu Val Asp
            20                  25

<210> SEQ ID NO 72
<211> LENGTH: 29
<212> TYPE: PRT
<213> ORGANISM: Artificial
<220> FEATURE:
<223> OTHER INFORMATION: Engineered polypeptide

<400> SEQUENCE: 72

Glu Leu Ile Ala Ala Ala Ala Glu Ile Asp Arg Leu Pro Asn Leu Asn
1               5                   10                  15

Arg Val Gln Trp Asn Ala Phe Ile Lys Ser Leu Val Asp
            20                  25

<210> SEQ ID NO 73
<211> LENGTH: 29
<212> TYPE: PRT
<213> ORGANISM: Artificial
<220> FEATURE:
<223> OTHER INFORMATION: Engineered polypeptide

<400> SEQUENCE: 73

Glu Leu Arg Ala Ala Ala Glu Glu Ile Asp Lys Leu Pro Asn Leu Asn
1               5                   10                  15

Arg Arg Gln Trp Asn Ala Phe Ile Lys Ser Leu Ile Asp
            20                  25

<210> SEQ ID NO 74
<211> LENGTH: 29
<212> TYPE: PRT
<213> ORGANISM: Artificial
<220> FEATURE:
<223> OTHER INFORMATION: Engineered polypeptide

<400> SEQUENCE: 74

Glu Leu Ile Trp Ala Ala Ala Glu Ile Asp Arg Leu Pro Asn Leu Asn
1               5                   10                  15

Arg Glu Gln Trp Asn Ala Phe Ile Arg Ser Leu Val Asp
            20                  25

```
<210> SEQ ID NO 75
<211> LENGTH: 29
<212> TYPE: PRT
<213> ORGANISM: Artificial
<220> FEATURE:
<223> OTHER INFORMATION: Engineered polypeptide

<400> SEQUENCE: 75

Glu Leu Arg Ala Ala Lys Glu Ile Asp Asn Leu Pro Asn Leu Asn
1               5                   10                  15

Arg Arg Gln Trp Asn Ala Phe Ile Lys Ser Leu Val Asp
            20                  25

<210> SEQ ID NO 76
<211> LENGTH: 29
<212> TYPE: PRT
<213> ORGANISM: Artificial
<220> FEATURE:
<223> OTHER INFORMATION: Engineered polypeptide

<400> SEQUENCE: 76

Glu Leu Val Gln Ala Ala Lys Glu Ile Asp Asn Leu Pro Asn Leu Asn
1               5                   10                  15

Arg Ser Gln Trp Asn Ala Phe Ile Arg Ser Leu Val Asp
            20                  25

<210> SEQ ID NO 77
<211> LENGTH: 29
<212> TYPE: PRT
<213> ORGANISM: Artificial
<220> FEATURE:
<223> OTHER INFORMATION: Engineered polypeptide

<400> SEQUENCE: 77

Glu Leu Ile Glu Ala Ala Gly Glu Ile Asp Ala Leu Pro Asn Leu Asn
1               5                   10                  15

Arg Arg Gln Trp Asn Ala Phe Ile Lys Ser Leu Val Asp
            20                  25

<210> SEQ ID NO 78
<211> LENGTH: 29
<212> TYPE: PRT
<213> ORGANISM: Artificial
<220> FEATURE:
<223> OTHER INFORMATION: Engineered polypeptide

<400> SEQUENCE: 78

Glu Leu Val Lys Ala Ala Ala Glu Ile Asp Ala Leu Pro Asn Leu Asn
1               5                   10                  15

Arg Arg Gln Trp Asn Ala Phe Ile Lys Ser Leu Val Asp
            20                  25

<210> SEQ ID NO 79
<211> LENGTH: 29
<212> TYPE: PRT
<213> ORGANISM: Artificial
<220> FEATURE:
<223> OTHER INFORMATION: Engineered polypeptide

<400> SEQUENCE: 79

Glu Leu Arg Glu Ala Ala Arg Glu Ile Asp Ser Leu Pro Asn Leu Asn
1               5                   10                  15

Arg Ser Gln Trp Asn Ala Phe Ile Lys Ser Leu Val Asp
```

20                  25

<210> SEQ ID NO 80
<211> LENGTH: 29
<212> TYPE: PRT
<213> ORGANISM: Artificial
<220> FEATURE:
<223> OTHER INFORMATION: Engineered polypeptide

<400> SEQUENCE: 80

Glu Leu Leu Glu Ala Ala Lys Glu Ile Asp Glu Leu Pro Asn Leu Asn
1               5                   10                  15

Arg Arg Gln Trp Asn Ala Phe Ile Lys Ser Leu Val Asp
            20                  25

<210> SEQ ID NO 81
<211> LENGTH: 29
<212> TYPE: PRT
<213> ORGANISM: Artificial
<220> FEATURE:
<223> OTHER INFORMATION: Engineered polypeptide

<400> SEQUENCE: 81

Glu Leu Val Glu Ala Ala Arg Glu Ile Asp Glu Leu Pro Asn Leu Asn
1               5                   10                  15

Arg Ser Gln Trp Asn Ala Phe Ile Lys Ser Leu Val Asp
            20                  25

<210> SEQ ID NO 82
<211> LENGTH: 29
<212> TYPE: PRT
<213> ORGANISM: Artificial
<220> FEATURE:
<223> OTHER INFORMATION: Engineered polypeptide

<400> SEQUENCE: 82

Glu Leu Arg Glu Ala Ala Ala Glu Ile Asp Ala Leu Pro Asn Leu Asn
1               5                   10                  15

Arg Ser Gln Trp Asn Ala Phe Ile Lys Ser Leu Val Asp
            20                  25

<210> SEQ ID NO 83
<211> LENGTH: 29
<212> TYPE: PRT
<213> ORGANISM: Artificial
<220> FEATURE:
<223> OTHER INFORMATION: Engineered polypeptide

<400> SEQUENCE: 83

Glu Leu Val Arg Ala Ala Glu Glu Ile Asp Arg Leu Pro Asn Leu Asn
1               5                   10                  15

Arg Ala Gln Trp Asn Ala Phe Ile Lys Ser Leu Val Asp
            20                  25

<210> SEQ ID NO 84
<211> LENGTH: 29
<212> TYPE: PRT
<213> ORGANISM: Artificial
<220> FEATURE:
<223> OTHER INFORMATION: Engineered polypeptide

<400> SEQUENCE: 84

Glu Leu Arg Ala Ala Ala Ala Glu Ile Asp Ser Leu Pro Asn Leu Asn
1               5                   10                  15

Arg Gly Gln Trp Asn Ala Phe Ile Lys Ser Leu Val Asp
            20                  25

<210> SEQ ID NO 85
<211> LENGTH: 29
<212> TYPE: PRT
<213> ORGANISM: Artificial
<220> FEATURE:
<223> OTHER INFORMATION: Engineered polypeptide

<400> SEQUENCE: 85

Glu Leu Ile Arg Ala Ala Arg Glu Ile Asp Glu Leu Pro Asn Leu Asn
1               5                   10                  15

Arg Met Gln Trp Asn Ala Phe Ile Lys Ser Leu Val Asp
            20                  25

<210> SEQ ID NO 86
<211> LENGTH: 29
<212> TYPE: PRT
<213> ORGANISM: Artificial
<220> FEATURE:
<223> OTHER INFORMATION: Engineered polypeptide

<400> SEQUENCE: 86

Glu Leu Arg Asp Ala Ala Arg Glu Ile Asp Ser Leu Pro Asn Leu Asn
1               5                   10                  15

Arg Arg Gln Trp Asn Ala Phe Ile Arg Ser Leu Val Asp
            20                  25

<210> SEQ ID NO 87
<211> LENGTH: 29
<212> TYPE: PRT
<213> ORGANISM: Artificial
<220> FEATURE:
<223> OTHER INFORMATION: Engineered polypeptide

<400> SEQUENCE: 87

Glu Leu Arg Glu Ala Ala Arg Glu Ile Asp Glu Leu Pro Asn Leu Asn
1               5                   10                  15

Arg Arg Gln Trp Asn Ala Phe Ile Lys Ser Leu Val Asp
            20                  25

<210> SEQ ID NO 88
<211> LENGTH: 29
<212> TYPE: PRT
<213> ORGANISM: Artificial
<220> FEATURE:
<223> OTHER INFORMATION: Engineered polypeptide

<400> SEQUENCE: 88

Glu Leu Ile Arg Ala Ala Glu Glu Ile Asp Lys Leu Pro Asn Leu Asn
1               5                   10                  15

Arg Lys Gln Trp Asn Ala Phe Ile Lys Ser Leu Val Asp
            20                  25

<210> SEQ ID NO 89
<211> LENGTH: 29
<212> TYPE: PRT
<213> ORGANISM: Artificial
<220> FEATURE:
<223> OTHER INFORMATION: Engineered polypeptide

<400> SEQUENCE: 89

Glu Leu Leu Lys Ala Ala Arg Glu Ile Asp Glu Leu Pro Asn Leu Asn
1               5                   10                  15

Arg Arg Gln Trp Asn Ala Phe Ile Arg Ser Leu Val Asp
            20                  25

<210> SEQ ID NO 90
<211> LENGTH: 29
<212> TYPE: PRT
<213> ORGANISM: Artificial
<220> FEATURE:
<223> OTHER INFORMATION: Engineered polypeptide

<400> SEQUENCE: 90

Glu Leu Ile Ala Ala Ala Arg Glu Ile Asp Gly Leu Pro Asn Leu Asn
1               5                   10                  15

Arg Lys Gln Trp Asn Ala Phe Ile Lys Ser Leu Val Asp
            20                  25

<210> SEQ ID NO 91
<211> LENGTH: 29
<212> TYPE: PRT
<213> ORGANISM: Artificial
<220> FEATURE:
<223> OTHER INFORMATION: Engineered polypeptide

<400> SEQUENCE: 91

Glu Leu Val Ala Ala Ala Ala Glu Ile Asp Gly Leu Pro Asn Leu Asn
1               5                   10                  15

Arg Lys Gln Trp Asn Ala Phe Ile His Ser Leu Val Asp
            20                  25

<210> SEQ ID NO 92
<211> LENGTH: 29
<212> TYPE: PRT
<213> ORGANISM: Artificial
<220> FEATURE:
<223> OTHER INFORMATION: Engineered polypeptide

<400> SEQUENCE: 92

Glu Leu Arg Asp Ala Ala Arg Glu Ile Asp Ala Leu Pro Asn Leu Asn
1               5                   10                  15

Arg Ala Gln Trp Asn Ala Phe Ile Lys Ser Leu Val Asp
            20                  25

<210> SEQ ID NO 93
<211> LENGTH: 29
<212> TYPE: PRT
<213> ORGANISM: Artificial
<220> FEATURE:
<223> OTHER INFORMATION: Engineered polypeptide

<400> SEQUENCE: 93

Glu Arg Ile Asn Ala Ala Lys Glu Ile Asp Ser Leu Pro Asn Leu Asn
1               5                   10                  15

Arg Arg Gln Trp Asn Ala Phe Ile Lys Ser Leu Val Asp
            20                  25

<210> SEQ ID NO 94
<211> LENGTH: 29
<212> TYPE: PRT
<213> ORGANISM: Artificial
<220> FEATURE:
<223> OTHER INFORMATION: Engineered polypeptide

<400> SEQUENCE: 94

Glu Leu Arg Gln Ala Ala Ala Glu Ile Asp Ala Leu Pro Asn Leu Asn

```
                1               5                   10                  15
Arg Gln Gln Trp Asn Ala Phe Ile Lys Ser Leu Val Asp
            20                  25

<210> SEQ ID NO 95
<211> LENGTH: 29
<212> TYPE: PRT
<213> ORGANISM: Artificial
<220> FEATURE:
<223> OTHER INFORMATION: Engineered polypeptide

<400> SEQUENCE: 95

Glu Leu Val Glu Ala Ala Ala Glu Ile Asp Arg Leu Pro Asn Leu Asn
1               5                   10                  15

Arg Gly Gln Trp Asn Ala Phe Ile Lys Ser Leu Val Asp
            20                  25

<210> SEQ ID NO 96
<211> LENGTH: 29
<212> TYPE: PRT
<213> ORGANISM: Artificial
<220> FEATURE:
<223> OTHER INFORMATION: Engineered polypeptide

<400> SEQUENCE: 96

Glu Leu Arg Glu Ala Ala Ala Glu Ile Asp Arg Leu Pro Asn Leu Asn
1               5                   10                  15

Arg Lys Gln Trp Asn Ala Phe Ile Lys Ser Leu Val Asp
            20                  25

<210> SEQ ID NO 97
<211> LENGTH: 29
<212> TYPE: PRT
<213> ORGANISM: Artificial
<220> FEATURE:
<223> OTHER INFORMATION: Engineered polypeptide

<400> SEQUENCE: 97

Glu Leu Ile Gln Ala Ala Lys Glu Ile Asp Ser Leu Pro Asn Leu Asn
1               5                   10                  15

Arg Arg Gln Trp Asn Ala Phe Ile Lys Ser Leu Val Asp
            20                  25

<210> SEQ ID NO 98
<211> LENGTH: 29
<212> TYPE: PRT
<213> ORGANISM: Artificial
<220> FEATURE:
<223> OTHER INFORMATION: Engineered polypeptide

<400> SEQUENCE: 98

Glu Arg Ser Met Ala Ala Lys Glu Ile Asp Ser Leu Pro Asn Leu Asn
1               5                   10                  15

Arg Arg Gln Trp Asn Ala Phe Ile Lys Ser Leu Val Asp
            20                  25

<210> SEQ ID NO 99
<211> LENGTH: 29
<212> TYPE: PRT
<213> ORGANISM: Artificial
<220> FEATURE:
<223> OTHER INFORMATION: Engineered polypeptide

<400> SEQUENCE: 99
```

```
Glu Leu Val Ala Ala Arg Glu Ile Asp Asp Leu Pro Asn Leu Asn
1               5                   10                  15

Arg Lys Gln Trp Asn Ala Phe Ile Arg Ser Leu Val Asp
            20                  25
```

<210> SEQ ID NO 100
<211> LENGTH: 29
<212> TYPE: PRT
<213> ORGANISM: Artificial
<220> FEATURE:
<223> OTHER INFORMATION: Engineered polypeptide

<400> SEQUENCE: 100

```
Glu Leu Val Arg Ala Ala Glu Glu Ile Asp Arg Leu Pro Asn Leu Asn
1               5                   10                  15

Arg Leu Gln Trp Asn Ala Phe Ile Lys Ser Leu Ile Asp
            20                  25
```

<210> SEQ ID NO 101
<211> LENGTH: 29
<212> TYPE: PRT
<213> ORGANISM: Artificial
<220> FEATURE:
<223> OTHER INFORMATION: Engineered polypeptide

<400> SEQUENCE: 101

```
Glu Leu Arg Glu Ala Ala Ala Glu Ile Asp Asp Leu Pro Asn Leu Asn
1               5                   10                  15

Arg Ala Gln Trp Asn Ala Phe Ile Lys Ser Leu Val Asp
            20                  25
```

<210> SEQ ID NO 102
<211> LENGTH: 29
<212> TYPE: PRT
<213> ORGANISM: Artificial
<220> FEATURE:
<223> OTHER INFORMATION: Engineered polypeptide

<400> SEQUENCE: 102

```
Glu Leu Val Glu Ala Ala Lys Glu Ile Asp Ser Leu Pro Asn Leu Asn
1               5                   10                  15

Arg Arg Gln Trp Asn Ala Phe Ile Lys Ser Leu Val Asp
            20                  25
```

<210> SEQ ID NO 103
<211> LENGTH: 29
<212> TYPE: PRT
<213> ORGANISM: Artificial
<220> FEATURE:
<223> OTHER INFORMATION: Engineered polypeptide

<400> SEQUENCE: 103

```
Glu Leu Ile Asn Ala Ala Gly Glu Ile Asp Arg Leu Pro Asn Leu Asn
1               5                   10                  15

Arg Arg Gln Trp Asn Ala Phe Ile Lys Ser Leu Val Asp
            20                  25
```

<210> SEQ ID NO 104
<211> LENGTH: 29
<212> TYPE: PRT
<213> ORGANISM: Artificial
<220> FEATURE:
<223> OTHER INFORMATION: Engineered polypeptide

<400> SEQUENCE: 104

```
Glu Leu Ser Ala Ala Ala Glu Ile Asp Ser Leu Pro Asn Leu Asn
1               5                   10                  15

Arg Lys Gln Trp Asn Ala Phe Ile Lys Ser Leu Val Asp
            20                  25
```

<210> SEQ ID NO 105
<211> LENGTH: 29
<212> TYPE: PRT
<213> ORGANISM: Artificial
<220> FEATURE:
<223> OTHER INFORMATION: Engineered polypeptide

<400> SEQUENCE: 105

```
Glu Leu Arg Asp Ala Ala Ala Glu Ile Asp Lys Leu Pro Asn Leu Asn
1               5                   10                  15

Arg Arg Gln Trp Asn Ala Phe Ile Lys Ser Leu Val Asp
            20                  25
```

<210> SEQ ID NO 106
<211> LENGTH: 29
<212> TYPE: PRT
<213> ORGANISM: Artificial
<220> FEATURE:
<223> OTHER INFORMATION: Engineered polypeptide

<400> SEQUENCE: 106

```
Glu Leu Arg Gln Ala Ala Ala Glu Ile Asp Lys Leu Pro Asn Leu Asn
1               5                   10                  15

Arg Ser Gln Trp Asn Ala Phe Ile Gln Ser Leu Val Asp
            20                  25
```

<210> SEQ ID NO 107
<211> LENGTH: 29
<212> TYPE: PRT
<213> ORGANISM: Artificial
<220> FEATURE:
<223> OTHER INFORMATION: Engineered polypeptide

<400> SEQUENCE: 107

```
Glu Leu Arg Glu Ala Ala Ala Glu Ile Asp Ala Leu Pro Asn Leu Asn
1               5                   10                  15

Arg Val Gln Trp Asn Ala Phe Ile Lys Ser Leu Arg Asp
            20                  25
```

<210> SEQ ID NO 108
<211> LENGTH: 29
<212> TYPE: PRT
<213> ORGANISM: Artificial
<220> FEATURE:
<223> OTHER INFORMATION: Engineered polypeptide

<400> SEQUENCE: 108

```
Glu Leu Val Ala Ala Ala Glu Glu Ile Asp Arg Leu Pro Asn Leu Asn
1               5                   10                  15

Arg Ala Gln Trp Asn Ala Phe Ile Lys Ser Leu Val Asp
            20                  25
```

<210> SEQ ID NO 109
<211> LENGTH: 29
<212> TYPE: PRT
<213> ORGANISM: Artificial
<220> FEATURE:
<223> OTHER INFORMATION: Engineered polypeptide

```
<400> SEQUENCE: 109

Glu Leu Ile Asp Ala Ala Ala Glu Ile Asp Lys Leu Pro Asn Leu Asn
1               5                   10                  15

Arg Asn Gln Trp Asn Ala Phe Ile Lys Ser Leu Val Asp
            20                  25

<210> SEQ ID NO 110
<211> LENGTH: 29
<212> TYPE: PRT
<213> ORGANISM: Artificial
<220> FEATURE:
<223> OTHER INFORMATION: Engineered polypeptide

<400> SEQUENCE: 110

Glu Arg Ile Asn Ala Ala Ala Glu Ile Asp Gly Leu Pro Asn Leu Asn
1               5                   10                  15

Arg Gln Gln Trp Asn Ala Phe Ile Lys Ser Leu Val Asp
            20                  25

<210> SEQ ID NO 111
<211> LENGTH: 29
<212> TYPE: PRT
<213> ORGANISM: Artificial
<220> FEATURE:
<223> OTHER INFORMATION: Engineered polypeptide

<400> SEQUENCE: 111

Glu Leu Val Arg Ala Ala Glu Glu Ile Asp Asn Leu Pro Asn Leu Asn
1               5                   10                  15

Arg Lys Gln Trp Asn Ala Phe Ile Lys Ser Leu Val Asp
            20                  25

<210> SEQ ID NO 112
<211> LENGTH: 29
<212> TYPE: PRT
<213> ORGANISM: Artificial
<220> FEATURE:
<223> OTHER INFORMATION: Engineered polypeptide

<400> SEQUENCE: 112

Glu Leu Ile Arg Ala Ala Lys Glu Ile Asp Glu Leu Pro Asn Leu Asn
1               5                   10                  15

Arg Arg Gln Trp Asn Ala Phe Ile Arg Ser Leu Val Asp
            20                  25

<210> SEQ ID NO 113
<211> LENGTH: 29
<212> TYPE: PRT
<213> ORGANISM: Artificial
<220> FEATURE:
<223> OTHER INFORMATION: Engineered polypeptide

<400> SEQUENCE: 113

Glu Leu Ile Gln Ala Ala Arg Glu Ile Asp Ser Leu Pro Asn Leu Asn
1               5                   10                  15

Arg Arg Gln Trp Asn Ala Phe Ile Lys Ser Leu Val Asp
            20                  25

<210> SEQ ID NO 114
<211> LENGTH: 29
<212> TYPE: PRT
<213> ORGANISM: Artificial
<220> FEATURE:
<223> OTHER INFORMATION: Engineered polypeptide
```

<400> SEQUENCE: 114

Glu Leu Ile Asp Ala Ala Arg Glu Ile Asp Asp Leu Pro Asn Leu Asn
1               5                   10                  15

Arg Gln Gln Trp Asn Ala Phe Ile Lys Ser Leu Leu Asp
            20                  25

<210> SEQ ID NO 115
<211> LENGTH: 29
<212> TYPE: PRT
<213> ORGANISM: Artificial
<220> FEATURE:
<223> OTHER INFORMATION: Engineered polypeptide

<400> SEQUENCE: 115

Glu Leu Leu Lys Ala Ala Asp Glu Ile Asp Ala Leu Pro Asn Leu Asn
1               5                   10                  15

Arg Ala Gln Trp Asn Ala Phe Ile Lys Ser Leu Val Asp
            20                  25

<210> SEQ ID NO 116
<211> LENGTH: 29
<212> TYPE: PRT
<213> ORGANISM: Artificial
<220> FEATURE:
<223> OTHER INFORMATION: Engineered polypeptide

<400> SEQUENCE: 116

Glu Leu Leu Glu Ala Ala Ala Glu Ile Asp Ser Leu Pro Asn Leu Asn
1               5                   10                  15

Arg Arg Gln Trp Asn Ala Phe Ile Lys Ser Leu Val Asp
            20                  25

<210> SEQ ID NO 117
<211> LENGTH: 29
<212> TYPE: PRT
<213> ORGANISM: Artificial
<220> FEATURE:
<223> OTHER INFORMATION: Engineered polypeptide

<400> SEQUENCE: 117

Glu Leu Val Asp Ala Ala Arg Glu Ile Asp Thr Leu Pro Asn Leu Asn
1               5                   10                  15

Arg Arg Gln Trp Asn Ala Phe Ile Lys Ser Leu Val Asp
            20                  25

<210> SEQ ID NO 118
<211> LENGTH: 29
<212> TYPE: PRT
<213> ORGANISM: Artificial
<220> FEATURE:
<223> OTHER INFORMATION: Engineered polypeptide

<400> SEQUENCE: 118

Glu Leu Ile Glu Ala Ala Arg Glu Ile Asp Lys Leu Pro Asn Leu Asn
1               5                   10                  15

Arg Arg Gln Trp Asn Ala Phe Ile Arg Ser Leu Val Asp
            20                  25

<210> SEQ ID NO 119
<211> LENGTH: 29
<212> TYPE: PRT
<213> ORGANISM: Artificial
<220> FEATURE:

<223> OTHER INFORMATION: Engineered polypeptide

<400> SEQUENCE: 119

Glu Leu Val Ala Ala Arg Glu Ile Asp Asn Leu Pro Asn Leu Asn
1               5                   10                  15

Arg Arg Gln Trp Asn Ala Phe Ile Lys Ser Leu Val Asp
            20                  25

<210> SEQ ID NO 120
<211> LENGTH: 29
<212> TYPE: PRT
<213> ORGANISM: Artificial
<220> FEATURE:
<223> OTHER INFORMATION: Engineered polypeptide

<400> SEQUENCE: 120

Glu Leu Val Glu Ala Ala Glu Ile Asp Gly Leu Pro Asn Leu Asn
1               5                   10                  15

Arg Asp Gln Trp Asn Ala Phe Ile Lys Ser Leu Arg Asp
            20                  25

<210> SEQ ID NO 121
<211> LENGTH: 29
<212> TYPE: PRT
<213> ORGANISM: Artificial
<220> FEATURE:
<223> OTHER INFORMATION: Engineered polypeptide

<400> SEQUENCE: 121

Glu Leu Arg Asn Ala Ala Lys Glu Ile Asp Gly Leu Pro Asn Leu Asn
1               5                   10                  15

Arg Arg Gln Trp Asn Ala Phe Ile Lys Ser Leu Val Asp
            20                  25

<210> SEQ ID NO 122
<211> LENGTH: 29
<212> TYPE: PRT
<213> ORGANISM: Artificial
<220> FEATURE:
<223> OTHER INFORMATION: Engineered polypeptide

<400> SEQUENCE: 122

Glu Leu Arg His Ala Ala Arg Glu Ile Asp Gly Leu Pro Asn Leu Asn
1               5                   10                  15

Arg Thr Gln Trp Asn Ala Phe Ile Lys Ser Leu Val Asp
            20                  25

<210> SEQ ID NO 123
<211> LENGTH: 29
<212> TYPE: PRT
<213> ORGANISM: Artificial
<220> FEATURE:
<223> OTHER INFORMATION: Engineered polypeptide

<400> SEQUENCE: 123

Glu Leu Val Glu Ala Ala Arg Glu Ile Asp Thr Leu Pro Asn Leu Asn
1               5                   10                  15

Arg Arg Gln Trp Asn Ala Phe Ile Lys Ser Leu Arg Asp
            20                  25

<210> SEQ ID NO 124
<211> LENGTH: 29
<212> TYPE: PRT
<213> ORGANISM: Artificial

```
<220> FEATURE:
<223> OTHER INFORMATION: Engineered polypeptide

<400> SEQUENCE: 124

Glu Leu Val Ala Ala Ala Glu Ile Asp Ala Leu Pro Asn Leu Asn
1               5                   10                  15

Arg Arg Gln Trp Asn Ala Phe Ile Lys Ser Leu Val Asp
                20                  25

<210> SEQ ID NO 125
<211> LENGTH: 29
<212> TYPE: PRT
<213> ORGANISM: Artificial
<220> FEATURE:
<223> OTHER INFORMATION: Engineered polypeptide

<400> SEQUENCE: 125

Glu Leu Arg Thr Ala Ala Lys Glu Ile Asp Asp Leu Pro Asn Leu Asn
1               5                   10                  15

Arg Lys Gln Trp Asn Ala Phe Ile Lys Ser Leu Val Asp
                20                  25

<210> SEQ ID NO 126
<211> LENGTH: 29
<212> TYPE: PRT
<213> ORGANISM: Artificial
<220> FEATURE:
<223> OTHER INFORMATION: Engineered polypeptide

<400> SEQUENCE: 126

Glu Leu Leu Arg Ala Ala Arg Glu Ile Asp Ser Leu Pro Asn Leu Asn
1               5                   10                  15

Arg Thr Gln Trp Asn Ala Phe Ile Lys Ser Leu Val Asp
                20                  25

<210> SEQ ID NO 127
<211> LENGTH: 29
<212> TYPE: PRT
<213> ORGANISM: Artificial
<220> FEATURE:
<223> OTHER INFORMATION: Engineered polypeptide

<400> SEQUENCE: 127

Glu Arg Ile Arg Ala Ala Arg Glu Ile Asp Ala Leu Pro Asn Leu Asn
1               5                   10                  15

Arg Gln Gln Trp Asn Ala Phe Ile Lys Ser Leu Val Asp
                20                  25

<210> SEQ ID NO 128
<211> LENGTH: 29
<212> TYPE: PRT
<213> ORGANISM: Artificial
<220> FEATURE:
<223> OTHER INFORMATION: Engineered polypeptide

<400> SEQUENCE: 128

Glu Leu Arg Ala Ala Ala Glu Glu Ile Asp Arg Leu Pro Asn Leu Asn
1               5                   10                  15

Arg Arg Gln Trp Asn Ala Phe Ile Lys Ser Leu Val Asp
                20                  25

<210> SEQ ID NO 129
<211> LENGTH: 29
<212> TYPE: PRT
```

```
<213> ORGANISM: Artificial
<220> FEATURE:
<223> OTHER INFORMATION: Engineered polypeptide

<400> SEQUENCE: 129

Glu Leu Ile Glu Ala Ala Ala Glu Ile Asp Ala Leu Pro Asn Leu Asn
1               5                   10                  15

Arg Lys Gln Trp Asn Ala Phe Ile Ser Ser Leu Val Asp
            20                  25

<210> SEQ ID NO 130
<211> LENGTH: 29
<212> TYPE: PRT
<213> ORGANISM: Artificial
<220> FEATURE:
<223> OTHER INFORMATION: Engineered polypeptide

<400> SEQUENCE: 130

Glu Arg Ile Glu Ala Ala Arg Glu Ile Asp Glu Leu Pro Asn Leu Asn
1               5                   10                  15

Arg Lys Gln Trp Asn Ala Phe Ile Ser Ser Leu Val Asp
            20                  25

<210> SEQ ID NO 131
<211> LENGTH: 29
<212> TYPE: PRT
<213> ORGANISM: Artificial
<220> FEATURE:
<223> OTHER INFORMATION: Engineered polypeptide

<400> SEQUENCE: 131

Glu Leu Leu Ala Ala Ala Lys Glu Ile Asp Glu Leu Pro Asn Leu Asn
1               5                   10                  15

Arg Ala Gln Trp Asn Ala Phe Ile Lys Ser Leu Val Asp
            20                  25

<210> SEQ ID NO 132
<211> LENGTH: 29
<212> TYPE: PRT
<213> ORGANISM: Artificial
<220> FEATURE:
<223> OTHER INFORMATION: Engineered polypeptide

<400> SEQUENCE: 132

Glu Leu Ile Asn Ala Ala Arg Glu Ile Asp Glu Leu Pro Asn Leu Asn
1               5                   10                  15

Arg Arg Gln Trp Asn Ala Phe Ile Lys Ser Leu Val Asp
            20                  25

<210> SEQ ID NO 133
<211> LENGTH: 29
<212> TYPE: PRT
<213> ORGANISM: Artificial
<220> FEATURE:
<223> OTHER INFORMATION: Engineered polypeptide

<400> SEQUENCE: 133

Glu Leu Val Lys Ala Ala Ala Glu Ile Asp Ala Leu Pro Asn Leu Asn
1               5                   10                  15

Arg Arg Gln Trp Asn Ala Phe Ile Lys Ser Leu Val Asp
            20                  25

<210> SEQ ID NO 134
<211> LENGTH: 29
```

<212> TYPE: PRT
<213> ORGANISM: Artificial
<220> FEATURE:
<223> OTHER INFORMATION: Engineered polypeptide

<400> SEQUENCE: 134

Glu Leu Ile Ala Ala Ala Lys Glu Ile Asp Glu Leu Pro Asn Leu Asn
1               5                   10                  15

Arg Arg Gln Trp Asn Ala Phe Ile Lys Ser Leu Val Asp
            20                  25

<210> SEQ ID NO 135
<211> LENGTH: 29
<212> TYPE: PRT
<213> ORGANISM: Artificial
<220> FEATURE:
<223> OTHER INFORMATION: Engineered polypeptide

<400> SEQUENCE: 135

Glu Leu Ile Ser Ala Ala Arg Glu Ile Asp Lys Leu Pro Asn Leu Asn
1               5                   10                  15

Arg Gln Gln Trp Asn Ala Phe Ile Lys Ser Leu Val Asp
            20                  25

<210> SEQ ID NO 136
<211> LENGTH: 29
<212> TYPE: PRT
<213> ORGANISM: Artificial
<220> FEATURE:
<223> OTHER INFORMATION: Engineered polypeptide

<400> SEQUENCE: 136

Glu Leu Arg Glu Ala Ala Glu Glu Ile Asp Lys Leu Pro Asn Leu Asn
1               5                   10                  15

Arg Trp Gln Trp Asn Ala Phe Ile Lys Ser Leu Val Asp
            20                  25

<210> SEQ ID NO 137
<211> LENGTH: 29
<212> TYPE: PRT
<213> ORGANISM: Artificial
<220> FEATURE:
<223> OTHER INFORMATION: Engineered polypeptide

<400> SEQUENCE: 137

Glu Leu Val Glu Ala Ala Arg Glu Ile Asp Gly Leu Pro Asn Leu Asn
1               5                   10                  15

Arg Ala Gln Trp Asn Ala Phe Ile Lys Ser Leu Val Asp
            20                  25

<210> SEQ ID NO 138
<211> LENGTH: 29
<212> TYPE: PRT
<213> ORGANISM: Artificial
<220> FEATURE:
<223> OTHER INFORMATION: Engineered polypeptide

<400> SEQUENCE: 138

Glu Leu Val Ala Ala Ala Gln Glu Ile Asp Asn Leu Pro Asn Leu Asn
1               5                   10                  15

Arg Lys Gln Trp Asn Ala Phe Ile Ser Ser Leu Val Asp
            20                  25

<210> SEQ ID NO 139

```
<211> LENGTH: 29
<212> TYPE: PRT
<213> ORGANISM: Artificial
<220> FEATURE:
<223> OTHER INFORMATION: Engineered polypeptide

<400> SEQUENCE: 139

Glu Leu Arg Asn Ala Ala Ala Glu Ile Asp Lys Leu Pro Asn Leu Asn
1               5                   10                  15

Arg Arg Gln Trp Asn Ala Phe Ile Lys Ser Leu Val Asp
            20                  25

<210> SEQ ID NO 140
<211> LENGTH: 29
<212> TYPE: PRT
<213> ORGANISM: Artificial
<220> FEATURE:
<223> OTHER INFORMATION: Engineered polypeptide

<400> SEQUENCE: 140

Glu Leu Ile Gln Ala Ala Ser Glu Ile Asp Ala Leu Pro Asn Leu Asn
1               5                   10                  15

Arg Thr Gln Trp Asn Ala Phe Ile Lys Ser Leu Val Asp
            20                  25

<210> SEQ ID NO 141
<211> LENGTH: 29
<212> TYPE: PRT
<213> ORGANISM: Artificial
<220> FEATURE:
<223> OTHER INFORMATION: Engineered polypeptide

<400> SEQUENCE: 141

Glu Leu Val Glu Ala Ala Ala Glu Ile Asp Ser Leu Pro Asn Leu Asn
1               5                   10                  15

Arg Arg Gln Trp Asn Ala Phe Ile Lys Ser Leu Val Asp
            20                  25

<210> SEQ ID NO 142
<211> LENGTH: 29
<212> TYPE: PRT
<213> ORGANISM: Artificial
<220> FEATURE:
<223> OTHER INFORMATION: Engineered polypeptide

<400> SEQUENCE: 142

Glu Arg Ile Ala Ala Ala Gln Glu Ile Asp Ala Leu Pro Asn Leu Asn
1               5                   10                  15

Arg Arg Gln Trp Asn Ala Phe Ile Arg Ser Leu Val Asp
            20                  25

<210> SEQ ID NO 143
<211> LENGTH: 29
<212> TYPE: PRT
<213> ORGANISM: Artificial
<220> FEATURE:
<223> OTHER INFORMATION: Engineered polypeptide

<400> SEQUENCE: 143

Glu Leu Arg Asp Ala Ala Lys Glu Ile Asp Ser Leu Pro Asn Leu Asn
1               5                   10                  15

Arg Arg Gln Trp Asn Ala Phe Ile Lys Ser Leu Val Asp
            20                  25
```

-continued

```
<210> SEQ ID NO 144
<211> LENGTH: 29
<212> TYPE: PRT
<213> ORGANISM: Artificial
<220> FEATURE:
<223> OTHER INFORMATION: Engineered polypeptide

<400> SEQUENCE: 144

Glu Leu Val Ala Ala Lys Glu Ile Asp Lys Leu Pro Asn Leu Asn
1               5                   10                  15

Arg Lys Gln Trp Asn Ala Phe Ile Lys Ser Leu Val Asp
            20                  25

<210> SEQ ID NO 145
<211> LENGTH: 29
<212> TYPE: PRT
<213> ORGANISM: Artificial
<220> FEATURE:
<223> OTHER INFORMATION: Engineered polypeptide

<400> SEQUENCE: 145

Glu Leu Ile Lys Ala Ala Arg Glu Ile Asp Glu Leu Pro Asn Leu Asn
1               5                   10                  15

Arg Lys Gln Trp Asn Ala Phe Ile Lys Ser Leu Ile Asp
            20                  25

<210> SEQ ID NO 146
<211> LENGTH: 29
<212> TYPE: PRT
<213> ORGANISM: Artificial
<220> FEATURE:
<223> OTHER INFORMATION: Engineered polypeptide

<400> SEQUENCE: 146

Glu Leu Val Glu Ala Ala Ser Glu Ile Asp Gly Leu Pro Asn Leu Asn
1               5                   10                  15

Arg Asn Gln Trp Asn Ala Phe Ile Lys Ser Leu Val Asp
            20                  25

<210> SEQ ID NO 147
<211> LENGTH: 29
<212> TYPE: PRT
<213> ORGANISM: Artificial
<220> FEATURE:
<223> OTHER INFORMATION: Engineered polypeptide

<400> SEQUENCE: 147

Glu Leu Leu Arg Ala Ala Glu Glu Ile Asp Asn Leu Pro Asn Leu Asn
1               5                   10                  15

Arg Ala Gln Trp Asn Ala Phe Ile Lys Ser Leu Val Asp
            20                  25

<210> SEQ ID NO 148
<211> LENGTH: 29
<212> TYPE: PRT
<213> ORGANISM: Artificial
<220> FEATURE:
<223> OTHER INFORMATION: Engineered polypeptide

<400> SEQUENCE: 148

Glu Leu Ile Lys Ala Ala Lys Glu Ile Asp Ala Leu Pro Asn Leu Asn
1               5                   10                  15

Arg Arg Gln Trp Asn Ala Phe Ile Lys Ser Leu Val Asp
            20                  25
```

<210> SEQ ID NO 149
<211> LENGTH: 29
<212> TYPE: PRT
<213> ORGANISM: Artificial
<220> FEATURE:
<223> OTHER INFORMATION: Engineered polypeptide

<400> SEQUENCE: 149

Glu Leu Arg Arg Ala Ala Ala Glu Ile Asp Ser Leu Pro Asn Leu Asn
1               5                   10                  15

Arg Asp Gln Trp Asn Ala Phe Ile Arg Ser Leu Ile Asp
            20                  25

<210> SEQ ID NO 150
<211> LENGTH: 29
<212> TYPE: PRT
<213> ORGANISM: Artificial
<220> FEATURE:
<223> OTHER INFORMATION: Engineered polypeptide

<400> SEQUENCE: 150

Glu Leu Val Glu Ala Ala Arg Glu Ile Asp Gly Leu Pro Asn Leu Asn
1               5                   10                  15

Arg Ala Gln Trp Asn Ala Phe Ile Lys Ser Leu Val Asp
            20                  25

<210> SEQ ID NO 151
<211> LENGTH: 29
<212> TYPE: PRT
<213> ORGANISM: Artificial
<220> FEATURE:
<223> OTHER INFORMATION: Engineered polypeptide

<400> SEQUENCE: 151

Glu Leu Val Glu Ala Ala Arg Glu Ile Asp Glu Leu Pro Asn Leu Asn
1               5                   10                  15

Arg Arg Gln Trp Asn Ala Phe Ile Arg Ser Leu Val Asp
            20                  25

<210> SEQ ID NO 152
<211> LENGTH: 29
<212> TYPE: PRT
<213> ORGANISM: Artificial
<220> FEATURE:
<223> OTHER INFORMATION: Engineered polypeptide

<400> SEQUENCE: 152

Glu Leu Val Trp Ala Ala Ala Glu Ile Asp Arg Leu Pro Asn Leu Asn
1               5                   10                  15

Arg Cys Gln Trp Asn Ala Phe Ile Lys Ser Leu Val Asp
            20                  25

<210> SEQ ID NO 153
<211> LENGTH: 29
<212> TYPE: PRT
<213> ORGANISM: Artificial
<220> FEATURE:
<223> OTHER INFORMATION: Engineered polypeptide

<400> SEQUENCE: 153

Glu Arg Ile Arg Ala Ala Arg Glu Ile Asp Glu Leu Pro Asn Leu Asn
1               5                   10                  15

Arg Glu Gln Trp Asn Ala Phe Ile Lys Ser Leu Val Asp
            20                  25

<210> SEQ ID NO 154
<211> LENGTH: 29
<212> TYPE: PRT
<213> ORGANISM: Artificial
<220> FEATURE:
<223> OTHER INFORMATION: Engineered polypeptide

<400> SEQUENCE: 154

Glu Leu Arg Gln Ala Ala Lys Glu Ile Asp Ala Leu Pro Asn Leu Asn
1               5                   10                  15

Arg Arg Gln Trp Asn Ala Phe Ile Lys Ser Leu Val Asp
            20                  25

<210> SEQ ID NO 155
<211> LENGTH: 29
<212> TYPE: PRT
<213> ORGANISM: Artificial
<220> FEATURE:
<223> OTHER INFORMATION: Engineered polypeptide

<400> SEQUENCE: 155

Glu Leu Arg Glu Ala Ala Ala Glu Ile Asp Lys Leu Pro Asn Leu Asn
1               5                   10                  15

Arg Lys Gln Trp Asn Ala Phe Ile Arg Ser Leu Val Asp
            20                  25

<210> SEQ ID NO 156
<211> LENGTH: 29
<212> TYPE: PRT
<213> ORGANISM: Artificial
<220> FEATURE:
<223> OTHER INFORMATION: Engineered polypeptide

<400> SEQUENCE: 156

Glu Leu Arg Arg Ala Ala Glu Glu Ile Asp Lys Leu Pro Asn Leu Asn
1               5                   10                  15

Arg Gln Gln Trp Asn Ala Phe Ile Lys Ser Leu Val Asp
            20                  25

<210> SEQ ID NO 157
<211> LENGTH: 29
<212> TYPE: PRT
<213> ORGANISM: Artificial
<220> FEATURE:
<223> OTHER INFORMATION: Engineered polypeptide

<400> SEQUENCE: 157

Glu Leu Val Gln Ala Ala Arg Glu Ile Asp Ala Leu Pro Asn Leu Asn
1               5                   10                  15

Arg Gln Gln Trp Asn Ala Phe Ile Lys Ser Leu Val Asp
            20                  25

<210> SEQ ID NO 158
<211> LENGTH: 29
<212> TYPE: PRT
<213> ORGANISM: Artificial
<220> FEATURE:
<223> OTHER INFORMATION: Engineered polypeptide

<400> SEQUENCE: 158

Glu Leu Arg Ala Ala Ala Ala Glu Ile Asp Ala Leu Pro Asn Leu Asn
1               5                   10                  15

Arg Arg Gln Trp Asn Ala Phe Ile Lys Ser Leu Val Asp 20                  25

<210> SEQ ID NO 159
<211> LENGTH: 29
<212> TYPE: PRT
<213> ORGANISM: Artificial
<220> FEATURE:
<223> OTHER INFORMATION: Engineered polypeptide

<400> SEQUENCE: 159

Glu Leu Arg Ala Ala Ala Ala Glu Ile Asp Lys Leu Pro Asn Leu Asn
1               5                   10                  15

Arg Lys Gln Trp Asn Ala Phe Ile Lys Ser Leu Val Asp
                20                  25

<210> SEQ ID NO 160
<211> LENGTH: 29
<212> TYPE: PRT
<213> ORGANISM: Artificial
<220> FEATURE:
<223> OTHER INFORMATION: Engineered polypeptide

<400> SEQUENCE: 160

Glu Arg Ile Gln Ala Ala Lys Glu Ile Asp Glu Leu Pro Asn Leu Asn
1               5                   10                  15

Arg Glu Gln Trp Asn Ala Phe Ile Lys Ser Leu Val Asp
                20                  25

<210> SEQ ID NO 161
<211> LENGTH: 29
<212> TYPE: PRT
<213> ORGANISM: Artificial
<220> FEATURE:
<223> OTHER INFORMATION: Engineered polypeptide

<400> SEQUENCE: 161

Glu Leu Val Ala Ala Ala Glu Glu Ile Asp Lys Leu Pro Asn Leu Asn
1               5                   10                  15

Arg Arg Gln Trp Asn Ala Phe Ile Lys Ser Leu Val Asp
                20                  25

<210> SEQ ID NO 162
<211> LENGTH: 29
<212> TYPE: PRT
<213> ORGANISM: Artificial
<220> FEATURE:
<223> OTHER INFORMATION: Engineered polypeptide

<400> SEQUENCE: 162

Glu Leu Val Arg Ala Ala Glu Glu Ile Asp Asn Leu Pro Asn Leu Asn
1               5                   10                  15

Arg Lys Gln Trp Asn Ala Phe Ile Lys Ser Leu Val Asp
                20                  25

<210> SEQ ID NO 163
<211> LENGTH: 29
<212> TYPE: PRT
<213> ORGANISM: Artificial
<220> FEATURE:
<223> OTHER INFORMATION: Engineered polypeptide

<400> SEQUENCE: 163

Glu Leu Arg Thr Ala Ala Ala Glu Ile Asp Ala Leu Pro Asn Leu Asn
1               5                   10                  15

Arg Glu Gln Trp Asn Ala Phe Ile Arg Ser Leu Val Asp
            20                  25

<210> SEQ ID NO 164
<211> LENGTH: 29
<212> TYPE: PRT
<213> ORGANISM: Artificial
<220> FEATURE:
<223> OTHER INFORMATION: Engineered polypeptide

<400> SEQUENCE: 164

Glu Leu Val Glu Ala Ala Ala Glu Ile Asp Ala Leu Pro Asn Leu Asn
1               5                   10                  15

Arg Lys Gln Trp Asn Ala Phe Ile Lys Ser Leu Val Asp
            20                  25

<210> SEQ ID NO 165
<211> LENGTH: 29
<212> TYPE: PRT
<213> ORGANISM: Artificial
<220> FEATURE:
<223> OTHER INFORMATION: Engineered polypeptide

<400> SEQUENCE: 165

Glu Leu Ile Lys Ala Ala Glu Glu Ile Asp Lys Leu Pro Asn Leu Asn
1               5                   10                  15

Arg Met Gln Trp Asn Ala Phe Ile Arg Ser Leu Val Asp
            20                  25

<210> SEQ ID NO 166
<211> LENGTH: 29
<212> TYPE: PRT
<213> ORGANISM: Artificial
<220> FEATURE:
<223> OTHER INFORMATION: Engineered polypeptide

<400> SEQUENCE: 166

Glu Leu Arg Glu Ala Ala Ala Glu Ile Asp Asn Leu Pro Asn Leu Asn
1               5                   10                  15

Arg Arg Gln Trp Asn Ala Phe Ile Lys Ser Leu Ile Asp
            20                  25

<210> SEQ ID NO 167
<211> LENGTH: 29
<212> TYPE: PRT
<213> ORGANISM: Artificial
<220> FEATURE:
<223> OTHER INFORMATION: Engineered polypeptide

<400> SEQUENCE: 167

Glu Leu Ile Glu Ala Ala Arg Glu Ile Asp Ala Leu Pro Asn Leu Asn
1               5                   10                  15

Arg Lys Gln Trp Asn Ala Phe Ile Arg Ser Leu Val Asp
            20                  25

<210> SEQ ID NO 168
<211> LENGTH: 29
<212> TYPE: PRT
<213> ORGANISM: Artificial
<220> FEATURE:
<223> OTHER INFORMATION: Engineered polypeptide

<400> SEQUENCE: 168

Glu Leu Arg Glu Ala Ala Gln Glu Ile Asp Ser Leu Pro Asn Leu Asn
1               5                   10                  15

Arg Gln Gln Trp Asn Ala Phe Ile Lys Ser Leu Val Asp
            20                  25

<210> SEQ ID NO 169
<211> LENGTH: 29
<212> TYPE: PRT
<213> ORGANISM: Artificial
<220> FEATURE:
<223> OTHER INFORMATION: Engineered polypeptide

<400> SEQUENCE: 169

Glu Leu Arg Ser Ala Ala Glu Glu Ile Asp Ser Leu Pro Asn Leu Asn
1               5                   10                  15

Arg Arg Gln Trp Asn Ala Phe Ile Lys Ser Leu Val Asp
            20                  25

<210> SEQ ID NO 170
<211> LENGTH: 29
<212> TYPE: PRT
<213> ORGANISM: Artificial
<220> FEATURE:
<223> OTHER INFORMATION: Engineered polypeptide

<400> SEQUENCE: 170

Glu Leu Val Glu Ala Ala Ala Glu Ile Asp Asn Leu Pro Asn Leu Asn
1               5                   10                  15

Arg Met Gln Trp Asn Ala Phe Ile Lys Ser Leu Val Asp
            20                  25

<210> SEQ ID NO 171
<211> LENGTH: 29
<212> TYPE: PRT
<213> ORGANISM: Artificial
<220> FEATURE:
<223> OTHER INFORMATION: Engineered polypeptide

<400> SEQUENCE: 171

Glu Leu Val Glu Ala Ala Gly Glu Ile Asp Asn Leu Pro Asn Leu Asn
1               5                   10                  15

Arg Arg Gln Trp Asn Ala Phe Ile Arg Ser Leu Val Asp
            20                  25

<210> SEQ ID NO 172
<211> LENGTH: 29
<212> TYPE: PRT
<213> ORGANISM: Artificial
<220> FEATURE:
<223> OTHER INFORMATION: Engineered polypeptide

<400> SEQUENCE: 172

Glu Leu Ser Lys Ala Ala Ala Glu Ile Asp Ala Leu Pro Asn Leu Asn
1               5                   10                  15

Arg Arg Gln Trp Asn Ala Phe Ile Lys Ser Leu Val Asp
            20                  25

<210> SEQ ID NO 173
<211> LENGTH: 29
<212> TYPE: PRT
<213> ORGANISM: Artificial
<220> FEATURE:
<223> OTHER INFORMATION: Engineered polypeptide

<400> SEQUENCE: 173

Glu Leu Leu Trp Ala Ala Gly Glu Ile Asp Arg Leu Pro Asn Leu Asn

```
1               5                   10                  15
Arg Gln Gln Trp Asn Ala Phe Ile Lys Ser Leu Val Asp
            20                  25

<210> SEQ ID NO 174
<211> LENGTH: 29
<212> TYPE: PRT
<213> ORGANISM: Artificial
<220> FEATURE:
<223> OTHER INFORMATION: Engineered polypeptide

<400> SEQUENCE: 174

Glu Leu Arg Gln Ala Ala Ala Glu Ile Asp Gly Leu Pro Asn Leu Asn
1               5                   10                  15

Arg Arg Gln Trp Asn Ala Phe Ile Lys Ser Leu Val Asp
            20                  25

<210> SEQ ID NO 175
<211> LENGTH: 29
<212> TYPE: PRT
<213> ORGANISM: Artificial
<220> FEATURE:
<223> OTHER INFORMATION: Engineered polypeptide

<400> SEQUENCE: 175

Glu Leu Val Lys Ala Ala Ala Glu Ile Asp Ala Leu Pro Asn Leu Thr
1               5                   10                  15

Arg Arg Gln Trp Asn Ala Phe Ile Lys Ser Leu Val Asp
            20                  25

<210> SEQ ID NO 176
<211> LENGTH: 29
<212> TYPE: PRT
<213> ORGANISM: Artificial
<220> FEATURE:
<223> OTHER INFORMATION: Engineered polypeptide

<400> SEQUENCE: 176

Glu Leu Val Lys Ala Ala Ala Glu Ile Asp Ala Leu Pro Asn Leu Asn
1               5                   10                  15

Arg Arg Gln Trp Asn Ala Phe Ile Lys Lys Leu Val Asp
            20                  25

<210> SEQ ID NO 177
<211> LENGTH: 29
<212> TYPE: PRT
<213> ORGANISM: Artificial
<220> FEATURE:
<223> OTHER INFORMATION: Engineered polypeptide

<400> SEQUENCE: 177

Glu Leu Val Lys Ala Ala Ala Glu Ile Asp Ala Leu Pro Asn Leu Thr
1               5                   10                  15

Arg Arg Gln Trp Asn Ala Phe Ile Lys Lys Leu Val Asp
            20                  25

<210> SEQ ID NO 178
<211> LENGTH: 29
<212> TYPE: PRT
<213> ORGANISM: Artificial
<220> FEATURE:
<223> OTHER INFORMATION: Engineered polypeptide

<400> SEQUENCE: 178
```

Glu Leu Val Lys Ala Ala Ala Glu Ile Asp Ala Leu Pro Asn Leu Thr
1               5                   10                  15

Arg Arg Gln Trp Asn Ala Phe Ile Lys Lys Leu Val Lys
            20                  25

<210> SEQ ID NO 179
<211> LENGTH: 29
<212> TYPE: PRT
<213> ORGANISM: Artificial
<220> FEATURE:
<223> OTHER INFORMATION: Engineered polypeptide

<400> SEQUENCE: 179

Glu Leu Ile Glu Ala Ala Ala Glu Ile Asp Ala Leu Pro Asn Leu Thr
1               5                   10                  15

Arg Arg Gln Trp Asn Ala Phe Ile Lys Lys Leu Val Asp
            20                  25

<210> SEQ ID NO 180
<211> LENGTH: 49
<212> TYPE: PRT
<213> ORGANISM: Artificial
<220> FEATURE:
<223> OTHER INFORMATION: Engineered polypeptide

<400> SEQUENCE: 180

Lys Glu Arg Ala Glu Ala Ala Gln Glu Ile Asp Gln Leu Pro Asn Leu
1               5                   10                  15

Asn Arg Gly Gln Trp Asn Ala Phe Ile Ala Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 181
<211> LENGTH: 49
<212> TYPE: PRT
<213> ORGANISM: Artificial
<220> FEATURE:
<223> OTHER INFORMATION: Engineered polypeptide

<400> SEQUENCE: 181

Lys Glu Arg Gln Val Ala Ala Glu Ile Asp Ala Leu Pro Asn Leu
1               5                   10                  15

Asn Arg Gly Gln Trp Asn Ala Phe Ile Ala Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 182
<211> LENGTH: 49
<212> TYPE: PRT
<213> ORGANISM: Artificial
<220> FEATURE:
<223> OTHER INFORMATION: Engineered polypeptide

<400> SEQUENCE: 182

Lys Glu Leu Ser Asp Ala Ala Gln Glu Ile Asp Ser Leu Pro Asn Leu
1               5                   10                  15

Asn Arg Ser Gln Trp Asn Ala Phe Ile Lys Ser Leu Ile Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 183
<211> LENGTH: 49
<212> TYPE: PRT
<213> ORGANISM: Artificial
<220> FEATURE:
<223> OTHER INFORMATION: Engineered polypeptide

<400> SEQUENCE: 183

Lys Glu Arg Arg Glu Ala Ala Ala Glu Ile Asp Asn Leu Pro Asn Leu
1               5                   10                  15

Asn Arg Ser Gln Trp Asn Ala Phe Ile Gln Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 184
<211> LENGTH: 49
<212> TYPE: PRT
<213> ORGANISM: Artificial
<220> FEATURE:
<223> OTHER INFORMATION: Engineered polypeptide

<400> SEQUENCE: 184

Lys Glu Arg Arg Glu Ala Ala Lys Glu Ile Asp Ser Leu Pro Asn Leu
1               5                   10                  15

Asn Arg Thr Gln Trp Asn Ala Phe Ile Arg Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 185
<211> LENGTH: 49
<212> TYPE: PRT
<213> ORGANISM: Artificial
<220> FEATURE:
<223> OTHER INFORMATION: Engineered polypeptide

<400> SEQUENCE: 185

Lys Glu Leu Arg His Ala Ala Ser Glu Ile Asp Asp Leu Pro Asn Leu
1               5                   10                  15

Asn Arg Ala Gln Trp Asn Ala Phe Ile Arg Ser Leu Arg Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 186
<211> LENGTH: 49
<212> TYPE: PRT
<213> ORGANISM: Artificial
<220> FEATURE:
<223> OTHER INFORMATION: Engineered polypeptide

<400> SEQUENCE: 186

-continued

```
Lys Glu Leu Val Arg Ala Ala Gln Glu Ile Asp Glu Leu Pro Asn Leu
1               5                   10                  15
Asn Arg Gly Gln Trp Asn Ala Phe Ile Lys Ser Leu Val Asp Asp Pro
            20                  25                  30
Ser Gln Ser Ala Asn Leu Leu Ala Glu Ala Lys Lys Leu Asn Asp Ala
        35                  40                  45
Gln
```

```
<210> SEQ ID NO 187
<211> LENGTH: 49
<212> TYPE: PRT
<213> ORGANISM: Artificial
<220> FEATURE:
<223> OTHER INFORMATION: Engineered polypeptide

<400> SEQUENCE: 187

Lys Glu Ile Lys Gln Ala Ala Arg Glu Ile Asp Ala Leu Pro Asn Leu
1               5                   10                  15
Asn Lys Lys Gln Trp Asn Ala Phe Ile Gln Ser Leu Ala Asp Asp Pro
            20                  25                  30
Ser Gln Ser Ala Asn Leu Leu Ala Glu Ala Lys Lys Leu Asn Asp Ala
        35                  40                  45
Gln
```

```
<210> SEQ ID NO 188
<211> LENGTH: 49
<212> TYPE: PRT
<213> ORGANISM: Artificial
<220> FEATURE:
<223> OTHER INFORMATION: Engineered polypeptide

<400> SEQUENCE: 188

Lys Glu Arg His Arg Ala Ala Gln Glu Ile Asp Gln Leu Pro Asn Leu
1               5                   10                  15
Asn Arg Arg Gln Trp Asn Ala Phe Ile Lys Ser Leu Val Asp Asp Pro
            20                  25                  30
Ser Gln Ser Ala Asn Leu Leu Ala Glu Ala Lys Lys Leu Asn Asp Ala
        35                  40                  45
Gln
```

```
<210> SEQ ID NO 189
<211> LENGTH: 49
<212> TYPE: PRT
<213> ORGANISM: Artificial
<220> FEATURE:
<223> OTHER INFORMATION: Engineered polypeptide

<400> SEQUENCE: 189

Lys Glu Ile Lys Phe Ala Ala Gly Glu Ile Asp Asn Leu Pro Asn Leu
1               5                   10                  15
Asn Arg Lys Gln Trp Asn Ala Phe Ile Gly Ser Leu Arg Asp Asp Pro
            20                  25                  30
Ser Gln Ser Ala Asn Leu Leu Ala Glu Ala Lys Lys Leu Asn Asp Ala
        35                  40                  45
Gln
```

```
<210> SEQ ID NO 190
<211> LENGTH: 49
<212> TYPE: PRT
<213> ORGANISM: Artificial
```

```
<220> FEATURE:
<223> OTHER INFORMATION: Engineered polypeptide

<400> SEQUENCE: 190

Lys Glu Arg Leu Lys Ala Ala Glu Ile Asp Ala Leu Pro Asn Leu
1               5                   10                  15

Asn Arg Lys Gln Trp Asn Ala Phe Ile Ser Ser Leu Arg Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 191
<211> LENGTH: 49
<212> TYPE: PRT
<213> ORGANISM: Artificial
<220> FEATURE:
<223> OTHER INFORMATION: Engineered polypeptide

<400> SEQUENCE: 191

Lys Glu Leu Arg Ala Ala Ala Glu Ile Asp Ser Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 192
<211> LENGTH: 49
<212> TYPE: PRT
<213> ORGANISM: Artificial
<220> FEATURE:
<223> OTHER INFORMATION: Engineered polypeptide

<400> SEQUENCE: 192

Lys Glu Arg Leu Glu Ala Ala Glu Ile Asp Ser Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 193
<211> LENGTH: 49
<212> TYPE: PRT
<213> ORGANISM: Artificial
<220> FEATURE:
<223> OTHER INFORMATION: Engineered polypeptide

<400> SEQUENCE: 193

Lys Glu Leu Ile Lys Ala Ala Ala Glu Ile Asp Ala Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln
```

```
<210> SEQ ID NO 194
<211> LENGTH: 49
<212> TYPE: PRT
<213> ORGANISM: Artificial
<220> FEATURE:
<223> OTHER INFORMATION: Engineered polypeptide

<400> SEQUENCE: 194

Lys Glu Arg Ile His Ala Ala Arg Glu Ile Asp Ala Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 195
<211> LENGTH: 49
<212> TYPE: PRT
<213> ORGANISM: Artificial
<220> FEATURE:
<223> OTHER INFORMATION: Engineered polypeptide

<400> SEQUENCE: 195

Lys Glu Leu Ile Lys Ala Ala Ala Glu Ile Asp Gly Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 196
<211> LENGTH: 49
<212> TYPE: PRT
<213> ORGANISM: Artificial
<220> FEATURE:
<223> OTHER INFORMATION: Engineered polypeptide

<400> SEQUENCE: 196

Lys Glu Leu Val Glu Ala Ala Arg Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 197
<211> LENGTH: 49
<212> TYPE: PRT
<213> ORGANISM: Artificial
<220> FEATURE:
<223> OTHER INFORMATION: Engineered polypeptide

<400> SEQUENCE: 197

Lys Glu Leu Ile Lys Ala Ala Arg Glu Ile Asp Glu Leu Pro Asn Leu
1               5                   10                  15

Asn Arg Arg Gln Trp Asn Ala Phe Ile Lys Ser Leu Val Asp Asp Pro
            20                  25                  30
```

Ser Gln Ser Ala Asn Leu Leu Ala Glu Ala Lys Lys Leu Asn Asp Ala
        35                  40                  45

Gln

<210> SEQ ID NO 198
<211> LENGTH: 49
<212> TYPE: PRT
<213> ORGANISM: Artificial
<220> FEATURE:
<223> OTHER INFORMATION: Engineered polypeptide

<400> SEQUENCE: 198

Lys Glu Leu Leu Ala Ala Ala Glu Ile Asp Ser Leu Pro Asn Leu
1               5                   10                  15

Asn Arg Ala Gln Trp Asn Ala Phe Ile Lys Ser Leu Val Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 199
<211> LENGTH: 49
<212> TYPE: PRT
<213> ORGANISM: Artificial
<220> FEATURE:
<223> OTHER INFORMATION: Engineered polypeptide

<400> SEQUENCE: 199

Lys Glu Leu Ile Asn Ala Ala Lys Glu Ile Asp Asp Leu Pro Asn Leu
1               5                   10                  15

Asn Arg Arg Gln Trp Asn Ala Phe Ile Lys Ser Leu Val Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 200
<211> LENGTH: 49
<212> TYPE: PRT
<213> ORGANISM: Artificial
<220> FEATURE:
<223> OTHER INFORMATION: Engineered polypeptide

<400> SEQUENCE: 200

Lys Glu Leu Val Glu Ala Ala Arg Glu Ile Asp Ala Leu Pro Asn Leu
1               5                   10                  15

Asn Arg Lys Gln Trp Asn Ala Phe Ile Lys Ser Leu Val Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 201
<211> LENGTH: 49
<212> TYPE: PRT
<213> ORGANISM: Artificial
<220> FEATURE:
<223> OTHER INFORMATION: Engineered polypeptide

<400> SEQUENCE: 201

Lys Glu Leu Arg Asp Ala Ala Ala Glu Ile Asp Arg Leu Pro Asn Leu

```
                1               5                  10                  15
Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 202
<211> LENGTH: 49
<212> TYPE: PRT
<213> ORGANISM: Artificial
<220> FEATURE:
<223> OTHER INFORMATION: Engineered polypeptide

<400> SEQUENCE: 202

Lys Glu Leu Ser Ala Ala Ala Arg Glu Ile Asp Asn Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 203
<211> LENGTH: 49
<212> TYPE: PRT
<213> ORGANISM: Artificial
<220> FEATURE:
<223> OTHER INFORMATION: Engineered polypeptide

<400> SEQUENCE: 203

Lys Glu Leu Ile Ser Ala Ala Glu Glu Ile Asp Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 204
<211> LENGTH: 49
<212> TYPE: PRT
<213> ORGANISM: Artificial
<220> FEATURE:
<223> OTHER INFORMATION: Engineered polypeptide

<400> SEQUENCE: 204

Lys Glu Leu Val Asp Ala Ala Arg Glu Ile Asp Glu Leu Pro Asn Leu
1               5                   10                  15

Asn Arg Val Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 205
<211> LENGTH: 49
<212> TYPE: PRT
<213> ORGANISM: Artificial
<220> FEATURE:
```

<223> OTHER INFORMATION: Engineered polypeptide

<400> SEQUENCE: 205

Lys Glu Leu Ile Glu Ala Ala Arg Glu Ile Asp Ala Leu Pro Asn Leu
1               5                   10                  15

Asn Arg Ser Gln Trp Asn Ala Phe Ile Lys Ser Leu Arg Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 206
<211> LENGTH: 49
<212> TYPE: PRT
<213> ORGANISM: Artificial
<220> FEATURE:
<223> OTHER INFORMATION: Engineered polypeptide

<400> SEQUENCE: 206

Lys Glu Leu Val Glu Ala Ala Lys Glu Ile Asp Lys Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 207
<211> LENGTH: 49
<212> TYPE: PRT
<213> ORGANISM: Artificial
<220> FEATURE:
<223> OTHER INFORMATION: Engineered polypeptide

<400> SEQUENCE: 207

Lys Glu Leu Arg Gln Ala Ala Lys Glu Ile Asp Asn Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 208
<211> LENGTH: 49
<212> TYPE: PRT
<213> ORGANISM: Artificial
<220> FEATURE:
<223> OTHER INFORMATION: Engineered polypeptide

<400> SEQUENCE: 208

Lys Glu Leu Val Ala Ala Ala Arg Glu Ile Asp Ser Leu Pro Asn Leu
1               5                   10                  15

Asn Arg Thr Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 209
<211> LENGTH: 49
<212> TYPE: PRT
<213> ORGANISM: Artificial
<220> FEATURE:
<223> OTHER INFORMATION: Engineered polypeptide

<400> SEQUENCE: 209

Lys Glu Leu Arg Asn Ala Ala Lys Glu Ile Asp Ser Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 210
<211> LENGTH: 49
<212> TYPE: PRT
<213> ORGANISM: Artificial
<220> FEATURE:
<223> OTHER INFORMATION: Engineered polypeptide

<400> SEQUENCE: 210

Lys Glu Leu Val Gln Ala Ala Arg Glu Ile Asp Glu Leu Pro Asn Leu
1               5                   10                  15

Asn Arg Thr Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 211
<211> LENGTH: 49
<212> TYPE: PRT
<213> ORGANISM: Artificial
<220> FEATURE:
<223> OTHER INFORMATION: Engineered polypeptide

<400> SEQUENCE: 211

Lys Glu Leu Arg Glu Ala Ala Glu Glu Ile Asp Asn Leu Pro Asn Leu
1               5                   10                  15

Asn Arg Val Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 212
<211> LENGTH: 49
<212> TYPE: PRT
<213> ORGANISM: Artificial
<220> FEATURE:
<223> OTHER INFORMATION: Engineered polypeptide

<400> SEQUENCE: 212

Lys Glu Leu Ile Glu Ala Ala Arg Glu Ile Asp Asn Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
```

-continued

```
                35                  40                  45
Gln

<210> SEQ ID NO 213
<211> LENGTH: 49
<212> TYPE: PRT
<213> ORGANISM: Artificial
<220> FEATURE:
<223> OTHER INFORMATION: Engineered polypeptide

<400> SEQUENCE: 213

Lys Glu Leu Ile Asn Ala Ala Arg Glu Ile Asp Gly Leu Pro Asn Leu
1               5                   10                  15

Asn Arg Met Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 214
<211> LENGTH: 49
<212> TYPE: PRT
<213> ORGANISM: Artificial
<220> FEATURE:
<223> OTHER INFORMATION: Engineered polypeptide

<400> SEQUENCE: 214

Lys Glu Arg Ile Ala Ala Ala Gln Glu Ile Asp Gly Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 215
<211> LENGTH: 49
<212> TYPE: PRT
<213> ORGANISM: Artificial
<220> FEATURE:
<223> OTHER INFORMATION: Engineered polypeptide

<400> SEQUENCE: 215

Lys Glu Leu Ile Asn Ala Ala Lys Glu Ile Asp Asp Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 216
<211> LENGTH: 49
<212> TYPE: PRT
<213> ORGANISM: Artificial
<220> FEATURE:
<223> OTHER INFORMATION: Engineered polypeptide

<400> SEQUENCE: 216

Lys Glu Arg Ser His Ala Ala Gln Glu Ile Asp Ala Leu Pro Asn Leu
1               5                   10                  15
```

Asn Arg Val Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 217
<211> LENGTH: 49
<212> TYPE: PRT
<213> ORGANISM: Artificial
<220> FEATURE:
<223> OTHER INFORMATION: Engineered polypeptide

<400> SEQUENCE: 217

Lys Glu Leu Ile Ala Ala Lys Glu Ile Asp Glu Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 218
<211> LENGTH: 49
<212> TYPE: PRT
<213> ORGANISM: Artificial
<220> FEATURE:
<223> OTHER INFORMATION: Engineered polypeptide

<400> SEQUENCE: 218

Lys Glu Arg Ile Arg Ala Ala Glu Glu Ile Asp Gly Leu Pro Asn Leu
1               5                   10                  15

Asn Arg Trp Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 219
<211> LENGTH: 49
<212> TYPE: PRT
<213> ORGANISM: Artificial
<220> FEATURE:
<223> OTHER INFORMATION: Engineered polypeptide

<400> SEQUENCE: 219

Lys Glu Leu Val Gln Ala Ala Arg Glu Ile Asp Ala Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 220
<211> LENGTH: 49
<212> TYPE: PRT
<213> ORGANISM: Artificial
<220> FEATURE:
<223> OTHER INFORMATION: Engineered polypeptide -continued

<400> SEQUENCE: 220

Lys Glu Arg Arg Glu Ala Ala Arg Glu Ile Asp Asn Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 221
<211> LENGTH: 49
<212> TYPE: PRT
<213> ORGANISM: Artificial
<220> FEATURE:
<223> OTHER INFORMATION: Engineered polypeptide

<400> SEQUENCE: 221

Lys Glu Leu Arg Trp Ala Ala Gly Glu Ile Asp Lys Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 222
<211> LENGTH: 49
<212> TYPE: PRT
<213> ORGANISM: Artificial
<220> FEATURE:
<223> OTHER INFORMATION: Engineered polypeptide

<400> SEQUENCE: 222

Lys Glu Leu Ser Arg Ala Ala Glu Glu Ile Asp Arg Leu Pro Asn Leu
1               5                   10                  15

Asn Arg Val Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 223
<211> LENGTH: 49
<212> TYPE: PRT
<213> ORGANISM: Artificial
<220> FEATURE:
<223> OTHER INFORMATION: Engineered polypeptide

<400> SEQUENCE: 223

Lys Glu Leu Ile Glu Ala Ala Arg Glu Ile Asp Glu Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 224

```
<211> LENGTH: 49
<212> TYPE: PRT
<213> ORGANISM: Artificial
<220> FEATURE:
<223> OTHER INFORMATION: Engineered polypeptide

<400> SEQUENCE: 224

Lys Glu Leu Ile Ala Ala Ala Lys Glu Ile Asp Asp Leu Pro Asn Leu
1               5                   10                  15

Asn Arg Glu Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 225
<211> LENGTH: 49
<212> TYPE: PRT
<213> ORGANISM: Artificial
<220> FEATURE:
<223> OTHER INFORMATION: Engineered polypeptide

<400> SEQUENCE: 225

Lys Glu Arg Val Arg Ala Ala Glu Glu Ile Asp Ser Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 226
<211> LENGTH: 49
<212> TYPE: PRT
<213> ORGANISM: Artificial
<220> FEATURE:
<223> OTHER INFORMATION: Engineered polypeptide

<400> SEQUENCE: 226

Lys Glu Leu Ile Asp Ala Ala Ala Glu Ile Asp Lys Leu Pro Asn Leu
1               5                   10                  15

Asn Arg Gly Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 227
<211> LENGTH: 49
<212> TYPE: PRT
<213> ORGANISM: Artificial
<220> FEATURE:
<223> OTHER INFORMATION: Engineered polypeptide

<400> SEQUENCE: 227

Lys Glu Leu Ile Asp Ala Ala Ala Glu Ile Asp Lys Leu Pro Asn Leu
1               5                   10                  15

Asn Arg Ser Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45
```

Gln

```
<210> SEQ ID NO 228
<211> LENGTH: 49
<212> TYPE: PRT
<213> ORGANISM: Artificial
<220> FEATURE:
<223> OTHER INFORMATION: Engineered polypeptide

<400> SEQUENCE: 228
```

Lys Glu Leu Ile Glu Ala Ala Glu Glu Ile Asp Arg Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 229
<211> LENGTH: 49
<212> TYPE: PRT
<213> ORGANISM: Artificial
<220> FEATURE:
<223> OTHER INFORMATION: Engineered polypeptide

<400> SEQUENCE: 229
```

Lys Glu Leu Ile Glu Ala Ala Arg Glu Ile Asp Glu Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 230
<211> LENGTH: 49
<212> TYPE: PRT
<213> ORGANISM: Artificial
<220> FEATURE:
<223> OTHER INFORMATION: Engineered polypeptide

<400> SEQUENCE: 230
```

Lys Glu Leu Arg Glu Ala Ala Glu Glu Ile Asp Ser Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 231
<211> LENGTH: 49
<212> TYPE: PRT
<213> ORGANISM: Artificial
<220> FEATURE:
<223> OTHER INFORMATION: Engineered polypeptide

<400> SEQUENCE: 231
```

Lys Glu Leu Val Asp Ala Ala Arg Glu Ile Asp Asp Leu Pro Asn Leu
1               5                   10                  15

```
Asn Arg Gly Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 232
<211> LENGTH: 49
<212> TYPE: PRT
<213> ORGANISM: Artificial
<220> FEATURE:
<223> OTHER INFORMATION: Engineered polypeptide

<400> SEQUENCE: 232

Lys Glu Leu Arg Glu Ala Ala Ala Glu Ile Asp Ala Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 233
<211> LENGTH: 49
<212> TYPE: PRT
<213> ORGANISM: Artificial
<220> FEATURE:
<223> OTHER INFORMATION: Engineered polypeptide

<400> SEQUENCE: 233

Lys Glu Leu Ile Glu Ala Ala Ala Glu Ile Asp Lys Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 234
<211> LENGTH: 49
<212> TYPE: PRT
<213> ORGANISM: Artificial
<220> FEATURE:
<223> OTHER INFORMATION: Engineered polypeptide

<400> SEQUENCE: 234

Lys Glu Leu Arg Glu Ala Ala Gly Glu Ile Asp Arg Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 235
<211> LENGTH: 49
<212> TYPE: PRT
<213> ORGANISM: Artificial
<220> FEATURE:
<223> OTHER INFORMATION: Engineered polypeptide
```

```
<400> SEQUENCE: 235

Lys Glu Leu Val Arg Ala Ala Glu Ile Asp Ala Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 236
<211> LENGTH: 49
<212> TYPE: PRT
<213> ORGANISM: Artificial
<220> FEATURE:
<223> OTHER INFORMATION: Engineered polypeptide

<400> SEQUENCE: 236

Lys Glu Arg Ser Arg Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 237
<211> LENGTH: 49
<212> TYPE: PRT
<213> ORGANISM: Artificial
<220> FEATURE:
<223> OTHER INFORMATION: Engineered polypeptide

<400> SEQUENCE: 237

Lys Glu Leu Ile Arg Ala Ala Ser Glu Ile Asp Lys Leu Pro Asn Leu
1               5                   10                  15

Asn Arg Arg Gln Trp Asn Ala Phe Ile Lys Ser Leu Arg Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 238
<211> LENGTH: 49
<212> TYPE: PRT
<213> ORGANISM: Artificial
<220> FEATURE:
<223> OTHER INFORMATION: Engineered polypeptide

<400> SEQUENCE: 238

Lys Glu Leu Ile Lys Ala Ala Gln Glu Ile Asp Arg Leu Pro Asn Leu
1               5                   10                  15

Asn Arg Thr Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 239
<211> LENGTH: 49
```

```
<212> TYPE: PRT
<213> ORGANISM: Artificial
<220> FEATURE:
<223> OTHER INFORMATION: Engineered polypeptide

<400> SEQUENCE: 239

Lys Glu Leu Ile Glu Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 240
<211> LENGTH: 49
<212> TYPE: PRT
<213> ORGANISM: Artificial
<220> FEATURE:
<223> OTHER INFORMATION: Engineered polypeptide

<400> SEQUENCE: 240

Lys Glu Leu Ile Trp Ala Ala Gly Glu Ile Asp Lys Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 241
<211> LENGTH: 49
<212> TYPE: PRT
<213> ORGANISM: Artificial
<220> FEATURE:
<223> OTHER INFORMATION: Engineered polypeptide

<400> SEQUENCE: 241

Lys Glu Arg Leu Ala Ala Ala Glu Glu Ile Asp Asn Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 242
<211> LENGTH: 49
<212> TYPE: PRT
<213> ORGANISM: Artificial
<220> FEATURE:
<223> OTHER INFORMATION: Engineered polypeptide

<400> SEQUENCE: 242

Lys Glu Leu Arg Lys Ala Ala Glu Glu Ile Asp Ala Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45
```

Gln

<210> SEQ ID NO 243
<211> LENGTH: 49
<212> TYPE: PRT
<213> ORGANISM: Artificial
<220> FEATURE:
<223> OTHER INFORMATION: Engineered polypeptide

<400> SEQUENCE: 243

Lys Glu Leu Ile Ala Ala Ala Arg Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 244
<211> LENGTH: 49
<212> TYPE: PRT
<213> ORGANISM: Artificial
<220> FEATURE:
<223> OTHER INFORMATION: Engineered polypeptide

<400> SEQUENCE: 244

Lys Glu Arg Val Lys Ala Ala Glu Glu Ile Asp Lys Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 245
<211> LENGTH: 49
<212> TYPE: PRT
<213> ORGANISM: Artificial
<220> FEATURE:
<223> OTHER INFORMATION: Engineered polypeptide

<400> SEQUENCE: 245

Lys Glu Leu Ile His Ala Ala Glu Glu Ile Asp Arg Leu Pro Asn Leu
1               5                   10                  15

Asn Arg Asn Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 246
<211> LENGTH: 49
<212> TYPE: PRT
<213> ORGANISM: Artificial
<220> FEATURE:
<223> OTHER INFORMATION: Engineered polypeptide

<400> SEQUENCE: 246

Lys Glu Leu Ile Asn Ala Ala Gly Glu Ile Asp Lys Leu Pro Asn Leu
1               5                   10                  15

Asn Arg Lys Gln Trp Asn Ala Phe Ile Lys Ser Leu Val Asp Asp Pro

```
                20                  25                  30

Ser Gln Ser Ala Asn Leu Leu Ala Glu Ala Lys Lys Leu Asn Asp Ala
        35                  40                  45

Gln

<210> SEQ ID NO 247
<211> LENGTH: 49
<212> TYPE: PRT
<213> ORGANISM: Artificial
<220> FEATURE:
<223> OTHER INFORMATION: Engineered polypeptide

<400> SEQUENCE: 247

Lys Glu Leu Ile Glu Ala Ala Ala Glu Ile Asp Ala Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 248
<211> LENGTH: 49
<212> TYPE: PRT
<213> ORGANISM: Artificial
<220> FEATURE:
<223> OTHER INFORMATION: Engineered polypeptide

<400> SEQUENCE: 248

Lys Glu Leu Ile Ala Ala Ala Arg Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 249
<211> LENGTH: 49
<212> TYPE: PRT
<213> ORGANISM: Artificial
<220> FEATURE:
<223> OTHER INFORMATION: Engineered polypeptide

<400> SEQUENCE: 249

Lys Glu Arg Val Asp Ala Ala Arg Glu Ile Asp Asn Leu Pro Asn Leu
1               5                   10                  15

Asn Arg Glu Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 250
<211> LENGTH: 49
<212> TYPE: PRT
<213> ORGANISM: Artificial
<220> FEATURE:
<223> OTHER INFORMATION: Engineered polypeptide

<400> SEQUENCE: 250
```

-continued

Lys Glu Leu Arg Asp Ala Ala Ala Glu Ile Asp Arg Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 251
<211> LENGTH: 49
<212> TYPE: PRT
<213> ORGANISM: Artificial
<220> FEATURE:
<223> OTHER INFORMATION: Engineered polypeptide

<400> SEQUENCE: 251

Lys Glu Leu Ile Ala Ala Ala Glu Ile Asp Arg Leu Pro Asn Leu
1               5                   10                  15

Asn Arg Val Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 252
<211> LENGTH: 49
<212> TYPE: PRT
<213> ORGANISM: Artificial
<220> FEATURE:
<223> OTHER INFORMATION: Engineered polypeptide

<400> SEQUENCE: 252

Lys Glu Leu Arg Ala Ala Ala Glu Ile Asp Lys Leu Pro Asn Leu
1               5                   10                  15

Asn Arg Arg Gln Trp Asn Ala Phe Ile Lys Ser Leu Ile Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 253
<211> LENGTH: 49
<212> TYPE: PRT
<213> ORGANISM: Artificial
<220> FEATURE:
<223> OTHER INFORMATION: Engineered polypeptide

<400> SEQUENCE: 253

Lys Glu Leu Ile Trp Ala Ala Ala Glu Ile Asp Arg Leu Pro Asn Leu
1               5                   10                  15

Asn Arg Glu Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 254
<211> LENGTH: 49
<212> TYPE: PRT

```
<213> ORGANISM: Artificial
<220> FEATURE:
<223> OTHER INFORMATION: Engineered polypeptide

<400> SEQUENCE: 254

Lys Glu Leu Arg Ala Ala Lys Glu Ile Asp Asn Leu Pro Asn Leu
1               5                   10                  15

Asn Arg Arg Gln Trp Asn Ala Phe Ile Lys Ser Leu Val Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 255
<211> LENGTH: 49
<212> TYPE: PRT
<213> ORGANISM: Artificial
<220> FEATURE:
<223> OTHER INFORMATION: Engineered polypeptide

<400> SEQUENCE: 255

Lys Glu Leu Val Gln Ala Ala Lys Glu Ile Asp Asn Leu Pro Asn Leu
1               5                   10                  15

Asn Arg Ser Gln Trp Asn Ala Phe Ile Arg Ser Leu Val Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 256
<211> LENGTH: 49
<212> TYPE: PRT
<213> ORGANISM: Artificial
<220> FEATURE:
<223> OTHER INFORMATION: Engineered polypeptide

<400> SEQUENCE: 256

Lys Glu Leu Ile Glu Ala Ala Gly Glu Ile Asp Ala Leu Pro Asn Leu
1               5                   10                  15

Asn Arg Arg Gln Trp Asn Ala Phe Ile Lys Ser Leu Val Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 257
<211> LENGTH: 49
<212> TYPE: PRT
<213> ORGANISM: Artificial
<220> FEATURE:
<223> OTHER INFORMATION: Engineered polypeptide

<400> SEQUENCE: 257

Lys Glu Leu Val Lys Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
                20                  25                  30

Ser Gln Ser Ala Asn Leu Leu Ala Glu Ala Lys Lys Leu Asn Asp Ala
        35                  40                  45

Gln
```

<210> SEQ ID NO 258
<211> LENGTH: 49
<212> TYPE: PRT
<213> ORGANISM: Artificial
<220> FEATURE:
<223> OTHER INFORMATION: Engineered polypeptide

<400> SEQUENCE: 258

Lys Glu Leu Arg Glu Ala Ala Arg Glu Ile Asp Ser Leu Pro Asn Leu
1               5                   10                  15

Asn Arg Ser Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 259
<211> LENGTH: 49
<212> TYPE: PRT
<213> ORGANISM: Artificial
<220> FEATURE:
<223> OTHER INFORMATION: Engineered polypeptide

<400> SEQUENCE: 259

Lys Glu Leu Leu Glu Ala Ala Lys Glu Ile Asp Glu Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 260
<211> LENGTH: 49
<212> TYPE: PRT
<213> ORGANISM: Artificial
<220> FEATURE:
<223> OTHER INFORMATION: Engineered polypeptide

<400> SEQUENCE: 260

Lys Glu Leu Val Glu Ala Ala Arg Glu Ile Asp Glu Leu Pro Asn Leu
1               5                   10                  15

Asn Arg Ser Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 261
<211> LENGTH: 49
<212> TYPE: PRT
<213> ORGANISM: Artificial
<220> FEATURE:
<223> OTHER INFORMATION: Engineered polypeptide

<400> SEQUENCE: 261

Lys Glu Leu Arg Glu Ala Ala Ala Glu Ile Asp Ala Leu Pro Asn Leu
1               5                   10                  15

Asn Arg Ser Gln Trp Asn Ala Phe Ile Lys Ser Leu Val Asp Asp Pro
            20                  25                  30

-continued

```
Ser Gln Ser Ala Asn Leu Leu Ala Glu Ala Lys Lys Leu Asn Asp Ala
        35                  40                  45

Gln

<210> SEQ ID NO 262
<211> LENGTH: 49
<212> TYPE: PRT
<213> ORGANISM: Artificial
<220> FEATURE:
<223> OTHER INFORMATION: Engineered polypeptide

<400> SEQUENCE: 262

Lys Glu Leu Val Arg Ala Ala Glu Glu Ile Asp Arg Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 263
<211> LENGTH: 49
<212> TYPE: PRT
<213> ORGANISM: Artificial
<220> FEATURE:
<223> OTHER INFORMATION: Engineered polypeptide

<400> SEQUENCE: 263

Lys Glu Leu Arg Ala Ala Ala Glu Ile Asp Ser Leu Pro Asn Leu
1               5                   10                  15

Asn Arg Gly Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 264
<211> LENGTH: 49
<212> TYPE: PRT
<213> ORGANISM: Artificial
<220> FEATURE:
<223> OTHER INFORMATION: Engineered polypeptide

<400> SEQUENCE: 264

Lys Glu Leu Ile Arg Ala Ala Arg Glu Ile Asp Glu Leu Pro Asn Leu
1               5                   10                  15

Asn Arg Met Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 265
<211> LENGTH: 49
<212> TYPE: PRT
<213> ORGANISM: Artificial
<220> FEATURE:
<223> OTHER INFORMATION: Engineered polypeptide

<400> SEQUENCE: 265
```

-continued

```
Lys Glu Leu Arg Asp Ala Ala Arg Glu Ile Asp Ser Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 266
<211> LENGTH: 49
<212> TYPE: PRT
<213> ORGANISM: Artificial
<220> FEATURE:
<223> OTHER INFORMATION: Engineered polypeptide

<400> SEQUENCE: 266

Lys Glu Leu Arg Glu Ala Ala Arg Glu Ile Asp Glu Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 267
<211> LENGTH: 49
<212> TYPE: PRT
<213> ORGANISM: Artificial
<220> FEATURE:
<223> OTHER INFORMATION: Engineered polypeptide

<400> SEQUENCE: 267

Lys Glu Leu Ile Arg Ala Ala Glu Glu Ile Asp Lys Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 268
<211> LENGTH: 49
<212> TYPE: PRT
<213> ORGANISM: Artificial
<220> FEATURE:
<223> OTHER INFORMATION: Engineered polypeptide

<400> SEQUENCE: 268

Lys Glu Leu Leu Lys Ala Ala Arg Glu Ile Asp Glu Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 269
<211> LENGTH: 49
<212> TYPE: PRT
<213> ORGANISM: Artificial
```

```
<220> FEATURE:
<223> OTHER INFORMATION: Engineered polypeptide

<400> SEQUENCE: 269

Lys Glu Leu Ile Ala Ala Ala Arg Glu Ile Asp Gly Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 270
<211> LENGTH: 49
<212> TYPE: PRT
<213> ORGANISM: Artificial
<220> FEATURE:
<223> OTHER INFORMATION: Engineered polypeptide

<400> SEQUENCE: 270

Lys Glu Leu Val Ala Ala Ala Ala Glu Ile Asp Gly Leu Pro Asn Leu
1               5                   10                  15

Asn Arg Lys Gln Trp Asn Ala Phe Ile His Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 271
<211> LENGTH: 49
<212> TYPE: PRT
<213> ORGANISM: Artificial
<220> FEATURE:
<223> OTHER INFORMATION: Engineered polypeptide

<400> SEQUENCE: 271

Lys Glu Leu Arg Asp Ala Ala Arg Glu Ile Asp Ala Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 272
<211> LENGTH: 49
<212> TYPE: PRT
<213> ORGANISM: Artificial
<220> FEATURE:
<223> OTHER INFORMATION: Engineered polypeptide

<400> SEQUENCE: 272

Lys Glu Arg Ile Asn Ala Ala Lys Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 273
<211> LENGTH: 49
<212> TYPE: PRT
<213> ORGANISM: Artificial
<220> FEATURE:
<223> OTHER INFORMATION: Engineered polypeptide

<400> SEQUENCE: 273

Lys Glu Leu Arg Gln Ala Ala Ala Glu Ile Asp Ala Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 274
<211> LENGTH: 49
<212> TYPE: PRT
<213> ORGANISM: Artificial
<220> FEATURE:
<223> OTHER INFORMATION: Engineered polypeptide

<400> SEQUENCE: 274

Lys Glu Leu Val Glu Ala Ala Ala Glu Ile Asp Arg Leu Pro Asn Leu
1               5                   10                  15

Asn Arg Gly Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 275
<211> LENGTH: 49
<212> TYPE: PRT
<213> ORGANISM: Artificial
<220> FEATURE:
<223> OTHER INFORMATION: Engineered polypeptide

<400> SEQUENCE: 275

Lys Glu Leu Arg Glu Ala Ala Ala Glu Ile Asp Arg Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 276
<211> LENGTH: 49
<212> TYPE: PRT
<213> ORGANISM: Artificial
<220> FEATURE:
<223> OTHER INFORMATION: Engineered polypeptide

<400> SEQUENCE: 276

Lys Glu Leu Ile Gln Ala Ala Lys Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

```
Ser Gln Ser Ala Asn Leu Leu Ala Glu Ala Lys Lys Leu Asn Asp Ala
        35                  40                  45

Gln

<210> SEQ ID NO 277
<211> LENGTH: 49
<212> TYPE: PRT
<213> ORGANISM: Artificial
<220> FEATURE:
<223> OTHER INFORMATION: Engineered polypeptide

<400> SEQUENCE: 277

Lys Glu Arg Ser Met Ala Ala Lys Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 278
<211> LENGTH: 49
<212> TYPE: PRT
<213> ORGANISM: Artificial
<220> FEATURE:
<223> OTHER INFORMATION: Engineered polypeptide

<400> SEQUENCE: 278

Lys Glu Leu Val Ala Ala Ala Arg Glu Ile Asp Asp Leu Pro Asn Leu
1               5                   10                  15

Asn Arg Lys Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 279
<211> LENGTH: 49
<212> TYPE: PRT
<213> ORGANISM: Artificial
<220> FEATURE:
<223> OTHER INFORMATION: Engineered polypeptide

<400> SEQUENCE: 279

Lys Glu Leu Val Arg Ala Ala Glu Glu Ile Asp Arg Leu Pro Asn Leu
1               5                   10                  15

Asn Arg Leu Gln Trp Asn Ala Phe Ile Lys Ser Leu Ile Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 280
<211> LENGTH: 49
<212> TYPE: PRT
<213> ORGANISM: Artificial
<220> FEATURE:
<223> OTHER INFORMATION: Engineered polypeptide

<400> SEQUENCE: 280

Lys Glu Leu Arg Glu Ala Ala Ala Glu Ile Asp Asp Leu Pro Asn Leu
```

```
                1               5                  10                 15
Asn Arg Ala Gln Trp Asn Ala Phe Ile Lys Ser Leu Val Asp Asp Pro
            20                  25                 30

Ser Gln Ser Ala Asn Leu Leu Ala Glu Ala Lys Lys Leu Asn Asp Ala
        35                  40                  45

Gln

<210> SEQ ID NO 281
<211> LENGTH: 49
<212> TYPE: PRT
<213> ORGANISM: Artificial
<220> FEATURE:
<223> OTHER INFORMATION: Engineered polypeptide

<400> SEQUENCE: 281

Lys Glu Leu Val Glu Ala Ala Lys Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 282
<211> LENGTH: 49
<212> TYPE: PRT
<213> ORGANISM: Artificial
<220> FEATURE:
<223> OTHER INFORMATION: Engineered polypeptide

<400> SEQUENCE: 282

Lys Glu Leu Ile Asn Ala Ala Gly Glu Ile Asp Arg Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 283
<211> LENGTH: 49
<212> TYPE: PRT
<213> ORGANISM: Artificial
<220> FEATURE:
<223> OTHER INFORMATION: Engineered polypeptide

<400> SEQUENCE: 283

Lys Glu Leu Leu Ser Ala Ala Ala Glu Ile Asp Ser Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 284
<211> LENGTH: 49
<212> TYPE: PRT
<213> ORGANISM: Artificial
<220> FEATURE:
```

-continued

<223> OTHER INFORMATION: Engineered polypeptide

<400> SEQUENCE: 284

Lys Glu Leu Arg Asp Ala Ala Ala Glu Ile Asp Lys Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 285
<211> LENGTH: 49
<212> TYPE: PRT
<213> ORGANISM: Artificial
<220> FEATURE:
<223> OTHER INFORMATION: Engineered polypeptide

<400> SEQUENCE: 285

Lys Glu Leu Arg Gln Ala Ala Ala Glu Ile Asp Lys Leu Pro Asn Leu
1               5                   10                  15

Asn Arg Ser Gln Trp Asn Ala Phe Ile Gln Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 286
<211> LENGTH: 49
<212> TYPE: PRT
<213> ORGANISM: Artificial
<220> FEATURE:
<223> OTHER INFORMATION: Engineered polypeptide

<400> SEQUENCE: 286

Lys Glu Leu Arg Glu Ala Ala Ala Glu Ile Asp Ala Leu Pro Asn Leu
1               5                   10                  15

Asn Arg Val Gln Trp Asn Ala Phe Ile Lys Ser Leu Arg Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 287
<211> LENGTH: 49
<212> TYPE: PRT
<213> ORGANISM: Artificial
<220> FEATURE:
<223> OTHER INFORMATION: Engineered polypeptide

<400> SEQUENCE: 287

Lys Glu Leu Val Ala Ala Ala Glu Ile Asp Arg Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 288
<211> LENGTH: 49
<212> TYPE: PRT
<213> ORGANISM: Artificial
<220> FEATURE:
<223> OTHER INFORMATION: Engineered polypeptide

<400> SEQUENCE: 288

Lys Glu Leu Ile Asp Ala Ala Ala Glu Ile Asp Lys Leu Pro Asn Leu
1               5                   10                  15

Asn Arg Asn Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 289
<211> LENGTH: 49
<212> TYPE: PRT
<213> ORGANISM: Artificial
<220> FEATURE:
<223> OTHER INFORMATION: Engineered polypeptide

<400> SEQUENCE: 289

Lys Glu Arg Ile Asn Ala Ala Ala Glu Ile Asp Gly Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 290
<211> LENGTH: 49
<212> TYPE: PRT
<213> ORGANISM: Artificial
<220> FEATURE:
<223> OTHER INFORMATION: Engineered polypeptide

<400> SEQUENCE: 290

Lys Glu Leu Val Arg Ala Ala Glu Glu Ile Asp Asn Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 291
<211> LENGTH: 49
<212> TYPE: PRT
<213> ORGANISM: Artificial
<220> FEATURE:
<223> OTHER INFORMATION: Engineered polypeptide

<400> SEQUENCE: 291

Lys Glu Leu Ile Arg Ala Ala Lys Glu Ile Asp Glu Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
```

```
                35                  40                  45
Gln

<210> SEQ ID NO 292
<211> LENGTH: 49
<212> TYPE: PRT
<213> ORGANISM: Artificial
<220> FEATURE:
<223> OTHER INFORMATION: Engineered polypeptide

<400> SEQUENCE: 292

Lys Glu Leu Ile Gln Ala Ala Arg Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 293
<211> LENGTH: 49
<212> TYPE: PRT
<213> ORGANISM: Artificial
<220> FEATURE:
<223> OTHER INFORMATION: Engineered polypeptide

<400> SEQUENCE: 293

Lys Glu Leu Ile Asp Ala Ala Arg Glu Ile Asp Asp Leu Pro Asn Leu
1               5                   10                  15

Asn Arg Gln Gln Trp Asn Ala Phe Ile Lys Ser Leu Leu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 294
<211> LENGTH: 49
<212> TYPE: PRT
<213> ORGANISM: Artificial
<220> FEATURE:
<223> OTHER INFORMATION: Engineered polypeptide

<400> SEQUENCE: 294

Lys Glu Leu Leu Lys Ala Ala Asp Glu Ile Asp Ala Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 295
<211> LENGTH: 49
<212> TYPE: PRT
<213> ORGANISM: Artificial
<220> FEATURE:
<223> OTHER INFORMATION: Engineered polypeptide

<400> SEQUENCE: 295

Lys Glu Leu Leu Glu Ala Ala Ala Glu Ile Asp Ser Leu Pro Asn Leu
1               5                   10                  15
```

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 296
<211> LENGTH: 49
<212> TYPE: PRT
<213> ORGANISM: Artificial
<220> FEATURE:
<223> OTHER INFORMATION: Engineered polypeptide

<400> SEQUENCE: 296

Lys Glu Leu Val Asp Ala Ala Arg Glu Ile Asp Thr Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 297
<211> LENGTH: 49
<212> TYPE: PRT
<213> ORGANISM: Artificial
<220> FEATURE:
<223> OTHER INFORMATION: Engineered polypeptide

<400> SEQUENCE: 297

Lys Glu Leu Ile Glu Ala Ala Arg Glu Ile Asp Lys Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 298
<211> LENGTH: 49
<212> TYPE: PRT
<213> ORGANISM: Artificial
<220> FEATURE:
<223> OTHER INFORMATION: Engineered polypeptide

<400> SEQUENCE: 298

Lys Glu Leu Val Ala Ala Ala Arg Glu Ile Asp Asn Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 299
<211> LENGTH: 49
<212> TYPE: PRT
<213> ORGANISM: Artificial
<220> FEATURE:
<223> OTHER INFORMATION: Engineered polypeptide

<400> SEQUENCE: 299

Lys Glu Leu Val Glu Ala Ala Ala Glu Ile Asp Gly Leu Pro Asn Leu
1               5                   10                  15

Asn Arg Asp Gln Trp Asn Ala Phe Ile Lys Ser Leu Arg Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 300
<211> LENGTH: 49
<212> TYPE: PRT
<213> ORGANISM: Artificial
<220> FEATURE:
<223> OTHER INFORMATION: Engineered polypeptide

<400> SEQUENCE: 300

Lys Glu Leu Arg Asn Ala Ala Lys Glu Ile Asp Gly Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 301
<211> LENGTH: 49
<212> TYPE: PRT
<213> ORGANISM: Artificial
<220> FEATURE:
<223> OTHER INFORMATION: Engineered polypeptide

<400> SEQUENCE: 301

Lys Glu Leu Arg His Ala Ala Arg Glu Ile Asp Gly Leu Pro Asn Leu
1               5                   10                  15

Asn Arg Thr Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 302
<211> LENGTH: 49
<212> TYPE: PRT
<213> ORGANISM: Artificial
<220> FEATURE:
<223> OTHER INFORMATION: Engineered polypeptide

<400> SEQUENCE: 302

Lys Glu Leu Val Glu Ala Ala Arg Glu Ile Asp Thr Leu Pro Asn Leu
1               5                   10                  15

Asn Arg Arg Gln Trp Asn Ala Phe Ile Lys Ser Leu Arg Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 303

```
<211> LENGTH: 49
<212> TYPE: PRT
<213> ORGANISM: Artificial
<220> FEATURE:
<223> OTHER INFORMATION: Engineered polypeptide

<400> SEQUENCE: 303

Lys Glu Leu Val Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 304
<211> LENGTH: 49
<212> TYPE: PRT
<213> ORGANISM: Artificial
<220> FEATURE:
<223> OTHER INFORMATION: Engineered polypeptide

<400> SEQUENCE: 304

Lys Glu Leu Arg Thr Ala Ala Lys Glu Ile Asp Asp Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 305
<211> LENGTH: 49
<212> TYPE: PRT
<213> ORGANISM: Artificial
<220> FEATURE:
<223> OTHER INFORMATION: Engineered polypeptide

<400> SEQUENCE: 305

Lys Glu Leu Leu Arg Ala Ala Arg Glu Ile Asp Ser Leu Pro Asn Leu
1               5                   10                  15

Asn Arg Thr Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 306
<211> LENGTH: 49
<212> TYPE: PRT
<213> ORGANISM: Artificial
<220> FEATURE:
<223> OTHER INFORMATION: Engineered polypeptide

<400> SEQUENCE: 306

Lys Glu Arg Ile Arg Ala Ala Arg Glu Ile Asp Ala Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45
```

Gln

<210> SEQ ID NO 307
<211> LENGTH: 49
<212> TYPE: PRT
<213> ORGANISM: Artificial
<220> FEATURE:
<223> OTHER INFORMATION: Engineered polypeptide

<400> SEQUENCE: 307

Lys Glu Leu Arg Ala Ala Ala Glu Glu Ile Asp Arg Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 308
<211> LENGTH: 49
<212> TYPE: PRT
<213> ORGANISM: Artificial
<220> FEATURE:
<223> OTHER INFORMATION: Engineered polypeptide

<400> SEQUENCE: 308

Lys Glu Leu Ile Glu Ala Ala Ala Glu Ile Asp Ala Leu Pro Asn Leu
1               5                   10                  15

Asn Arg Lys Gln Trp Asn Ala Phe Ile Ser Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 309
<211> LENGTH: 49
<212> TYPE: PRT
<213> ORGANISM: Artificial
<220> FEATURE:
<223> OTHER INFORMATION: Engineered polypeptide

<400> SEQUENCE: 309

Lys Glu Arg Ile Glu Ala Ala Arg Glu Ile Asp Glu Leu Pro Asn Leu
1               5                   10                  15

Asn Arg Lys Gln Trp Asn Ala Phe Ile Ser Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 310
<211> LENGTH: 49
<212> TYPE: PRT
<213> ORGANISM: Artificial
<220> FEATURE:
<223> OTHER INFORMATION: Engineered polypeptide

<400> SEQUENCE: 310

Lys Glu Leu Leu Ala Ala Ala Lys Glu Ile Asp Glu Leu Pro Asn Leu
1               5                   10                  15

-continued

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 311
<211> LENGTH: 49
<212> TYPE: PRT
<213> ORGANISM: Artificial
<220> FEATURE:
<223> OTHER INFORMATION: Engineered polypeptide

<400> SEQUENCE: 311

Lys Glu Leu Ile Asn Ala Ala Arg Glu Ile Asp Glu Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 312
<211> LENGTH: 49
<212> TYPE: PRT
<213> ORGANISM: Artificial
<220> FEATURE:
<223> OTHER INFORMATION: Engineered polypeptide

<400> SEQUENCE: 312

Lys Glu Leu Val Lys Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 313
<211> LENGTH: 49
<212> TYPE: PRT
<213> ORGANISM: Artificial
<220> FEATURE:
<223> OTHER INFORMATION: Engineered polypeptide

<400> SEQUENCE: 313

Lys Glu Leu Ile Ala Ala Ala Lys Glu Ile Asp Glu Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 314
<211> LENGTH: 49
<212> TYPE: PRT
<213> ORGANISM: Artificial
<220> FEATURE:
<223> OTHER INFORMATION: Engineered polypeptide

```
<400> SEQUENCE: 314

Lys Glu Leu Ile Ser Ala Ala Arg Glu Ile Asp Lys Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 315
<211> LENGTH: 49
<212> TYPE: PRT
<213> ORGANISM: Artificial
<220> FEATURE:
<223> OTHER INFORMATION: Engineered polypeptide

<400> SEQUENCE: 315

Lys Glu Leu Arg Glu Ala Ala Glu Glu Ile Asp Lys Leu Pro Asn Leu
1               5                   10                  15

Asn Arg Trp Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 316
<211> LENGTH: 49
<212> TYPE: PRT
<213> ORGANISM: Artificial
<220> FEATURE:
<223> OTHER INFORMATION: Engineered polypeptide

<400> SEQUENCE: 316

Lys Glu Leu Val Glu Ala Ala Arg Glu Ile Asp Gly Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 317
<211> LENGTH: 49
<212> TYPE: PRT
<213> ORGANISM: Artificial
<220> FEATURE:
<223> OTHER INFORMATION: Engineered polypeptide

<400> SEQUENCE: 317

Lys Glu Leu Val Ala Ala Ala Gln Glu Ile Asp Asn Leu Pro Asn Leu
1               5                   10                  15

Asn Arg Lys Gln Trp Asn Ala Phe Ile Ser Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 318
<211> LENGTH: 49
```

-continued

```
<212> TYPE: PRT
<213> ORGANISM: Artificial
<220> FEATURE:
<223> OTHER INFORMATION: Engineered polypeptide

<400> SEQUENCE: 318

Lys Glu Leu Arg Asn Ala Ala Ala Glu Ile Asp Lys Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 319
<211> LENGTH: 49
<212> TYPE: PRT
<213> ORGANISM: Artificial
<220> FEATURE:
<223> OTHER INFORMATION: Engineered polypeptide

<400> SEQUENCE: 319

Lys Glu Leu Ile Gln Ala Ala Ser Glu Ile Asp Ala Leu Pro Asn Leu
1               5                   10                  15

Asn Arg Thr Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 320
<211> LENGTH: 49
<212> TYPE: PRT
<213> ORGANISM: Artificial
<220> FEATURE:
<223> OTHER INFORMATION: Engineered polypeptide

<400> SEQUENCE: 320

Lys Glu Leu Val Glu Ala Ala Ala Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 321
<211> LENGTH: 49
<212> TYPE: PRT
<213> ORGANISM: Artificial
<220> FEATURE:
<223> OTHER INFORMATION: Engineered polypeptide

<400> SEQUENCE: 321

Lys Glu Arg Ile Ala Ala Ala Gln Glu Ile Asp Ala Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45
```

Gln

<210> SEQ ID NO 322
<211> LENGTH: 49
<212> TYPE: PRT
<213> ORGANISM: Artificial
<220> FEATURE:
<223> OTHER INFORMATION: Engineered polypeptide

<400> SEQUENCE: 322

Lys Glu Leu Arg Asp Ala Ala Lys Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 323
<211> LENGTH: 49
<212> TYPE: PRT
<213> ORGANISM: Artificial
<220> FEATURE:
<223> OTHER INFORMATION: Engineered polypeptide

<400> SEQUENCE: 323

Lys Glu Leu Val Ala Ala Ala Lys Glu Ile Asp Lys Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 324
<211> LENGTH: 49
<212> TYPE: PRT
<213> ORGANISM: Artificial
<220> FEATURE:
<223> OTHER INFORMATION: Engineered polypeptide

<400> SEQUENCE: 324

Lys Glu Leu Ile Lys Ala Ala Arg Glu Ile Asp Glu Leu Pro Asn Leu
1               5                   10                  15

Asn Arg Lys Gln Trp Asn Ala Phe Ile Lys Ser Leu Ile Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 325
<211> LENGTH: 49
<212> TYPE: PRT
<213> ORGANISM: Artificial
<220> FEATURE:
<223> OTHER INFORMATION: Engineered polypeptide

<400> SEQUENCE: 325

Lys Glu Leu Val Glu Ala Ala Ser Glu Ile Asp Gly Leu Pro Asn Leu
1               5                   10                  15

Asn Arg Asn Gln Trp Asn Ala Phe Ile Lys Ser Leu Val Asp Asp Pro

```
                    20                  25                  30
Ser Gln Ser Ala Asn Leu Leu Ala Glu Ala Lys Lys Leu Asn Asp Ala
        35                  40                  45
Gln

<210> SEQ ID NO 326
<211> LENGTH: 49
<212> TYPE: PRT
<213> ORGANISM: Artificial
<220> FEATURE:
<223> OTHER INFORMATION: Engineered polypeptide

<400> SEQUENCE: 326

Lys Glu Leu Leu Arg Ala Ala Glu Glu Ile Asp Asn Leu Pro Asn Leu
1               5                   10                  15

Asn Arg Ala Gln Trp Asn Ala Phe Ile Lys Ser Leu Val Asp Asp Pro
                20                  25                  30

Ser Gln Ser Ala Asn Leu Leu Ala Glu Ala Lys Lys Leu Asn Asp Ala
        35                  40                  45
Gln

<210> SEQ ID NO 327
<211> LENGTH: 49
<212> TYPE: PRT
<213> ORGANISM: Artificial
<220> FEATURE:
<223> OTHER INFORMATION: Engineered polypeptide

<400> SEQUENCE: 327

Lys Glu Leu Ile Lys Ala Ala Lys Glu Ile Asp Ala Leu Pro Asn Leu
1               5                   10                  15

Asn Arg Arg Gln Trp Asn Ala Phe Ile Lys Ser Leu Val Asp Asp Pro
                20                  25                  30

Ser Gln Ser Ala Asn Leu Leu Ala Glu Ala Lys Lys Leu Asn Asp Ala
        35                  40                  45
Gln

<210> SEQ ID NO 328
<211> LENGTH: 49
<212> TYPE: PRT
<213> ORGANISM: Artificial
<220> FEATURE:
<223> OTHER INFORMATION: Engineered polypeptide

<400> SEQUENCE: 328

Lys Glu Leu Arg Arg Ala Ala Ala Glu Ile Asp Ser Leu Pro Asn Leu
1               5                   10                  15

Asn Arg Asp Gln Trp Asn Ala Phe Ile Arg Ser Leu Ile Asp Asp Pro
                20                  25                  30

Ser Gln Ser Ala Asn Leu Leu Ala Glu Ala Lys Lys Leu Asn Asp Ala
        35                  40                  45
Gln

<210> SEQ ID NO 329
<211> LENGTH: 49
<212> TYPE: PRT
<213> ORGANISM: Artificial
<220> FEATURE:
<223> OTHER INFORMATION: Engineered polypeptide

<400> SEQUENCE: 329
```

```
Lys Glu Leu Val Glu Ala Ala Arg Glu Ile Asp Gly Leu Pro Asn Leu
1               5                   10                  15

Asn Arg Ala Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 330
<211> LENGTH: 49
<212> TYPE: PRT
<213> ORGANISM: Artificial
<220> FEATURE:
<223> OTHER INFORMATION: Engineered polypeptide

<400> SEQUENCE: 330

```
Lys Glu Leu Val Glu Ala Ala Arg Glu Ile Asp Glu Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 331
<211> LENGTH: 49
<212> TYPE: PRT
<213> ORGANISM: Artificial
<220> FEATURE:
<223> OTHER INFORMATION: Engineered polypeptide

<400> SEQUENCE: 331

```
Lys Glu Leu Val Trp Ala Ala Ala Glu Ile Asp Arg Leu Pro Asn Leu
1               5                   10                  15

Asn Arg Cys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 332
<211> LENGTH: 49
<212> TYPE: PRT
<213> ORGANISM: Artificial
<220> FEATURE:
<223> OTHER INFORMATION: Engineered polypeptide

<400> SEQUENCE: 332

```
Lys Glu Arg Ile Arg Ala Ala Arg Glu Ile Asp Glu Leu Pro Asn Leu
1               5                   10                  15

Asn Arg Glu Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 333
<211> LENGTH: 49
<212> TYPE: PRT

```
<213> ORGANISM: Artificial
<220> FEATURE:
<223> OTHER INFORMATION: Engineered polypeptide

<400> SEQUENCE: 333

Lys Glu Leu Arg Gln Ala Ala Lys Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 334
<211> LENGTH: 49
<212> TYPE: PRT
<213> ORGANISM: Artificial
<220> FEATURE:
<223> OTHER INFORMATION: Engineered polypeptide

<400> SEQUENCE: 334

Lys Glu Leu Arg Glu Ala Ala Ala Glu Ile Asp Lys Leu Pro Asn Leu
1               5                   10                  15

Asn Arg Lys Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 335
<211> LENGTH: 49
<212> TYPE: PRT
<213> ORGANISM: Artificial
<220> FEATURE:
<223> OTHER INFORMATION: Engineered polypeptide

<400> SEQUENCE: 335

Lys Glu Leu Arg Arg Ala Ala Glu Glu Ile Asp Lys Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 336
<211> LENGTH: 49
<212> TYPE: PRT
<213> ORGANISM: Artificial
<220> FEATURE:
<223> OTHER INFORMATION: Engineered polypeptide

<400> SEQUENCE: 336

Lys Glu Leu Val Gln Ala Ala Arg Glu Ile Asp Ala Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 337
<211> LENGTH: 49
<212> TYPE: PRT
<213> ORGANISM: Artificial
<220> FEATURE:
<223> OTHER INFORMATION: Engineered polypeptide

<400> SEQUENCE: 337

Lys Glu Leu Arg Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 338
<211> LENGTH: 49
<212> TYPE: PRT
<213> ORGANISM: Artificial
<220> FEATURE:
<223> OTHER INFORMATION: Engineered polypeptide

<400> SEQUENCE: 338

Lys Glu Leu Arg Ala Ala Ala Ala Glu Ile Asp Lys Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 339
<211> LENGTH: 49
<212> TYPE: PRT
<213> ORGANISM: Artificial
<220> FEATURE:
<223> OTHER INFORMATION: Engineered polypeptide

<400> SEQUENCE: 339

Lys Glu Arg Ile Gln Ala Ala Lys Glu Ile Asp Glu Leu Pro Asn Leu
1               5                   10                  15

Asn Arg Glu Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 340
<211> LENGTH: 49
<212> TYPE: PRT
<213> ORGANISM: Artificial
<220> FEATURE:
<223> OTHER INFORMATION: Engineered polypeptide

<400> SEQUENCE: 340

Lys Glu Leu Val Ala Ala Ala Glu Glu Ile Asp Lys Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 341
<211> LENGTH: 49
<212> TYPE: PRT
<213> ORGANISM: Artificial
<220> FEATURE:
<223> OTHER INFORMATION: Engineered polypeptide

<400> SEQUENCE: 341

Lys Glu Leu Val Arg Ala Ala Glu Glu Ile Asp Asn Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 342
<211> LENGTH: 49
<212> TYPE: PRT
<213> ORGANISM: Artificial
<220> FEATURE:
<223> OTHER INFORMATION: Engineered polypeptide

<400> SEQUENCE: 342

Lys Glu Leu Arg Thr Ala Ala Glu Ile Asp Ala Leu Pro Asn Leu
1               5                   10                  15

Asn Arg Glu Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 343
<211> LENGTH: 49
<212> TYPE: PRT
<213> ORGANISM: Artificial
<220> FEATURE:
<223> OTHER INFORMATION: Engineered polypeptide

<400> SEQUENCE: 343

Lys Glu Leu Val Glu Ala Ala Glu Ile Asp Ala Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 344
<211> LENGTH: 49
<212> TYPE: PRT
<213> ORGANISM: Artificial
<220> FEATURE:
<223> OTHER INFORMATION: Engineered polypeptide

<400> SEQUENCE: 344

Lys Glu Leu Ile Lys Ala Ala Glu Glu Ile Asp Lys Leu Pro Asn Leu
1               5                   10                  15

Asn Arg Met Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 345
<211> LENGTH: 49
<212> TYPE: PRT
<213> ORGANISM: Artificial
<220> FEATURE:
<223> OTHER INFORMATION: Engineered polypeptide

<400> SEQUENCE: 345

Lys Glu Leu Arg Glu Ala Ala Ala Glu Ile Asp Asn Leu Pro Asn Leu
1               5                   10                  15

Asn Arg Arg Gln Trp Asn Ala Phe Ile Lys Ser Leu Ile Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 346
<211> LENGTH: 49
<212> TYPE: PRT
<213> ORGANISM: Artificial
<220> FEATURE:
<223> OTHER INFORMATION: Engineered polypeptide

<400> SEQUENCE: 346

Lys Glu Leu Ile Glu Ala Ala Arg Glu Ile Asp Ala Leu Pro Asn Leu
1               5                   10                  15

Asn Arg Lys Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 347
<211> LENGTH: 49
<212> TYPE: PRT
<213> ORGANISM: Artificial
<220> FEATURE:
<223> OTHER INFORMATION: Engineered polypeptide

<400> SEQUENCE: 347

Lys Glu Leu Arg Glu Ala Ala Gln Glu Ile Asp Ser Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 348
<211> LENGTH: 49
<212> TYPE: PRT
<213> ORGANISM: Artificial

```
<220> FEATURE:
<223> OTHER INFORMATION: Engineered polypeptide

<400> SEQUENCE: 348

Lys Glu Leu Arg Ser Ala Ala Glu Glu Ile Asp Ser Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 349
<211> LENGTH: 49
<212> TYPE: PRT
<213> ORGANISM: Artificial
<220> FEATURE:
<223> OTHER INFORMATION: Engineered polypeptide

<400> SEQUENCE: 349

Lys Glu Leu Val Glu Ala Ala Glu Ile Asp Asn Leu Pro Asn Leu
1               5                   10                  15

Asn Arg Met Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 350
<211> LENGTH: 49
<212> TYPE: PRT
<213> ORGANISM: Artificial
<220> FEATURE:
<223> OTHER INFORMATION: Engineered polypeptide

<400> SEQUENCE: 350

Lys Glu Leu Val Glu Ala Ala Gly Glu Ile Asp Asn Leu Pro Asn Leu
1               5                   10                  15

Asn Arg Arg Gln Trp Asn Ala Phe Ile Arg Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 351
<211> LENGTH: 49
<212> TYPE: PRT
<213> ORGANISM: Artificial
<220> FEATURE:
<223> OTHER INFORMATION: Engineered polypeptide

<400> SEQUENCE: 351

Lys Glu Leu Ser Lys Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 352
<211> LENGTH: 49
<212> TYPE: PRT
<213> ORGANISM: Artificial
<220> FEATURE:
<223> OTHER INFORMATION: Engineered polypeptide

<400> SEQUENCE: 352

Lys Glu Leu Leu Trp Ala Ala Gly Glu Ile Asp Arg Leu Pro Asn Leu
1               5                   10                  15

Asn Arg Gln Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 353
<211> LENGTH: 49
<212> TYPE: PRT
<213> ORGANISM: Artificial
<220> FEATURE:
<223> OTHER INFORMATION: Engineered polypeptide

<400> SEQUENCE: 353

Lys Glu Leu Arg Gln Ala Ala Ala Glu Ile Asp Gly Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 354
<211> LENGTH: 49
<212> TYPE: PRT
<213> ORGANISM: Artificial
<220> FEATURE:
<223> OTHER INFORMATION: Engineered polypeptide

<400> SEQUENCE: 354

Lys Glu Leu Val Lys Ala Ala Ala Glu Ile Asp Ala Leu Pro Asn Leu
1               5                   10                  15

Thr Arg Arg Gln Trp Asn Ala Phe Ile Lys Ser Leu Val Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 355
<211> LENGTH: 49
<212> TYPE: PRT
<213> ORGANISM: Artificial
<220> FEATURE:
<223> OTHER INFORMATION: Engineered polypeptide

<400> SEQUENCE: 355

Lys Glu Leu Val Lys Ala Ala Ala Glu Ile Asp Ala Leu Pro Asn Leu
1               5                   10                  15

Asn Arg Arg Gln Trp Asn Ala Phe Ile Lys Lys Leu Val Asp Asp Pro
            20                  25                  30

Ser Gln Ser Ser Glu Leu Leu Ser Glu Ala Lys Lys Leu Asn Asp Ser
         35                  40                  45

Gln

<210> SEQ ID NO 356
<211> LENGTH: 49
<212> TYPE: PRT
<213> ORGANISM: Artificial
<220> FEATURE:
<223> OTHER INFORMATION: Engineered polypeptide

<400> SEQUENCE: 356

Lys Glu Leu Val Lys Ala Ala Ala Glu Ile Asp Ala Leu Pro Asn Leu
1               5                   10                  15

Thr Arg Arg Gln Trp Asn Ala Phe Ile Lys Lys Leu Val Asp Asp Pro
            20                  25                  30

Ser Gln Ser Ser Glu Leu Leu Ser Glu Ala Lys Lys Leu Asn Asp Ser
         35                  40                  45

Gln

<210> SEQ ID NO 357
<211> LENGTH: 49
<212> TYPE: PRT
<213> ORGANISM: Artificial
<220> FEATURE:
<223> OTHER INFORMATION: Engineered polypeptide

<400> SEQUENCE: 357

Lys Glu Leu Val Lys Ala Ala Ala Glu Ile Asp Ala Leu Pro Asn Leu
1               5                   10                  15

Thr Arg Arg Gln Trp Asn Ala Phe Ile Lys Lys Leu Val Lys Asp Pro
            20                  25                  30

Ser Gln Ser Ser Glu Leu Leu Ser Glu Ala Lys Lys Leu Asn Asp Ser
         35                  40                  45

Gln

<210> SEQ ID NO 358
<211> LENGTH: 49
<212> TYPE: PRT
<213> ORGANISM: Artificial
<220> FEATURE:
<223> OTHER INFORMATION: Engineered polypeptide

<400> SEQUENCE: 358

Lys Glu Leu Ile Glu Ala Ala Ala Glu Ile Asp Ala Leu Pro Asn Leu
1               5                   10                  15

Thr Arg Arg Gln Trp Asn Ala Phe Ile Lys Lys Leu Val Asp Asp Pro
            20                  25                  30

Ser Gln Ser Ser Glu Leu Leu Ser Glu Ala Lys Lys Leu Asn Asp Ser
         35                  40                  45

Gln

<210> SEQ ID NO 359
<211> LENGTH: 58
<212> TYPE: PRT
<213> ORGANISM: Artificial
<220> FEATURE:
<223> OTHER INFORMATION: Engineered polypeptide

<400> SEQUENCE: 359

Val Asp Asn Lys Phe Asn Lys Glu Arg Ala Glu Ala Ala Gln Glu Ile

```
                1               5                   10                  15
Asp Gln Leu Pro Asn Leu Asn Arg Gly Gln Trp Asn Ala Phe Ile Ala
                20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 360
<211> LENGTH: 58
<212> TYPE: PRT
<213> ORGANISM: Artificial
<220> FEATURE:
<223> OTHER INFORMATION: Engineered polypeptide

<400> SEQUENCE: 360

Val Asp Asn Lys Phe Asn Lys Glu Arg Gln Val Ala Ala Ala Glu Ile
1               5                   10                  15

Asp Ala Leu Pro Asn Leu Asn Arg Gly Gln Trp Asn Ala Phe Ile Ala
                20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 361
<211> LENGTH: 58
<212> TYPE: PRT
<213> ORGANISM: Artificial
<220> FEATURE:
<223> OTHER INFORMATION: Engineered polypeptide

<400> SEQUENCE: 361

Val Asp Asn Lys Phe Asn Lys Glu Leu Ser Asp Ala Ala Gln Glu Ile
1               5                   10                  15

Asp Ser Leu Pro Asn Leu Asn Arg Ser Gln Trp Asn Ala Phe Ile Lys
                20                  25                  30

Ser Leu Ile Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 362
<211> LENGTH: 58
<212> TYPE: PRT
<213> ORGANISM: Artificial
<220> FEATURE:
<223> OTHER INFORMATION: Engineered polypeptide

<400> SEQUENCE: 362

Val Asp Asn Lys Phe Asn Lys Glu Arg Arg Glu Ala Ala Ala Glu Ile
1               5                   10                  15

Asp Asn Leu Pro Asn Leu Asn Arg Ser Gln Trp Asn Ala Phe Ile Gln
                20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 363
```

<211> LENGTH: 58
<212> TYPE: PRT
<213> ORGANISM: Artificial
<220> FEATURE:
<223> OTHER INFORMATION: Engineered polypeptide

<400> SEQUENCE: 363

Val Asp Asn Lys Phe Asn Lys Glu Arg Arg Glu Ala Ala Lys Glu Ile
1               5                   10                  15

Asp Ser Leu Pro Asn Leu Asn Arg Thr Gln Trp Asn Ala Phe Ile Arg
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 364
<211> LENGTH: 58
<212> TYPE: PRT
<213> ORGANISM: Artificial
<220> FEATURE:
<223> OTHER INFORMATION: Engineered polypeptide

<400> SEQUENCE: 364

Val Asp Asn Lys Phe Asn Lys Glu Leu Arg His Ala Ala Ser Glu Ile
1               5                   10                  15

Asp Asp Leu Pro Asn Leu Asn Arg Ala Gln Trp Asn Ala Phe Ile Arg
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 365
<211> LENGTH: 58
<212> TYPE: PRT
<213> ORGANISM: Artificial
<220> FEATURE:
<223> OTHER INFORMATION: Engineered polypeptide

<400> SEQUENCE: 365

Val Asp Asn Lys Phe Asn Lys Glu Leu Val Arg Ala Ala Gln Glu Ile
1               5                   10                  15

Asp Glu Leu Pro Asn Leu Asn Arg Gly Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 366
<211> LENGTH: 58
<212> TYPE: PRT
<213> ORGANISM: Artificial
<220> FEATURE:
<223> OTHER INFORMATION: Engineered polypeptide

<400> SEQUENCE: 366

Val Asp Asn Lys Phe Asn Lys Glu Ile Lys Gln Ala Ala Arg Glu Ile
1               5                   10                  15

Asp Ala Leu Pro Asn Leu Asn Lys Lys Gln Trp Asn Ala Phe Ile Gln
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 367
<211> LENGTH: 58
<212> TYPE: PRT
<213> ORGANISM: Artificial
<220> FEATURE:
<223> OTHER INFORMATION: Engineered polypeptide

<400> SEQUENCE: 367

Val Asp Asn Lys Phe Asn Lys Glu Arg His Arg Ala Ala Gln Glu Ile
1               5                   10                  15

Asp Gln Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 368
<211> LENGTH: 58
<212> TYPE: PRT
<213> ORGANISM: Artificial
<220> FEATURE:
<223> OTHER INFORMATION: Engineered polypeptide

<400> SEQUENCE: 368

Val Asp Asn Lys Phe Asn Lys Glu Ile Lys Phe Ala Ala Gly Glu Ile
1               5                   10                  15

Asp Asn Leu Pro Asn Leu Asn Arg Lys Gln Trp Asn Ala Phe Ile Gly
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 369
<211> LENGTH: 58
<212> TYPE: PRT
<213> ORGANISM: Artificial
<220> FEATURE:
<223> OTHER INFORMATION: Engineered polypeptide

<400> SEQUENCE: 369

Val Asp Asn Lys Phe Asn Lys Glu Arg Leu Lys Ala Ala Ala Glu Ile
1               5                   10                  15

Asp Ala Leu Pro Asn Leu Asn Arg Lys Gln Trp Asn Ala Phe Ile Ser
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 370
<211> LENGTH: 58
<212> TYPE: PRT
<213> ORGANISM: Artificial
<220> FEATURE:

<223> OTHER INFORMATION: Engineered polypeptide

<400> SEQUENCE: 370

Val Asp Asn Lys Phe Asn Lys Glu Leu Arg Ala Ala Ala Glu Ile
1               5                   10                  15

Asp Ser Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 371
<211> LENGTH: 58
<212> TYPE: PRT
<213> ORGANISM: Artificial
<220> FEATURE:
<223> OTHER INFORMATION: Engineered polypeptide

<400> SEQUENCE: 371

Val Asp Asn Lys Phe Asn Lys Glu Arg Leu Glu Ala Ala Glu Glu Ile
1               5                   10                  15

Asp Ser Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 372
<211> LENGTH: 58
<212> TYPE: PRT
<213> ORGANISM: Artificial
<220> FEATURE:
<223> OTHER INFORMATION: Engineered polypeptide

<400> SEQUENCE: 372

Val Asp Asn Lys Phe Asn Lys Glu Leu Ile Lys Ala Ala Ala Glu Ile
1               5                   10                  15

Asp Ala Leu Pro Asn Leu Asn Arg Arg Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 373
<211> LENGTH: 58
<212> TYPE: PRT
<213> ORGANISM: Artificial
<220> FEATURE:
<223> OTHER INFORMATION: Engineered polypeptide

<400> SEQUENCE: 373

Val Asp Asn Lys Phe Asn Lys Glu Arg Ile His Ala Ala Arg Glu Ile
1               5                   10                  15

Asp Ala Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

```
Lys Lys Leu Asn Asp Ala Gln Ala Pro Lys
    50                  55

<210> SEQ ID NO 374
<211> LENGTH: 58
<212> TYPE: PRT
<213> ORGANISM: Artificial
<220> FEATURE:
<223> OTHER INFORMATION: Engineered polypeptide

<400> SEQUENCE: 374

Val Asp Asn Lys Phe Asn Lys Glu Leu Ile Lys Ala Ala Glu Ile
1               5                   10                  15

Asp Gly Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 375
<211> LENGTH: 58
<212> TYPE: PRT
<213> ORGANISM: Artificial
<220> FEATURE:
<223> OTHER INFORMATION: Engineered polypeptide

<400> SEQUENCE: 375

Val Asp Asn Lys Phe Asn Lys Glu Leu Val Glu Ala Ala Arg Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 376
<211> LENGTH: 58
<212> TYPE: PRT
<213> ORGANISM: Artificial
<220> FEATURE:
<223> OTHER INFORMATION: Engineered polypeptide

<400> SEQUENCE: 376

Val Asp Asn Lys Phe Asn Lys Glu Leu Ile Lys Ala Ala Arg Glu Ile
1               5                   10                  15

Asp Glu Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 377
<211> LENGTH: 58
<212> TYPE: PRT
<213> ORGANISM: Artificial
<220> FEATURE:
<223> OTHER INFORMATION: Engineered polypeptide

<400> SEQUENCE: 377
```

Val Asp Asn Lys Phe Asn Lys Glu Leu Leu Ala Ala Ala Glu Ile
1               5                   10                  15

Asp Ser Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 378
<211> LENGTH: 58
<212> TYPE: PRT
<213> ORGANISM: Artificial
<220> FEATURE:
<223> OTHER INFORMATION: Engineered polypeptide

<400> SEQUENCE: 378

Val Asp Asn Lys Phe Asn Lys Glu Leu Ile Asn Ala Ala Lys Glu Ile
1               5                   10                  15

Asp Asp Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 379
<211> LENGTH: 58
<212> TYPE: PRT
<213> ORGANISM: Artificial
<220> FEATURE:
<223> OTHER INFORMATION: Engineered polypeptide

<400> SEQUENCE: 379

Val Asp Asn Lys Phe Asn Lys Glu Leu Val Glu Ala Ala Arg Glu Ile
1               5                   10                  15

Asp Ala Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 380
<211> LENGTH: 58
<212> TYPE: PRT
<213> ORGANISM: Artificial
<220> FEATURE:
<223> OTHER INFORMATION: Engineered polypeptide

<400> SEQUENCE: 380

Val Asp Asn Lys Phe Asn Lys Glu Leu Arg Asp Ala Ala Ala Glu Ile
1               5                   10                  15

Asp Arg Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 381
<211> LENGTH: 58
<212> TYPE: PRT
<213> ORGANISM: Artificial
<220> FEATURE:
<223> OTHER INFORMATION: Engineered polypeptide

<400> SEQUENCE: 381

Val Asp Asn Lys Phe Asn Lys Glu Leu Ser Ala Ala Arg Glu Ile
1               5                   10                  15

Asp Asn Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 382
<211> LENGTH: 58
<212> TYPE: PRT
<213> ORGANISM: Artificial
<220> FEATURE:
<223> OTHER INFORMATION: Engineered polypeptide

<400> SEQUENCE: 382

Val Asp Asn Lys Phe Asn Lys Glu Leu Ile Ser Ala Ala Glu Glu Ile
1               5                   10                  15

Asp Asp Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 383
<211> LENGTH: 58
<212> TYPE: PRT
<213> ORGANISM: Artificial
<220> FEATURE:
<223> OTHER INFORMATION: Engineered polypeptide

<400> SEQUENCE: 383

Val Asp Asn Lys Phe Asn Lys Glu Leu Val Asp Ala Ala Arg Glu Ile
1               5                   10                  15

Asp Glu Leu Pro Asn Leu Asn Arg Val Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 384
<211> LENGTH: 58
<212> TYPE: PRT
<213> ORGANISM: Artificial
<220> FEATURE:
<223> OTHER INFORMATION: Engineered polypeptide

<400> SEQUENCE: 384

Val Asp Asn Lys Phe Asn Lys Glu Leu Ile Glu Ala Ala Arg Glu Ile
1               5                   10                  15

Asp Ala Leu Pro Asn Leu Asn Arg Ser Gln Trp Asn Ala Phe Ile Lys
```

```
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 385
<211> LENGTH: 58
<212> TYPE: PRT
<213> ORGANISM: Artificial
<220> FEATURE:
<223> OTHER INFORMATION: Engineered polypeptide

<400> SEQUENCE: 385

```
Val Asp Asn Lys Phe Asn Lys Glu Leu Val Glu Ala Ala Lys Glu Ile
1               5                   10                  15

Asp Lys Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 386
<211> LENGTH: 58
<212> TYPE: PRT
<213> ORGANISM: Artificial
<220> FEATURE:
<223> OTHER INFORMATION: Engineered polypeptide

<400> SEQUENCE: 386

```
Val Asp Asn Lys Phe Asn Lys Glu Leu Arg Gln Ala Ala Lys Glu Ile
1               5                   10                  15

Asp Asn Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 387
<211> LENGTH: 58
<212> TYPE: PRT
<213> ORGANISM: Artificial
<220> FEATURE:
<223> OTHER INFORMATION: Engineered polypeptide

<400> SEQUENCE: 387

```
Val Asp Asn Lys Phe Asn Lys Glu Leu Val Ala Ala Ala Arg Glu Ile
1               5                   10                  15

Asp Ser Leu Pro Asn Leu Asn Arg Thr Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 388
<211> LENGTH: 58
<212> TYPE: PRT
<213> ORGANISM: Artificial

```
<220> FEATURE:
<223> OTHER INFORMATION: Engineered polypeptide

<400> SEQUENCE: 388

Val Asp Asn Lys Phe Asn Lys Glu Leu Arg Asn Ala Ala Lys Glu Ile
1               5                   10                  15

Asp Ser Leu Pro Asn Leu Asn Arg Arg Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 389
<211> LENGTH: 58
<212> TYPE: PRT
<213> ORGANISM: Artificial
<220> FEATURE:
<223> OTHER INFORMATION: Engineered polypeptide

<400> SEQUENCE: 389

Val Asp Asn Lys Phe Asn Lys Glu Leu Val Gln Ala Ala Arg Glu Ile
1               5                   10                  15

Asp Glu Leu Pro Asn Leu Asn Arg Thr Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 390
<211> LENGTH: 58
<212> TYPE: PRT
<213> ORGANISM: Artificial
<220> FEATURE:
<223> OTHER INFORMATION: Engineered polypeptide

<400> SEQUENCE: 390

Val Asp Asn Lys Phe Asn Lys Glu Leu Arg Glu Ala Ala Glu Glu Ile
1               5                   10                  15

Asp Asn Leu Pro Asn Leu Asn Arg Val Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 391
<211> LENGTH: 58
<212> TYPE: PRT
<213> ORGANISM: Artificial
<220> FEATURE:
<223> OTHER INFORMATION: Engineered polypeptide

<400> SEQUENCE: 391

Val Asp Asn Lys Phe Asn Lys Glu Leu Ile Glu Ala Ala Arg Glu Ile
1               5                   10                  15

Asp Asn Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45
```

Lys Lys Leu Asn Asp Ala Gln Ala Pro Lys
    50                  55

<210> SEQ ID NO 392
<211> LENGTH: 58
<212> TYPE: PRT
<213> ORGANISM: Artificial
<220> FEATURE:
<223> OTHER INFORMATION: Engineered polypeptide

<400> SEQUENCE: 392

Val Asp Asn Lys Phe Asn Lys Glu Leu Ile Asn Ala Ala Arg Glu Ile
1               5                   10                  15

Asp Gly Leu Pro Asn Leu Asn Arg Met Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 393
<211> LENGTH: 58
<212> TYPE: PRT
<213> ORGANISM: Artificial
<220> FEATURE:
<223> OTHER INFORMATION: Engineered polypeptide

<400> SEQUENCE: 393

Val Asp Asn Lys Phe Asn Lys Glu Arg Ile Ala Ala Ala Gln Glu Ile
1               5                   10                  15

Asp Gly Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 394
<211> LENGTH: 58
<212> TYPE: PRT
<213> ORGANISM: Artificial
<220> FEATURE:
<223> OTHER INFORMATION: Engineered polypeptide

<400> SEQUENCE: 394

Val Asp Asn Lys Phe Asn Lys Glu Leu Ile Asn Ala Ala Lys Glu Ile
1               5                   10                  15

Asp Asp Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 395
<211> LENGTH: 58
<212> TYPE: PRT
<213> ORGANISM: Artificial
<220> FEATURE:
<223> OTHER INFORMATION: Engineered polypeptide

<400> SEQUENCE: 395

Val Asp Asn Lys Phe Asn Lys Glu Arg Ser His Ala Ala Gln Glu Ile
1               5                   10                  15

Asp Ala Leu Pro Asn Leu Asn Arg Val Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 396
<211> LENGTH: 58
<212> TYPE: PRT
<213> ORGANISM: Artificial
<220> FEATURE:
<223> OTHER INFORMATION: Engineered polypeptide

<400> SEQUENCE: 396

Val Asp Asn Lys Phe Asn Lys Glu Leu Ile Ala Ala Lys Glu Ile
1               5                   10                  15

Asp Glu Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 397
<211> LENGTH: 58
<212> TYPE: PRT
<213> ORGANISM: Artificial
<220> FEATURE:
<223> OTHER INFORMATION: Engineered polypeptide

<400> SEQUENCE: 397

Val Asp Asn Lys Phe Asn Lys Glu Arg Ile Arg Ala Ala Glu Glu Ile
1               5                   10                  15

Asp Gly Leu Pro Asn Leu Asn Arg Trp Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 398
<211> LENGTH: 58
<212> TYPE: PRT
<213> ORGANISM: Artificial
<220> FEATURE:
<223> OTHER INFORMATION: Engineered polypeptide

<400> SEQUENCE: 398

Val Asp Asn Lys Phe Asn Lys Glu Leu Val Gln Ala Ala Arg Glu Ile
1               5                   10                  15

Asp Ala Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 399
<211> LENGTH: 58
<212> TYPE: PRT
<213> ORGANISM: Artificial
<220> FEATURE:
<223> OTHER INFORMATION: Engineered polypeptide

<400> SEQUENCE: 399

Val Asp Asn Lys Phe Asn Lys Glu Arg Arg Glu Ala Ala Arg Glu Ile
1               5                   10                  15

Asp Asn Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 400
<211> LENGTH: 58
<212> TYPE: PRT
<213> ORGANISM: Artificial
<220> FEATURE:
<223> OTHER INFORMATION: Engineered polypeptide

<400> SEQUENCE: 400

Val Asp Asn Lys Phe Asn Lys Glu Leu Arg Trp Ala Ala Gly Glu Ile
1               5                   10                  15

Asp Lys Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 401
<211> LENGTH: 58
<212> TYPE: PRT
<213> ORGANISM: Artificial
<220> FEATURE:
<223> OTHER INFORMATION: Engineered polypeptide

<400> SEQUENCE: 401

Val Asp Asn Lys Phe Asn Lys Glu Leu Ser Arg Ala Ala Glu Glu Ile
1               5                   10                  15

Asp Arg Leu Pro Asn Leu Asn Arg Val Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 402
<211> LENGTH: 58
<212> TYPE: PRT
<213> ORGANISM: Artificial
<220> FEATURE:
<223> OTHER INFORMATION: Engineered polypeptide

<400> SEQUENCE: 402

Val Asp Asn Lys Phe Asn Lys Glu Leu Ile Glu Ala Ala Arg Glu Ile
1               5                   10                  15

Asp Glu Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 403
<211> LENGTH: 58
<212> TYPE: PRT
<213> ORGANISM: Artificial
<220> FEATURE:
<223> OTHER INFORMATION: Engineered polypeptide

<400> SEQUENCE: 403

Val Asp Asn Lys Phe Asn Lys Glu Leu Ile Ala Ala Lys Glu Ile
1               5                   10                  15

Asp Asp Leu Pro Asn Leu Asn Arg Glu Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 404
<211> LENGTH: 58
<212> TYPE: PRT
<213> ORGANISM: Artificial
<220> FEATURE:
<223> OTHER INFORMATION: Engineered polypeptide

<400> SEQUENCE: 404

Val Asp Asn Lys Phe Asn Lys Glu Arg Val Arg Ala Ala Glu Glu Ile
1               5                   10                  15

Asp Ser Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 405
<211> LENGTH: 58
<212> TYPE: PRT
<213> ORGANISM: Artificial
<220> FEATURE:
<223> OTHER INFORMATION: Engineered polypeptide

<400> SEQUENCE: 405

Val Asp Asn Lys Phe Asn Lys Glu Leu Ile Asp Ala Ala Glu Ile
1               5                   10                  15

Asp Lys Leu Pro Asn Leu Asn Arg Gly Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 406
<211> LENGTH: 58
<212> TYPE: PRT

<213> ORGANISM: Artificial
<220> FEATURE:
<223> OTHER INFORMATION: Engineered polypeptide

<400> SEQUENCE: 406

Val Asp Asn Lys Phe Asn Lys Glu Leu Ile Asp Ala Ala Ala Glu Ile
1               5                   10                  15

Asp Lys Leu Pro Asn Leu Asn Arg Ser Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 407
<211> LENGTH: 58
<212> TYPE: PRT
<213> ORGANISM: Artificial
<220> FEATURE:
<223> OTHER INFORMATION: Engineered polypeptide

<400> SEQUENCE: 407

Val Asp Asn Lys Phe Asn Lys Glu Leu Ile Glu Ala Ala Glu Glu Ile
1               5                   10                  15

Asp Arg Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 408
<211> LENGTH: 58
<212> TYPE: PRT
<213> ORGANISM: Artificial
<220> FEATURE:
<223> OTHER INFORMATION: Engineered polypeptide

<400> SEQUENCE: 408

Val Asp Asn Lys Phe Asn Lys Glu Leu Ile Glu Ala Ala Arg Glu Ile
1               5                   10                  15

Asp Glu Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 409
<211> LENGTH: 58
<212> TYPE: PRT
<213> ORGANISM: Artificial
<220> FEATURE:
<223> OTHER INFORMATION: Engineered polypeptide

<400> SEQUENCE: 409

Val Asp Asn Lys Phe Asn Lys Glu Leu Arg Glu Ala Ala Glu Glu Ile
1               5                   10                  15

Asp Ser Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala

```
                    35                  40                  45

Lys Lys Leu Asn Asp Ala Gln Ala Pro Lys
    50                  55

<210> SEQ ID NO 410
<211> LENGTH: 58
<212> TYPE: PRT
<213> ORGANISM: Artificial
<220> FEATURE:
<223> OTHER INFORMATION: Engineered polypeptide

<400> SEQUENCE: 410

Val Asp Asn Lys Phe Asn Lys Glu Leu Val Asp Ala Ala Arg Glu Ile
1               5                   10                  15

Asp Asp Leu Pro Asn Leu Asn Arg Gly Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 411
<211> LENGTH: 58
<212> TYPE: PRT
<213> ORGANISM: Artificial
<220> FEATURE:
<223> OTHER INFORMATION: Engineered polypeptide

<400> SEQUENCE: 411

Val Asp Asn Lys Phe Asn Lys Glu Leu Arg Glu Ala Ala Ala Glu Ile
1               5                   10                  15

Asp Ala Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 412
<211> LENGTH: 58
<212> TYPE: PRT
<213> ORGANISM: Artificial
<220> FEATURE:
<223> OTHER INFORMATION: Engineered polypeptide

<400> SEQUENCE: 412

Val Asp Asn Lys Phe Asn Lys Glu Leu Ile Glu Ala Ala Ala Glu Ile
1               5                   10                  15

Asp Lys Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 413
<211> LENGTH: 58
<212> TYPE: PRT
<213> ORGANISM: Artificial
<220> FEATURE:
<223> OTHER INFORMATION: Engineered polypeptide
```

```
<400> SEQUENCE: 413

Val Asp Asn Lys Phe Asn Lys Glu Leu Arg Glu Ala Ala Gly Glu Ile
1               5                   10                  15

Asp Arg Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 414
<211> LENGTH: 58
<212> TYPE: PRT
<213> ORGANISM: Artificial
<220> FEATURE:
<223> OTHER INFORMATION: Engineered polypeptide

<400> SEQUENCE: 414

Val Asp Asn Lys Phe Asn Lys Glu Leu Val Arg Ala Ala Glu Glu Ile
1               5                   10                  15

Asp Ala Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 415
<211> LENGTH: 58
<212> TYPE: PRT
<213> ORGANISM: Artificial
<220> FEATURE:
<223> OTHER INFORMATION: Engineered polypeptide

<400> SEQUENCE: 415

Val Asp Asn Lys Phe Asn Lys Glu Arg Ser Arg Ala Ala Ala Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 416
<211> LENGTH: 58
<212> TYPE: PRT
<213> ORGANISM: Artificial
<220> FEATURE:
<223> OTHER INFORMATION: Engineered polypeptide

<400> SEQUENCE: 416

Val Asp Asn Lys Phe Asn Lys Glu Leu Ile Arg Ala Ala Ser Glu Ile
1               5                   10                  15

Asp Lys Leu Pro Asn Leu Asn Arg Arg Gln Trp Asn Ala Phe Ile Lys
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 417
<211> LENGTH: 58
<212> TYPE: PRT
<213> ORGANISM: Artificial
<220> FEATURE:
<223> OTHER INFORMATION: Engineered polypeptide

<400> SEQUENCE: 417

Val Asp Asn Lys Phe Asn Lys Glu Leu Ile Lys Ala Ala Gln Glu Ile
1               5                   10                  15

Asp Arg Leu Pro Asn Leu Asn Arg Thr Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 418
<211> LENGTH: 58
<212> TYPE: PRT
<213> ORGANISM: Artificial
<220> FEATURE:
<223> OTHER INFORMATION: Engineered polypeptide

<400> SEQUENCE: 418

Val Asp Asn Lys Phe Asn Lys Glu Leu Ile Glu Ala Ala Ala Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 419
<211> LENGTH: 58
<212> TYPE: PRT
<213> ORGANISM: Artificial
<220> FEATURE:
<223> OTHER INFORMATION: Engineered polypeptide

<400> SEQUENCE: 419

Val Asp Asn Lys Phe Asn Lys Glu Leu Ile Trp Ala Ala Gly Glu Ile
1               5                   10                  15

Asp Lys Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 420
<211> LENGTH: 58
<212> TYPE: PRT
<213> ORGANISM: Artificial
<220> FEATURE:
<223> OTHER INFORMATION: Engineered polypeptide

<400> SEQUENCE: 420

Val Asp Asn Lys Phe Asn Lys Glu Arg Leu Ala Ala Ala Glu Glu Ile
1               5                   10                  15

Asp Asn Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 421
<211> LENGTH: 58
<212> TYPE: PRT
<213> ORGANISM: Artificial
<220> FEATURE:
<223> OTHER INFORMATION: Engineered polypeptide

<400> SEQUENCE: 421

Val Asp Asn Lys Phe Asn Lys Glu Leu Arg Lys Ala Ala Glu Glu Ile
1               5                   10                  15

Asp Ala Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 422
<211> LENGTH: 58
<212> TYPE: PRT
<213> ORGANISM: Artificial
<220> FEATURE:
<223> OTHER INFORMATION: Engineered polypeptide

<400> SEQUENCE: 422

Val Asp Asn Lys Phe Asn Lys Glu Leu Ile Ala Ala Ala Arg Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 423
<211> LENGTH: 58
<212> TYPE: PRT
<213> ORGANISM: Artificial
<220> FEATURE:
<223> OTHER INFORMATION: Engineered polypeptide

<400> SEQUENCE: 423

Val Asp Asn Lys Phe Asn Lys Glu Arg Val Lys Ala Ala Glu Glu Ile
1               5                   10                  15

Asp Lys Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 424
<211> LENGTH: 58

```
<212> TYPE: PRT
<213> ORGANISM: Artificial
<220> FEATURE:
<223> OTHER INFORMATION: Engineered polypeptide

<400> SEQUENCE: 424

Val Asp Asn Lys Phe Asn Lys Glu Leu Ile His Ala Ala Glu Glu Ile
1               5                   10                  15

Asp Arg Leu Pro Asn Leu Asn Arg Asn Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 425
<211> LENGTH: 58
<212> TYPE: PRT
<213> ORGANISM: Artificial
<220> FEATURE:
<223> OTHER INFORMATION: Engineered polypeptide

<400> SEQUENCE: 425

Val Asp Asn Lys Phe Asn Lys Glu Leu Ile Asn Ala Ala Gly Glu Ile
1               5                   10                  15

Asp Lys Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 426
<211> LENGTH: 58
<212> TYPE: PRT
<213> ORGANISM: Artificial
<220> FEATURE:
<223> OTHER INFORMATION: Engineered polypeptide

<400> SEQUENCE: 426

Val Asp Asn Lys Phe Asn Lys Glu Leu Ile Glu Ala Ala Ala Glu Ile
1               5                   10                  15

Asp Ala Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 427
<211> LENGTH: 58
<212> TYPE: PRT
<213> ORGANISM: Artificial
<220> FEATURE:
<223> OTHER INFORMATION: Engineered polypeptide

<400> SEQUENCE: 427

Val Asp Asn Lys Phe Asn Lys Glu Leu Ile Ala Ala Ala Arg Glu Ile
1               5                   10                  15

Asp Ser Leu Pro Asn Leu Asn Arg Arg Gln Trp Asn Ala Phe Ile Lys
            20                  25                  30
```

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 428
<211> LENGTH: 58
<212> TYPE: PRT
<213> ORGANISM: Artificial
<220> FEATURE:
<223> OTHER INFORMATION: Engineered polypeptide

<400> SEQUENCE: 428

Val Asp Asn Lys Phe Asn Lys Glu Arg Val Asp Ala Ala Arg Glu Ile
1               5                   10                  15

Asp Asn Leu Pro Asn Leu Asn Arg Glu Gln Trp Asn Ala Phe Ile Arg
             20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 429
<211> LENGTH: 58
<212> TYPE: PRT
<213> ORGANISM: Artificial
<220> FEATURE:
<223> OTHER INFORMATION: Engineered polypeptide

<400> SEQUENCE: 429

Val Asp Asn Lys Phe Asn Lys Glu Leu Arg Asp Ala Ala Ala Glu Ile
1               5                   10                  15

Asp Arg Leu Pro Asn Leu Asn Arg Lys Gln Trp Asn Ala Phe Ile Lys
             20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 430
<211> LENGTH: 58
<212> TYPE: PRT
<213> ORGANISM: Artificial
<220> FEATURE:
<223> OTHER INFORMATION: Engineered polypeptide

<400> SEQUENCE: 430

Val Asp Asn Lys Phe Asn Lys Glu Leu Ile Ala Ala Ala Ala Glu Ile
1               5                   10                  15

Asp Arg Leu Pro Asn Leu Asn Arg Val Gln Trp Asn Ala Phe Ile Lys
             20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 431
<211> LENGTH: 58
<212> TYPE: PRT
<213> ORGANISM: Artificial
<220> FEATURE:
<223> OTHER INFORMATION: Engineered polypeptide

<400> SEQUENCE: 431

Val Asp Asn Lys Phe Asn Lys Glu Leu Arg Ala Ala Ala Glu Ile
1               5                   10                  15

Asp Lys Leu Pro Asn Leu Asn Arg Arg Gln Trp Asn Ala Phe Ile Lys
            20                  25                  30

Ser Leu Ile Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 432
<211> LENGTH: 58
<212> TYPE: PRT
<213> ORGANISM: Artificial
<220> FEATURE:
<223> OTHER INFORMATION: Engineered polypeptide

<400> SEQUENCE: 432

Val Asp Asn Lys Phe Asn Lys Glu Leu Ile Trp Ala Ala Ala Glu Ile
1               5                   10                  15

Asp Arg Leu Pro Asn Leu Asn Arg Glu Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 433
<211> LENGTH: 58
<212> TYPE: PRT
<213> ORGANISM: Artificial
<220> FEATURE:
<223> OTHER INFORMATION: Engineered polypeptide

<400> SEQUENCE: 433

Val Asp Asn Lys Phe Asn Lys Glu Leu Arg Ala Ala Ala Lys Glu Ile
1               5                   10                  15

Asp Asn Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 434
<211> LENGTH: 58
<212> TYPE: PRT
<213> ORGANISM: Artificial
<220> FEATURE:
<223> OTHER INFORMATION: Engineered polypeptide

<400> SEQUENCE: 434

Val Asp Asn Lys Phe Asn Lys Glu Leu Val Gln Ala Ala Lys Glu Ile
1               5                   10                  15

Asp Asn Leu Pro Asn Leu Asn Arg Ser Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys

<210> SEQ ID NO 435
<211> LENGTH: 58
<212> TYPE: PRT
<213> ORGANISM: Artificial
<220> FEATURE:
<223> OTHER INFORMATION: Engineered polypeptide

<400> SEQUENCE: 435

Val Asp Asn Lys Phe Asn Lys Glu Leu Ile Glu Ala Ala Gly Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 436
<211> LENGTH: 58
<212> TYPE: PRT
<213> ORGANISM: Artificial
<220> FEATURE:
<223> OTHER INFORMATION: Engineered polypeptide

<400> SEQUENCE: 436

Val Asp Asn Lys Phe Asn Lys Glu Leu Val Lys Ala Ala Ala Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 437
<211> LENGTH: 58
<212> TYPE: PRT
<213> ORGANISM: Artificial
<220> FEATURE:
<223> OTHER INFORMATION: Engineered polypeptide

<400> SEQUENCE: 437

Val Asp Asn Lys Phe Asn Lys Glu Leu Arg Glu Ala Ala Arg Glu Ile
1               5                   10                  15

Asp Ser Leu Pro Asn Leu Asn Arg Ser Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 438
<211> LENGTH: 58
<212> TYPE: PRT
<213> ORGANISM: Artificial
<220> FEATURE:
<223> OTHER INFORMATION: Engineered polypeptide

<400> SEQUENCE: 438

Val Asp Asn Lys Phe Asn Lys Glu Leu Leu Glu Ala Ala Lys Glu Ile

```
1               5                   10                  15
Asp Glu Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 439
<211> LENGTH: 58
<212> TYPE: PRT
<213> ORGANISM: Artificial
<220> FEATURE:
<223> OTHER INFORMATION: Engineered polypeptide

<400> SEQUENCE: 439

Val Asp Asn Lys Phe Asn Lys Glu Leu Val Glu Ala Ala Arg Glu Ile
1               5                   10                  15

Asp Glu Leu Pro Asn Leu Asn Arg Ser Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 440
<211> LENGTH: 58
<212> TYPE: PRT
<213> ORGANISM: Artificial
<220> FEATURE:
<223> OTHER INFORMATION: Engineered polypeptide

<400> SEQUENCE: 440

Val Asp Asn Lys Phe Asn Lys Glu Leu Arg Glu Ala Ala Ala Glu Ile
1               5                   10                  15

Asp Ala Leu Pro Asn Leu Asn Arg Ser Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 441
<211> LENGTH: 58
<212> TYPE: PRT
<213> ORGANISM: Artificial
<220> FEATURE:
<223> OTHER INFORMATION: Engineered polypeptide

<400> SEQUENCE: 441

Val Asp Asn Lys Phe Asn Lys Glu Leu Val Arg Ala Ala Glu Glu Ile
1               5                   10                  15

Asp Arg Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 442
```

```
<211> LENGTH: 58
<212> TYPE: PRT
<213> ORGANISM: Artificial
<220> FEATURE:
<223> OTHER INFORMATION: Engineered polypeptide

<400> SEQUENCE: 442

Val Asp Asn Lys Phe Asn Lys Glu Leu Arg Ala Ala Ala Ala Glu Ile
1               5                   10                  15

Asp Ser Leu Pro Asn Leu Asn Arg Gly Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 443
<211> LENGTH: 58
<212> TYPE: PRT
<213> ORGANISM: Artificial
<220> FEATURE:
<223> OTHER INFORMATION: Engineered polypeptide

<400> SEQUENCE: 443

Val Asp Asn Lys Phe Asn Lys Glu Leu Ile Arg Ala Ala Arg Glu Ile
1               5                   10                  15

Asp Glu Leu Pro Asn Leu Asn Arg Met Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 444
<211> LENGTH: 58
<212> TYPE: PRT
<213> ORGANISM: Artificial
<220> FEATURE:
<223> OTHER INFORMATION: Engineered polypeptide

<400> SEQUENCE: 444

Val Asp Asn Lys Phe Asn Lys Glu Leu Arg Asp Ala Ala Arg Glu Ile
1               5                   10                  15

Asp Ser Leu Pro Asn Leu Asn Arg Arg Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 445
<211> LENGTH: 58
<212> TYPE: PRT
<213> ORGANISM: Artificial
<220> FEATURE:
<223> OTHER INFORMATION: Engineered polypeptide

<400> SEQUENCE: 445

Val Asp Asn Lys Phe Asn Lys Glu Leu Arg Glu Ala Ala Arg Glu Ile
1               5                   10                  15

Asp Glu Leu Pro Asn Leu Asn Arg Arg Gln Trp Asn Ala Phe Ile Lys
            20                  25                  30
```

```
Ser Leu Val Asp Asp Pro Ser Gln Ser Ala Asn Leu Leu Ala Glu Ala
        35                  40                  45

Lys Lys Leu Asn Asp Ala Gln Ala Pro Lys
 50                  55
```

<210> SEQ ID NO 446
<211> LENGTH: 58
<212> TYPE: PRT
<213> ORGANISM: Artificial
<220> FEATURE:
<223> OTHER INFORMATION: Engineered polypeptide

<400> SEQUENCE: 446

```
Val Asp Asn Lys Phe Asn Lys Glu Leu Ile Arg Ala Ala Glu Glu Ile
 1               5                  10                  15

Asp Lys Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
 50                  55
```

<210> SEQ ID NO 447
<211> LENGTH: 58
<212> TYPE: PRT
<213> ORGANISM: Artificial
<220> FEATURE:
<223> OTHER INFORMATION: Engineered polypeptide

<400> SEQUENCE: 447

```
Val Asp Asn Lys Phe Asn Lys Glu Leu Leu Lys Ala Ala Arg Glu Ile
 1               5                  10                  15

Asp Glu Leu Pro Asn Leu Asn Arg Arg Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
 50                  55
```

<210> SEQ ID NO 448
<211> LENGTH: 58
<212> TYPE: PRT
<213> ORGANISM: Artificial
<220> FEATURE:
<223> OTHER INFORMATION: Engineered polypeptide

<400> SEQUENCE: 448

```
Val Asp Asn Lys Phe Asn Lys Glu Leu Ile Ala Ala Ala Arg Glu Ile
 1               5                  10                  15

Asp Gly Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
 50                  55
```

<210> SEQ ID NO 449
<211> LENGTH: 58
<212> TYPE: PRT
<213> ORGANISM: Artificial
<220> FEATURE:

<223> OTHER INFORMATION: Engineered polypeptide

<400> SEQUENCE: 449

Val Asp Asn Lys Phe Asn Lys Glu Leu Val Ala Ala Ala Glu Ile
1               5                   10                  15

Asp Gly Leu Pro Asn Leu Asn Arg Lys Gln Trp Asn Ala Phe Ile His
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 450
<211> LENGTH: 58
<212> TYPE: PRT
<213> ORGANISM: Artificial
<220> FEATURE:
<223> OTHER INFORMATION: Engineered polypeptide

<400> SEQUENCE: 450

Val Asp Asn Lys Phe Asn Lys Glu Leu Arg Asp Ala Ala Arg Glu Ile
1               5                   10                  15

Asp Ala Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 451
<211> LENGTH: 58
<212> TYPE: PRT
<213> ORGANISM: Artificial
<220> FEATURE:
<223> OTHER INFORMATION: Engineered polypeptide

<400> SEQUENCE: 451

Val Asp Asn Lys Phe Asn Lys Glu Arg Ile Asn Ala Ala Lys Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 452
<211> LENGTH: 58
<212> TYPE: PRT
<213> ORGANISM: Artificial
<220> FEATURE:
<223> OTHER INFORMATION: Engineered polypeptide

<400> SEQUENCE: 452

Val Asp Asn Lys Phe Asn Lys Glu Leu Arg Gln Ala Ala Ala Glu Ile
1               5                   10                  15

Asp Ala Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
        35                  40                  45

```
Lys Lys Leu Asn Asp Ala Gln Ala Pro Lys
    50                  55
```

<210> SEQ ID NO 453
<211> LENGTH: 58
<212> TYPE: PRT
<213> ORGANISM: Artificial
<220> FEATURE:
<223> OTHER INFORMATION: Engineered polypeptide

<400> SEQUENCE: 453

```
Val Asp Asn Lys Phe Asn Lys Glu Leu Val Glu Ala Ala Ala Glu Ile
1               5                   10                  15

Asp Arg Leu Pro Asn Leu Asn Arg Gly Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 454
<211> LENGTH: 58
<212> TYPE: PRT
<213> ORGANISM: Artificial
<220> FEATURE:
<223> OTHER INFORMATION: Engineered polypeptide

<400> SEQUENCE: 454

```
Val Asp Asn Lys Phe Asn Lys Glu Leu Arg Glu Ala Ala Ala Glu Ile
1               5                   10                  15

Asp Arg Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 455
<211> LENGTH: 58
<212> TYPE: PRT
<213> ORGANISM: Artificial
<220> FEATURE:
<223> OTHER INFORMATION: Engineered polypeptide

<400> SEQUENCE: 455

```
Val Asp Asn Lys Phe Asn Lys Glu Leu Ile Gln Ala Ala Lys Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 456
<211> LENGTH: 58
<212> TYPE: PRT
<213> ORGANISM: Artificial
<220> FEATURE:
<223> OTHER INFORMATION: Engineered polypeptide

<400> SEQUENCE: 456

-continued

Val Asp Asn Lys Phe Asn Lys Glu Arg Ser Met Ala Ala Lys Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 457
<211> LENGTH: 58
<212> TYPE: PRT
<213> ORGANISM: Artificial
<220> FEATURE:
<223> OTHER INFORMATION: Engineered polypeptide

<400> SEQUENCE: 457

Val Asp Asn Lys Phe Asn Lys Glu Leu Val Ala Ala Arg Glu Ile
1               5                   10                  15

Asp Asp Leu Pro Asn Leu Asn Arg Lys Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 458
<211> LENGTH: 58
<212> TYPE: PRT
<213> ORGANISM: Artificial
<220> FEATURE:
<223> OTHER INFORMATION: Engineered polypeptide

<400> SEQUENCE: 458

Val Asp Asn Lys Phe Asn Lys Glu Leu Val Arg Ala Ala Glu Ile
1               5                   10                  15

Asp Arg Leu Pro Asn Leu Asn Arg Leu Gln Trp Asn Ala Phe Ile Lys
            20                  25                  30

Ser Leu Ile Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 459
<211> LENGTH: 58
<212> TYPE: PRT
<213> ORGANISM: Artificial
<220> FEATURE:
<223> OTHER INFORMATION: Engineered polypeptide

<400> SEQUENCE: 459

Val Asp Asn Lys Phe Asn Lys Glu Leu Arg Glu Ala Ala Ala Glu Ile
1               5                   10                  15

Asp Asp Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 460
<211> LENGTH: 58
<212> TYPE: PRT
<213> ORGANISM: Artificial
<220> FEATURE:
<223> OTHER INFORMATION: Engineered polypeptide

<400> SEQUENCE: 460

Val Asp Asn Lys Phe Asn Lys Glu Leu Val Glu Ala Ala Lys Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 461
<211> LENGTH: 58
<212> TYPE: PRT
<213> ORGANISM: Artificial
<220> FEATURE:
<223> OTHER INFORMATION: Engineered polypeptide

<400> SEQUENCE: 461

Val Asp Asn Lys Phe Asn Lys Glu Leu Ile Asn Ala Ala Gly Glu Ile
1               5                   10                  15

Asp Arg Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 462
<211> LENGTH: 58
<212> TYPE: PRT
<213> ORGANISM: Artificial
<220> FEATURE:
<223> OTHER INFORMATION: Engineered polypeptide

<400> SEQUENCE: 462

Val Asp Asn Lys Phe Asn Lys Glu Leu Leu Ser Ala Ala Ala Glu Ile
1               5                   10                  15

Asp Ser Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 463
<211> LENGTH: 58
<212> TYPE: PRT
<213> ORGANISM: Artificial
<220> FEATURE:
<223> OTHER INFORMATION: Engineered polypeptide

<400> SEQUENCE: 463

Val Asp Asn Lys Phe Asn Lys Glu Leu Arg Asp Ala Ala Ala Glu Ile
1               5                   10                  15

Asp Lys Leu Pro Asn Leu Asn Arg Arg Gln Trp Asn Ala Phe Ile Lys
```

20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 464
<211> LENGTH: 58
<212> TYPE: PRT
<213> ORGANISM: Artificial
<220> FEATURE:
<223> OTHER INFORMATION: Engineered polypeptide

<400> SEQUENCE: 464

Val Asp Asn Lys Phe Asn Lys Glu Leu Arg Gln Ala Ala Ala Glu Ile
1               5                   10                  15

Asp Lys Leu Pro Asn Leu Asn Arg Ser Gln Trp Asn Ala Phe Ile Gln
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 465
<211> LENGTH: 58
<212> TYPE: PRT
<213> ORGANISM: Artificial
<220> FEATURE:
<223> OTHER INFORMATION: Engineered polypeptide

<400> SEQUENCE: 465

Val Asp Asn Lys Phe Asn Lys Glu Leu Arg Glu Ala Ala Ala Glu Ile
1               5                   10                  15

Asp Ala Leu Pro Asn Leu Asn Arg Val Gln Trp Asn Ala Phe Ile Lys
                20                  25                  30

Ser Leu Arg Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 466
<211> LENGTH: 58
<212> TYPE: PRT
<213> ORGANISM: Artificial
<220> FEATURE:
<223> OTHER INFORMATION: Engineered polypeptide

<400> SEQUENCE: 466

Val Asp Asn Lys Phe Asn Lys Glu Leu Val Ala Ala Ala Glu Glu Ile
1               5                   10                  15

Asp Arg Leu Pro Asn Leu Asn Arg Ala Gln Trp Asn Ala Phe Ile Lys
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 467
<211> LENGTH: 58
<212> TYPE: PRT
<213> ORGANISM: Artificial

```
<220> FEATURE:
<223> OTHER INFORMATION: Engineered polypeptide

<400> SEQUENCE: 467

Val Asp Asn Lys Phe Asn Lys Glu Leu Ile Asp Ala Ala Ala Glu Ile
1               5                   10                  15

Asp Lys Leu Pro Asn Leu Asn Arg Asn Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 468
<211> LENGTH: 58
<212> TYPE: PRT
<213> ORGANISM: Artificial
<220> FEATURE:
<223> OTHER INFORMATION: Engineered polypeptide

<400> SEQUENCE: 468

Val Asp Asn Lys Phe Asn Lys Glu Arg Ile Asn Ala Ala Ala Glu Ile
1               5                   10                  15

Asp Gly Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 469
<211> LENGTH: 58
<212> TYPE: PRT
<213> ORGANISM: Artificial
<220> FEATURE:
<223> OTHER INFORMATION: Engineered polypeptide

<400> SEQUENCE: 469

Val Asp Asn Lys Phe Asn Lys Glu Leu Val Arg Ala Ala Glu Glu Ile
1               5                   10                  15

Asp Asn Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 470
<211> LENGTH: 58
<212> TYPE: PRT
<213> ORGANISM: Artificial
<220> FEATURE:
<223> OTHER INFORMATION: Engineered polypeptide

<400> SEQUENCE: 470

Val Asp Asn Lys Phe Asn Lys Glu Leu Ile Arg Ala Ala Lys Glu Ile
1               5                   10                  15

Asp Glu Leu Pro Asn Leu Asn Arg Arg Gln Trp Asn Ala Phe Ile Arg
            20                  25                  30

Ser Leu Val Asp Asp Pro Ser Gln Ser Ala Asn Leu Leu Ala Glu Ala
        35                  40                  45
```

```
<210> SEQ ID NO 471
<211> LENGTH: 58
<212> TYPE: PRT
<213> ORGANISM: Artificial
<220> FEATURE:
<223> OTHER INFORMATION: Engineered polypeptide

<400> SEQUENCE: 471
```

Val Asp Asn Lys Phe Asn Lys Glu Leu Ile Gln Ala Ala Arg Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 472
<211> LENGTH: 58
<212> TYPE: PRT
<213> ORGANISM: Artificial
<220> FEATURE:
<223> OTHER INFORMATION: Engineered polypeptide

<400> SEQUENCE: 472
```

Val Asp Asn Lys Phe Asn Lys Glu Leu Ile Asp Ala Ala Arg Glu Ile
1               5                   10                  15

Asp Asp Leu Pro Asn Leu Asn Arg Gln Gln Trp Asn Ala Phe Ile Lys
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 473
<211> LENGTH: 58
<212> TYPE: PRT
<213> ORGANISM: Artificial
<220> FEATURE:
<223> OTHER INFORMATION: Engineered polypeptide

<400> SEQUENCE: 473
```

Val Asp Asn Lys Phe Asn Lys Glu Leu Leu Lys Ala Ala Asp Glu Ile
1               5                   10                  15

Asp Ala Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 474
<211> LENGTH: 58
<212> TYPE: PRT
<213> ORGANISM: Artificial
<220> FEATURE:
<223> OTHER INFORMATION: Engineered polypeptide

<400> SEQUENCE: 474
```

```
Val Asp Asn Lys Phe Asn Lys Glu Leu Leu Glu Ala Ala Ala Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 475
<211> LENGTH: 58
<212> TYPE: PRT
<213> ORGANISM: Artificial
<220> FEATURE:
<223> OTHER INFORMATION: Engineered polypeptide

<400> SEQUENCE: 475

Val Asp Asn Lys Phe Asn Lys Glu Leu Val Asp Ala Ala Arg Glu Ile
1               5                   10                  15

Asp Thr Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 476
<211> LENGTH: 58
<212> TYPE: PRT
<213> ORGANISM: Artificial
<220> FEATURE:
<223> OTHER INFORMATION: Engineered polypeptide

<400> SEQUENCE: 476

Val Asp Asn Lys Phe Asn Lys Glu Leu Ile Glu Ala Ala Arg Glu Ile
1               5                   10                  15

Asp Lys Leu Pro Asn Leu Asn Arg Arg Gln Trp Asn Ala Phe Ile Arg
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 477
<211> LENGTH: 58
<212> TYPE: PRT
<213> ORGANISM: Artificial
<220> FEATURE:
<223> OTHER INFORMATION: Engineered polypeptide

<400> SEQUENCE: 477

Val Asp Asn Lys Phe Asn Lys Glu Leu Val Ala Ala Ala Arg Glu Ile
1               5                   10                  15

Asp Asn Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 478
<211> LENGTH: 58
<212> TYPE: PRT
<213> ORGANISM: Artificial
<220> FEATURE:
<223> OTHER INFORMATION: Engineered polypeptide

<400> SEQUENCE: 478

Val Asp Asn Lys Phe Asn Lys Glu Leu Val Glu Ala Ala Ala Glu Ile
1               5                   10                  15

Asp Gly Leu Pro Asn Leu Asn Arg Asp Gln Trp Asn Ala Phe Ile Lys
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 479
<211> LENGTH: 58
<212> TYPE: PRT
<213> ORGANISM: Artificial
<220> FEATURE:
<223> OTHER INFORMATION: Engineered polypeptide

<400> SEQUENCE: 479

Val Asp Asn Lys Phe Asn Lys Glu Leu Arg Asn Ala Ala Lys Glu Ile
1               5                   10                  15

Asp Gly Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 480
<211> LENGTH: 58
<212> TYPE: PRT
<213> ORGANISM: Artificial
<220> FEATURE:
<223> OTHER INFORMATION: Engineered polypeptide

<400> SEQUENCE: 480

Val Asp Asn Lys Phe Asn Lys Glu Leu Arg His Ala Ala Arg Glu Ile
1               5                   10                  15

Asp Gly Leu Pro Asn Leu Asn Arg Thr Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 481
<211> LENGTH: 58
<212> TYPE: PRT
<213> ORGANISM: Artificial
<220> FEATURE:
<223> OTHER INFORMATION: Engineered polypeptide

<400> SEQUENCE: 481

Val Asp Asn Lys Phe Asn Lys Glu Leu Val Glu Ala Ala Arg Glu Ile
1               5                   10                  15

```
Asp Thr Leu Pro Asn Leu Asn Arg Arg Gln Trp Asn Ala Phe Ile Lys
            20                  25                  30

Ser Leu Arg Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 482
<211> LENGTH: 58
<212> TYPE: PRT
<213> ORGANISM: Artificial
<220> FEATURE:
<223> OTHER INFORMATION: Engineered polypeptide

<400> SEQUENCE: 482

```
Val Asp Asn Lys Phe Asn Lys Glu Leu Val Ala Ala Ala Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 483
<211> LENGTH: 58
<212> TYPE: PRT
<213> ORGANISM: Artificial
<220> FEATURE:
<223> OTHER INFORMATION: Engineered polypeptide

<400> SEQUENCE: 483

```
Val Asp Asn Lys Phe Asn Lys Glu Leu Arg Thr Ala Ala Lys Glu Ile
1               5                   10                  15

Asp Asp Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 484
<211> LENGTH: 58
<212> TYPE: PRT
<213> ORGANISM: Artificial
<220> FEATURE:
<223> OTHER INFORMATION: Engineered polypeptide

<400> SEQUENCE: 484

```
Val Asp Asn Lys Phe Asn Lys Glu Leu Leu Arg Ala Ala Arg Glu Ile
1               5                   10                  15

Asp Ser Leu Pro Asn Leu Asn Arg Thr Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 485
<211> LENGTH: 58
<212> TYPE: PRT

<213> ORGANISM: Artificial
<220> FEATURE:
<223> OTHER INFORMATION: Engineered polypeptide

<400> SEQUENCE: 485

Val Asp Asn Lys Phe Asn Lys Glu Arg Ile Arg Ala Ala Arg Glu Ile
1               5                   10                  15

Asp Ala Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 486
<211> LENGTH: 58
<212> TYPE: PRT
<213> ORGANISM: Artificial
<220> FEATURE:
<223> OTHER INFORMATION: Engineered polypeptide

<400> SEQUENCE: 486

Val Asp Asn Lys Phe Asn Lys Glu Leu Arg Ala Ala Ala Glu Glu Ile
1               5                   10                  15

Asp Arg Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 487
<211> LENGTH: 58
<212> TYPE: PRT
<213> ORGANISM: Artificial
<220> FEATURE:
<223> OTHER INFORMATION: Engineered polypeptide

<400> SEQUENCE: 487

Val Asp Asn Lys Phe Asn Lys Glu Leu Ile Glu Ala Ala Ala Glu Ile
1               5                   10                  15

Asp Ala Leu Pro Asn Leu Asn Arg Lys Gln Trp Asn Ala Phe Ile Ser
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 488
<211> LENGTH: 58
<212> TYPE: PRT
<213> ORGANISM: Artificial
<220> FEATURE:
<223> OTHER INFORMATION: Engineered polypeptide

<400> SEQUENCE: 488

Val Asp Asn Lys Phe Asn Lys Glu Arg Ile Glu Ala Ala Arg Glu Ile
1               5                   10                  15

Asp Glu Leu Pro Asn Leu Asn Arg Lys Gln Trp Asn Ala Phe Ile Ser
            20                  25                  30

Ser Leu Val Asp Asp Pro Ser Gln Ser Ala Asn Leu Leu Ala Glu Ala

Lys Lys Leu Asn Asp Ala Gln Ala Pro Lys
    50                  55

<210> SEQ ID NO 489
<211> LENGTH: 58
<212> TYPE: PRT
<213> ORGANISM: Artificial
<220> FEATURE:
<223> OTHER INFORMATION: Engineered polypeptide

<400> SEQUENCE: 489

Val Asp Asn Lys Phe Asn Lys Glu Leu Leu Ala Ala Ala Lys Glu Ile
1               5                   10                  15

Asp Glu Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 490
<211> LENGTH: 58
<212> TYPE: PRT
<213> ORGANISM: Artificial
<220> FEATURE:
<223> OTHER INFORMATION: Engineered polypeptide

<400> SEQUENCE: 490

Val Asp Asn Lys Phe Asn Lys Glu Leu Ile Asn Ala Ala Arg Glu Ile
1               5                   10                  15

Asp Glu Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 491
<211> LENGTH: 58
<212> TYPE: PRT
<213> ORGANISM: Artificial
<220> FEATURE:
<223> OTHER INFORMATION: Engineered polypeptide

<400> SEQUENCE: 491

Val Asp Asn Lys Phe Asn Lys Glu Leu Val Lys Ala Ala Ala Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 492
<211> LENGTH: 58
<212> TYPE: PRT
<213> ORGANISM: Artificial
<220> FEATURE:
<223> OTHER INFORMATION: Engineered polypeptide -continued

<400> SEQUENCE: 492

Val Asp Asn Lys Phe Asn Lys Glu Leu Ile Ala Ala Ala Lys Glu Ile
1               5                   10                  15

Asp Glu Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 493
<211> LENGTH: 58
<212> TYPE: PRT
<213> ORGANISM: Artificial
<220> FEATURE:
<223> OTHER INFORMATION: Engineered polypeptide

<400> SEQUENCE: 493

Val Asp Asn Lys Phe Asn Lys Glu Leu Ile Ser Ala Ala Arg Glu Ile
1               5                   10                  15

Asp Lys Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 494
<211> LENGTH: 58
<212> TYPE: PRT
<213> ORGANISM: Artificial
<220> FEATURE:
<223> OTHER INFORMATION: Engineered polypeptide

<400> SEQUENCE: 494

Val Asp Asn Lys Phe Asn Lys Glu Leu Arg Glu Ala Ala Glu Glu Ile
1               5                   10                  15

Asp Lys Leu Pro Asn Leu Asn Arg Trp Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 495
<211> LENGTH: 58
<212> TYPE: PRT
<213> ORGANISM: Artificial
<220> FEATURE:
<223> OTHER INFORMATION: Engineered polypeptide

<400> SEQUENCE: 495

Val Asp Asn Lys Phe Asn Lys Glu Leu Val Glu Ala Ala Arg Glu Ile
1               5                   10                  15

Asp Gly Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 496
<211> LENGTH: 58
<212> TYPE: PRT
<213> ORGANISM: Artificial
<220> FEATURE:
<223> OTHER INFORMATION: Engineered polypeptide

<400> SEQUENCE: 496

Val Asp Asn Lys Phe Asn Lys Glu Leu Val Ala Ala Ala Gln Glu Ile
1               5                   10                  15

Asp Asn Leu Pro Asn Leu Asn Arg Lys Gln Trp Asn Ala Phe Ile Ser
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 497
<211> LENGTH: 58
<212> TYPE: PRT
<213> ORGANISM: Artificial
<220> FEATURE:
<223> OTHER INFORMATION: Engineered polypeptide

<400> SEQUENCE: 497

Val Asp Asn Lys Phe Asn Lys Glu Leu Arg Asn Ala Ala Ala Glu Ile
1               5                   10                  15

Asp Lys Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 498
<211> LENGTH: 58
<212> TYPE: PRT
<213> ORGANISM: Artificial
<220> FEATURE:
<223> OTHER INFORMATION: Engineered polypeptide

<400> SEQUENCE: 498

Val Asp Asn Lys Phe Asn Lys Glu Leu Ile Gln Ala Ala Ser Glu Ile
1               5                   10                  15

Asp Ala Leu Pro Asn Leu Asn Arg Thr Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 499
<211> LENGTH: 58
<212> TYPE: PRT
<213> ORGANISM: Artificial
<220> FEATURE:
<223> OTHER INFORMATION: Engineered polypeptide

<400> SEQUENCE: 499

Val Asp Asn Lys Phe Asn Lys Glu Leu Val Glu Ala Ala Ala Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 500
<211> LENGTH: 58
<212> TYPE: PRT
<213> ORGANISM: Artificial
<220> FEATURE:
<223> OTHER INFORMATION: Engineered polypeptide

<400> SEQUENCE: 500

Val Asp Asn Lys Phe Asn Lys Glu Arg Ile Ala Ala Gln Glu Ile
1               5                   10                  15

Asp Ala Leu Pro Asn Leu Asn Arg Arg Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 501
<211> LENGTH: 58
<212> TYPE: PRT
<213> ORGANISM: Artificial
<220> FEATURE:
<223> OTHER INFORMATION: Engineered polypeptide

<400> SEQUENCE: 501

Val Asp Asn Lys Phe Asn Lys Glu Leu Arg Asp Ala Ala Lys Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 502
<211> LENGTH: 58
<212> TYPE: PRT
<213> ORGANISM: Artificial
<220> FEATURE:
<223> OTHER INFORMATION: Engineered polypeptide

<400> SEQUENCE: 502

Val Asp Asn Lys Phe Asn Lys Glu Leu Val Ala Ala Ala Lys Glu Ile
1               5                   10                  15

Asp Lys Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 503
<211> LENGTH: 58

```
<212> TYPE: PRT
<213> ORGANISM: Artificial
<220> FEATURE:
<223> OTHER INFORMATION: Engineered polypeptide

<400> SEQUENCE: 503

Val Asp Asn Lys Phe Asn Lys Glu Leu Ile Lys Ala Ala Arg Glu Ile
1               5                   10                  15

Asp Glu Leu Pro Asn Leu Asn Arg Lys Gln Trp Asn Ala Phe Ile Lys
            20                  25                  30

Ser Leu Ile Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 504
<211> LENGTH: 58
<212> TYPE: PRT
<213> ORGANISM: Artificial
<220> FEATURE:
<223> OTHER INFORMATION: Engineered polypeptide

<400> SEQUENCE: 504

Val Asp Asn Lys Phe Asn Lys Glu Leu Val Glu Ala Ala Ser Glu Ile
1               5                   10                  15

Asp Gly Leu Pro Asn Leu Asn Arg Asn Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 505
<211> LENGTH: 58
<212> TYPE: PRT
<213> ORGANISM: Artificial
<220> FEATURE:
<223> OTHER INFORMATION: Engineered polypeptide

<400> SEQUENCE: 505

Val Asp Asn Lys Phe Asn Lys Glu Leu Leu Arg Ala Ala Glu Glu Ile
1               5                   10                  15

Asp Asn Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 506
<211> LENGTH: 58
<212> TYPE: PRT
<213> ORGANISM: Artificial
<220> FEATURE:
<223> OTHER INFORMATION: Engineered polypeptide

<400> SEQUENCE: 506

Val Asp Asn Lys Phe Asn Lys Glu Leu Ile Lys Ala Ala Lys Glu Ile
1               5                   10                  15

Asp Ala Leu Pro Asn Leu Asn Arg Arg Gln Trp Asn Ala Phe Ile Lys
            20                  25                  30
```

```
Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 507
<211> LENGTH: 58
<212> TYPE: PRT
<213> ORGANISM: Artificial
<220> FEATURE:
<223> OTHER INFORMATION: Engineered polypeptide

<400> SEQUENCE: 507

```
Val Asp Asn Lys Phe Asn Lys Glu Leu Arg Arg Ala Ala Ala Glu Ile
1               5                   10                  15

Asp Ser Leu Pro Asn Leu Asn Arg Asp Gln Trp Asn Ala Phe Ile Arg
            20                  25                  30

Ser Leu Ile Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 508
<211> LENGTH: 58
<212> TYPE: PRT
<213> ORGANISM: Artificial
<220> FEATURE:
<223> OTHER INFORMATION: Engineered polypeptide

<400> SEQUENCE: 508

```
Val Asp Asn Lys Phe Asn Lys Glu Leu Val Glu Ala Ala Arg Glu Ile
1               5                   10                  15

Asp Gly Leu Pro Asn Leu Asn Arg Ala Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 509
<211> LENGTH: 58
<212> TYPE: PRT
<213> ORGANISM: Artificial
<220> FEATURE:
<223> OTHER INFORMATION: Engineered polypeptide

<400> SEQUENCE: 509

```
Val Asp Asn Lys Phe Asn Lys Glu Leu Val Glu Ala Ala Arg Glu Ile
1               5                   10                  15

Asp Glu Leu Pro Asn Leu Asn Arg Arg Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 510
<211> LENGTH: 58
<212> TYPE: PRT
<213> ORGANISM: Artificial
<220> FEATURE:
<223> OTHER INFORMATION: Engineered polypeptide

<400> SEQUENCE: 510

Val Asp Asn Lys Phe Asn Lys Glu Leu Val Trp Ala Ala Ala Glu Ile
1               5                   10                  15

Asp Arg Leu Pro Asn Leu Asn Arg Cys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 511
<211> LENGTH: 58
<212> TYPE: PRT
<213> ORGANISM: Artificial
<220> FEATURE:
<223> OTHER INFORMATION: Engineered polypeptide

<400> SEQUENCE: 511

Val Asp Asn Lys Phe Asn Lys Glu Arg Ile Arg Ala Ala Arg Glu Ile
1               5                   10                  15

Asp Glu Leu Pro Asn Leu Asn Arg Glu Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 512
<211> LENGTH: 58
<212> TYPE: PRT
<213> ORGANISM: Artificial
<220> FEATURE:
<223> OTHER INFORMATION: Engineered polypeptide

<400> SEQUENCE: 512

Val Asp Asn Lys Phe Asn Lys Glu Leu Arg Gln Ala Ala Lys Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 513
<211> LENGTH: 58
<212> TYPE: PRT
<213> ORGANISM: Artificial
<220> FEATURE:
<223> OTHER INFORMATION: Engineered polypeptide

<400> SEQUENCE: 513

Val Asp Asn Lys Phe Asn Lys Glu Leu Arg Glu Ala Ala Ala Glu Ile
1               5                   10                  15

Asp Lys Leu Pro Asn Leu Asn Arg Lys Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys

```
                        50                  55

<210> SEQ ID NO 514
<211> LENGTH: 58
<212> TYPE: PRT
<213> ORGANISM: Artificial
<220> FEATURE:
<223> OTHER INFORMATION: Engineered polypeptide

<400> SEQUENCE: 514

Val Asp Asn Lys Phe Asn Lys Glu Leu Arg Arg Ala Ala Glu Glu Ile
1               5                   10                  15

Asp Lys Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 515
<211> LENGTH: 58
<212> TYPE: PRT
<213> ORGANISM: Artificial
<220> FEATURE:
<223> OTHER INFORMATION: Engineered polypeptide

<400> SEQUENCE: 515

Val Asp Asn Lys Phe Asn Lys Glu Leu Val Gln Ala Ala Arg Glu Ile
1               5                   10                  15

Asp Ala Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 516
<211> LENGTH: 58
<212> TYPE: PRT
<213> ORGANISM: Artificial
<220> FEATURE:
<223> OTHER INFORMATION: Engineered polypeptide

<400> SEQUENCE: 516

Val Asp Asn Lys Phe Asn Lys Glu Leu Arg Ala Ala Ala Ala Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 517
<211> LENGTH: 58
<212> TYPE: PRT
<213> ORGANISM: Artificial
<220> FEATURE:
<223> OTHER INFORMATION: Engineered polypeptide

<400> SEQUENCE: 517

Val Asp Asn Lys Phe Asn Lys Glu Leu Arg Ala Ala Ala Ala Glu Ile
```

```
            1               5                  10                  15
Asp Lys Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
            50                  55
```

<210> SEQ ID NO 518
<211> LENGTH: 58
<212> TYPE: PRT
<213> ORGANISM: Artificial
<220> FEATURE:
<223> OTHER INFORMATION: Engineered polypeptide

<400> SEQUENCE: 518

```
Val Asp Asn Lys Phe Asn Lys Glu Arg Ile Gln Ala Ala Lys Glu Ile
1               5                   10                  15

Asp Glu Leu Pro Asn Leu Asn Arg Glu Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
            50                  55
```

<210> SEQ ID NO 519
<211> LENGTH: 58
<212> TYPE: PRT
<213> ORGANISM: Artificial
<220> FEATURE:
<223> OTHER INFORMATION: Engineered polypeptide

<400> SEQUENCE: 519

```
Val Asp Asn Lys Phe Asn Lys Glu Leu Val Ala Ala Ala Glu Glu Ile
1               5                   10                  15

Asp Lys Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
            50                  55
```

<210> SEQ ID NO 520
<211> LENGTH: 58
<212> TYPE: PRT
<213> ORGANISM: Artificial
<220> FEATURE:
<223> OTHER INFORMATION: Engineered polypeptide

<400> SEQUENCE: 520

```
Val Asp Asn Lys Phe Asn Lys Glu Leu Val Arg Ala Ala Glu Glu Ile
1               5                   10                  15

Asp Asn Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
            50                  55
```

<210> SEQ ID NO 521

<211> LENGTH: 58
<212> TYPE: PRT
<213> ORGANISM: Artificial
<220> FEATURE:
<223> OTHER INFORMATION: Engineered polypeptide

<400> SEQUENCE: 521

Val Asp Asn Lys Phe Asn Lys Glu Leu Arg Thr Ala Ala Ala Glu Ile
1               5                   10                  15

Asp Ala Leu Pro Asn Leu Asn Arg Glu Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 522
<211> LENGTH: 58
<212> TYPE: PRT
<213> ORGANISM: Artificial
<220> FEATURE:
<223> OTHER INFORMATION: Engineered polypeptide

<400> SEQUENCE: 522

Val Asp Asn Lys Phe Asn Lys Glu Leu Val Glu Ala Ala Ala Glu Ile
1               5                   10                  15

Asp Ala Leu Pro Asn Leu Asn Arg Lys Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 523
<211> LENGTH: 58
<212> TYPE: PRT
<213> ORGANISM: Artificial
<220> FEATURE:
<223> OTHER INFORMATION: Engineered polypeptide

<400> SEQUENCE: 523

Val Asp Asn Lys Phe Asn Lys Glu Leu Ile Lys Ala Ala Glu Glu Ile
1               5                   10                  15

Asp Lys Leu Pro Asn Leu Asn Arg Met Gln Trp Asn Ala Phe Ile Arg
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 524
<211> LENGTH: 58
<212> TYPE: PRT
<213> ORGANISM: Artificial
<220> FEATURE:
<223> OTHER INFORMATION: Engineered polypeptide

<400> SEQUENCE: 524

Val Asp Asn Lys Phe Asn Lys Glu Leu Arg Glu Ala Ala Ala Glu Ile
1               5                   10                  15

Asp Asn Leu Pro Asn Leu Asn Arg Arg Gln Trp Asn Ala Phe Ile Lys
            20                  25                  30

Ser Leu Ile Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 525
<211> LENGTH: 58
<212> TYPE: PRT
<213> ORGANISM: Artificial
<220> FEATURE:
<223> OTHER INFORMATION: Engineered polypeptide

<400> SEQUENCE: 525

Val Asp Asn Lys Phe Asn Lys Glu Leu Ile Glu Ala Ala Arg Glu Ile
1               5                   10                  15

Asp Ala Leu Pro Asn Leu Asn Arg Lys Gln Trp Asn Ala Phe Ile Arg
            20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 526
<211> LENGTH: 58
<212> TYPE: PRT
<213> ORGANISM: Artificial
<220> FEATURE:
<223> OTHER INFORMATION: Engineered polypeptide

<400> SEQUENCE: 526

Val Asp Asn Lys Phe Asn Lys Glu Leu Arg Glu Ala Ala Gln Glu Ile
1               5                   10                  15

Asp Ser Leu Pro Asn Leu Asn Arg Gln Gln Trp Asn Ala Phe Ile Lys
            20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 527
<211> LENGTH: 58
<212> TYPE: PRT
<213> ORGANISM: Artificial
<220> FEATURE:
<223> OTHER INFORMATION: Engineered polypeptide

<400> SEQUENCE: 527

Val Asp Asn Lys Phe Asn Lys Glu Leu Arg Ser Ala Ala Glu Glu Ile
1               5                   10                  15

Asp Ser Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 528
<211> LENGTH: 58
<212> TYPE: PRT
<213> ORGANISM: Artificial
<220> FEATURE:

<223> OTHER INFORMATION: Engineered polypeptide

<400> SEQUENCE: 528

Val Asp Asn Lys Phe Asn Lys Glu Leu Val Glu Ala Ala Ala Glu Ile
1               5                   10                  15

Asp Asn Leu Pro Asn Leu Asn Arg Met Gln Trp Asn Ala Phe Ile Lys
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 529
<211> LENGTH: 58
<212> TYPE: PRT
<213> ORGANISM: Artificial
<220> FEATURE:
<223> OTHER INFORMATION: Engineered polypeptide

<400> SEQUENCE: 529

Val Asp Asn Lys Phe Asn Lys Glu Leu Val Glu Ala Ala Gly Glu Ile
1               5                   10                  15

Asp Asn Leu Pro Asn Leu Asn Arg Arg Gln Trp Asn Ala Phe Ile Arg
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 530
<211> LENGTH: 58
<212> TYPE: PRT
<213> ORGANISM: Artificial
<220> FEATURE:
<223> OTHER INFORMATION: Engineered polypeptide

<400> SEQUENCE: 530

Val Asp Asn Lys Phe Asn Lys Glu Leu Ser Lys Ala Ala Ala Glu Ile
1               5                   10                  15

Asp Ala Leu Pro Asn Leu Asn Arg Arg Gln Trp Asn Ala Phe Ile Lys
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 531
<211> LENGTH: 58
<212> TYPE: PRT
<213> ORGANISM: Artificial
<220> FEATURE:
<223> OTHER INFORMATION: Engineered polypeptide

<400> SEQUENCE: 531

Val Asp Asn Lys Phe Asn Lys Glu Leu Leu Trp Ala Ala Gly Glu Ile
1               5                   10                  15

Asp Arg Leu Pro Asn Leu Asn Arg Gln Gln Trp Asn Ala Phe Ile Lys
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 532
<211> LENGTH: 58
<212> TYPE: PRT
<213> ORGANISM: Artificial
<220> FEATURE:
<223> OTHER INFORMATION: Engineered polypeptide

<400> SEQUENCE: 532

Val Asp Asn Lys Phe Asn Lys Glu Leu Arg Gln Ala Ala Ala Glu Ile
1               5                   10                  15

Asp Gly Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 533
<211> LENGTH: 58
<212> TYPE: PRT
<213> ORGANISM: Artificial
<220> FEATURE:
<223> OTHER INFORMATION: Engineered polypeptide

<400> SEQUENCE: 533

Val Asp Ala Lys Phe Ala Lys Glu Leu Val Lys Ala Ala Ala Glu Ile
1               5                   10                  15

Asp Ala Leu Pro Asn Leu Thr Arg Arg Gln Trp Asn Ala Phe Ile Lys
            20                  25                  30

Ser Leu Val Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 534
<211> LENGTH: 58
<212> TYPE: PRT
<213> ORGANISM: Artificial
<220> FEATURE:
<223> OTHER INFORMATION: Engineered polypeptide

<400> SEQUENCE: 534

Val Asp Ala Lys Phe Ala Lys Glu Leu Val Lys Ala Ala Ala Glu Ile
1               5                   10                  15

Asp Ala Leu Pro Asn Leu Asn Arg Arg Gln Trp Asn Ala Phe Ile Lys
            20                  25                  30

Lys Leu Val Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 535
<211> LENGTH: 58
<212> TYPE: PRT
<213> ORGANISM: Artificial
<220> FEATURE:
<223> OTHER INFORMATION: Engineered polypeptide

<400> SEQUENCE: 535

```
Val Asp Ala Lys Phe Ala Lys Glu Leu Val Lys Ala Ala Ala Glu Ile
1               5                   10                  15

Asp Ala Leu Pro Asn Leu Thr Arg Arg Gln Trp Asn Ala Phe Ile Lys
            20                  25                  30

Lys Leu Val Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 536
<211> LENGTH: 58
<212> TYPE: PRT
<213> ORGANISM: Artificial
<220> FEATURE:
<223> OTHER INFORMATION: Engineered polypeptide

<400> SEQUENCE: 536

```
Val Asp Ala Lys Phe Ala Lys Glu Leu Val Lys Ala Ala Ala Glu Ile
1               5                   10                  15

Asp Ala Leu Pro Asn Leu Thr Arg Arg Gln Trp Asn Ala Phe Ile Lys
            20                  25                  30

Lys Leu Val Lys Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 537
<211> LENGTH: 58
<212> TYPE: PRT
<213> ORGANISM: Artificial
<220> FEATURE:
<223> OTHER INFORMATION: Engineered polypeptide

<400> SEQUENCE: 537

```
Ala Glu Ala Lys Tyr Ala Lys Glu Leu Ile Glu Ala Ala Ala Glu Ile
1               5                   10                  15

Asp Ala Leu Pro Asn Leu Thr Arg Arg Gln Trp Asn Ala Phe Ile Lys
            20                  25                  30

Lys Leu Val Asp Asp Pro Ser Gln Ser Ser Glu Leu Leu Ser Glu Ala
        35                  40                  45

Lys Lys Leu Asn Asp Ser Gln Ala Pro Ser
    50                  55
```

<210> SEQ ID NO 538
<211> LENGTH: 58
<212> TYPE: PRT
<213> ORGANISM: Artificial
<220> FEATURE:
<223> OTHER INFORMATION: Engineered polypeptide

<400> SEQUENCE: 538

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

```
<210> SEQ ID NO 539
<211> LENGTH: 1132
<212> TYPE: PRT
<213> ORGANISM: Homo sapiens

<400> SEQUENCE: 539

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380
```

```
Arg Val Lys Val Ala Glu Gly His Tyr Thr Met Arg Ala Phe His
385                 390                 395                 400

Glu Asp Ala Glu Val Gln Leu Ser Phe Gln Leu Gln Ile Asn Val Pro
            405                 410                 415

Val Arg Val Leu Glu Leu Ser Glu Ser His Pro Asp Ser Gly Glu Gln
        420                 425                 430

Thr Val Arg Cys Arg Gly Arg Gly Met Pro Gln Pro Asn Ile Ile Trp
    435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
        515                 520                 525

Pro Phe Lys Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
```

```
                       805                 810                 815
Leu Ala Ser Lys Asn Cys Val His Arg Asp Leu Ala Ala Arg Asn Val
                820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe
850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
                900                 905                 910

Phe Tyr Asn Ala Ile Lys Arg Gly Tyr Arg Met Ala Gln Pro Ala His
                915                 920                 925

Ala Ser Asp Glu Ile Tyr Glu Ile Met Gln Lys Cys Trp Glu Glu Lys
            930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
                980                 985                 990

Pro Gly Phe His Gly Leu Arg Ser Pro Leu Asp Thr Ser Ser Val Leu
            995                1000                1005

Tyr Thr Ala Val Gln Pro Asn Glu Gly Asp Asn Asp Tyr Ile Ile
    1010                1015                1020

Pro Leu Pro Asp Pro Lys Pro Glu Val Ala Asp Glu Gly Pro Leu
    1025                1030                1035

Glu Gly Ser Pro Ser Leu Ala Ser Ser Thr Leu Asn Glu Val Asn
    1040                1045                1050

Thr Ser Ser Thr Ile Ser Cys Asp Ser Pro Leu Glu Pro Gln Asp
    1055                1060                1065

Glu Pro Glu Pro Glu Pro Gln Leu Glu Leu Gln Val Glu Pro Glu
    1070                1075                1080

Pro Glu Leu Glu Gln Leu Pro Asp Ser Gly Cys Pro Ala Pro Arg
    1085                1090                1095

Ala Glu Ala Glu Asp Ser Phe Leu Glu Pro Glu Pro Glu Leu Glu
    1100                1105                1110

Gln Leu Pro Asp Ser Gly Cys Pro Ala Pro Arg Ala Glu Ala Glu
    1115                1120                1125

Asp Ser Phe Leu
    1130

<210> SEQ ID NO 540
<211> LENGTH: 498
<212> TYPE: PRT
<213> ORGANISM: Homo sapiens

<400> SEQUENCE: 540

Val Val Thr Pro Pro Gly Pro Glu Leu Val Leu Asn Val Ser Ser Thr
1               5                  10                  15

Phe Val Leu Thr Cys Ser Gly Ser Ala Pro Val Val Trp Glu Arg Met
            20                  25                  30
```

-continued

```
Ser Gln Glu Pro Pro Gln Glu Met Ala Lys Ala Gln Asp Gly Thr Phe
         35                  40                  45

Ser Ser Val Leu Thr Leu Thr Asn Leu Thr Gly Leu Asp Thr Gly Glu
 50                  55                  60

Tyr Phe Cys Thr His Asn Asp Ser Arg Gly Leu Glu Thr Asp Glu Arg
 65                  70                  75                  80

Lys Arg Leu Tyr Ile Phe Val Pro Asp Pro Thr Val Gly Phe Leu Pro
                 85                  90                  95

Asn Asp Ala Glu Glu Leu Phe Ile Phe Leu Thr Glu Ile Thr Glu Ile
            100                 105                 110

Thr Ile Pro Cys Arg Val Thr Asp Pro Gln Leu Val Val Thr Leu His
            115                 120                 125

Glu Lys Lys Gly Asp Val Ala Leu Pro Val Pro Tyr Asp His Gln Arg
130                 135                 140

Gly Phe Ser Gly Ile Phe Glu Asp Arg Ser Tyr Ile Cys Lys Thr Thr
145                 150                 155                 160

Ile Gly Asp Arg Glu Val Asp Ser Asp Ala Tyr Tyr Val Tyr Arg Leu
                165                 170                 175

Gln Val Ser Ser Ile Asn Val Ser Val Asn Ala Val Gln Thr Val Val
            180                 185                 190

Arg Gln Gly Glu Asn Ile Thr Leu Met Cys Ile Val Ile Gly Asn Glu
        195                 200                 205

Val Val Asn Phe Glu Trp Thr Tyr Pro Arg Lys Glu Ser Gly Arg Leu
    210                 215                 220

Val Glu Pro Val Thr Asp Phe Leu Leu Asp Met Pro Tyr His Ile Arg
225                 230                 235                 240

Ser Ile Leu His Ile Pro Ser Ala Glu Leu Glu Asp Ser Gly Thr Tyr
                245                 250                 255

Thr Cys Asn Val Thr Glu Ser Val Asn Asp His Gln Asp Glu Lys Ala
            260                 265                 270

Ile Asn Ile Thr Val Val Glu Ser Gly Tyr Val Arg Leu Leu Gly Glu
        275                 280                 285

Val Gly Thr Leu Gln Phe Ala Glu Leu His Arg Ser Arg Thr Leu Gln
    290                 295                 300

Val Val Phe Glu Ala Tyr Pro Pro Pro Thr Val Leu Trp Phe Lys Asp
305                 310                 315                 320

Asn Arg Thr Leu Gly Asp Ser Ser Ala Gly Glu Ile Ala Leu Ser Thr
                325                 330                 335

Arg Asn Val Ser Glu Thr Arg Tyr Val Ser Glu Leu Thr Leu Val Arg
            340                 345                 350

Val Lys Val Ala Glu Ala Gly His Tyr Thr Met Arg Ala Phe His Glu
        355                 360                 365

Asp Ala Glu Val Gln Leu Ser Phe Gln Leu Gln Ile Asn Val Pro Val
    370                 375                 380

Arg Val Leu Glu Leu Ser Glu Ser His Pro Asp Ser Gly Glu Gln Thr
385                 390                 395                 400

Val Arg Cys Arg Gly Arg Gly Met Pro Gln Pro Asn Ile Ile Trp Ser
                405                 410                 415

Ala Cys Arg Asp Leu Lys Arg Cys Pro Arg Glu Leu Pro Pro Thr Leu
            420                 425                 430

Leu Gly Asn Ser Ser Glu Glu Ser Gln Leu Glu Thr Asn Val Thr
        435                 440                 445

Tyr Trp Glu Glu Glu Gln Glu Phe Glu Val Val Ser Thr Leu Arg Leu
```

```
                450                 455                 460

Gln His Val Asp Arg Pro Leu Ser Val Arg Cys Thr Leu Arg Asn Ala
465                 470                 475                 480

Val Gly Gln Asp Thr Gln Glu Val Ile Val Val Pro His Ser Leu Pro
                485                 490                 495

Phe Lys

<210> SEQ ID NO 541
<211> LENGTH: 29
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (2)..(2)
<223> OTHER INFORMATION: X2 is selected from L, R and I;
<220> FEATURE:
<221> NAME/KEY: VARIANT
<222> LOCATION: (3)..(3)
<223> OTHER INFORMATION: X3 is selected from R, I, L, V, K, Q, S, H, and
      A;
<220> FEATURE:
<221> NAME/KEY: VARIANT
<222> LOCATION: (4)..(4)
<223> OTHER INFORMATION: X4 is selected from A, R, N, D, Q, E, H, K, M,
      S, T, W, F and V
<220> FEATURE:
<221> NAME/KEY: VARIANT
<222> LOCATION: (7)..(7)
<223> OTHER INFORMATION: X7 is selected from A, R, D, Q, E, G, K and S
<220> FEATURE:
<221> NAME/KEY: VARIANT
<222> LOCATION: (11)..(11)
<223> OTHER INFORMATION: X11 is selected from A, R, N, D, E, G, K, S, T
      and Q
<220> FEATURE:
<221> NAME/KEY: VARIANT
<222> LOCATION: (16)..(16)
<223> OTHER INFORMATION: X16 is selected from N and T;
<220> FEATURE:
<221> NAME/KEY: VARIANT
<222> LOCATION: (17)..(17)
<223> OTHER INFORMATION: X17 is selected from R and K
<220> FEATURE:
<221> NAME/KEY: VARIANT
<222> LOCATION: (18)..(18)
<223> OTHER INFORMATION: X18 is selected from A, R, N, D, C, Q, E, G, L,
      K, M, S, T, W and V
<220> FEATURE:
<221> NAME/KEY: VARIANT
<222> LOCATION: (25)..(25)
<223> OTHER INFORMATION: X25 is selected from K, R, Q, H, S, G and A
<220> FEATURE:
<221> NAME/KEY: VARIANT
<222> LOCATION: (26)..(26)
<223> OTHER INFORMATION: X26 is selected from S and K
<220> FEATURE:
<221> NAME/KEY: VARIANT
<222> LOCATION: (28)..(28)
<223> OTHER INFORMATION: X28 is selected from V, R, I, L and A;
<220> FEATURE:
<221> NAME/KEY: VARIANT
<222> LOCATION: (29)..(29)
<223> OTHER INFORMATION: X29 is selected from D and K

<400> SEQUENCE: 541

Glu Xaa Xaa Xaa Ala Ala Xaa Glu Ile Asp Xaa Leu Pro Asn Leu Xaa
1               5                   10                  15

Xaa Xaa Gln Trp Asn Ala Phe Ile Xaa Xaa Leu Xaa Xaa
            20                  25
```

```
<210> SEQ ID NO 542
<211> LENGTH: 49
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (3)..(3)
<223> OTHER INFORMATION: X is selected from L, R and I
<220> FEATURE:
<221> NAME/KEY: VARIANT
<222> LOCATION: (4)..(4)
<223> OTHER INFORMATION: X3 is selected from R, I, L, V, K, Q, S, H, and
      A;
<220> FEATURE:
<221> NAME/KEY: VARIANT
<222> LOCATION: (5)..(5)
<223> OTHER INFORMATION: X is selected from A, R, N, D, Q, E, H, K, M,
      S, T, W, F and V
<220> FEATURE:
<221> NAME/KEY: VARIANT
<222> LOCATION: (8)..(8)
<223> OTHER INFORMATION: X is selected from A, R, D, Q, E, G, K and S
<220> FEATURE:
<221> NAME/KEY: VARIANT
<222> LOCATION: (12)..(12)
<223> OTHER INFORMATION: X is selected from A, R, N, D, E, G, K, S, T
      and Q
<220> FEATURE:
<221> NAME/KEY: VARIANT
<222> LOCATION: (17)..(17)
<223> OTHER INFORMATION: X is selected from N and T
<220> FEATURE:
<221> NAME/KEY: VARIANT
<222> LOCATION: (18)..(18)
<223> OTHER INFORMATION: X is selected from R and K
<220> FEATURE:
<221> NAME/KEY: VARIANT
<222> LOCATION: (19)..(19)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (26)..(26)
<223> OTHER INFORMATION: X is selected from K, R, Q, H, S, G and A
<220> FEATURE:
<221> NAME/KEY: VARIANT
<222> LOCATION: (27)..(27)
<223> OTHER INFORMATION: X is selected from S and K
<220> FEATURE:
<221> NAME/KEY: VARIANT
<222> LOCATION: (29)..(29)
<223> OTHER INFORMATION: X is selected from V, R, I, L and A
<220> FEATURE:
<221> NAME/KEY: VARIANT
<222> LOCATION: (30)..(30)
<223> OTHER INFORMATION: X is selected from D and K
<220> FEATURE:
<221> NAME/KEY: VARIANT
<222> LOCATION: (36)..(36)
<223> OTHER INFORMATION: X is selected from A and S
<220> FEATURE:
<221> NAME/KEY: VARIANT
<222> LOCATION: (37)..(37)
<223> OTHER INFORMATION: X is selected from N and E
<220> FEATURE:
<221> NAME/KEY: VARIANT
<222> LOCATION: (40)..(40)
<223> OTHER INFORMATION: X is selected from A and S
<220> FEATURE:
<221> NAME/KEY: VARIANT
<222> LOCATION: (48)..(48)
<223> OTHER INFORMATION: X is selected from A and S

<400> SEQUENCE: 542

Lys Glu Xaa Xaa Xaa Ala Ala Xaa Glu Ile Asp Xaa Leu Pro Asn Leu
1               5                   10                  15
```

```
Xaa Xaa Xaa Gln Trp Asn Ala Phe Ile Xaa Xaa Leu Xaa Xaa Asp Pro
            20                  25                  30

Ser Gln Ser Xaa Xaa Leu Leu Xaa Glu Ala Lys Lys Leu Asn Asp Xaa
        35                  40                  45

Gln

<210> SEQ ID NO 543
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (9)..(9)
<223> OTHER INFORMATION: X is selected from L, R and I
<220> FEATURE:
<221> NAME/KEY: VARIANT
<222> LOCATION: (10)..(10)
<223> OTHER INFORMATION: X is selected from R, I, L, V, K, Q, S, H, and
      A
<220> FEATURE:
<221> NAME/KEY: VARIANT
<222> LOCATION: (11)..(11)
<223> OTHER INFORMATION: X is selected from A, R, N, D, Q, E, H, K, M,
      S, T, W, F and V
<220> FEATURE:
<221> NAME/KEY: VARIANT
<222> LOCATION: (14)..(14)
<223> OTHER INFORMATION: X is selected from A, R, D, Q, E, G, K and S
<220> FEATURE:
<221> NAME/KEY: VARIANT
<222> LOCATION: (18)..(18)
<223> OTHER INFORMATION: X is selected from A, R, N, D, E, G, K, S, T
      and Q
<220> FEATURE:
<221> NAME/KEY: VARIANT
<222> LOCATION: (23)..(23)
<223> OTHER INFORMATION: X is selected from N and T
<220> FEATURE:
<221> NAME/KEY: VARIANT
<222> LOCATION: (24)..(24)
<223> OTHER INFORMATION: X is selected from R and K
<220> FEATURE:
<221> NAME/KEY: VARIANT
<222> LOCATION: (25)..(25)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (32)..(32)
<223> OTHER INFORMATION: X is selected from K, R, Q, H, S, G and A
<220> FEATURE:
<221> NAME/KEY: VARIANT
<222> LOCATION: (33)..(33)
<223> OTHER INFORMATION: X is selected from S and K
<220> FEATURE:
<221> NAME/KEY: VARIANT
<222> LOCATION: (35)..(35)
<223> OTHER INFORMATION: X is selected from V, R, I, L and A
<220> FEATURE:
<221> NAME/KEY: VARIANT
<222> LOCATION: (36)..(36)
<223> OTHER INFORMATION: X is selected from D and K

<400> SEQUENCE: 543

Ala Asp Asn Asn Phe Asn Lys Glu Xaa Xaa Xaa Ala Ala Xaa Glu Ile
1               5                   10                  15

Asp Xaa Leu Pro Asn Leu Xaa Xaa Xaa Gln Trp Asn Ala Phe Ile Xaa
            20                  25                  30

Xaa Leu Xaa Xaa Asp Pro Ser Gln Ser Ala Asn Leu Leu Ser Glu Ala
            35                  40                  45
```

Lys Lys Leu Asn Glu Ser Gln Ala Pro Lys
    50                  55

<210> SEQ ID NO 544
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (9)..(9)
<223> OTHER INFORMATION: X is selected from L, R and I
<220> FEATURE:
<221> NAME/KEY: VARIANT
<222> LOCATION: (10)..(10)
<223> OTHER INFORMATION: X is selected from R, I, L, V, K, Q, S, H, and
      A
<220> FEATURE:
<221> NAME/KEY: VARIANT
<222> LOCATION: (11)..(11)
<223> OTHER INFORMATION: X is selected from A, R, N, D, Q, E, H, K, M,
      S, T, W, F and V
<220> FEATURE:
<221> NAME/KEY: VARIANT
<222> LOCATION: (14)..(14)
<223> OTHER INFORMATION: X is selected from A, R, D, Q, E, G, K and S
<220> FEATURE:
<221> NAME/KEY: VARIANT
<222> LOCATION: (18)..(18)
<223> OTHER INFORMATION: X is selected from A, R, N, D, E, G, K, S, T
      and Q
<220> FEATURE:
<221> NAME/KEY: VARIANT
<222> LOCATION: (23)..(23)
<223> OTHER INFORMATION: X is selected from N and T
<220> FEATURE:
<221> NAME/KEY: VARIANT
<222> LOCATION: (24)..(24)
<223> OTHER INFORMATION: X is selected from R and K
<220> FEATURE:
<221> NAME/KEY: VARIANT
<222> LOCATION: (25)..(25)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (32)..(32)
<223> OTHER INFORMATION: X is selected from K, R, Q, H, S, G and A
<220> FEATURE:
<221> NAME/KEY: VARIANT
<222> LOCATION: (33)..(33)
<223> OTHER INFORMATION: X is selected from S and K
<220> FEATURE:
<221> NAME/KEY: VARIANT
<222> LOCATION: (35)..(35)
<223> OTHER INFORMATION: X is selected from V, R, I, L and A
<220> FEATURE:
<221> NAME/KEY: VARIANT
<222> LOCATION: (36)..(36)
<223> OTHER INFORMATION: X is selected from D and K

<400> SEQUENCE: 544

Ala Asp Asn Lys Phe Asn Lys Glu Xaa Xaa Xaa Ala Ala Xaa Glu Ile
1               5                   10                  15

Asp Xaa Leu Pro Asn Leu Xaa Xaa Xaa Gln Trp Asn Ala Phe Ile Xaa
            20                  25                  30

Xaa Leu Xaa Xaa Asp Pro Ser Gln Ser Ala Asn Leu Leu Ala Glu Ala
        35                  40                  45

Lys Lys Leu Asn Asp Ala Gln Ala Pro Lys
    50                  55

-continued

```
<210> SEQ ID NO 545
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (9)..(9)
<223> OTHER INFORMATION: X is selected from L, R and I
<220> FEATURE:
<221> NAME/KEY: VARIANT
<222> LOCATION: (10)..(10)
<223> OTHER INFORMATION: X is selected from R, I, L, V, K, Q, S, H, and
      A
<220> FEATURE:
<221> NAME/KEY: VARIANT
<222> LOCATION: (11)..(11)
<223> OTHER INFORMATION: X is selected from A, R, N, D, Q, E, H, K, M,
      S, T, W, F and V
<220> FEATURE:
<221> NAME/KEY: VARIANT
<222> LOCATION: (14)..(14)
<223> OTHER INFORMATION: X is selected from A, R, D, Q, E, G, K and S
<220> FEATURE:
<221> NAME/KEY: VARIANT
<222> LOCATION: (18)..(18)
<223> OTHER INFORMATION: X is selected from A, R, N, D, E, G, K, S, T
      and Q
<220> FEATURE:
<221> NAME/KEY: VARIANT
<222> LOCATION: (23)..(23)
<223> OTHER INFORMATION: X is selected from N and T
<220> FEATURE:
<221> NAME/KEY: VARIANT
<222> LOCATION: (24)..(24)
<223> OTHER INFORMATION: X is selected from R and K
<220> FEATURE:
<221> NAME/KEY: VARIANT
<222> LOCATION: (25)..(25)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (32)..(32)
<223> OTHER INFORMATION: X is selected from K, R, Q, H, S, G and A
<220> FEATURE:
<221> NAME/KEY: VARIANT
<222> LOCATION: (33)..(33)
<223> OTHER INFORMATION: X is selected from S and K
<220> FEATURE:
<221> NAME/KEY: VARIANT
<222> LOCATION: (35)..(35)
<223> OTHER INFORMATION: X is selected from V, R, I, L and A
<220> FEATURE:
<221> NAME/KEY: VARIANT
<222> LOCATION: (36)..(36)
<223> OTHER INFORMATION: X is selected from D and K

<400> SEQUENCE: 545

Ala Asp Asn Lys Phe Asn Lys Glu Xaa Xaa Xaa Ala Ala Xaa Glu Ile
1               5                   10                  15

Asp Xaa Leu Pro Asn Leu Xaa Xaa Xaa Gln Trp Asn Ala Phe Ile Xaa
            20                  25                  30

Xaa Leu Xaa Xaa Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 546
<211> LENGTH: 61
<212> TYPE: PRT
<213> ORGANISM: Artificial Sequence
<220> FEATURE:
```

```
<223> OTHER INFORMATION: Engineered polypeptide
<220> FEATURE:
<221> NAME/KEY: VARIANT
<222> LOCATION: (12)..(12)
<223> OTHER INFORMATION: X is selected from L, R and I
<220> FEATURE:
<221> NAME/KEY: VARIANT
<222> LOCATION: (13)..(13)
<223> OTHER INFORMATION: X is selected from R, I, L, V, K, Q, S, H, and
      A
<220> FEATURE:
<221> NAME/KEY: VARIANT
<222> LOCATION: (14)..(14)
<223> OTHER INFORMATION: X is selected from A, R, N, D, Q, E, H, K, M,
      S, T, W, F and V
<220> FEATURE:
<221> NAME/KEY: VARIANT
<222> LOCATION: (17)..(17)
<223> OTHER INFORMATION: X is selected from A, R, D, Q, E, G, K and S
<220> FEATURE:
<221> NAME/KEY: VARIANT
<222> LOCATION: (21)..(21)
<223> OTHER INFORMATION: X is selected from A, R, N, D, E, G, K, S, T
      and Q
<220> FEATURE:
<221> NAME/KEY: VARIANT
<222> LOCATION: (26)..(26)
<223> OTHER INFORMATION: X is selected from N and T
<220> FEATURE:
<221> NAME/KEY: VARIANT
<222> LOCATION: (27)..(27)
<223> OTHER INFORMATION: X is selected from R and K
<220> FEATURE:
<221> NAME/KEY: VARIANT
<222> LOCATION: (28)..(28)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (35)..(35)
<223> OTHER INFORMATION: X is selected from K, R, Q, H, S, G and A
<220> FEATURE:
<221> NAME/KEY: VARIANT
<222> LOCATION: (36)..(36)
<223> OTHER INFORMATION: X is selected from S and K
<220> FEATURE:
<221> NAME/KEY: VARIANT
<222> LOCATION: (38)..(38)
<223> OTHER INFORMATION: X is selected from V, R, I, L and A
<220> FEATURE:
<221> NAME/KEY: VARIANT
<222> LOCATION: (39)..(39)
<223> OTHER INFORMATION: X is selected from D and K

<400> SEQUENCE: 546

Ala Asp Ala Gln Gln Asn Asn Phe Asn Lys Glu Xaa Xaa Xaa Ala Ala
1               5                   10                  15

Xaa Glu Ile Asp Xaa Leu Pro Asn Leu Xaa Xaa Xaa Gln Trp Asn Ala
                20                  25                  30

Phe Ile Xaa Xaa Leu Xaa Xaa Asp Pro Ser Gln Ser Thr Asn Val Leu
            35                  40                  45

Gly Glu Ala Lys Lys Leu Asn Glu Ser Gln Ala Pro Lys
    50                  55                  60

<210> SEQ ID NO 547
<211> LENGTH: 56
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (7)..(7)
<223> OTHER INFORMATION: X is selected from L, R and I
```

```
<220> FEATURE:
<221> NAME/KEY: VARIANT
<222> LOCATION: (8)..(8)
<223> OTHER INFORMATION: X is selected from R, I, L, V, K, Q, S, H, and
      A
<220> FEATURE:
<221> NAME/KEY: VARIANT
<222> LOCATION: (9)..(9)
<223> OTHER INFORMATION: X is selected from A, R, N, D, Q, E, H, K, M,
      S, T, W, F and V
<220> FEATURE:
<221> NAME/KEY: VARIANT
<222> LOCATION: (12)..(12)
<223> OTHER INFORMATION: X is selected from A, R, D, Q, E, G, K and S
<220> FEATURE:
<221> NAME/KEY: VARIANT
<222> LOCATION: (16)..(16)
<223> OTHER INFORMATION: X is selected from A, R, N, D, E, G, K, S, T
      and Q
<220> FEATURE:
<221> NAME/KEY: VARIANT
<222> LOCATION: (21)..(21)
<223> OTHER INFORMATION: X is selected from N and T
<220> FEATURE:
<221> NAME/KEY: VARIANT
<222> LOCATION: (22)..(22)
<223> OTHER INFORMATION: X is selected from R and K
<220> FEATURE:
<221> NAME/KEY: VARIANT
<222> LOCATION: (23)..(23)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (30)..(30)
<223> OTHER INFORMATION: X is selected from K, R, Q, H, S, G and A
<220> FEATURE:
<221> NAME/KEY: VARIANT
<222> LOCATION: (31)..(31)
<223> OTHER INFORMATION: X is selected from S and K
<220> FEATURE:
<221> NAME/KEY: VARIANT
<222> LOCATION: (33)..(33)
<223> OTHER INFORMATION: X is selected from V, R, I, L and A
<220> FEATURE:
<221> NAME/KEY: VARIANT
<222> LOCATION: (34)..(34)
<223> OTHER INFORMATION: X is selected from D and K

<400> SEQUENCE: 547

Ala Gln His Asp Glu Glu Xaa Xaa Xaa Ala Ala Xaa Glu Ile Asp Xaa
1               5                   10                  15

Leu Pro Asn Leu Xaa Xaa Xaa Gln Trp Asn Ala Phe Ile Xaa Xaa Leu
                20                  25                  30

Xaa Xaa Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 548
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (9)..(9)
<223> OTHER INFORMATION: X is selected from L, R and I
<220> FEATURE:
<221> NAME/KEY: VARIANT
<222> LOCATION: (10)..(10)
<223> OTHER INFORMATION: X is selected from R, I, L, V, K, Q, S, H, and
      A
```

```
<220> FEATURE:
<221> NAME/KEY: VARIANT
<222> LOCATION: (11)..(11)
<223> OTHER INFORMATION: X is selected from A, R, N, D, Q, E, H, K, M,
      S, T, W, F and V
<220> FEATURE:
<221> NAME/KEY: VARIANT
<222> LOCATION: (14)..(14)
<223> OTHER INFORMATION: X is selected from A, R, D, Q, E, G, K and S
<220> FEATURE:
<221> NAME/KEY: VARIANT
<222> LOCATION: (18)..(18)
<223> OTHER INFORMATION: X is selected from A, R, N, D, E, G, K, S, T
      and Q
<220> FEATURE:
<221> NAME/KEY: VARIANT
<222> LOCATION: (23)..(23)
<223> OTHER INFORMATION: X is selected from N and T
<220> FEATURE:
<221> NAME/KEY: VARIANT
<222> LOCATION: (24)..(24)
<223> OTHER INFORMATION: X is selected from R and K
<220> FEATURE:
<221> NAME/KEY: VARIANT
<222> LOCATION: (25)..(25)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (32)..(32)
<223> OTHER INFORMATION: X is selected from K, R, Q, H, S, G and A
<220> FEATURE:
<221> NAME/KEY: VARIANT
<222> LOCATION: (33)..(33)
<223> OTHER INFORMATION: X is selected from S and K
<220> FEATURE:
<221> NAME/KEY: VARIANT
<222> LOCATION: (35)..(35)
<223> OTHER INFORMATION: X is selected from V, R, I, L and A
<220> FEATURE:
<221> NAME/KEY: VARIANT
<222> LOCATION: (36)..(36)
<223> OTHER INFORMATION: X is selected from D and K

<400> SEQUENCE: 548

Val Asp Asn Lys Phe Asn Lys Glu Xaa Xaa Xaa Ala Ala Xaa Glu Ile
1               5                   10                  15

Asp Xaa Leu Pro Asn Leu Xaa Xaa Xaa Gln Trp Asn Ala Phe Ile Xaa
            20                  25                  30

Xaa Leu Xaa Xaa Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 549
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (9)..(9)
<223> OTHER INFORMATION: X is selected from L, R and I
<220> FEATURE:
<221> NAME/KEY: VARIANT
<222> LOCATION: (10)..(10)
<223> OTHER INFORMATION: X is selected from R, I, L, V, K, Q, S, H, and
      A
<220> FEATURE:
<221> NAME/KEY: VARIANT
<222> LOCATION: (11)..(11)
<223> OTHER INFORMATION: X is selected from A, R, N, D, Q, E, H, K, M,
      S, T, W, F and V
```

```
<220> FEATURE:
<221> NAME/KEY: VARIANT
<222> LOCATION: (14)..(14)
<223> OTHER INFORMATION: X is selected from A, R, D, Q, E, G, K and S
<220> FEATURE:
<221> NAME/KEY: VARIANT
<222> LOCATION: (18)..(18)
<223> OTHER INFORMATION: X is selected from A, R, N, D, E, G, K, S, T
      and Q
<220> FEATURE:
<221> NAME/KEY: VARIANT
<222> LOCATION: (23)..(23)
<223> OTHER INFORMATION: X is selected from N and T
<220> FEATURE:
<221> NAME/KEY: VARIANT
<222> LOCATION: (24)..(24)
<223> OTHER INFORMATION: X is selected from R and K
<220> FEATURE:
<221> NAME/KEY: VARIANT
<222> LOCATION: (25)..(25)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (32)..(32)
<223> OTHER INFORMATION: X is selected from K, R, Q, H, S, G and A
<220> FEATURE:
<221> NAME/KEY: VARIANT
<222> LOCATION: (33)..(33)
<223> OTHER INFORMATION: X is selected from S and K
<220> FEATURE:
<221> NAME/KEY: VARIANT
<222> LOCATION: (35)..(35)
<223> OTHER INFORMATION: X is selected from V, R, I, L and A
<220> FEATURE:
<221> NAME/KEY: VARIANT
<222> LOCATION: (36)..(36)
<223> OTHER INFORMATION: X is selected from D and K

<400> SEQUENCE: 549

Val Asp Ala Lys Phe Ala Lys Glu Xaa Xaa Xaa Ala Ala Xaa Glu Ile
1               5                   10                  15

Asp Xaa Leu Pro Asn Leu Xaa Xaa Xaa Gln Trp Asn Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 550
<211> LENGTH: 58
<212> TYPE: PRT
<213> ORGANISM: Artificial Sequence
<220> FEATURE:
<223> OTHER INFORMATION: Engineered polypeptide
<220> FEATURE:
<221> NAME/KEY: VARIANT
<222> LOCATION: (9)..(9)
<223> OTHER INFORMATION: X is selected from L, R and I
<220> FEATURE:
<221> NAME/KEY: VARIANT
<222> LOCATION: (10)..(10)
<223> OTHER INFORMATION: X is selected from R, I, L, V, K, Q, S, H, and
      A
<220> FEATURE:
<221> NAME/KEY: VARIANT
<222> LOCATION: (11)..(11)
<223> OTHER INFORMATION: X is selected from A, R, N, D, Q, E, H, K, M,
      S, T, W, F and V
<220> FEATURE:
<221> NAME/KEY: VARIANT
<222> LOCATION: (14)..(14)
<223> OTHER INFORMATION: X is selected from A, R, D, Q, E, G, K and S
<220> FEATURE:
```

```
<221> NAME/KEY: VARIANT
<222> LOCATION: (18)..(18)
<223> OTHER INFORMATION: X is selected from A, R, N, D, E, G, K, S, T
      and Q
<220> FEATURE:
<221> NAME/KEY: VARIANT
<222> LOCATION: (23)..(23)
<223> OTHER INFORMATION: X is selected from N and T
<220> FEATURE:
<221> NAME/KEY: VARIANT
<222> LOCATION: (24)..(24)
<223> OTHER INFORMATION: X is selected from R and K
<220> FEATURE:
<221> NAME/KEY: VARIANT
<222> LOCATION: (25)..(25)
<223> OTHER INFORMATION: X is selected from A, R, N, D, C, Q, E, G, L,
      K, M, S, T, W and V
<220> FEATURE:
<221> NAME/KEY: VARIANT
<222> LOCATION: (32)..(32)
<223> OTHER INFORMATION: X is selected from K, R, Q, H, S, G and A
<220> FEATURE:
<221> NAME/KEY: VARIANT
<222> LOCATION: (33)..(33)
<223> OTHER INFORMATION: X is selected from S and K
<220> FEATURE:
<221> NAME/KEY: VARIANT
<222> LOCATION: (35)..(35)
<223> OTHER INFORMATION: X is selected from V, R, I, L and A
<220> FEATURE:
<221> NAME/KEY: VARIANT
<222> LOCATION: (36)..(36)
<223> OTHER INFORMATION: X is selected from D and K

<400> SEQUENCE: 550

Ala Glu Ala Lys Tyr Ala Lys Glu Xaa Xaa Xaa Ala Ala Xaa Glu Ile
1               5                   10                  15

Asp Xaa Leu Pro Asn Leu Xaa Xaa Xaa Gln Trp Asn Ala Phe Ile Xaa
            20                  25                  30

Xaa Leu Xaa Xaa Asp Pro Ser Gln Ser Ser Glu Leu Leu Ser Glu Ala
        35                  40                  45

Lys Lys Leu Asn Asp Ser Gln Ala Pro Ser
50                  55
```

POLYPEPTIDE DERIVED FROM PROTEIN A AND ABLE TO BIND PDGF

CROSS-REFERENCE TO RELATED APPLICATIONS

This application is a U.S. National Stage application of International Patent Application No. PCT/EP2008/010776 filed 17 Dec. 2008, which is a CIP of U.S. patent application Ser. No. 12/002,972 filed 19 Dec. 2007 now U.S. Pat. No. 8,937,047. This application also claims the benefit of U.S. Provisional Patent Application Ser. No. 61/009,171 filed 26 Dec. 2007.

FIELD OF THE INVENTION

The present invention relates to polypeptides that bind to platelet-derived growth factor receptor beta (PDGF-Rβ). It also relates to new methods and uses of such polypeptides in treatment and diagnosis of different PDGF-Rβ related conditions.

BACKGROUND

The platelet-derived growth factor receptor beta (PDGF-Rβ) is a membrane-spanning tyrosine kinase. The ligand PDGF is composed of combinations of the homologous chains A, B, C and D, combined to either homo- or heterodimers. PDGF-Rβ binds PDGF-BB with high affinity and PDGF-AB with lower affinity. Ligand binding leads to dimerization and trans-phosphorylation of tyrosines in the intracellular kinase domain of the receptors.

PDGF is an important factor for regulating cell proliferation, cellular differentiation, cell growth and development. PDGF-Rβ is implicated in angiogenesis and in early stages of fibrosis. This receptor represents an attractive and potentially valuable target, e.g. for treatment and molecular imaging in for example oncologic and fibrotic diseases.

Antibodies blocking the effect of PDGF-Rβ are in clinical development and the continued provision of agents with a comparable affinity for this receptor remains a matter of substantial interest within the field. Of great interest is also the provision of uses of such molecules in the treatment and diagnosis of disease. It is an object of the invention to provide new PDGF-Rβ-binding agents, which could for example be used for diagnostic, in vitro or in vivo imaging, and therapeutic applications.

SUMMARY OF THE INVENTION

According to one aspect of the invention, there is provided a platelet derived growth factor receptor beta (PDGF-Rβ) binding polypeptide, comprising a platelet derived growth factor receptor beta binding motif, PBM, which motif consists of an amino acid sequence selected from i) $EX_2X_3X_4AAX_7EID$ $X_{11}LPNLX_{16}X_{17}X_{18}QW$ $NAFIX_{25}X_{26}LX_{28}X_{29}$ SEQ ID NO:541,
wherein, independently of each other,
$X_2$ is selected from L, R and I;
$X_3$ is selected from R, I, L, V, K, Q, S, H, and A;
$X_4$ is selected from A, R, N, D, Q, E, H, K, M, S, T, W, F and V;
$X_7$ is selected from A, R, D, Q, E, G, K and S;
$X_{11}$ is selected from A, R, N, D, E, G, K, S, T and Q;
$X_{16}$ is selected from N and T;
$X_{17}$ is selected from R and K;
$X_{18}$ is selected from A, R, N, D, C, Q, E, G, L, K, M, S, T, W and V;
$X_{25}$ is selected from K, R, Q, H, S, G and A;
$X_{26}$ is selected from S and K;
$X_{28}$ is selected from V, R, I, L and A;
$X_{29}$ is selected from D and K; and
ii) an amino acid sequence which has at least 90% identity to the sequence defined in i),
and wherein the PDGF-Rβ-binding polypeptide binds to PDGF-Rβ such that the $K_D$ value of the interaction is at most $1\times10^{-6}$ M.

The above definition of a class of sequence related, PDGF-Rβ-binding polypeptides according to the invention is based on an analysis of a number of random polypeptide variants of a parent scaffold, that were selected for their interaction with PDGF-Rβ in selection experiments. The identified PDGF-Rβ-binding motif, or "PBM", corresponds to the target binding region of the parent scaffold, which region constitutes two alpha helices within a three-helical bundle protein domain. In the parent scaffold, the varied amino acid residues of the two PBM helices constitute a binding surface for interaction with the constant Fc part of antibodies. In the present invention, the random variation of binding surface residues and the subsequent selection of variants have replaced the Fc interaction capacity with a capacity for interaction with PDGF-Rβ.

As the skilled person will realize, the function of any polypeptide, such as the PDGF-Rβ-binding capacity of the polypeptides according to the invention, is dependent on the tertiary structure of the polypeptide. It is therefore possible to make minor changes to the sequence of amino acids in a polypeptide without affecting the function thereof. Thus, the invention encompasses modified variants of the PBM of i), which are such that the resulting sequence is at least 90% identical to a sequence belonging to the class defined by i), such as at least 93% identical, such as at least 97% identical. For example, it is possible that an amino acid residue belonging to a certain functional grouping of amino acid residues (e.g. hydrophobic, hydrophilic, polar etc) could be exchanged for another amino acid residue from the same functional group.

In one embodiment of the polypeptide according to the invention, $X_{17}$ is R.

In one embodiment of the polypeptide according to the invention, $X_{11}$ is selected from A, R, N, D, E, G, K, S and T.

In one embodiment of the polypeptide according to the invention, $X_2$ is selected from L and R.

In one embodiment of the polypeptide according to the invention, $X_3$ is selected from R, I, L, V and S.

In one embodiment of the polypeptide according to the invention, $X_4$ is selected from A, R, N, D, Q, E, H, K, M, S, T and W.

In one embodiment of the polypeptide according to the invention, $X_{25}$ is selected from K, R, Q, H and S.

In one embodiment of the polypeptide according to the invention, $X_{28}$ is selected from V, R, I and L.

In one embodiment of the polypeptide according to the invention, $X_{29}$ is D. In one embodiment of the polypeptide according to the invention, $X_{25}$ is K. In one embodiment of the polypeptide according to the invention, $X_{28}$ is V.

In one embodiment of the polypeptide according to the invention, $X_3$ is selected from I and V.

In one embodiment of the polypeptide according to the invention, $X_4$ is selected from A, R, E and K.

In one embodiment of the polypeptide according to the invention, $X_7$ is selected from A, R and E.

In one embodiment of the polypeptide according to the invention, $X_{11}$ is selected from A, R, N and E.

In one embodiment of the polypeptide according to the invention, $X_{18}$ is selected from R, E, K and V.

In one embodiment of the polypeptide according to the invention, $X_2$ is L.

As described in detail in the experimental section to follow, the selection of PDGF-Rβ-binding variants has led to the identification of individual PDGF-Rβ-binding motif (PBM) sequences. These sequences constitute individual embodiments of the PBM sequence i) in the definition of PDGF-Rβ-binding polypeptides according to this aspect of the present invention. The sequences of individual PDGF-Rβ-binding motifs are presented in FIG. 1A-G and as SEQ ID NO:1-179. In some embodiments of this aspect of the invention, the PBM sequence i) is selected from any one of SEQ ID NO:2-3, SEQ ID NO:5, SEQ ID NO:7, SEQ ID NO:11-12, SEQ ID NO:18-19, SEQ ID NO:38, SEQ ID NO:42, SEQ ID NO:44, SEQ ID NO:47, SEQ ID NO:60-62, SEQ ID NO:64, SEQ ID NO:67-68, SEQ ID NO:71-72, SEQ ID NO:78, SEQ ID NO:80-81, SEQ ID NO:83, SEQ ID NO:86, SEQ ID NO:91-92, SEQ ID NO:94-97, SEQ ID NO: 101-103, SEQ ID NO:105, SEQ ID NO:109, SEQ ID NO:111, SEQ ID NO:116, SEQ ID NO:119, SEQ ID NO:133, SEQ ID NO:137, SEQ ID NO:139-140, SEQ ID NO:149, SEQ ID NO:153, SEQ ID NO:160, SEQ ID NO:164, SEQ ID NO:170, SEQ ID NO:174 and SEQ ID NO:179.

In one embodiment, the PDGF-Rβ-binding polypeptide according to the invention comprises a platelet derived growth factor receptor beta binding motif, PBM, which motif consists of the amino acid sequence selected from $EX_2X_3X_4AAX_7EID\ X_{11}LPNLX_{16}RX_{18}QWNAFIX_{25}X_{26}LX_{28}D$ SEQ ID NO:541 with $X_{29}$=D, wherein, independently of each other, $X_2$ is selected from L and R;

$X_3$ is selected from R, I, L, V, Q and S;

$X_4$ is selected from A, R, D, E, K and V;

$X_7$ is selected from A, Q and K;

$X_{11}$ is selected from A, R, E and S;

$X_{16}$ is selected from N and T;

$X_{18}$ is selected from R, G, K, S, T and V;

$X_{25}$ is selected from K, R, S and A;

$X_{26}$ is selected from S and K;

$X_{28}$ is selected from V, R, I and A.

The amino acid sequence of the PBM may for example be selected from any one of SEQ ID NO:2-3, SEQ ID NO:5, SEQ ID NO:7, SEQ ID NO:11, SEQ ID NO:60, SEQ ID NO:72, SEQ ID NO:78, SEQ ID NO:111 and SEQ ID NO:153.

In particular embodiments of the present invention, the PBM forms part of a three-helix bundle protein domain. For example, the PBM may essentially constitute two alpha helices with an interconnecting loop, within said three-helix bundle protein domain. In these embodiments, the PDGF-Rβ-binding polypeptide according to the invention may in particular comprise an amino acid sequence selected from:

i) K-[PBM]-DPSQS$X_aX_b$LL$X_c$EAKKLNDX$_d$Q SEQ ID NO:542;

wherein

[PBM] is a PDGF-Rβ-binding motif as defined above;

$X_a$ is selected from A and S;

$X_b$ is selected from N and E;

$X_c$ is selected from A and S;

$X_d$ is selected from A and S;

and ii) an amino acid sequence which has at least 80% identity to any one of the sequences defined above.

Said amino acid sequence may have at least 82%, such as at least 84%, such as at least 86%, such as at least 88%, such as at least 90%, such as at least 92%, such as at least 94%, such as at least 96%, such as at least 98% identity to the sequences defined above. The amino acid sequence may for example be selected from SEQ ID NO:180-358. In some embodiments of this aspect of the invention, the amino acid sequence i) may be selected from any one of SEQ ID NO:181-182, SEQ ID NO:184, SEQ ID NO:186, SEQ ID NO: 190-191, SEQ ID NO:197-198, SEQ ID NO:217, SEQ ID NO:221, SEQ ID NO:223, SEQ ID NO:226, SEQ ID NO:239-241, SEQ ID NO:243, SEQ ID NO:246-247, SEQ ID NO:250-251, SEQ ID NO:257, SEQ ID NO:259-260, SEQ ID NO:262, SEQ ID NO:265, SEQ ID NO:270-271, SEQ ID NO:273-276, SEQ ID NO:280-282, SEQ ID NO:284, SEQ ID NO:288, SEQ ID NO:290, SEQ ID NO:295, SEQ ID NO:298, SEQ ID NO:312, SEQ ID NO:316, SEQ ID NO:318-319, SEQ ID NO:328, SEQ ID NO:332, SEQ ID NO:339, SEQ ID NO:343, SEQ ID NO:343, SEQ ID NO:349, SEQ ID NO:353 and SEQ ID NO:358, and may in particular be selected from any one of SEQ ID NO:181-182, SEQ ID NO:184, SEQ ID NO:186, SEQ ID NO: 190, SEQ ID NO:239, SEQ ID NO:251, SEQ ID NO:257, SEQ ID NO: 290, SEQ ID NO:332 and SEQ ID NO:358.

In particular embodiments of the invention, said three-helix bundle protein domain is selected from domains of bacterial receptor proteins. Non-limiting examples of such domains are the five different three-helical domains of Protein A from *Staphylococcus aureus*, and derivatives thereof.

Thus, a PDGF-Rβ-binding polypeptide according the invention may comprise an amino acid sequence selected from:

ADNNFNK-[PBM]-DPSQSANLLSEAKKLNESQAPK SEQ ID NO:543 (PBM within domain A of staphylococcal protein A);

ADNKFNK-[PBM]-DPSQSANLLAE-AKKLNDAQAPK SEQ ID NO:544 (PBM within domain B of staphylococcal protein A);

ADNKFNK-[PBM]-DPSVSKEILAEAKKLNDAQAPK SEQ ID NO:545 (PBM within domain C of staphylococcal protein A);

ADAQQNNFNK-[PBM]-DPSQSTNVLGEAKKL-NESQAPK SEQ ID NO:546 (PBM within domain D of staphylococcal protein A);

AQHDE-[PBM]-DPSQSANVLGEAQKLNDSQAPK SEQ ID NO:547 (PBM within domain E of staphylococcal protein A);

VDNKFNK-[PBM]-DPSQSANLLAE-AKKLNDAQAPK SEQ ID NO:548 (PBM within the protein Z derivative of domain B of staphylococcal protein A);

VDAKFAK[PBM]-DPSQSSELLSEAKKLNDSQAPK SEQ ID NO:549 (PBM within a variant of a protein Z derivative of domain B of staphylococcal protein A);

AEAKYAK[PBM]-DPSQSSELLSEAKKLNDSQAPS SEQ ID NO:550 (PBM within a variant of a protein Z derivative of domain B of staphylococcal protein A); and an amino acid sequence which has at least 80% identity to any one of the sequences defined above, and wherein [PBM] is an PDGF-Rβ-binding motif as defined above. The inventive polypeptide may for example have a sequence which is at least 81%, at least 83%, at least 84%, at least 86%, at least 88%, at least 90%, at least 91% at least 93%, at least 95%, at least 97% or at least 98% identical to the sequence described herein. In some embodiments of this aspect of the invention, said amino acid sequence comprises a sequence selected from any one of SEQ ID NO:359-537. The amino acid sequence may for example comprise a sequence selected from SEQ ID NO:360-361, SEQ ID NO:363, SEQ ID NO:365, SEQ ID NO:369-370, SEQ ID NO:376-377, SEQ ID NO:396, SEQ ID NO:400, SEQ ID NO:402, SEQ ID NO:405, SEQ ID NO:418-420, SEQ ID NO:422, SEQ ID NO:425-426, SEQ ID NO:429-430, SEQ ID NO:436, SEQ ID NO:438-439, SEQ ID NO:441, SEQ ID NO:444, SEQ ID NO:449-450, SEQ ID NO:452-455, SEQ ID NO:459-461, SEQ ID NO:463, SEQ ID NO:467, SEQ ID NO:469, SEQ ID NO:474, SEQ ID NO:477, SEQ ID NO:491, SEQ ID NO:495, SEQ ID NO:497-498, SEQ ID NO:507, SEQ ID NO:511, SEQ ID NO:518, SEQ ID NO:522, SEQ ID NO:528, SEQ ID NO:532 and SEQ ID NO:537, and may in particular comprise an amino acid sequence selected from SEQ ID NO:360-361, SEQ ID NO:363, SEQ ID NO:365, SEQ ID NO:369, SEQ ID NO:418, SEQ ID NO:430, SEQ ID NO:436, SEQ ID NO:469, SEQ ID NO:511 and SEQ ID NO:537.

A PDGF-Rβ-binding polypeptide according to any aspect of the invention may bind to PDGF-Rβ such that the $K_D$ value of the interaction is at most $1\times10^{-7}$ M, for example at most $1\times10^{-8}$ M.

The polypeptides according to the invention are advantageous in that they bind well to PDGF-Rβ. The polypeptides may in particular bind to the extra-cellular domain of PDGF-Rβ. Typically, the polypeptides can be relatively short. By virtue of their small size, they are expected to exhibit a more efficient penetration in tumor tissue than antibodies, as well as to have better systemic circulation properties than monoclonal antibodies (which often have too long circulation times). Thus, they are considered suitable candidates for the development of molecular imaging agents. Additional possible applications include use in drug development and in screening procedures where specific imaging agents are desired in order to measure the outcome of treatment in in vivo models, and subsequently during clinical development. Molecular imaging provides a direct read-out efficacy of a pharmaceutical aimed at down-regulating a growth factor receptor, as well as for assessing the anti-tumor effect.

The skilled person will appreciate that various modifications and/or additions can be made to a polypeptide according to the invention in order to tailor the polypeptide to a specific application without departing from the scope of the present invention. For example, a PDGF-Rβ-binding polypeptide according to any aspect of the invention may be extended by C terminal and/or N terminal amino acids. Said extended polypeptide is a polypeptide which has additional amino acids residues at the very first and/or the very last position in the polypeptide chain, i.e. at the N- and/or C-terminus. The polypeptide may be extended by any suitable number of additional amino acid residues, for example at least one amino acid residue. Each additional amino acid residue may individually or collectively be added in order to, for example, improve production, purification, stabilization in vivo or in vitro, coupling, or detection of the polypeptide. Such additional amino acid residues may comprise one or more amino acid residues added for the purpose of chemical coupling. One example of this is the addition of a cysteine residue. Such additional amino acid residues may also provide a "tag" for purification or detection of the polypeptide such as a $His_6$ tag or a "myc" (c-myc) tag or a "FLAG" tag for interaction with antibodies specific to the tag.

The amino acid extensions discussed above may also provide one or more polypeptide domains with any desired function, such as the same binding function as the first PDGF-Rβ-binding domain, or another binding function, or an enzymatic function, toxic function (e.g. an immunotoxin), or a fluorescent signaling function, or combinations thereof. In such an extended polypeptide according to the invention, a PDGF-Rβ-binding polypeptide as described above is present as an PDGF-Rβ-binding domain to which additional peptides or proteins or other functional groups are coupled N- and/or C-terminally, or to any other residues (specifically or non-specifically). One example is an amino acid extension comprising the albumin-binding domain (ABD) of streptococcal protein G, or a derivative thereof. Such an ABD-extended polypeptide binds to serum albumin in vivo, and benefits from its longer half life, which increases the net half life of the polypeptide itself (see e.g. WO91/01743). Alternatively, the amino acid extension may comprise any other polypeptide with affinity for a serum protein.

Also covered by the present invention are modifications and/or additions to the polypeptide of the invention such as labels and/or therapeutic agents that are chemically conjugated or otherwise bound to the polypeptide.

The amino acid extensions, modifications and additions as discussed above may be coupled to the polypeptide of the invention by means of chemical conjugation (using known organic chemistry methods) or by any other means, such as expression of the polypeptide according to the invention as a fusion protein.

In one specific embodiment of the present invention, the polypeptide binds to the same epitope as PDGF-BB, or sufficiently close to it to block the binding of the ligand PDGF-BB to PDGF-Rβ. The polypeptide may for example be used to inhibit cell signaling by binding to a PDGF-Rβ on the cell surface. Such blocking of receptor function may be utilized to obtain a therapeutic effect. Alternatively, binding of the polypeptide to PDGF-Rβ may stimulate receptor activation by providing receptor dimerization.

In some embodiments of the invention, the polypeptide is present in multimeric form, comprising at least two PDGF-Rβ-binding polypeptide monomer units, the amino acid sequences of which may be the same or different. Multimeric forms of the polypeptide may be advantageous in that they may have enhanced binding properties. Preferred multimeric forms include dimeric forms. Such a dimeric form of the inventive polypeptide may for example be used to stimulate receptor activation. Multimeric forms of the polypeptides may comprise a suitable number of domains, each having a PDGF-Rβ-binding motif, and each forming a "monomer" within the multimer. These domains may all have the same amino acid sequence, but alternatively, they may have different amino acid sequences. The monomer units of a multimeric polypeptide may be joined by covalent coupling using known organic chemistry methods, or expressed as one or more fusion polypeptides, for example in a system for recombinant expression of polypeptides, or joined in any other fashion, either directly or via a linker, for example an amino acid linker.

In related aspects of the invention, there is provided a polynucleotide encoding a polypeptide as described above, as well as a method of producing such a polypeptide, the method comprising expression of the polynucleotide.

A polypeptide of the invention may be used as an alternative to conventional antibodies or low molecular weight substances in various medical, veterinary and diagnostic applications. The skilled addressee will understand that the polypeptides of the invention may be useful in any method which relies on affinity for PDGF-Rβ of a reagent. Thus, the inventive polypeptide may be used as a detection reagent, a capture reagent or a separation reagent in such methods, but also as a therapeutic or diagnostic agent in its own right or as a means for targeting other therapeutic or diagnostic agents, with direct (e.g. toxic molecules, toxins) or indirect (e.g. cancer vaccines, immunostimulatory molecules) effects on the PDGF-Rβ protein. Diagnostic applications include for example molecular imaging in order to reveal, diagnose and examine the presence of a disease, such as a tumor, in vivo in the body of a mammalian subject.

In one aspect of the invention, there is thus provided a PDGF-Rβ-binding polypeptide according to the invention for use as a medicament, for example for the treatment of a PDGF-Rβ-related condition. In this case, the PDGF-Rβ-binding polypeptide of the invention is used in vivo to obtain a therapeutic effect, for example by inhibiting cell signaling by binding to a PDGF-Rβ on a cell surface. There is also provided a PDGF-Rβ-binding polypeptide for use in diagnosis, such as in the diagnosis of a PDGF-Rβ-related condition.

In other aspects of the invention, the PDGF-Rβ-binding polypeptides may be used in targeting therapeutic or diagnostic agents, both in vivo and in vitro, to cells expressing PDGF-Rβ, particularly to cells which over-express PDGF-Rβ. There is thus provided a combination of a PDGF-Rβ-binding polypeptide according to the invention and a therapeutic agent. In one embodiment, said combination is used as a medicament, for example for the treatment of a PDGF-Rβ-related condition. There is moreover provided, in a related aspect of the invention, a combination of a PDGF-Rβ-binding polypeptide according to the invention and a diagnostic agent. Such a combination may be used in the diagnosis of a PDGF-Rβ-related condition, for example in molecular imaging of cells over-expressing PDGF-Rβ. In addition to the development of molecular imaging agents for the clinic, an application exists for specific preclinical imaging agents to measure the outcome of treatment in in vivo models and subsequently during clinical development. Molecular imaging should provide a direct read-out of the efficacy of a pharmaceutical aimed to down-regulate a receptor e.g. PDGF-Rβ, as well as for assessing the anti-tumor effect.

In a related aspect of the present invention, there is provided a Method of treatment of a PDGF-Rβ-related condition, comprising administering of a PDGF-Rβ-binding polypeptide or combination as described above to a mammalian subject in need thereof. Thus, in the inventive method of treatment, the subject is treated with a PDGF-Rβ-binding polypeptide or a combination according to the invention. In a more specific embodiment of said method, said binding of said PDGF-Rβ-binding polypeptide or said combination to a PDGF-Rβ of the subject inhibits or stimulates activation of the receptor. Said binding may for example inhibit receptor signaling. Also provided is a method for diagnosis of a PDGF-Rβ-related condition in a mammalian subject, comprising administering a PDGF-Rβ-binding polypeptide according to the invention, or a diagnostic combination as described above, to the subject for the purposes of obtaining a diagnosis.

In embodiments of the above described uses and methods of treatment, said condition may be selected from cancer disease, such as gliomas, sarcomas, and leukemias; vascular disorders, such as atherosclerosis, restenosis, pulmonary hypertension, and retinal diseases; fibrotic diseases, such as pulmonary fibrosis, liver cirrhosis, scleroderma, glomerulosclerosis, and cardiac fibrosis.

The terms "PDGF-Rβ-binding" and "binding affinity for PDGF-Rβ" as used in this specification refers to a property of a polypeptide which may be tested for example by the use of surface plasmon resonance technology, such as in a Biacore instrument (GE Healthcare). For example as described in the examples below, PDGF-Rβ-binding affinity may be tested in an experiment in which PDGF-Rβ, or a fragment of PDGF-Rβ such as the extracellular domain, is immobilized on a sensor chip of the instrument, and the sample containing the polypeptide to be tested is passed over the chip. Alternatively, the polypeptide to be tested is immobilized on a sensor chip of the instrument, and a sample containing PDGF-Rβ, or fragment thereof, is passed over the chip. The skilled person may then interpret the results obtained by such experiments to establish at least a qualitative measure of the binding of the polypeptide to PDGF-Rβ. If a quantitative measure is desired, for example to determine a $K_D$ value for the interaction, surface plasmon resonance methods may also be used. Binding values may for example be defined in a Biacore 2000 instrument (GE Healthcare). PDGF-Rβ is immobilized on a sensor chip of the measurement, and samples of the polypeptide whose affinity is to be determined are prepared by serial dilution and injected over the chip. $K_D$ values may then be calculated from the results using for example the 1:1 Langmuir binding model of the BIAevaluation 4.1 software provided by the instrument manufacturer. The PDGF-Rβ or fragment thereof may for example comprise the amino acid sequence represented by SEQ ID NO:540 (PDGF-Rβ extracellular domain) or SEQ ID NO: 539 (PDGF-Rβ). The extracellular domain of recombinant human PDGF-Rβ (amino acid residue 1-530, Gronwald et al, 1998, PNAS 85) provided by R&D Systems, #385-PR/CF may for example be used.

BRIEF DESCRIPTION OF THE FIGURES

FIG. 1A-T is a listing of the amino acid sequences of examples of PDGF-Rβ-binding motifs comprised in PDGF-Rβ-binding polypeptides of the invention (SEQ ID NO:1-179), examples of 49 amino acid residues long PDGF-Rβ-binding polypeptides according to the invention (SEQ ID NO:180-358) and examples of 58 amino acid residues long PDGF-Rβ-binding polypeptides according to the invention (SEQ ID NO:359-537), as well as the sequences of protein Z (SEQ ID NO:538), the Swiss-Prot entry P09619 of human PDGF-Rβ (amino acid residues 1-1106, SEQ ID NO:539) and the Swiss-Prot entry P09619 of the extra-cellular domain of human PDGF-Rβ (amino acid residues 33-531 of PDGF-Rβ, SEQ ID NO:540).

FIG. 4 is an overview of the selections performed in Example 1 (A) and in Example 4 (B) showing target concentrations (nM) and number of washes (in parenthesis). Selection from the first library, (A), was performed in four cycles initially divided into two tracks (I and II). In the second selection cycle, these were further divided into two tracks (Ia and Ib, IIa and IIb), resulting in totally four tracks. Track Ia and Ib selections were performed against non-biotinylated PDGF-Rβ and track IIa and IIb selections were performed against biotinylated PDGF-Rβ. Selection from the maturated library, (B), was initially performed in four tracks. These were further divided in cycle two, resulting in totally six tracks. Selection was performed in four cycles.

FIGS. 5A-C show the result of a binding analysis performed in a Biacore instrument. Different monomeric Z variants from the maturated library (Example 4) were tested for their binding to PDGF receptors. A) shows binding to human PDGF-Rβ, B) shows binding to murine PDGF-Rβ, and C) shows binding to human PDGF-Rα. Five different Z variants were injected in duplicates or triplicates over Biacore chip surfaces with immobilized PDGF receptors; Z02558, Z02516, Z02483, Z02477 and Z02465. Two Z variants from the selection in Example 1 were run as references (Z01977 and Z01982), as well as an injection of running buffer HBS-EP.

FIGS. 6A-C show sensorgrams from kinetic experiments performed in a Biacore instrument with curve fitting in a Langmuir 1:1 binding model. Varying concentrations of the different Z variants A) Z01982, B) Z02465 and C) Z02483 were injected over immobilized human PDGF-Rβ. The straight curves represent the fitted model.

EXAMPLES

Figure 2:
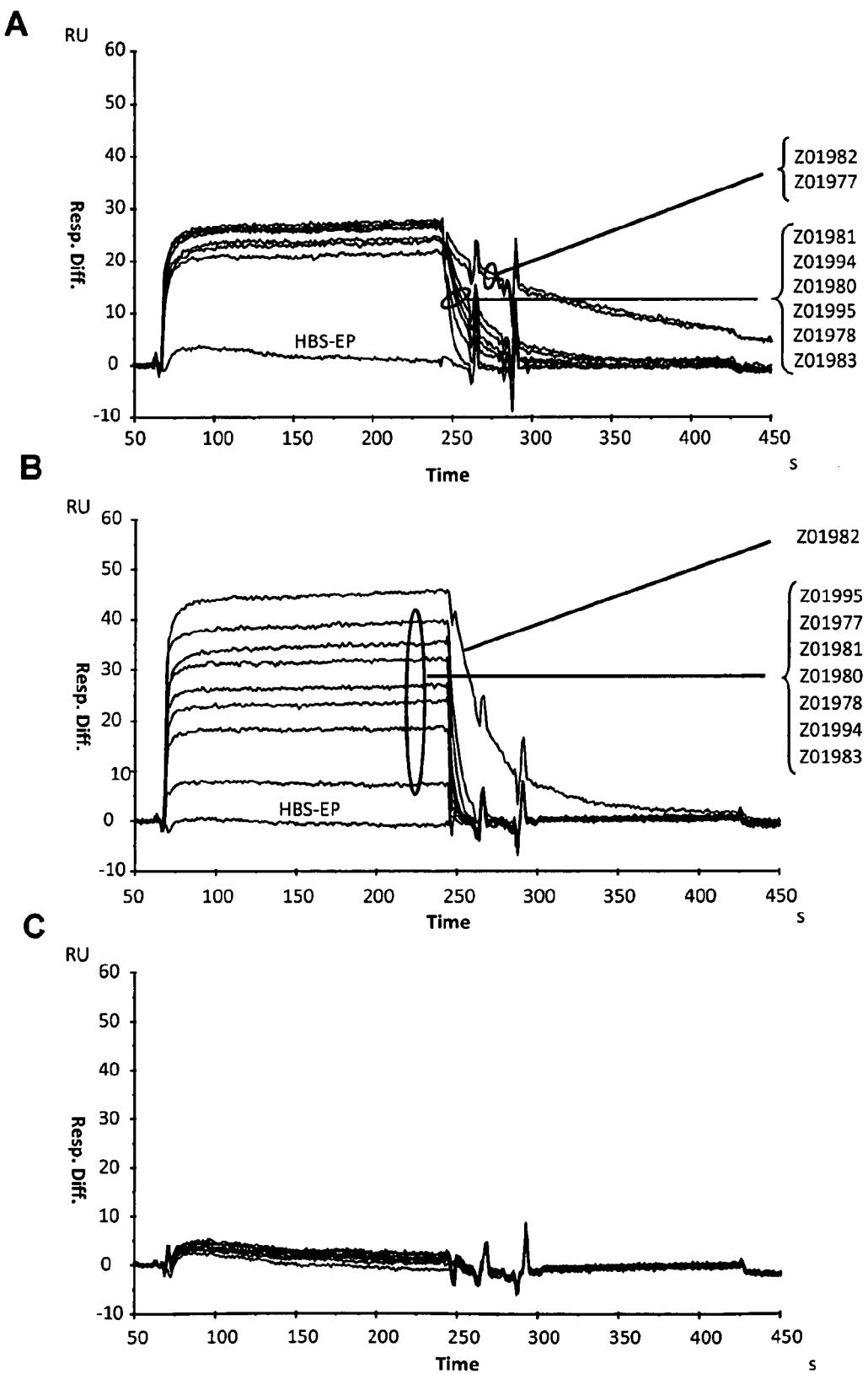
FIGS. 2A-C show the result of binding analysis performed in a Biacore instrument for investigating the binding of different monomeric Z variants to PDGF receptors. Eight different Z variants were injected in duplicates over Biacore chip surfaces with immobilized PDGF receptors. A) shows injection over human PDGF-Rβ, B) shows injection over murine PDGF-Rβ, and C) shows injection over human PDGF-Rα. The Z variants are listed in two groups, the individual Z variants in each Z variant group corresponding top-down to individual curves in each group of curves.

The following materials where used throughout this work except where otherwise noted.

*Escherichia coli* strain RR1ΔM15 (Rüther, Nucleic Acids Res 10:5765-5772, 1982)

The extracellular domain of recombinant human PDGF-Rβ with a C-terminal Fc fusion and $His_6$-tag (R&D Systems, #385-PR/CF)

Murine PDGF-Rβ-Fc (R&D Systems, #1042-PR/CF)

Human PDGF-sRα (R&D Systems, #322-PR/CF)

PDGF-BB (R&D Systems #220-BB/CF)

Example 1

Selection and Screening of PDGF-Rβ-Binding Polypeptides

Materials and Methods
Biotinylation of Target Protein:

The extracellular domain of recombinant human PDGF-Rβ was biotinylated with a 10× molar excess of EZ-link Sulfo-NHS-LC-Biotin (Pierce #21327) in PBS (10 mM phosphate, 137 mM NaCl, 2.68 mM KCl, pH 7.4). In order to remove any excess biotin, a buffer exchange was made on desalting PD-10 columns (GE Healthcare #17-0851-01), pre-equilibrated with PBS according to the manufacturer's instructions.

Preparation of Z00000-Coupled and Fc-Coated Streptavidin Beads:

Biotinylated Z00000 (Affibody AB, #10.0623.02.0005), i.e. protein Z (SEQ ID NO:538) as described in Nilsson et al, Prot Eng 1:107-113, 1987, was coupled to streptavidin coated magnetic beads (Dynabeads® M-280 Streptavidin, Dynal #112.06). 15 μg $(Z00000)_2$-Cys-biotin was added per mg beads, and the beads were incubated for 30 minutes at room temperature (RT). The beads were washed with PBS-T 0.1 (PBS supplemented with 0.1% Tween 20). The Z00000 coupled beads were thereafter coated with polyclonal human IgG1-Fc (Jackson Immuno Research #009-000-008) by end-over-end incubation for 1 hour at RT using 4 μg Fc per mg Z00000 coupled beads. The beads were washed with PBS-T 0.01 prior to use in the pre-selection described below.

Phage Display Selection of PDGF-Rβ-Binding Polypeptides:

A library of random variants of protein Z displayed on bacteriophage, constructed in phagemid pAffi1/pAY00065 as described in Gronwall et al, J Biotechnol 128:162-183 (2007), was used to select PDGF-Rβ-binding polypeptides. Selection was performed in four cycles initially divided into two tracks (I and II). In the second selection cycle, these were further divided into two tracks, resulting in totally four tracks (Ia=high target concentration, Ib=low target concentration, IIa=high target concentration, and IIb=low target concentration). Tracks Ia and Ib were performed against non-biotinylated PDGF-Rβ, and tracks IIa and IIb against biotinylated PDGF-Rβ. An overview of the selection strategy is shown in FIG. 4A.

Phage library stock was prepared according to previously described procedures (Nord et al, Nat Biotech 15:772-777 (1997); Hansson et al, Immunotechnology 4:237-252 (1999)). Prior to selection, the phage stock was twice precipitated in PEG/NaCl (20% polyethyleneglycol (PEG), 2.5 M NaCl) and dissolved in 1 ml selection buffer (0.1% gelatin in PBS-T 0.1). In order to reduce the amount of background binders, a pre-selection was performed by incubation of phage stock with biotinylated Z00000-coupled streptavidin beads coated with Fc protein (track I) or with streptavidin beads (track II) for 1 hour at RT. All tubes and beads used in the selection were pre-blocked with selection buffer.

In cycle 1 of the selection, the supernatant resulting from the pre-selection was mixed with 100 nM PDGF-Rβ (track I) or 100 nM biotinylated PDGF-Rβ (track II), followed by incubation under continuous rotation for 2 hours at RT. Target-phage complexes were captured on streptavidin beads via biotinylated Z00000 (0.5 mg beads, 20 minutes, track I) or directly to streptavidin beads (0.77 mg beads, 15 minutes, track II). The bead-bound phages were washed 2 times with 1000 μl PBS-T 0.1. After the wash, the bound phages were eluted with 500 μl 0.1 M glycine-HCl, pH 2.2 followed by immediate neutralization with 50 μl Tris-HCl, pH 8.0 and 450 μl PBS. Selected phage particles were amplified as described below and new phage stocks were prepared between each cycle. Phage stock, i.e. phages entering the selection cycle, and eluted phage particles were titrated after each selection cycle.

In cycle 2, selection tracks I and II were respectively split into selection tracks Ia and Ib, and tracks IIa and IIb. Thus, the newly prepared phage stocks were incubated with 50 nM (Ia) or 20 nM (Ib) PDGF-Rβ in selection buffer under continuous rotation for 2 hours at RT. Phage particle-target complexes were captured as in cycle 1 with 0.25 mg (Ia) or 0.1 mg (Ib) beads for 20 (Ia) or 15 (Ib) minutes. Similarly, phage stocks were incubated with 50 nM (IIa) or 20 nM (IIb) biotinylated PDGF-Rβ in selection buffer, followed by capturing with 0.4 mg (IIa) or 0.15 mg (IIb) beads. The wash was performed as in cycle 1 but with 4 washes. Elution was performed as in cycle 1.

In cycle 3, phage stocks were incubated with 25 nM (Ia) or 4 nM (Ib) PDGF-Rβ under continuous rotation as described above, followed by capturing with 0.15 mg (Ia) or 0.1 mg (Ib) beads. Similarly, phage stocks were incubated with 25 nM (IIa) or 4 nM (IIb) biotinylated PDGF-Rβ and captured with 0.2 mg (IIa) or 0.1 mg (IIb) beads. The wash was performed as in cycle 2 but with 6 washes. Elution was performed as in cycle 1.

In the last selection cycle, phage stocks were incubated with 12.5 nM (Ia) or 0.8 nM (Ib) PDGF-Rβ under continuous rotation and captured with 0.15 mg (Ia) or 0.1 mg (Ib) beads. Similarly, phage stocks were incubated with 12.5 nM (IIa) or 0.8 nM (IIb) biotinylated PDGF-Rβ under continuous rotation and captured with 0.2 mg (IIa) or 0.1 mg (IIb) beads. The wash was performed as in cycle 3 but with 12 washes. Elution was performed as in cycle 1.

Amplification of Phage Particles:

Log phase *E. coli* RR1ΔM15 cells were infected with 950 µl eluted phage particles for 20 min at 37° C. after each cycle of selection. The phages that were still bead-bound after elution were similarly amplified. After 20 minutes of incubation at 37° C., the cells infected with eluted phage and the cells infected with bead-bound phage originating from the same selection cycle and track, were pooled and pelleted by centrifugation. The pellet was dissolved in a small volume of TSB-YE medium (30 g/l TSB, 5 g/l yeast extract) and spread on tryptone yeast extract plates (TYE: 15 g/l agar, 10 g/l tryptone water (Merck), 5 g/l yeast extract, 3 g/l NaCl, 2% glucose and 0.1 g/l ampicillin), followed by incubation overnight at 37° C. In the final selection cycle, bacteria were diluted before spreading onto TYE plates in order to form single colonies to be used in ELISA screening.

Phage infected bacteria grown on the TYE plates were re-suspended in TSB medium. An amount of the re-suspended cells was prepared as glycerol stock and stored at −20° C. Suspended cells corresponding to 100-1000 times the number of eluted phage were inoculated in TSB-YE medium supplemented with 2% glucose and 100 µg/ml ampicillin. The cells were grown to log phase at 37° C. An amount of cells corresponding to the same amount of cells used for inoculation was infected with a 20× excess of M13K07 helper phage (New England Biolabs #NO315S) during 30 min at 37° C. Cells were pelleted by centrifugation, re-suspended in TSB-YE medium supplemented with 100 µM IPTG (1 M isopropyl-β-D-1-thiogalactopyranoside), 25 µg/ml kanamycin and 100 µg/ml ampicillin, and grown overnight at 30° C. The overnight cultures were centrifuged, and phage particles in the supernatant were precipitated twice with PEG/NaCl buffer. Finally, the phages were re-suspended in selection buffer before entering the next selection cycle.

ELISA Screening of Z Variants:

To test if the Z variant molecules could indeed interact with the PDGF-Rβ, an ELISA was performed. The Z variants were produced by inoculating single colonies, prepared as described above, in 1 ml TSB-YE medium supplemented with 100 µg/ml ampicillin and 0.1 mM IPTG in deep-well plates (Nunc #278752). The plates were incubated for 18-24 h at 37° C. After incubation, replicate plates were made by transferring a small fraction of each culture to 96-well plates with 15% glycerol for storage at −20° C. Remaining cells were pelleted by centrifugation, re-suspended in 300 µl PBS-T 0.05 (PBS supplemented with 0.05% Tween 20) and frozen at −80° C. to release the periplasmic fraction of the cells. Frozen samples were thawed in a water bath and cells were pelleted by centrifugation. The periplasmic supernatant contained the Z variants as fusions to an albumin binding domain (ABD, GA3 of protein G from *Streptococcus* strain G148), expressed as AQHDEALE-[Z#####]-VDYV-[ABD]-YVPG (Gronwall et al, supra). Z##### refers to individual Z variants.

Half area 96 well ELISA plates (Costar #3690) were coated with 50 µl/well of coating buffer (50 mM sodium carbonate, pH 9.6) containing 6 µg/ml human serum albumin (HSA, Sigma #A3782), and incubated over night. The HSA solution was poured off and the wells were blocked with 100 µl of PBS-T 0.1 supplemented with 2% non-fat dry milk solution (Semper AB) for 1 h at RT. The blocking solution was discarded and 50 µl of periplasmic solution were added to the wells and incubated for 1.5 h at RT under slow shaking. The supernatants were poured off and the wells were washed 4 times with PBS-T 0.05. 50 µl of a mixture containing both biotinylated and non-biotinylated PDGF-Rβ at a concentration of 4.5 µg/ml in PBS-T 0.1 was added to each well. The plates were incubated for 1.5 h at RT followed by wash 4× in PBS-T 0.05. IgG-Fc control plates were prepared by addition of 3 µg/ml Fc from human IgG in 50 µl PBS-T to the wells. The control plates were incubated for 1.5 h at RT and washed as described above. An antibody against Fc (DAKO, #P0214), labeled with horseradish peroxidase and diluted 1:4000 in PBS-T 0.1, was added to the wells. After washing as described above, 50 µl ImmunoPure TMB substrate (Pierce #34021) was added to the wells and the plates were treated according to the manufacturer's recommendations. All steps from blocking to reading were performed in a Tecan Genesis Freedom 200 robot (Tecan Group LTD). Absorbance of the wells was read at 450 nm in an ELISA reader Tecan Ultra 384 (Tecan) and evaluated with Magellan v. 5.0 software (Tecan).

Sequencing:

From the ELISA screening, clones regarded as positive were picked for sequencing. PCR fragments were amplified from single colonies using a standard PCR program and the primers AFFI-21 (5'-tgcttccggctcgtatgttgtgtg) and AFFI-22 (5'-cggaaccagagccaccaccgg). Sequencing of amplified fragments was performed using the biotinylated oligonucleotide AFFI-72 (5'-biotin-cggaaccagagccaccaccgg) and a BigDye® Terminator v3.1 Cycle Sequencing Kit (Applied Biosystems), used in accordance with the manufacturer's protocol. The sequencing reactions were purified by binding to magnetic streptavidin coated beads using a Magnatrix 8000 (Magnetic Biosolution), and analyzed on ABI PRISM® 3100 Genetic Analyzer (PE Applied Biosystems). The sequencing results were imported and analyzed with an ALD LIMS Nautilus™ 2003 R2 B3 software (Thermo Electronics Corp.).

Subcloning of Z Variants:

Monomeric and dimeric Z variants were amplified from pAffi1/pAY00065 vectors. A PCR was performed using different primer pairs and the resulting gene fragments were purified and hybridized in ligase buffer.

The hybridized gene fragments were subcloned in the pAY01448 vector, providing an N-terminal $His_6$ tag ($His_6$ Z#####), and in the pAY01449 vector, providing an N-terminal $His_6$ tag and a C-terminal cysteine ($His_6$-(Z#####)$_2$-Cys). The PDGF-Rβ-binding Z variants were subcloned as monomers in pAY01448 and as dimers in pAY01449, and the constructs encoded by the expression vectors were MGSSH-HHHHHLQ-[Z#####]-VD for the monomers and MGSSH-HHHHHLQ-[Z#####][Z#####]-VDC for the dimers. For the dimers, a three parts ligation was used for insertion of both insert fragments into the vector at the same step. Hybridized gene fragments and AccI-digested and dephosphorylated expression vectors were ligated in ligase buffer and electroporated into electrocompetent *E. coli* TOP10 cells. The transformed cells were spread on TBAB plates (30 g/l tryptose blood agar base) supplemented with 50 µg/ml of kanamycin, followed by incubation at 37° C. overnight. The colonies were screened using PCR and the lengths of the PCR fragments were verified on agarose gels. To verify the sequences, sequencing was performed with BigDye® Terminator v3.1 Cycle Sequencing Kit (Applied Biosystems), followed by analysis in an ABI PRISM® 3100 Genetic Analyzer (PE Applied Biosystems) and evaluation using Sequencher™ 4.0.5. software (Gene Codes Corporation).

Plasmid DNA stock was prepared from the sequenced clones and deposited in −80° C. In addition, *E. coli* BL21 (DE3) cells were transformed with the plasmids, either through electroporation (monomeric constructs) or through transformation of chemically competent cells (dimeric constructs).

Results

Phage Display Selection of PDGF-Rβ-Binding Polypeptides:

Four cycles of phage display selections were run against non-biotinylated (track I) and biotinylated (track II) human PDGF-Rβ fused to the Fc part of IgG. Phage particle-target complexes were captured onto streptavidin-coated beads with (I) or without (II) bead-coupled Z00000-biotin. The four selection cycles were performed with Ia) non-biotinylated target, high target concentration, Ib) non-biotinylated target, low target concentration, IIa) biotinylated target, high target concentration, and IIb) biotinylated target, low target concentration. For each selection cycle, the number of washes was increased. The phage particle titers and yields were calculated after each selection cycle. The phage particle yield (phage particles out/phage particles in) increased for each cycle (except the second one), indicating an enrichment in target binding clones.

ELISA Screening of Z Variants:

The clones obtained after four cycles of selection were produced in 96-well plates and screened for PDGF-Rβ-binding activity in an ELISA. In parallel, binding to Fc was tested for each clone. In total, 93 clones from each selection track (Ia, Ib, IIa, IIb) were screened. The absorbance measurements showed many clearly PDGF-Rβ positive clones and a few Fc positive clones. A Z variant molecule from selections against CD33 was used as negative and positive controls. The positive control was detected with human CD33-Fc and the negative control was not detected.

Sequencing:

Sequencing was performed for the clones with the highest absorbance values against PDGF-Rβ and with low absorbance values against Fc, i.e. values equal to values of background absorbance, in the ELISA screening. In total, 147 PDGF-Rβ positive clones were run. Most of the clones were found in several copies. However, eleven new Z variants were identified. Each variant was given a unique identification number, #####, and individual variants are referred to as Z#####. The amino acid sequences of the 58 amino acid residues long Z variants are listed in FIG. 1M and in the sequence listing as SEQ ID NO:359-369. The deduced PDGF-Rβ-binding motifs of these Z variants are listed in FIG. 1A and in the sequence listing as SEQ ID NO:1-11. The amino acid sequences of the 49 amino acid residues long polypeptides predicted to constitute the complete three-helix bundle within each of these Z variants are listed in FIG. 1G and in the sequence listing as SEQ ID NO:180-190.

The unique sequences were grouped together in a cluster of similar sequences with an internal dissimilarity lower than approximately 25% (results not shown). The sequence similarities suggest that the Z variants bind to the same binding surface on the PDGF-Rβ receptor.

Subcloning of Z Variants:

The unique clones were chosen for subcloning in the expression vectors pAY01448 and pAY01449 as monomers and dimers, respectively. The cloning resulted in eight monomers (Z01977, Z01978, Z01980, Z01981, Z01982, Z01983, Z01994 and Z01995) and seven dimers (dimers of Z01976, Z01977, Z01980, Z01982, Z01983, Z01994 and Z01995).

Example 2

Production and Characterization of Z Variants

Materials and Methods
Protein Expression and Purification:

Transformed *E. coli* BL21(DE3) cultures as subcloned in Example 1 were grown to an optical density of approximately 1 (diluted 10×) and protein expression was induced by addition of 1 M IPTG (0.5 ml/l culture). Cultures were harvested 5 h after induction, by 20 min of centrifugation at 15900 g. The supernatants were discarded and the cell pellets were collected and stored at −20° C. prior to further use.

The PDGF-Rβ-binding Z variants were purified from cell pellets under denatured conditions on Ni-NTA Superflow Columns (Qiagen), and buffer was exchanged to PBS using PD-10 columns (GE Healthcare). Expression levels of soluble and unsoluble proteins were analyzed using SDS-PAGE by ocular determination of Coomassie stained gels. Purified Z variants that were not to be used directly were aliquoted and stored at −80° C.

Protein Characterization:

The concentration of purified Z variants (in $His_6$-Z##### form and in $His_6$-(Z#####)$_2$ Cys form) was determined by absorbance measurements at 280 nm using theoretical extinction coefficients. The purity was estimated by SDS-PAGE analysis on 10 wells 4-12% NuPAGE™ gels (Invitrogen) using Coomassie blue staining. To verify the identity and to determine the molecular weights of purified Z variants, LC/MS-analyses were performed on an Agilent 1100 LC/MSD system (Agilent Technologies).

CD Analysis:

The purified Z variants were thawed and diluted to 0.5 mg/ml in PBS. For each diluted Z variant, a CD spectrum at 250-195 nm was obtained at 37° C. In addition, a variable temperature measurement (VTM) was performed to determine the melting temperature (Tm). In the VTM, the absorbance was measured at 221 nm while the temperature was raised from 20 to 90° C., with a temperature slope of 5° C./min. The CD measurements were performed on a Jasco J-810 spectropolarimeter (Jasco Scandinavia AB) using a cell with an optical path-length of 1 mm.

Biacore Binding Analysis:

The interactions of eight $His_6$-tagged monomeric PDGF-Rβ-binding Z variants with human PDGF-Rβ, murine PDGF-Rβ-Fc and human PDGF-sRα were analyzed in a Biacore instrument (GE Healthcare). The three receptors were immobilized in different flow cells on the carboxylated dextran layer of a CM5 chip surface (GE Healthcare). The immobilization was performed using amine coupling chemistry according to the manufacturer's protocol. One flow cell surface on the chip was activated and deactivated for use as blank during analyte injections. The analytes, i.e. Z variants diluted in HBS-EP running buffer (GE Healthcare) to a final concentration of 5 μM, were injected in random order in duplicates at a flow-rate of 10 μl/minute for 3 minutes. After 3 minutes of dissociation, the surfaces were regenerated with one injection of 25 mM HCl. The results were analyzed in BiaEvaluation software (GE Healthcare). Curves of the blank surface were subtracted from the curves of the ligand surfaces.

Epitope Test:

The interaction of the human PDGF-Rβ receptor with its natural ligand PDGF-BB in the presence of three different Z variants (Z01977, Z01980 and Z01982 in $His_6$ Z##### form) was analyzed in a Biacore instrument (GE Healthcare). Human PDGF-BB was immobilized on the carboxylated dextran layer of two flow cells on a Biacore CM5 chip surface. The ligand density was different in the two flow cells. Analytes containing 100 nM PDGF-Rβ mixed with varying concentrations of monomeric $His_6$-tagged Z variants were prepared by dilution in the running buffer HBS-EP. A Z variant specific for an irrelevant protein (amyloid β peptide, Aβ) was used as a negative control. The analytes were injected at a flow-rate of 10 μl/minute for 3 minutes. After 3 minutes of dissociation, the surfaces were regenerated with two injections of 10 mM HCl. The results were analyzed as described above.

Dot Blot Analysis:

Seven PDGF-Rβ-binding Z variants were tested for specificity by dot blot analysis. The Z variants were tested against alpha-2 macroglobulin (MP biomedicals/Cappel, #55833), alpha-1 acid glycoprotein (RDI, #RDI-SCP-153-1), alpha-1 antichymotrypsin (RDI, #RDI-SCP-159-0), alpha-1-antitrypsin (RDI, #RDI-SCP-165-5), C3 complement (RDI, #RDI-SCP-150-0), C4 complement (RDI, #RDI-SCP-151-0), fibrinogen (Enzyme research, #031015E), haptoglobulin (RDI, #RDI-SCP-119-1), hemopexin (Agilent), human IgG1 Fc, polyclonal (Jackson Immuno Research, #009-000-008), holo-transferrin (Sigma, #T0665), human IgA (Bethyl, #P80-102), human IgE (Fitzgerald, #30 A101), human IgG (Sigma, #G4386), human IgM (Sigma, #18260), human PDGF-sRα (R&D Systems, #322-PR/CF), human Serum Albumine (HSA, Sigma, #A3782), murine PDGF-Rβ-Fc (R&D Systems, #1042-PR/CF), neutravidin (Pierce, #31000), streptavidin (Pierce, #21122), transthyretin (Sigma, #P1742), and human PDGF-Rβ-Fc. Nitrocellulose membranes (Invitrogen) were dotted with 1 μl of each protein at a concentration of 0.1 mg/ml. The membranes were blocked for 1 h in PBS supplemented with 0.5% casein (blocking solution) at RT. After removal of the solution, the membranes were incubated for 1 h with 2 μg/ml of different dimeric Z variants, with N terminal $His_6$ tags and C terminal cysteines. The membranes were washed 4×5 minutes in PBS-T 0.1. The Z variants were detected with a polyclonal goat IgG against an epitope common to all Z variants (Affibody AB, #20.1000.01.0005). This goat anti-Z IgG, diluted to 1 μg/ml in blocking solution, was added to the membranes which were incubated for 1 h at RT. After washing, an antibody against goat IgG conjugated to HRP (DAKO #P0449), diluted 1:10000 in blocking solution, was added to the membranes, followed by incubation of the membranes for 1 h at RT. The membranes were washed, rinsed in PBS and soaked with Supersignal (Pierce #34075). Light emissions were photographed with a ChemiImager 5500 (Alpha Innotech Corp.).

Results

Protein Production:

Both monomeric (in $His_6$-Z##### form) and dimeric (in $His_6$-(Z#####)$_2$ Cys form) Z variant molecules yielded acceptable expression levels of soluble gene product. The purity of produced batches was assessed by SDS-PAGE analysis. The purity was estimated to exceed 95% for the monomeric molecules and to be approximately 90% for dimeric molecules.

The LC/MS analysis verified the correct molecular weight for all Z variant molecules.

CD Analysis:

In the CD analysis, the spectrum measurements were performed at 37° C. At that temperature, the α-helical structures of the Z variants molecules had attained a partly unfolded state. This result was also verified in the variable temperature measurements where the melting temperatures (Tm) were determined (Table 1).

TABLE 1

Melting temperatures for a number of Z variants

| Z variant | Tm (° C.) |
|---|---|
| $His_6$-Z01977 | 30 |
| $His_6$-Z01978 | 43 |
| $His_6$-Z01980 | 35 |
| $His_6$-Z01981 | 37 |
| $His_6$-Z01982 | 37 |
| $His_6$-Z01983 | 37 |
| $His_6$-Z01994 | 30 |
| $His_6$-Z01995 | 36 |
| $His_6$-(Z01976)$_2$-Cys | 34 |
| $His_6$-(Z01977)$_2$-Cys | 35 |
| $His_6$-(Z01980)$_2$-Cys | 35 |
| $His_6$-(Z01982)$_2$-Cys | 41 |
| $His_6$-(Z01983)$_2$-Cys | 38 |
| $His_6$-(Z01994)$_2$-Cys | 31 |
| $His_6$-(Z01995)$_2$-Cys | 37 |

Biacore Binding Analysis:

The binding of eight monomeric Z variants (Z01977, Z01978, Z01980, Z01981, Z01982, Z01983, Z01994 and Z01995) to human and murine PDGF-Rβ, as well as to human PDGF-sRα, was tested in a Biacore instrument by injecting the Z variants over surfaces containing the three receptors. The ligand immobilization levels on the surfaces were: human PDGF-Rβ (flow cell 2): 2240 RU, murine PDGF-Rβ (flow cell 3): 2010 RU and human PDGF-sRα (flow cell 4): 1900 RU. All tested Z variants showed binding to both human and murine PDGF-Rβ, but no binding to human PDGF-Rα. The result is displayed in FIGS. 2. Z01982 and Z01977 showed the slowest dissociation curves to human PDGF-Rβ. Z01982 also showed the slowest dissociation curve to murine PDGF-Rβ.

Figure 3:
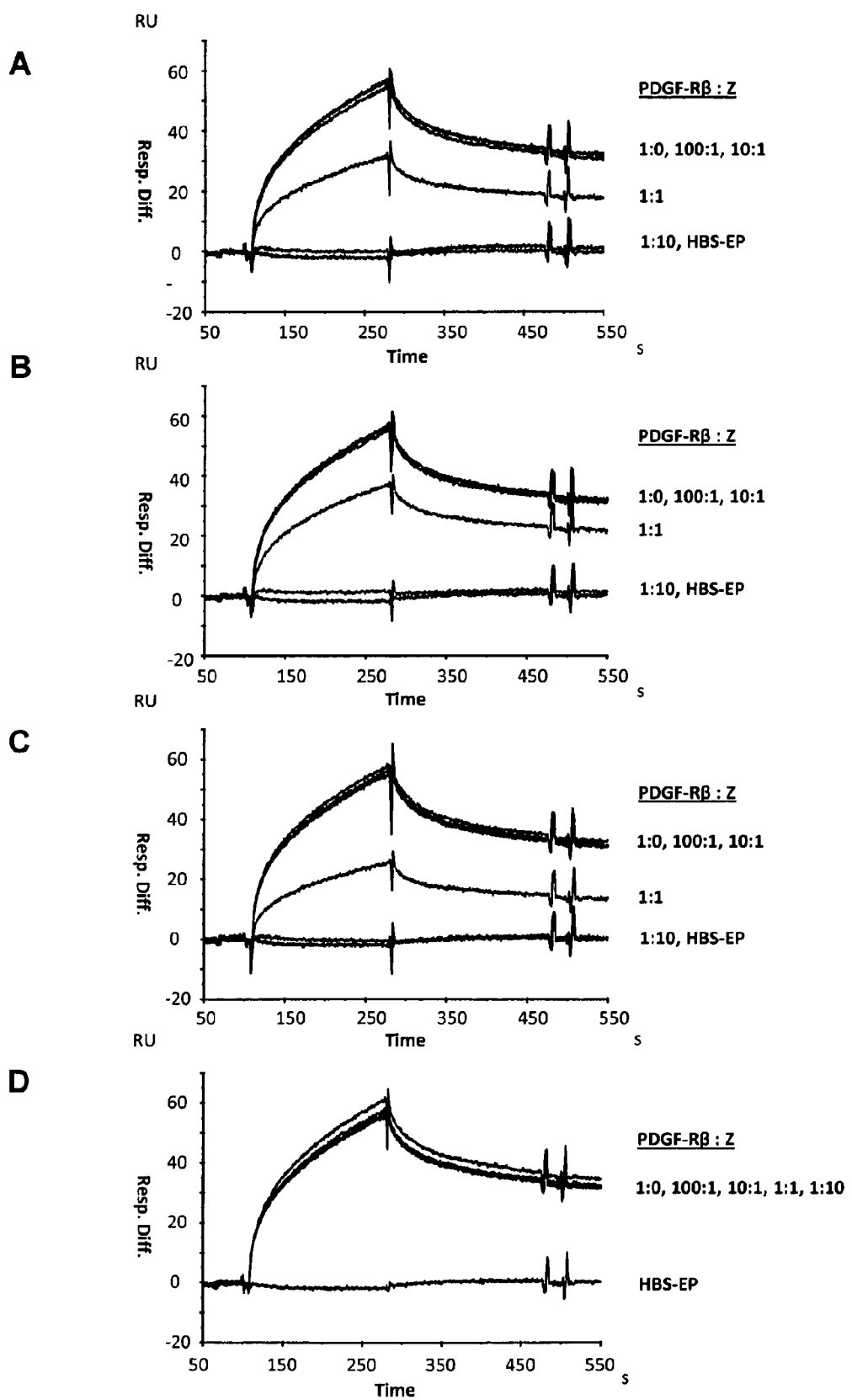
FIGS. 3A-D show the result of an epitope test of Z variant molecules on PDGF-Rβ. Analytes containing varying concentrations of Z variant molecules and a constant concentration of PDGF-Rβ were injected over immobilised PDGF-BB. A) shows Z01977, B) shows Z01980, C) shows Z01982 and D) shows a negative control (ZAβ). The relative concentrations of PDGF-Rβ and Z variant are shown in relation to each group of curves. Analytes containing higher Z variant molecule concentrations and buffer HBS-EP are seen near the baseline.

Epitope Test:

The binding of human PDGF-Rβ to its natural ligand PDGF-BB in the presence of monomeric Z variants was tested. The ligand immobilization levels on the surfaces were: flow cell 2 (PDGF-BB): 1130 RU and flow cell 3 (PDGF-BB): 5090 RU. All three tested Z variants, Z01977, Z01980 and Z01982, blocked the PDGF-Rβ-PDGF-BB binding partially at a 1:1 molar ratio (i.e. 100 nM Z variant and 100 nM PDGF-Rβ). The result is displayed in FIG. 3. When a ten times excess of Z variant compared to PDGF-Rβ was used, the blocking effect was almost complete. For the AR-binding Z variant used as negative control, no blocking effect was seen.

Dot Blot Analysis:

A specificity test was made by adding purified dimeric Z variants to nitrocellulose membranes with 0.1 μg dots of different proteins.

Bound Z variants were detected with chemiluminescence reacting HRP-conjugated antibodies. Seven binders were analyzed: Z01976, Z01977, Z01980, Z01982, Z01983, Z01994 and Z01995. The strongest signals were achieved for human and murine PDGF-Rβ for all tested Z variants (data not shown). Some background signals were seen for all Z variants, particularly to the immunoglobulins.

In summary, binding to both human and murine PDGF-Rβ, which are 79% identical on an amino acid level, was exhibited by the Z variants in binding analyses and in dot blot. When assayed against PDGF-Rα, Fc and serum proteins in a Biacore instrument and in dot blot, the binders were shown to be negative, i.e. their binding was satisfactory concerning specificity with respect to PDGF-Rβ. Three of the binders (Z01977, Z01980 and Z01982) were shown to block binding of the receptor PDGF-Rβ to its natural ligand PDGF-BB in a Biacore assay. The result suggests that the three binders share an epitope on the receptor, as they showed the same blocking result. It is likely that the non-tested binders in the sequence cluster would show the same type of binding pattern.

Example 3

Design and Construction of a Maturated Library of PDGF-Rβ-Binding Z Variants

In this Example, a maturated library was constructed. The library was used for selections of PDGF-Rβ-binding polypeptides. Selections from maturated libraries are usually expected to result in binders with increased affinity (Orlova et al, Cancer Res 66(8):4339-48 (2006)).

Materials and Methods

Library Design:

The library was based on the sequences of the PDGF-Rβ-binding Z variants described in Examples 1 and 2. In the new library, 13 variable positions in the Z molecule scaffold were biased towards certain amino acid residues, according to a strategy based on the Z variant sequences defined in SEQ ID NO: 1-11. A degenerated 129 bp oligonucleotide encoding the possible variants was obtained from Scandinavian Gene Synthesis AB and denoted AFFI-1011. The theoretical frequencies (in %) and distributions of amino acid residues in the new library for the 13 variable Z positions are given in Table 2:

ward primer AFFI-47 (5'-cmcccccctcgaggtagacaacaaattcaa) and 50 pmol reverse primer AFFI-50 (5'-cmccctgctagcaagttagcgctttggcttgggtcatc). An explanation of the nomenclature of degenerated nucleotides can be found in e.g. Biochemical Nomenclature and Related Documents, Portland Press, 1992. 95 PCR reactions were performed using AmpliTaq Gold polymerase (Applied Biosystems #N808-0244) in 10 cycles, each cycle consisting of one 15 s denaturation period at 96° C., one 15 s annealing period at 60° C. and one 1 min extension period at 72° C. After the amplification, the PCR products were pooled and purified using QIAquick® PCR purification kit (Qiagen). Fragment concentration and quality were determined by absorbance measurement and by analysis on an agarose gel. The amplified fragment was restriction cleaved at a concentration of 14 ng/µl using 1000 U of the enzymes XhoI and NheI (New England Biolabs, #R0146L, #0131 M). The 1500 µl reaction mixture was incubated at 37° C. for 3.5 hours. The cleaved fragments were purified using a QIAquick® PCR purification kit. Fragment concentrations were determined by absorbance measurements, and fragment quality by agarose gel analysis.

The phagemid vector pAY00065 was restricted with the same enzymes, purified and ligated with the amplified fragments. The amplified fragments (1.93 µg) and the vector (12 µg), in a molar ratio of 5:1, were ligated for 2 hours at RT. 50 U of T4 DNA ligase (Fermentas #EL0012) was used per µg of DNA in a ligation mixture of 6000 µl, and aliquoted into eppendorf tubes with 500 µl in each. The ligase was inactivated at 65° C. for 10 minutes and DNA was recovered by phenol/chloroform (Invitrogen) extraction and ethanol precipitation, followed by dissolution in sterile deionized water.

The ligation reactions (2 µl of approximately 150 ng/µl) were transformed into electrocompetent E. coli RRIΔM15 cells (100 µl). Immediately after electroporation, approxi-

| Possible amino acids | Amino acid positions in the Z variant molecule | | | | | | | | | | | | |
|---|---|---|---|---|---|---|---|---|---|---|---|---|---|
| | Pos 2 | Pos 3 | Pos 4 | Pos 6 | Pos 7 | Pos 10 | Pos 11 | Pos 17 | Pos 18 | Pos 20 | Pos 21 | Pos 25 | Pos 28 |
| Ala (A) | 0 | 0 | 6.25 | 100 | 6.25 | 25 | 17 | 0 | 6.25 | 0 | 0 | 0 | 0 |
| Arg (R) | 50 | 17 | 9.375 | 0 | 9.375 | 0 | 8.25 | 100 | 9.375 | 45 | 0 | 37.5 | 17 |
| Asn (N) | 0 | 0 | 3.125 | 0 | 3.125 | 12.5 | 8.25 | 0 | 3.125 | 0 | 100 | 12.5 | 0 |
| Asp (D) | 0 | 0 | 3.125 | 0 | 3.125 | 12.5 | 8.25 | 0 | 3.125 | 0 | 0 | 0 | 0 |
| Cys (C) | 0 | 0 | 3.125 | 0 | 3.125 | 0 | 0 | 0 | 3.125 | 0 | 0 | 0 | 0 |
| Gln (Q) | 0 | 0 | 3.125 | 0 | 3.125 | 0 | 0 | 0 | 3.125 | 0 | 0 | 12.5 | 0 |
| Glu (E) | 0 | 0 | 3.125 | 0 | 3.125 | 12.5 | 8.25 | 0 | 3.125 | 0 | 0 | 0 | 0 |
| Gly (G) | 0 | 16.5 | 6.25 | 0 | 6.25 | 0 | 16.5 | 0 | 6.25 | 0 | 0 | 0 | 16.5 |
| His (H) | 0 | 0 | 3.125 | 0 | 3.125 | 0 | 0 | 0 | 3.125 | 0 | 0 | 12.5 | 0 |
| Ile (I) | 0 | 16.5 | 3.125 | 0 | 3.125 | 0 | 0 | 0 | 3.125 | 0 | 0 | 0 | 16.5 |
| Leu (L) | 50 | 17 | 9.375 | 0 | 9.375 | 0 | 0 | 0 | 9.375 | 0 | 0 | 0 | 17 |
| Lys (K) | 0 | 0 | 3.125 | 0 | 3.125 | 12.5 | 8.25 | 0 | 3.125 | 5 | 0 | 12.5 | 0 |
| Met (M) | 0 | 0 | 3.125 | 0 | 3.125 | 0 | 0 | 0 | 3.125 | 0 | 0 | 0 | 0 |
| Phe (F) | 0 | 0 | 3.125 | 0 | 3.125 | 0 | 0 | 0 | 3.125 | 0 | 0 | 0 | 0 |
| Pro (P) | 0 | 0 | 6.25 | 0 | 6.25 | 0 | 0 | 0 | 6.25 | 0 | 0 | 0 | 0 |
| Ser (S) | 0 | 16.5 | 9.375 | 0 | 9.375 | 0 | 8.25 | 0 | 9.375 | 0 | 0 | 12.5 | 16.5 |
| Thr (T) | 0 | 0 | 6.25 | 0 | 6.25 | 25 | 17 | 0 | 6.25 | 0 | 0 | 0 | 0 |
| Trp (W) | 0 | 0 | 3.125 | 0 | 3.125 | 0 | 0 | 0 | 3.125 | 45 | 0 | 0 | 0 |
| Tyr (Y) | 0 | 0 | 3.125 | 0 | 3.125 | 0 | 0 | 0 | 3.125 | 0 | 0 | 0 | 0 |
| Val (V) | 0 | 16.5 | 6.25 | 0 | 6.25 | 0 | 0 | 0 | 6.25 | 0 | 0 | 0 | 16.5 |
| Amber stop (q) | 0 | 0 | 3.125 | 0 | 3.125 | 0 | 0 | 0 | 3.125 | 5 | 0 | 0 | 0 |
| Stop (.) | 0 | 0 | 0 | 0 | 0 | 0 | 0 | 0 | 0 | 0 | 0 | 0 | 0 |
| # of aa | 2 | 6 | 20 | 1 | 20 | 6 | 9 | 1 | 20 | 4 | 1 | 6 | 6 |

Library Construction:

The degenerated oligonucleotide AFFI-1011 (5'-ctcgaggtagacaacaaattcaacaaagaackkvkynnkgcggctnnkgagatcrmmrvsttacctaacttaaaccgtnnkcaawrgaacgccttcatcmrwagtttavktgatgacccaagccaaagc) was amplified by PCR using 100 fmol AFFI-1011, 50 pmol formately 1 ml of SOC medium (TSB-YE media, 1% glucose, 50 µM MgCl₂, 50 µM MgSO₄, 50 µM NaCl and 12.5 µM KCl) was added. The transformed cells were incubated at 37° C. for 40-50 min. Samples were taken for titration and for determination of the number of transformants. The cells were thereafter divided into 6 fractions which were inoculated in 1000 ml TSB-YE medium, supplemented with 2% glucose and 100 µg/ml ampicillin, and cultivated overnight at 37° C. The cells were pelleted for 8 min at 6000 g, re-suspended in a PBS/glycerol solution (approximately 20% glycerol). The different cell fractions were aliquoted and stored at −80° C.

Preparation of Phage Stock:

Cells from the glycerol stock containing the phagemid vector were inoculated in 2×1000 ml TSB-YE medium, supplemented with 2% glucose and 100 µg/ml ampicillin, and grown at 37° C. When the cells reached an optical density (OD) of 0.65, the same amount of cells as initially inoculated was infected using a 10× molar excess of M13K07 helper phage (New England Biolabs). The cells were incubated for 30 minutes, centrifuged at 2000 g for 10 min and re-suspended. Subsequently, the cells were cultivated in 2×1000 ml TSB-YE medium, supplemented with 100 µM IPTG for induction of expression, 25 µg/ml kanamycin and 100 µg/ml ampicillin, and grown overnight at 30° C. The induced culture was harvested by centrifugation at 2500 g for 10 min. In order to separate the phage particles from the cells, the supernatant was precipitated in PEG/NaCl. The precipitation buffer was added to the supernatant in a 1:4 volume ratio and the resulting mixture was incubated on ice for 1 hour. Precipitated phages were pelleted by centrifugation at 10500 g at 4° C. for 30 min and re-suspended in sterile $H_2O$. The precipitation procedure was repeated once and the phages were re-suspended in 1 ml PBS. The resulting phage solution was clarified from cells and cell debris by centrifugation, followed by filtration through a 0.45 µm filter. Glycerol was added to a final concentration of approximately 40%. Phage stocks were stored at −80° C.

Sequencing:

Clones from the phage stock library of Z variants were sequenced in order to verify the content and to evaluate the outcome of the constructed library in relation to the library design. Sequencing was performed as described in Example 1. The amino acid distribution was calculated.

Results

Library Construction:

The new library was designed based on a set of PDGF-Rβ-binding Z variants with verified binding properties (Example 1 and 2). The theoretical size of the designed library was $7.5 \times 10^8$ Z variants. The actual size of the library, determined by titration and after transformation to E. coli. RRIΔM15 cells, was $5.3 \times 10^9$ transformants.

The library quality was tested by sequencing of 95 transformants and by comparing their actual sequences with the theoretical design. The contents of the actual library compared to the designed library were shown to be satisfying. The locked positions in the designed amino acid sequence were reflected in the actual sequence in that only the expected amino acids occurred in these positions. Similarly, the biased or doped positions in the design were also reflected in the actual sequence in that most of the expected amino acids occurred in these positions.

A maturated library of PDGF-Rβ-binding polypeptides was thus successfully constructed.

Example 4

Selection, Screening and Characterization of Z Variants from a Maturated Library Materials and Methods The target protein, human recombinant PDGF-Rβ, was biotinylated as described in Example 1. Biotinylated dimeric Z00000 was coupled to streptavidin beads as described in Example 1.

Phage Display Selection of PDGF-Rβ-Binding Polypeptides:

Phage display selections were performed against PDGF-Rβ essentially as described in Example 1 using the new library of Z variant molecules described in Example 3. Selection was initially performed in four tracks. These were further divided in two cycles, resulting in totally six tracks. Selection was performed in four cycles. See FIG. 4B for an overview of target concentrations and number of washes. In order to reduce the number of background binders, phages were pre-incubated with Z00000-coupled streptavidin beads coated with Fc protein for 1 hour at RT prior to selection cycles 1-3.

Thereafter, non-biotinylated (1a, 1b and 2) and biotinylated human PDGF-Rβ (3a, 3b and 4) was added to the phage solution. Selection took place in blocked tubes (pre-blocked in selection buffer) incubated under agitation for two hours. To capture the phage-protein complexes, the selection solution was incubated with pre-blocked Z00000-coupled streptavidin beads (1a, 1b and 2) or streptavidin beads (3a, 3b and 4) for 20 min and for 15 min, respectively. Thereafter, unbound phage particles were removed by washing with PBS-T 0.1. The number of washes was increased for each selection cycle, starting with 4 washes in the first cycle and ending with up to 20 washes in the last cycle. Washing was performed at RT (2 and 4), 37° C. (1b and 3b) and 45° C. (1a and 3a). The wash length was less than 1 minute in all steps, except for the last wash step in the last cycle which lasted 30 minutes. Bound phages were eluted using a low pH strategy where 500 µl of 50 mM glycine-HCl, pH 2.2, was added to the streptavidin beads. After 10 min incubation at RT, the solution was neutralized by addition of 450 µl PBS and 50 µl 1 M Tris-HCl, pH 8.

Amplification of Phage Particles:

After each selection cycle, approximately 950 µl of the eluted phages from the different selection tracks were used to infect log phase E. coli RR1ΔM15 cells. Bead-bound phage were similarly infected. After 20 min of incubation at 37° C., the cells infected with eluted phage and bead-bound phage from the same selection were pooled (cycle 1-3) or kept separate (cycle 4). The infected cells were harvested by centrifugation. The pellet was dissolved in a small volume of TSB-YE and subsequently spread onto TYE plates. The plates were thereafter incubated overnight at 37° C. In the final selection cycle, bacteria were diluted before spreading onto TYE plates in order to form single colonies to be used in ELISA screening.

The cells from the TYE plates were re-suspended in TSB medium. A part of the re-suspended cells were stored in glycerol at −20° C. An amount of suspended cells corresponding to 100-1000 times the number of eluted phages was inoculated in TSB-YE medium, supplemented with 2% glucose and 100 µg/ml ampicillin. The cells were grown to log phase at 37° C. The same amount of cells as inoculated before were infected with 10× excess of M13K07 helper phages (New England Biolabs) during 30 min at 37° C. The cells were pelleted by centrifugation and re-suspended in TSB-YE medium supplemented with 25 µg/ml kanamycin, 100 µg/ml ampicillin and 100 µM IPTG to induce the production of Z variant molecules. The cultivations were incubated overnight at 30° C. The phage particles were harvested by centrifugation and precipitation as described earlier.

ELISA Screening of Z Variants:

Z variant molecules were produced by inoculation of single colonies, prepared as described above, in TSB-YE medium as described in Example 1. Half area 96 well ELISA plates were prepared as described in the same Example. After removal of the blocking solution from the wells, 50 µl of the periplasmic solution containing Z variant molecules was added to each well. The plates were incubated at RT for 1.5 hours. The plates were washed four times with PBS-T 0.05. Human PDGF-Rβ, at a concentration of 4.5 µg/ml in 50 µl PBS-T 0.1, was added to the wells and the plates were incubated for 1.5 h at RT. After washing as described above, target bound to the Z variants was detected by addition of the antibody against Fc conjugated to HRP, diluted 1:4000 in PBS-T 0.1. This was followed by incubation for 1 h at RT. Thereafter, developing was performed as described earlier. Absorbance was measured at 450 nm in an ELISA spectrophotometer. All steps from blocking to reading were performed manually.

Sequencing of Potential Binders:

From the ELISA screening, individual clones from the different selection tracks were picked for sequencing. Clones with absorbance values from at least twice the background absorbance to ten times the background absorbance were sequenced. Amplification of gene fragments and sequence analysis of gene fragments were performed as described in Example 1.

Biacore Binding Analysis:

In order to rank the sequenced clones, periplasmic fractions containing ABD tagged PDGF-Rβ-binding Z variants, previously prepared for ELISA, were analyzed in a Biacore instrument (GE Healthcare). Human PDGF-Rβ and HSA were immobilized onto a Biacore CM5 chip; PDGF-Rβ in flow cell 2 and HSA in flow cell 3 and 4. One flow cell surface on the chip (flow cell 1) was activated and deactivated for use as blank during analyte injections. The immobilization was performed according to the manufacturer's protocol. The periplasmic fractions were clarified at 16000 g for 5 min and injected at RT. In addition, some binders were analyzed at 37° C. The running buffer was HBS-EP and the analytes were injected at a flow-rate of 10 µl/min for 5 minutes. After 5 minutes of dissociation, the surfaces were regenerated with one injection of 0.05% SDS and one injection of 15 mM HCl. The results were analyzed using BiaEvaluation software. Sensorgrams from the blank surface (flow cell 1) were subtracted from the sensorgrams from the ligand surfaces.

Subcloning of Z Variant Molecules into Expression Vectors:

Based on sequence analysis and binding analysis in Biacore, a number of clones were selected for subcloning into the expression vector pAY01449 as described in Example 1. Monomer and dimer Z variant fragments were amplified from the pAffi1/pAY00065 vectors as described earlier in Example 1.

AccI-digested pAY01449 vector and amplified Z variant fragments were ligated using T4 DNA ligase. The ligation mix was electroporated into electrocompetent E. coli TOP-10 cells. The resulting transformants were plated on TBAB plates, supplemented with 50 µg/ml of kanamycin, followed by incubation at 37° C. overnight. Thereafter, colonies with the different Z variant molecules were screened using PCR and the lengths of the PCR fragments were verified on agarose gels.

To verify the sequences, sequencing was performed with BigDye® Terminator v3.1 Cycle Sequencing Kit using biotinylated primers in separate reactions. The sequencing products were purified using a Magnatrix 8000 with streptavidin coated magnetic beads, and analyzed on an ABI PRISM® 3100 Genetic Analyser. The sequences were evaluated with Sequencher™ software.

Plasmid DNA was prepared from clones with confirmed sequence. The bacteria were grown overnight in TSB medium, supplemented with 50 µg/ml of kanamycin. The cells were pelleted by centrifugation. Plasmids were prepared using QIAprep Spin Miniprep Kit, and electroporated into electrocompetent E. coli BL21(DE3) cells. The new plasmids were deposited at −80° C. Aliquots of the TOP-10 and BL21 DE3 cultures were similarly stored in glycerol at −80° C.

Results

Phage Display Selection of PDGF-Rβ-Binding Polypeptides:

Selection was performed in totally six parallel tracks with four cycles each. The different selection tracks differed in target concentration and wash conditions as follows: 1a) non-biotinylated target, high concentration, 37/45° C. wash, 1 b) non-biotinylated target, low concentration, 37° C. wash, 2) non-biotinylated target, low concentration, RT wash, 3a) biotinylated target, high concentration, 37/45° C. wash, 3b) biotinylated target, low concentration, 37° C. wash, and 4) biotinylated target, low concentration, RT wash. For each selection cycle, the target concentration was decreased and the washing conditions were more stringent. A pressure for structural stability was introduced in the selections by the high temperature wash (37° C. and 45° C.) of phage-target complexes. Phage particle titers and phage particle yield (% phage out/phage in) were determined after each cycle. For each selection cycle, the phage particle yield was higher (not shown), which indicated an enrichment of target binding clones.

ELISA Screening of Z Variants:

Clones obtained after four selection cycles were produced in 96-well plates and screened for PDGF-Rβ-binding activity using ELISA. In total, 2×93 clones from the group of eluted phage and 2×93 clones from the group of bead-bound phage were analyzed. Many clearly positive clones were found with signals of up to 2.2 absorbance units (AU). Clones from all selection tracks (and from both eluted and bead-bound phage) showed positive signals. The negative controls (lysates from a negative clone, basically pAffi1/pAY00065, without Z variant insert) were clearly negative (absorbance <0.2 AU). The positive control (Z01977 from Example 1) gave an absorbance signal (0.5-1.4 AU) which was lower than most of the positive clones.

Sequencing:

192 clones with positive ELISA signals were sequenced (96 clones from the group "eluted phage" and 96 clones from the group "bead-bound phage"). Each individual Z variant was given an identification number, Z#####, as described earlier. In total, 163 new Z variant molecules were identified. The amino acid sequences of the 58 amino acid residues long Z variants are listed in FIG. 1M-S and in the sequence listing as SEQ ID NO:370-532. The deduced PDGF-Rβ-binding motifs of these Z variants are listed in FIG. 1A-F and in the sequence listing as SEQ ID NO:12-174. The amino acid sequences of the 49 amino acid residues long polypeptides predicted to constitute the complete three-helix bundle within each of these Z variants are listed in FIG. 1G-M and in the sequence listing as SEQ ID NO:191-353. Among the sequenced clones, fifteen sequences occurred twice and one sequence occurred three times.

Clustering of the sequenced PDGF-Rβ-binding Z variants showed that the variants had similar sequences with an internal dissimilarity of down to 2%, corresponding to a difference in one single amino acid.

Biacore Binding Analysis:

Due to the large number of different Z variants with strong signals in ELISA, a second screening was performed using Biacore binding analysis. Clones with high ELISA signals, frequent occurrence (>1), origin in selections with washes at 37/45° C. and sequences similar to Z01982 (a sequence variant with high affinity from PDGF-Rβ) and Z01978 (a sequence variant with high Tm), were chosen for binding analysis. In total, 45 clones were chosen. Z01977 and Z01982 were included for comparison. A Z variant molecule binding to CD22 was used as negative control. The response levels acquired from the RT experiment against HSA were used for approximation of the relative concentrations. Apart from the response differences due to varying levels of Z variant molecule expression, the shapes of the sensorgrams in the RT experiment for the clones screened against PDGF-Rβ were similar. However, small dissimilarities were seen, and by relating the Z variant molecule expression levels to the sensorgrams from the PDGF-Rβ surface, the Z variants could be graded. In the experiment performed at 37° C., small distinctions between the Z variants could be seen by relating the responses against PDGF-Rβ with the responses against HSA. Thus, five Z variants (Z02465, Z02477, Z02483, Z02516 and Z02558) were picked for subcloning and further analysis, based on their low response to HSA and high response to PDGF-Rβ, their slow dissociation curve, their occurrence in duplicate in the selection, and/or their strong binding at 37° C.

Subcloning of Z Variant Molecules into Expression Vectors:

Five clones, Z02465, Z02477, Z02483, Z0516 and Z02558, were successfully subcloned into the expression vector pAY01449 as monomers and dimers as described previously in this Example.

Example 5

Production and Characterization of a Subset of PDGF-Rβ-Binding Z Variants

Materials and Methods
Protein Expression and Purification:

Transformed *E. coli* BL21(DE3) cultures from the subcloning described in Example 4 were grown at 37° C. to an optical density of approximately 1 (diluted 10×), and protein expression was induced by addition of 1 M IPTG (0.5 ml/l culture). Cultures were harvested by centrifugation (20 min, 15900 g) 5 h after induction. The supernatants were discarded and the cell pellets were collected and stored at −20° C. Expression levels of soluble and unsoluble proteins were analyzed using SDS-PAGE by ocular determination of Coomassie-stained gels.

PDGF-Rβ-binding Z variants constituting monomers and dimers of Z02465, Z02477, Z02483, Z0516 and Z02558 (in $His_6$-Z#####-Cys form and in $His_6$-(Z#####)$_2$ Cys form; i.e. expressed as the constructs MGSSHHHHHHLQ-[Z#####]-VDC and MGSSHHHHHHLQ-[Z#####][Z#####]-VDC, respectively) were purified from cell pellets under denatured conditions on Ni-NTA Superflow Columns (Qiagen), buffer exchanged to PBS using PD-10 columns (GE Healthcare), aliquoted and stored at −80° C.

Protein characterization was performed essentially as in Example 2.

CD Analysis:

The purified monomeric Z variants were thawed and diluted to 0.5 mg/ml in PBS. For each diluted Z variant, a CD spectrum at 250-195 nm was obtained at 20° C., followed by a variable temperature measurement (VTM) to determine the melting temperature (Tm). After incubation at 20° C., a second CD spectrum 250-195 nm was obtained at 20° C. to verify that the Z variant molecule retained its α-helical structure after the VTM. In the VTM, the absorbance was measured at 221 nm while the temperature was raised from 20 to 90° C., with a temperature slope of 5° C./min. The CD measurements were performed on a Jasco J-810 spectropolarimeter using a cell with an optical path-length of 1 mm.

Biacore Binding and Kinetic Analysis:

Five monomeric Z variant molecules, with NEM-blocked (N-ethylmaleimide, Pierce #23030) cysteines and with $His_6$-tags ($His_6$-Z#####-Cys-NEM), were subjected to interaction studies in a Biacore instrument (GE Healthcare) with human PDGF-Rβ, murine PDGF-Rβ and human PDGF-Rα. The three PDGF receptors had previously (Example 2) been immobilized onto different flow cells of a CM5 chip. The analytes were diluted in the running buffer HBS-EP to a final concentration of 100 nM, injected in duplicates or triplicates at a flow-rate of 20 μl/minute during 3 minutes. After 3 minutes of dissociation, the surfaces were regenerated with one injection of 10 mM HCl.

The binding affinities of Z variants Z02465 and Z02483 (in $His_6$-Z#####-Cys-NEM form) and the first generation binder Z01982 (in $His_6$-Z##### form) for human and murine PDGF-Rβ were determined in Biacore. Human and murine PDGF-Rβ were immobilized in different flow cells of a Biacore CM5 chip as described earlier. Different concentrations of the Z variants (100 nM, 40 nM, 16 nM, 6.4 nM and 2.56 nM) in HBS-EP buffer were injected at a flow-rate of 50 μl/minute for 1 minute. After 1 minute of dissociation, the surfaces were regenerated with one injection of 0.05% SDS and one injection of 10 mM HCl.

One flow cell surface of the chip was activated and deactivated for use as blank during analyte injections. Sensorgrams from the blank surface were subtracted from the sensorgrams from the ligand surfaces. BiaEvaluation software (GE Healthcare) was used for analyzing the results and calculating the dissociation constants ($K_D$).

Dot Blot Analysis:

Three PDGF-Rβ-binding Z variants were tested for specificity by dot blot analysis performed as described in Example 2 using dimeric Z variant molecules with N terminal $His_6$ tags and C terminal cysteines.

Flow Cytometry:

Five different dimeric Z variant molecules (20 or 5 μg/ml in PBS), were added to 0.5×10$^6$ cells PDGF-Rβ expressing AU565 (human mammary gland carcinoma cells, ATCC) in a 5 ml Falcon tube. The mixtures were incubated for 1 hour on ice. Subsequently, the cells were washed in PBS and pelleted in a centrifuge at 200 g for 3 minutes. The bound Z variant molecules were detected by addition of goat antibody against Z variants, followed by Alexa Fluor® 647 conjugated anti-goat Ig (Invitrogen #A20347, 5 μg/ml). After each addition, the cells were incubated for 45-60 minutes and thereafter washed twice in PBS. As a control, AU565-cells were stained with a commercially available goat anti-PDGF-Rβ antibody (R&D systems) followed by an Alexa Fluor® 647 conjugated anti-goat Ig antibody (Invitrogen). After staining, cells were washed, re-suspended and analyzed using a FACSCanto II flow cytometer (BD Biosciences). In a second set of flow cytometry analysis, Alexa Fluor® 647-conjugated $His_6$-(Z02465)$_2$-Cys, $His_6$-(Z02483)$_2$-Cys, and $His_6$-(Z02516)$_2$-Cys were used for staining. The Z variants were conjugated using Alexa Fluor® 647 C2-maleimid reagent (Invitrogen). AU565 cells, 0.5×10$^6$ per tube (5 ml Falcon tube) were mixed with a 3-fold dilution series of the three conjugated binders.

After one hour of incubation on ice, cells were washed as described above and resuspended in PBS for Flow Cytometry analysis using FACSCanto II.

Immunofluorescence:

AU565 cells were grown overnight on multiwell slides (Histolab) to yield a monolayer of cells. The next day, cells were rinsed with PBS and subjected to staining. The cells were stained with any one of three Z variant molecules (10 μg/ml) or a goat anti-PDGF-Rβ antibody (5 μg/ml), diluted in PBS on unfixed cells. After one hour of incubation, the wells were washed. The Z variant molecules were detected with a purified goat anti-Z Ig (5 μg/ml), followed by anti-goat IgG Alexa488 (5 μg/ml, Invitrogen #A21467). The goat anti-PDGF-Rβ antibody was detected by anti-goat IgG Alexa488. After each antibody addition, the wells were incubated for 1 hour and washed with PBS. The cells were fixed for 10 minutes with 3% formaldehyde in PBS, followed by wash with PBS. The wells were dried and the glass slides were mounted with anti-fading solution (Vectashield mounting medium for fluorescence with DAPI, Vector Laboratories #H-1200), and analyzed using a Leica DM-LA microscope (Leica Microsystems) equipped with a live imaging video camera.

Results

Protein Expression and Purification:

All expressed variants, Z02465, Z02477, Z02483, Z02516 and Z02558 (in $His_6$-Z#####-Cys and in $His_6$-(Z#####)$_2$ Cys form) gave good yields of soluble gene product. The amount of IMAC-purified Z variant molecules ranged from 5.5 mg to 12.1 mg per purified batch and the in vitro solubility for all variants were good. The purity was estimated on SDS-PAGE to exceed 90% for all variants. The correct molecular weights were verified with LC-MS.

CD Analysis:

CD spectrum measurements were performed at 20° C. At that temperature, the α-helical structures of the Z variants were almost fully developed. An overlay of the spectrums obtained after the variable temperature measurements (heating to 90° C. followed by cooling to 20° C.) on the spectrums obtained before the variable temperature measurement showed that all Z variants fold back to their α-helical structures after heating to 90° C. (result not shown). The melting temperatures were determined from the variable temperature measurements and are shown in Table 3.

TABLE 3

Melting temperatures of Z variants.

| Z variant molecule | Tm (° C.) |
| --- | --- |
| $His_6$-Z02465-Cys | 46 |
| $His_6$-Z02477-Cys | 46 |
| $His_6$-Z02483-Cys | 44 |
| $His_6$-Z02516-Cys | 42 |
| $His_6$-Z02558-Cys | 39 |
| $His_6$-(Z02477)$_2$-Cys | 46 |

Biacore Binding and Kinetic Analysis:

The binding of five Z variant molecules (in $His_6$-Z#####-Cys-NEM form) to human and murine PDGF-Rβ as well as to human PDGF-Rα was tested in Biacore by injecting each of the monomeric Z variant molecules Z02465, Z02477, Z02483, Z02516 and Z02558 over surfaces containing the three receptors. Comparisons were made with two variants from the first selection (Example 1), Z01977 and Z01982 (in $His_6$-Z##### form). All tested Z variants showed binding to both human and murine PDGF-Rβ but no binding to human PDGF-Rα. Z02465 and Z02483 showed the highest response curves against both the human and the murine receptor. The results are displayed in FIG. 5.

The binding affinities of two maturated Z variants (Z02465 and Z02483) and one Z variant from the first selection (Z01982; Example 1), were determined by calculation of the dissociation constant $K_D$. The calculation was based on the results from a Biacore experiment where the Z variant molecules, in five different concentrations, were run over a Biacore chip containing human and murine PDGF-Rβ. The ligand immobilisation grades on the surfaces were: flow cell 2 (hPDGF-Rβ): 1110 RU, flow cell 3 (hPDGF-Rβ): 3010 RU and flow cell 4 (mPDGF-Rβ): 3080 RU.

The calculations of $K_D$ were performed using a Langmuir 1:1 binding model on sensorgrams from the concentration series against the human (flow cell 2) and the murine (flow cell 4) receptor. Good curve fitting was achieved for Z01982 (all five concentrations) as well as for Z02465 and Z02483 (all except one concentration) against human PDGF-Rβ (FIG. 6). For the murine receptor, all Z variant concentrations were used in the calculations (sensorgrams not shown). The calculated dissociation constants are shown in Table 4 below.

TABLE 4

Dissociation constants ($K_D$) for PDGF-Rβ-binding Z variants

| Z variant | human PDGF-Rβ | murine PDGF-Rβ |
| --- | --- | --- |
| $His_6$-Z01982 | 4 nM | 27 nM |
| $His_6$-Z02465-Cys-NEM | 500 pM | 7 nM |
| $His_6$-Z02483-Cys-NEM | 400 pM | 6 nM |

Dot Blot Analysis:

The specificities of Z02516, Z02483 and Z02465 (in $His_6$-(Z#####)$_2$-Cys form) for PDGF-Rβ were tested using dot blot analysis. 22 different proteins were blotted onto nitrocellulose membranes. The 22 proteins included 16 high abundant human serum proteins, PDGF-Rα□ and recombinant human and mouse PDGF-Rβ. The three Z variant molecules bound to human and mouse PDGF-Rβ, but not to PDGF-Rα or to any of the other 19 molecules. Thus, the specificity of the tested Z variants was satisfying (data not shown).

Flow Cytometry:

The cell binding capacity of PDGF-Rβ-binding Z variant molecules were analyzed using flow cytometry. PDGF-Rβ expressing AU565 cells were stained with 20 μg/ml of Z02465, Z02483, Z02477, Z02516 or Z02558 (in $His_6$-(Z#####)$_2$ Cys form). The Z variant molecules were detected with a goat anti-Z antibody and Alexa Fluor® 647 conjugated anti-goat IgG. A goat anti-PDGF-Rβ antibody was used as a control. All five Z variant molecules gave shifts in fluorescence intensity (data not shown).

Figure 8:
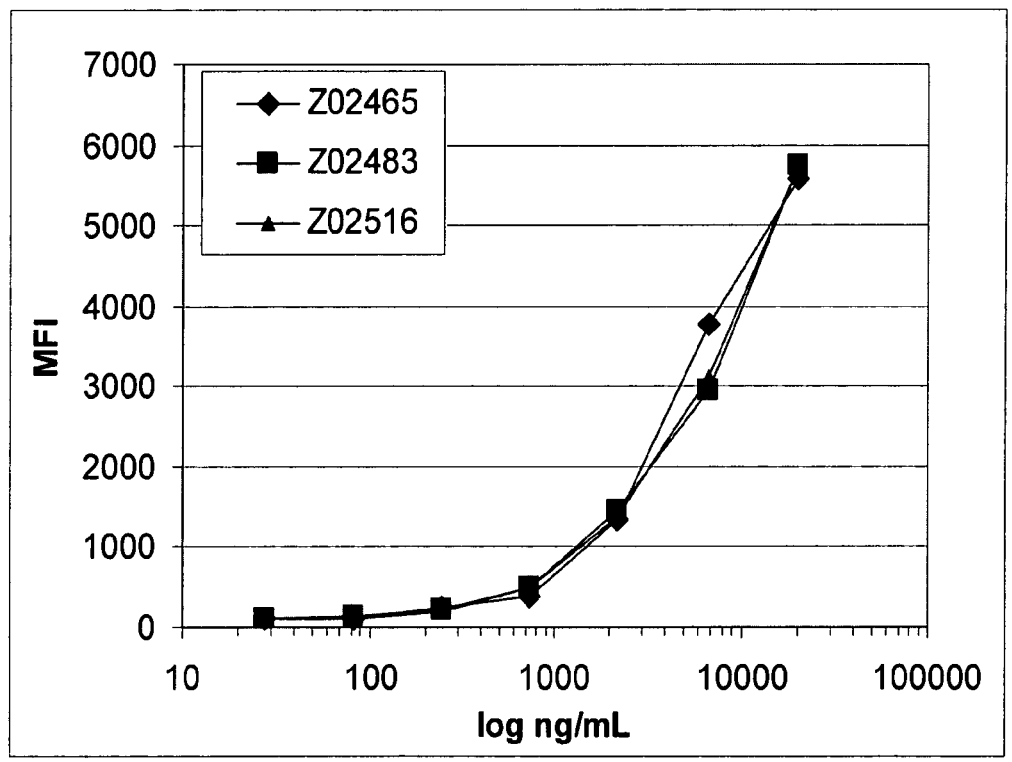
FIG. 8 shows the result from the flow cytometry experiment described in Example 5. The Figure shows titration of Alexa Fluor® 647 conjugated $His_6$-$(Z02465)_2$-Cys (♦), His6-$(Z02483)_2$-Cys (■) and His6-$(Z02516)_2$-Cys (▲) on PDGF-Rβ-expressing AU565 cells. Mean fluorescence intensity was plotted against log concentration (ng/ml) of Z variants.

In addition, the three Z variants molecules Z02465, Z02483 and Z02516 (in $His_6$-(Z#####)$_2$ Cys form) were conjugated with Alexa Fluor® 647 on the C-terminal cysteine and their abilities to bind to AU565 cells were compared. The cells were incubated with the molecules in a 3-fold titration series, ranging between 20000 to 1 ng/ml. The three Z variant molecules showed an equivalent binding to AU565 cells. The result is displayed in FIG. 8.

Figure 7:
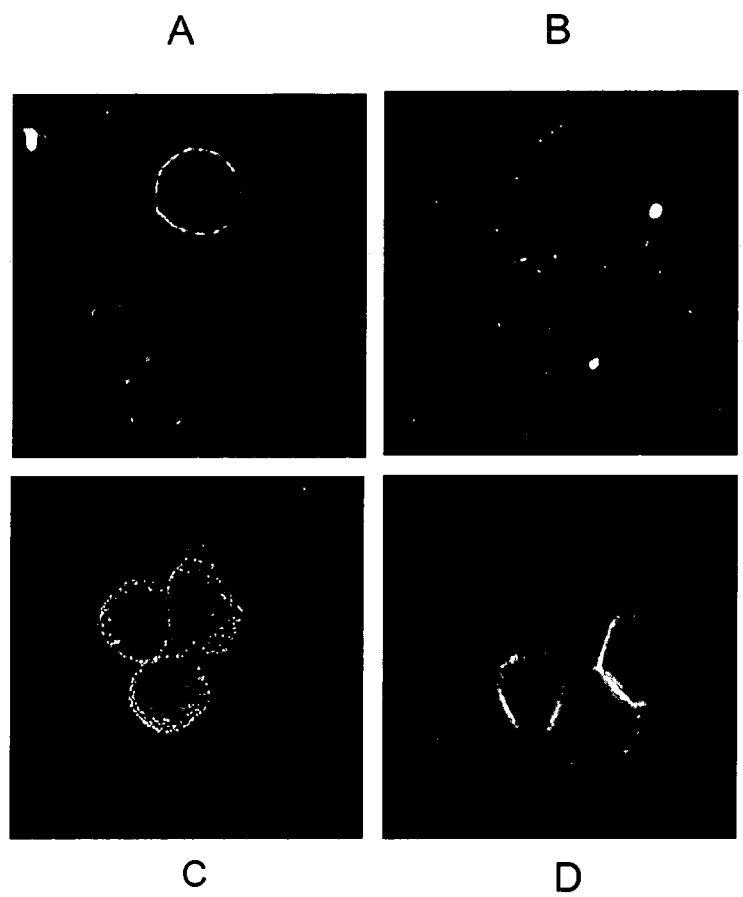
FIGS. 7A-D show images from the immunofluorescence experiment described in Example 5. The images show PDGF-Rβ-expressing AU565 cells stained with different antibodies or Z variants: A) goat anti-PDGF-Rβ antibody, B) or $His_6$-$(Z02465)_2$-Cys, C) $His_6$-$(Z02483)_2$-Cys, and D) $His_6$-$(Z02516)_2$-Cys.

Immunofluorescence:

PDGF-Rβ, expressed on the membranes of AU565 cells, was detected by immunofluorescence staining using any one of the dimeric Z variants Z02465, Z02483 and Z02516 (in $His_6$-(Z#####)$_2$ Cys form) or a goat anti-PDGF-Rβ antibody. Membrane staining was observed with the control antibody as well as with the three Z variants (FIG. 7). Staining with Z02483 resulted in a spotted staining pattern in addition to membranous staining which could be due to internalized PDGF-Rβ.

In conclusion, binding to both human and murine PDGF-Rβ was shown by the six investigated Z variants in a Biacore instrument and in dot blot analysis. When assayed against PDGF-Rα, Fc and serum proteins (Biacore and dot blot), the Z variants were shown to be negative, i.e. the Z variants showed specificity for PDGF-Rβ. In flow cytometry experiments, five dimeric Z variants showed binding to PDGF-Rβ-expressing cells. The microscopic analysis showed that the three strongest Z variants bound to the membrane of cells, reminiscent of the PDGF-Rβ specific control antibody. The variant Z02483 also bound to other structures, which most likely were internal vesicles. This suggests that PDGF-Rβ resides inside the cell. The melting temperatures for the maturated Z variants were improved compared to the Z variants from the first library selection. The variants Z02465 and Z02477 reached a Tm of 46° C.

Example 6

Characterization and Binding Analyses of Mutated Z Variants

Two Z variants from the selection described in Example 4 were subjected to site-directed mutagenesis in order to create new PDGF-Rβ-binding polypeptides.
Materials and Methods The PDGF-Rβ binding motifs of Z variants Z02465 (SEQ ID NO:60) and Z02483 (SEQ ID NO:78) were mutated to create the new Z variants Z03358 (from Z02465, PBM listed as SEQ ID NO:179 and the sequences of the 49 and 58 amino acid residues long polypeptides listed as SEQ ID NO:358 and SEQ ID NO:537, respectively), Z02831, Z02832, Z02833 and Z02834 (all four from Z02483, PBM:s listed as SEQ ID NO:175-178 and the sequences of the 49 and 58 amino acid residues long polypeptides listed as SEQ ID NO:354-357 and SEQ ID NO:533-536, respectively).

New amino acids were introduced in relevant positions of the parent scaffold in different expression vectors. The constructs encoded by the expression vectors were MGSSLQ-[Z#####]-VDC (Z02465), M-[Z#####]-C (Z03358) and MGSSHHHHHHLQ-[Z#####]-VD (Z02831, Z02832, Z02833 and Z02834), each M being removed by the host cell during production. The Z variants were generated using oligonucleotides with varied codons and a PCR based mutagenesis technique. Obtained PCR fragments were ligated into a restriction enzyme cleaved expression vector, as described in Example 1 or by using In-Fusion technology (Clontech, #639607, and transformed into *E. coli* TOP10 cells. Colonies were screened by PCR and sequences were verified essentially as described in Example 1. Plasmids were prepared and transformed into *E. coli* BL21(DE3).

His$_6$-tagged proteins were expressed, released by sonication and purified essentially as described in Example 2. Proteins without His$_6$-tag were expressed and then purified as follows: *E. coli* cells harboring soluble Z02465-Cys or Z03358-Cys were suspended in 20 mM Tris-HCl, pH 7.1. To disrupt the cells and release the intracellular content, the cell suspensions were heated to 85° C. for 3 minutes. The lysates were clarified by centrifugation followed by filtration and loaded on 25 ml Q Sepharose FF (GE Healthcare) packed in an XK26 column (GE Healthcare), previously equilibrated with 20 mM Tris-HCl, pH 7.1. After column wash with 5 column volumes (CV) 20 mM Tris-HCl, pH 7.1, bound proteins were eluted with a linear gradient of 0-0.5 M NaCl in 20 mM Tris-HCl, pH 7.1, during 10 CV. The flow rate was 5 ml/min and the 280 nm signal was monitored. Fractions containing Z02465-Cys or Z03358-Cys were identified by SDS-PAGE analysis. Relevant fractions were pooled and pH was adjusted to 8.0 by addition of 1 M Tris-HCl, pH 8.0, to a final concentration of 50 mM.

The C-terminal cysteine on the constructs was reduced by addition of DTT to 20 mM, followed by incubation at 40° C. for 3 minutes. After reduction, acetonitrile (ACN) was added to a final concentration of 5%, and reduced Z02465-Cys or Z03358-Cys was loaded on 1 ml Resource 15 RPC columns (GE Healthcare), previously equilibrated with RPC A-buffer (0.1% TFA, 5% ACN, 95% water). After column wash with 10 CV RPC A-buffer, bound proteins were eluted with a linear gradient of 0-40% RPC B-Buffer (0.1% TFA, 80% ACN, 20% water). The flow rate was 1 ml/min and the 280 nm-signal was monitored. Fractions containing pure Z02465-Cys or Z03358-Cys were identified by SDS-PAGE analysis. Relevant fractions were pooled and the buffer was changed to 10 mM NH$_4$HCO$_3$, pH 8.0, using PD10 columns (GE Healthcare). The new Z variants were analyzed by LC-MS for verification of the molecular weights.

The purified Z variants were diluted to 0.2 or 0.5 mg/ml in PBS and CD analyses were performed between 250-195 nm at 20° C. Subsequently, VTM:s were performed at 220 nm between 20-90° C. Another CD spectrum was obtained for the Z variants after the VTM.

Binding of Z variants Z02831, Z02832, Z02833, Z02834 and Z02483 (parent molecule; protein produced in Example 4 and NEM treated as described in Example 5) to PDGF receptors (human and murine) was tested in a Biacore instrument. The receptors were immobilized in different flow cells on Biacore chips as described in Example 2, and the Z variants, diluted in HBS-EP buffer, were injected over the chip surface in different concentrations. The results were analyzed as described in Example 2. Kinetic analysis of Z variants Z02465 and Z03358 (NEM treated as described in Example 5) was performed essentially as described in Example 5, using the Z variant concentrations 4 nM, 20 nM and 100 nM and the flow rate 30 µl/min.
Results All variants were successfully expressed and showed satisfying purity. Their theoretical molecular weights were verified by LC-MS. The melting temperatures (Tm), an estimate of the molecular stability, were determined with CD analyses: Z02831 Tm=44° C., Z02832 Tm=42° C., Z02833 Tm=49° C., Z02834 Tm=49° C. and Z003358 Tm=42° C. The Z variants regained their helical structure after the VTM, i.e. melting was reversible.

One of the mutated Z variants, Z02834, showed a faster off-rate from human PDGF-Rβ than its parent molecule Z02483. The other Z02483 mutants (Z02831, Z02832 and Z02833) showed similar binding for human PDGF-Rβ as Z02483. All mutated Z variants showed better binding to human PDGF-Rβ than to murine PDGF-Rβ. The dissociation constants ($K_D$) were calculated as described in Example 5 using sensorgrams from the 4 nM and 20 nM injections. The calculated $K_D$ values are shown in Table 5 below.

TABLE 5

Dissociation constants ($K_D$) for PDGF-Rβ binding Z variants

| Z variant | human PDGF-Rβ | murine PDGF-Rβ |
|---|---|---|
| Z02465-Cys-NEM | 640 pM | 7 nM |
| Z03358-Cys-NEM | 440 pM | 7 nM |

The invention claimed is:

1. Platelet derived growth factor receptor beta (PDGF-Rβ) binding polypeptide, comprising a platelet derived growth factor receptor beta binding motif, PBM, which motif consists of the amino acid sequence selected from i) $EX_2X_3X_4AAX_7EIDX_{11}LPNLX_{16}X_{17}X_{18}QWNAFIX_{25}X_{26}LX_{28}X_{29}$, SEQ ID NO:541 wherein, independently of each other, $X_2$ is selected from L, R and I;
$X_3$ is selected from R, I, L, V, K, Q and S;
$X_4$ is selected from A, R, N, D, Q, E, H, K, M, S, T, W, F and V;
$X_7$ is selected from A, R, D, Q, E, G, K and S;
$X_{11}$ is selected from A, R, N, D, E, G, K, S and T;
$X_{16}$ is selected from N and T;
$X_{17}$ is selected from R and K;
$X_{18}$ is selected from A, R, N, D, C, Q, E, G, L, K, M, S, T and V;
$X_{25}$ is selected from K, R, H, S, G and A;
$X_{26}$ is selected from S and K;
$X_{28}$ is selected from V, R, I and L;
$X_{29}$ is selected from D and K; and ii) an amino acid sequence which has at least 90% identity to the sequence defined in i), and wherein the PDGF-Rβ-binding polypeptide binds to PDGF-Rβ such that the $K_D$ value of the interaction is at most $1\times10^{-6}$ M.

2. PDGF-Rβ-binding polypeptide according to claim 1, wherein $X_{17}$ is R.

3. PDGF-Rβ-binding polypeptide according to claim 1, wherein $X_{11}$ is selected from A, R, N, D, E, G, K, S and T.

4. PDGF-Rβ-binding polypeptide according to claim 1, wherein $X_2$ is selected from L and R.

5. PDGF-Rβ-binding polypeptide according to claim 1, wherein $X_3$ is selected from R, I, L, V and S.

6. PDGF-Rβ-binding polypeptide according to claim 1, wherein $X_4$ is selected from A, R, N, D, Q, E, H, K, M, S, T and W.

7. PDGF-Rβ-binding polypeptide according to claim 1, wherein $X_{28}$ is selected from V, R, I and L.

8. PDGF-Rβ-binding polypeptide according to claim 1, wherein $X_{29}$ is D.

9. PDGF-Rβ-binding polypeptide according to claim 1, wherein $X_{25}$ is K.

10. PDGF-Rβ-binding polypeptide according to claim 1, wherein $X_{28}$ is V.

11. PDGF-Rβ-binding polypeptide according to claim 1, wherein $X_3$ is selected from I and V.

12. PDGF-Rβ-binding polypeptide according to claim 1, wherein $X_4$ is selected from A, R, E and K.

13. PDGF-Rβ-binding polypeptide according to claim 1, wherein $X_7$ is selected from A, R and E.

14. PDGF-Rβ-binding polypeptide according to claim 1, wherein $X_{11}$ is selected from A, R, N and E.

15. PDGF-Rβ-binding polypeptide according to claim 1, wherein $X_{18}$ is selected from R, E, K and V.

16. PDGF-Rβ-binding polypeptide according to claim 1, wherein $X_2$ is L.

17. PDGF-Rβ-binding polypeptide according to claim 1, whose amino acid sequence comprises a sequence selected from SEQ ID NO: 1-179.

18. PDGF-Rβ-binding polypeptide according to claim 17, wherein the amino acid sequence is selected from SEQ ID NO:2-3, SEQ ID NO:5, SEQ ID NO:7, SEQ ID NO:11-12, SEQ ID NO:18-19, SEQ ID NO:38, SEQ ID NO:42, SEQ ID NO:44, SEQ ID NO:47, SEQ ID NO:60-62, SEQ ID NO:64, SEQ ID NO:67-68, SEQ ID NO:71-72, SEQ ID NO:78, SEQ ID NO:80-81, SEQ ID NO:83, SEQ ID NO:86, SEQ ID NO:91-92, SEQ ID NO:94-97, SEQ ID NO: 101-103, SEQ ID NO:105, SEQ ID NO:109, SEQ ID NO:111, SEQ ID NO:116, SEQ ID NO:119, SEQ ID NO:133, SEQ ID NO:137, SEQ ID NO:139-140, SEQ ID NO:149, SEQ ID NO:153, SEQ ID NO:160, SEQ ID NO:164, SEQ ID NO:170, SEQ ID NO:174 and SEQ ID NO:179.

19. PDGF-Rβ-binding polypeptide according to claim 1, comprising a platelet derived growth factor receptor beta binding motif, PBM, which motif consists of the amino acid sequence selected from
$EX_2X_3X_4AAX_7EIDX_{11}LPNLX_{16}RX_{18}QWNAFIX_{25}X_{26}LX_{28}D$, SEQ ID NO:541 with $X_{29}$=D wherein, independently of each other,
$X_2$ is selected from L and R;
$X_3$ is selected from R, I, L, V, Q and S;
$X_4$ is selected from A, R, D, E, K and V;
$X_7$ is selected from A, Q, E and K;
$X_{11}$ is selected from A, R, E, N and S;
$X_{16}$ is selected from N and T;
$X_{18}$ is selected from R, G, K, S, T and V;
$X_{25}$ is selected from K, R, S and A;
$X_{26}$ is selected from S and K;
$X_{28}$ is selected from V, R and I.

20. PDGF-Rβ-binding polypeptide according to claim 19, wherein the amino acid sequence is selected from SEQ ID NO SEQ ID NO:2-3, SEQ ID NO:5, SEQ ID NO:7, SEQ ID NO:11, SEQ ID NO:60, SEQ ID NO:72, SEQ ID NO:78, SEQ ID NO:111 and SEQ ID NO:153.

21. PDGF-Rβ-binding polypeptide according to claim 1, in which said PDGF-Rβ-binding motif forms part of a three-helix bundle protein domain.

22. PDGF-Rβ-binding polypeptide according to claim 21, in which said PDGF-Rβ-binding motif essentially forms part of two alpha helices with an interconnecting loop, within said three-helix bundle protein domain.

23. PDGF-Rβ-binding polypeptide according to claim 1, which comprises an amino acid sequence selected from:
i) K-[PBM]-DPSQS$X_aX_b$LL$X_c$EAKKLND$X_d$Q; SEQ ID NO:542 wherein
[PBM] is a PDGF-Rβ-binding motif as defined in claim 1;
$X_a$ is selected from A and S;
$X_b$ is selected from N and E;
$X_c$ is selected from A and S;
$X_d$ is selected from A and S; and
ii) an amino acid sequence which has at least 80% identity to any one of the sequences defined above.

24. PDGF-Rβ-binding polypeptide according to claim 23, wherein the amino acid sequence is selected from SEQ ID NO: 180-358.

25. PDGF-Rβ-binding polypeptide according to claim 24, wherein the amino acid sequence is selected from SEQ ID NO:181-182, SEQ ID NO:184, SEQ ID NO:186, SEQ ID NO: 190, SEQ ID NO:239, SEQ ID NO:251, SEQ ID NO:257, SEQ ID NO: 290, SEQ ID NO:332 and SEQ ID NO:358.

26. PDGF-Rβ-binding polypeptide according to claim 21, in which said three-helix bundle protein domain is selected from domains of bacterial receptor proteins.

27. PDGF-Rβ-binding polypeptide according to claim 26, in which said three-helix bundle protein domain is selected from domains of Protein A from *Staphylococcus aureus* and derivates thereof.

28. PDGF-Rβ-binding polypeptide according to claim 1, which comprises an amino acid sequence selected from:
ADNNFNK[PBM]-DPSQSANLLSEAKKLNESQAPK SEQ ID NO:543;
ADNKFNK-[PBM]-DPSQSANLLAE-AKKLNDAQAPK SEQ ID NO:544;
ADNKFNK-[PBM]-DPSVSKEILAEAKKLNDAQAPK SEQ ID NO:545;
ADAQQNNFNK-[PBM]-DPSQSTNVLGEAKKL-NESQAPK SEQ ID NO:546;
AQHDE-[PBM]-DPSQSANVLGEAQKLNDSQAPK SEQ ID NO:547;
VDNKFNK-[PBM]-DPSQSANLLAE-AKKLNDAQAPK SEQ ID NO:548;
VDAKFAK-[PBM]-DPSQSSELLSEAKKLNDSQAPK SEQ ID NO:549;
AEAKYAK-[PBM]-DPSQSSELLSEAKKLNDSQAPS SEQ ID NO:550; and
an amino acid sequence which has at least 80% identity to any one of the sequences defined above, and wherein [PBM] is an PDGF-Rβ-binding motif as defined in claim 1.

29. PDGF-Rβ-binding polypeptide according to claim 28, the amino acid sequence of which comprises a sequence selected from SEQ ID NO:359-537.

30. PDGF-Rβ-binding polypeptide according to claim 29, the amino acid sequence of which comprises a sequence selected from SEQ ID NO:360-361, SEQ ID NO:363, SEQ ID NO:365, SEQ ID NO:369, SEQ ID NO:418, SEQ ID NO:430, SEQ ID NO:436, SEQ ID NO:469, SEQ ID NO:511 and SEQ ID NO:537.

31. PDGF-Rβ-binding polypeptide according to claim 1, which has been extended by C terminal and/or N terminal amino acids.

32. PDGF-Rβ-binding polypeptide according to claim 31, in which each amino acid extension improves production, purification, stabilization in vivo or in vitro, coupling, or detection of the polypeptide.

33. PDGF-Rβ-binding polypeptide according to claim 32, in which the extension comprises an albumin-binding domain of streptococcal protein G, or a derivative thereof.

34. PDGF-Rβ-binding polypeptide according to claim 1, which binds to PDGF-Rβ such that the $K_D$ value of the interaction is at most $1\times10^{-7}$.

35. PDGF-Rβ-binding polypeptide according to claim 34, wherein said $K_D$ value is at most $1\times10^{-8}$.

36. PDGF-Rβ-binding polypeptide according to claim 1, which binds to the extra-cellular domain of PDGF-Rβ.

37. PDGF-Rβ-binding polypeptide according to claim 1, which blocks the binding of PDGF-BB to PDGF-Rβ.

38. PDGF-Rβ-binding polypeptide according to claim 1 in multimeric form, comprising at least two PDGF-Rβ-binding polypeptide monomer units, the amino acid sequences of which may be the same or different.

39. PDGF-Rβ-binding polypeptide according to claim 38, in which the PDGF-Rβ-binding polypeptide monomer units are covalently coupled together.

40. PDGF-Rβ-binding polypeptide according to claim 38, in which the PDGF-Rβ-binding polypeptide monomer units are expressed as a fusion protein.

41. PDGF-Rβ-binding polypeptide according to claim 38, in dimeric form.

42. A polynucleotide encoding a polypeptide according to claim 1.

43. Method of producing a polypeptide, comprising expressing a polynucleotide according to claim 42.

44. A composition of a PDGF-Rβ-binding polypeptide according to claim 1 and a therapeutic agent.

* * * * *